(12) United States Patent
Jakob-Roetne et al.

(10) Patent No.: US 8,163,728 B2
(45) Date of Patent: Apr. 24, 2012

(54) PYRAZOLES

(75) Inventors: Roland Jakob-Roetne, Inzlingen (DE);
Matthew C. Lucas, Verona, NJ (US);
Andrew Thomas, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 107 days.

(21) Appl. No.: 12/768,770

(22) Filed: Apr. 28, 2010

(65) Prior Publication Data

US 2010/0286115 A1 Nov. 11, 2010

(30) Foreign Application Priority Data

May 5, 2009 (EP) .................................... 09159364

(51) Int. Cl.
| | | |
|---|---|---|
| *A61K 31/422* | (2006.01) | |
| *A61K 31/541* | (2006.01) | |
| *A61K 31/5377* | (2006.01) | |
| *A61K 31/454* | (2006.01) | |
| *A61K 31/4439* | (2006.01) | |
| *C07D 417/14* | (2006.01) | |
| *C07D 413/14* | (2006.01) | |
| *C07D 413/12* | (2006.01) | |

(52) U.S. Cl. ............. 514/210.18; 514/227.8; 514/236.5; 514/326; 514/341; 514/374; 544/131; 544/137; 546/209; 546/272.1; 548/247

(58) Field of Classification Search ........................ None
See application file for complete search history.

(56) References Cited

U.S. PATENT DOCUMENTS

| | | | |
|---|---|---|---|
| 4,639,266 | A | 1/1987 | Heubach et al. |
| 2003/0055085 | A1 | 3/2003 | Wagenen et al. |
| 2004/0006226 | A1 | 1/2004 | Ladduwahetty et al. |

FOREIGN PATENT DOCUMENTS

| | | |
|---|---|---|
| DE | 3525205 | 3/1986 |
| GB | 2336589 | 10/1999 |
| JP | 2007230909 | 9/2007 |
| WO | 0129015 | 4/2001 |
| WO | 0134603 | 5/2001 |
| WO | 0250062 | 6/2002 |
| WO | 02081474 | 10/2002 |
| WO | 03004027 | 1/2003 |
| WO | 03015771 | 2/2003 |
| WO | 03044017 | 5/2003 |
| WO | 2004048349 | 6/2004 |
| WO | 2005014553 | 2/2005 |
| WO | 2005118568 | 12/2005 |
| WO | 2005123672 | 12/2005 |
| WO | 2006037480 | 4/2006 |
| WO | 2006044617 | 4/2006 |
| WO | 2006069155 | 6/2006 |
| WO | 2007009275 | 1/2007 |
| WO | 2007/039389 | 4/2007 |
| WO | 2007039389 | 4/2007 |
| WO | 2007052843 | 5/2007 |
| WO | 2007076260 | 7/2007 |
| WO | 2007092751 | 8/2007 |
| WO | 2007/137954 | 12/2007 |
| WO | 2008025539 | 3/2008 |
| WO | 2008025540 | 3/2008 |

OTHER PUBLICATIONS

McNamara et al., Psychobiology (1993), vol. 21, pp. 101-108.
Goodman et al., Tetrahedron (1999) vol. 55 pp. 15067-15070.
Abstract corresponding to JP 2007/230909.
Roy et al., Synthesis, 2003 pp. 1347-1356.
White, et al., Journal of Organic Chemistry (1981), vol. 46(11) pp. 2273-2280.
Shi Shun et al., J. Org. Chem. vol. 68 (2003) pp. 6810-6813.
Lam et al., Bioorganic & Medicinal Chemistry Letters (2003) vol. 13(10) pp. 1795-1799.
Wang et al., Journal of Fluorine Chemistry, vol. 111(2) pp. 241-246 (2001).
Hamper et al., J. Agric. Food Chem. (1995), vol. 43, pp. 219-228.
Kumar, et al., Tetrahedron Letters, vol. 47, (2006), p. 1457-1460.
Burke, et al., Journal of Natural Products, 1986, vol. 49, pp. 522-523.
Hormi, Organic Syntheses, vol. 8, p. 247 (1993) & vol. 66, (1988), p. 173.
Andosova et al., Pharmaceutical Chemistry Journal (English Translation), vol. 12, No. 8, 1978, pp. 1019-1022.
Doyle, et al., Journal of the Chem. Society, 1963, pp. 5838-5845.
Anderson, et al., Journal of Organic Chem. vol. 51(6), 1986, pp. 945-947.
Bourbeau et al., Organic Letters, vol. 8(17), 2006, pp. 3679-3680.
Waldo et al., Org. Lett. vol. (7) pp. 5203-5205 (2005).
Seydel et al., J. Med. Chem. vol. (19) pp. 483-492 (1976).
Kirk, K. L., J. Org. Chem. vol. (43) pp. 4381-4383 (1978).
Ley et al., Angew Chem, 2003 vol. 115 p. 5558-5606.
Hüttel et al., Liebigs, Ann. Chem. vol. 593, pp. 200-207 (1955) (English translation).
Austin et al., J. Org. Chem. vol. 46, pp. 2280-2286 (1981).
Schlosser et al., Eur. J. Org. Chem. vol. (24), p. 4181-4184 (2002).
Félix et al., J. Org. Chem. 1995, vol. 60 p. 3907-3909.

(Continued)

*Primary Examiner* — Kamal Saeed
(74) *Attorney, Agent, or Firm* — George W. Johnston; Patricia S. Rocha-Tramaloni; Kimberly J. Prior

(57) ABSTRACT

The present invention is concerned with isoxazole-pyrazoles of formula I, having affinity and selectivity for GABA A α5 receptor, their manufacture, pharmaceutical compositions containing them and their use as therapeutics. The active compounds of the present invention are useful as cognitive enhancer or for the therapeutic and/or prophylactic treatment of cognitive disorders like Alzheimer's disease.

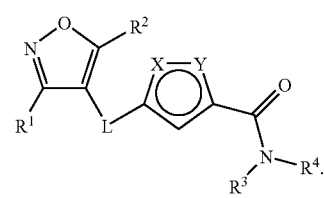

57 Claims, No Drawings

OTHER PUBLICATIONS

Otani et al., Neuroscience Letters, 2005, vol. 381 pp. 108-113.
Papadimitriou et al., Neuropsychobiology, 2001, vol. 43(3) pp. 141-144.
McCauley et al., American J. Med. Genetics, 2004, 131B, pp. 51-59.
Delong et al., Autism, 2007, vol. 11(2) pp. 135-147.
Solis Anez et al., Investigacion Clinica, 2007 vol. 28, pp. 529-541.
Fernandez et al., Nature, Neuroscience, 2007, vol. 10 pp. 411-413.
Rueda et al., Neuroscience Letters, 2008, vol. 433 pp. 22-27.
Cui et al., Cell. 2008, vol. 135, pp. 549-560.
Deshayes et al., Synthesis, 1984, pp. 868-870.
International Search Report by EPO for PCT/EP2010/055694 mailed Aug. 17, 2010.

PYRAZOLES

PRIORITY TO RELATED APPLICATION(S)

This application claims the benefit of European Patent Application No. 09159364.0, filed May 5, 2009, which is hereby incorporated by reference in its entirety.

FIELD OF THE INVENTION

The present invention is concerned with isoxazole-pyrazole derivatives having affinity and selectivity for GABA A α5 receptor, their manufacture, pharmaceutical compositions containing them and their use as medicaments.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in Psychobiology, 1993, 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor can be used to provide a medicament which is useful for enhancing cognition with reduced or without proconvulsant activity. It is also possible to use GABA A α5 inverse agonists which are not free of activity at GABA A α1 and/or α2 and/or α3 receptor but which are functionally selective for α5 containing subunits. However, inverse agonists which are selective for GABA A α5 subunits and are relatively free of activity at GABA A α1, α2 and α3 receptor are preferred.

Literature has been published to establish the link between GABA A α5 subunits and the therapeutic and/or prophylactic treatment of various diseases and disorders of the Central Nervous System, like Neuroscience Letts., 2005, 381,108-13, Neuropsychobiology, 2001, 43(3), 141-44, Amer. J. Med. Genetics, 2004, 131B, 51-9, Autism 2007, 11(2): 135-47, Investigacion Clinica, 2007, 48, 529-41, Nature Neuroscience, 2007, 10, 411-13, Neuroscience Letts., 2008, 433, 22-7 and Cell 2008, 135, 549-60.

SUMMARY OF THE INVENTION

In particular, the present invention provides isoxazole-pyrazoles of formula I

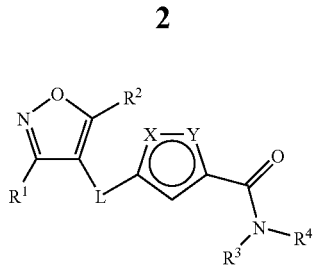

wherein

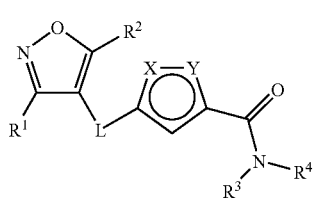

wherein
L is —$CH_2$—O—, —$CH_2$—NH— or —CH=CH—;
X is N—$R^5$ and Y is N, or X is N and Y is N—$R^6$;
$R^1$ is selected from the group consisting of
  i) lower alkyl,
  ii) lower alkyl substituted by 1-5 halogen atoms,
  iii) aryl,
  iv) aryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl,H)N—, N(lower alkyl, lower alkyl)-lower alkyl, N(lower alkyl,H)-lower alkyl, nitro, lower alkyl-S(O)$_2$—, carboxy, carboxy-lower alkyl, lower alkyl-COO-lower alkyl, COO-lower alkyl, CO—N(lower alkyl,H)-lower alkyl, CO—N(lower alkyl,lower alkyl)-lower alkyl, CO—$NH_2$-lower alkyl and lower alkyl-CO—,
  v) heteroaryl,
  vi) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl,H)N—, N(lower alkyl, lower alkyl)-lower alkyl, N(lower alkyl,H)-lower alkyl, nitro, lower alkyl-S(O)$_2$—, carboxy, carboxy-lower alkyl, lower alkyl-COO-lower alkyl, lower alkyl-COO—, CO—N(lower alkyl,H)-lower alkyl, CO—N(lower alkyl,lower alkyl)-lower alkyl, CO—$NH_2$-lower alkyl and lower alkyl-CO—, and
  vii) heterocyclyl;
$R^2$ is H, lower alkyl or lower alkyl substituted by 1-5 substituents individually selected from halogen and hydroxy;
$R^3$ is selected from the group consisting of
  i) H,
  ii) lower alkyl,
  iii) lower alkyl substituted by 1-5 substituents individually selected from acetamidyl, acetyl, acetylamino, amido, amino, carboxy, cyano, cycloalkyl, halogen, halogen-lower alkoxy, heterocyclyl, hydroxy, lower alkoxy, (lower alkyl,lower alkyl)N—, (lower alkyl,H)N—, nitro and lower alkyl-S(O)$_2$—, iv) heteroaryl,
v) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl,H)N—, N(lower alkyl, lower alkyl)-lower alkyl, N(lower alkyl,H)-lower alkyl, nitro, lower alkyl-S(O)$_2$—, carboxy, carboxy-lower alkyl, lower alkyl-COO-lower alkyl, lower alkyl-COO—, CO—N(lower alkyl,H)-lower alkyl, CO—N (lower alkyl,lower alkyl)-lower alkyl, CO—NH$_2$-lower alkyl, and lower alkyl-CO—,
vi) cycloalkyl,
vii) cycloalkyl substituted by 1-4 substituents individually selected from halogen and hydroxy,
viii) heterocyclyl,
ix) heterocyclyl substituted by 1-4 substituents individually selected from halogen and lower alkyl, and
x) —NR$^7$R$^8$;
R$^4$ is H, lower alkyl or lower alkyl substituted by 1-5 halogen atoms; or R$^3$ and R$^4$ together with the nitrogen to which they are attached form a heterocyclyl or a heterocyclyl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, lower alkyl-COO—, CO—N(lower alkyl,H)-lower alkyl, CO—N(lower alkyl,lower alkyl)-lower alkyl, CO—NH$_2$-lower alkyl and lower alkyl-CO—;
R$^5$ is H or lower alkyl;
R$^6$ is H or lower alkyl;
R$^7$ is lower alkyl; and
R$^8$ is lower alkyl,
or a pharmaceutically acceptable salt or ester thereof.

DETAILED DESCRIPTION OF THE INVENTION

The present invention provides compounds of formula I and their pharmaceutically acceptable salts and esters pharmaceutical compositions containing them. The invention also provides methods for the manufacture of the compounds and compositions of the invention. The invention further provides for methods of therapeutic and/or prophylactic treatment of diseases and disorders related to the GABA A α5 receptor. The compounds of present invention are preferably inverse agonists of GABA A α5.

The compounds of present invention and their pharmaceutically acceptable salts and esters can be used, alone or in combination with other drugs, as cognitive enhancers or for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders.

In particular, the compounds of the invention are useful for the therapeutic and/or prophylactic treatment of cognitive disorders, schizophrenia, positive, negative and/or cognitive symptoms associated with schizophrenia and Alzheimer's disease. Most preferred indications are schizophrenia and Alzheimer's disease. Particularly preferred is the therapeutic and/or prophylactic treatment of Alzheimer's disease.

The following definitions of the general terms used in the present description apply irrespective of whether the terms in question appear alone or in combination.

The term "lower alkyl", alone or in combination with other groups, stands for a hydrocarbon radical that is linear or branched, with single or multiple branching, whereby the alkyl group in general contains 1 to 6 carbon atoms, for example, methyl (Me), ethyl (Et), propyl, isopropyl (i-propyl), n-butyl, i-butyl (iso-butyl), 2-butyl (sec-butyl), t-butyl (tert-butyl) and the like. Preferred alkyl groups are groups with 1 to 4 carbon atoms. Most preferred are methyl, ethyl, isopropyl and n-butyl.

The phrase "lower alkyl substituted by", alone or in combination with other groups, refers to lower alkyl group that is substituted by one or multiple substituents, preferably 1-5 substituents, individually selected from the group consisting of acetamidyl, acetyl, acetylamino, amido, amino, carboxy, cyano, cycloalkyl, halogen, halogen-lower alkoxy, heterocyclyl, hydroxy, lower alkoxy, (lower alkyl,lower alkyl)N—, (lower alkyl,H)N—, nitro, lower alkyl-S(O)$_2$— and the like. Preferred substituents are hydroxy, fluoro, methyl, oxetanyl, methoxy, acetylamino and cyclopropyl. Preferred "lower alkyl substituted by" are hydroxy-lower alkyl, halogen-lower alkyl, fluoro-lower alkyl, cycloalkyl-lower alkyl and acetylamino-lower alkyl. Most preferred are 1-hydroxy-cyclopropyl-methyl, 1-hydroxymethyl-propyl, 1-oxetanyl-ethyl, 2,2,2-trifluoro-1-methyl-ethyl, 2,2,2-trifluoro-ethyl, 2,2,3,3,3-pentafluoro-propyl, 2-acetylamino-ethyl, 2-hydroxy-1,1-dimethyl-ethyl, 2-hydroxy-1-hydroxymethyl-ethyl, 2-hydroxy-1-methyl-ethyl, 2-hydroxy-2-methyl-propyl, 2-hydroxy-ethyl, 2-methoxy-ethyl, 3,3,3-trifluoro-2-hydroxy-propyl, 3-hydroxy-2,2-dimethyl-propyl. The most preferred are cyclopropyl-methyl, 1-hydroxy-cyclopropyl-methyl, 1-hydroxymethyl-propyl, 1-oxetanyl-ethyl, 2,2,2-trifluoro-1-methyl-ethyl, 2,2,2-trifluoro-ethyl, 2,2,3,3,3-pentafluoro-propyl, 2-acetylamino-ethyl, 2-hydroxy-1,1-dimethyl-ethyl, 2-hydroxy-1-hydroxymethyl-ethyl, 2-hydroxy-1-methyl-ethyl, 2-hydroxy-2-methyl-propyl, 2-hydroxy-ethyl, 2-methoxy-ethyl, 3,3,3-trifluoro-2-hydroxy-propyl, 3-hydroxy-2,2-dimethyl-propyl.

The term "halogen", alone or in combination with other groups, denotes chlorine (Cl), iodine (I), fluorine (F) and bromine (Br). Preferred halogen is fluorine.

The term "aryl", alone or in combination with other groups, refers to an aromatic carbocyclic group containing 6 to 14, preferably 6 to 10, carbon atoms and having at least one aromatic ring or multiple condensed rings in which at least one ring is aromatic, for example phenyl (Ph), benzyl, naphthyl, biphenyl or indanyl. Preferred aryl group is phenyl.

The phrase "aryl substituted by", alone or in combination with other groups, refer to an aryl group that is substituted by one or multiple substituents, preferably 1-4 substituents, whereby substitution at each ring atom individually is possible, with a substituent individually selected from the group consisting of amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, COO-lower alkyl, CO—N(lower alkyl,H)-lower alkyl, CO—N(lower alkyl,lower alkyl)-lower alkyl, CO—NH$_2$-lower alkyl, lower alkyl-CO— and the like. Preferred substituents are F and Cl. Preferred "aryl substituted by" are halogen-aryl, chloro-aryl, fluoro-aryl, fluoro-phenyl and chloro-phenyl. Most preferred are 4-fluoro-phenyl and 4-chloro-phenyl.

The term "heteroaryl", alone or in combination with other groups, refers to a cyclic aromatic group having a single 4 to 8 membered ring or multiple condensed rings comprising 6 to 14, more preferably 6 to 10, ring atoms and containing 1, 2 or 3 heteroatoms, in which group at least one heterocyclic ring is aromatic. Examples of such groups include pyrrolyl, thienyl, furyl, pyrazolyl, imidazolyl, triazolyl, tetrazolyl, thiazolyl, isothiazolyl, oxazolyl, isoxazolyl, pyridinyl, pyrimidinyl, pyrazinyl, pyridazinyl, indolyl, indazolyl, quinolinyl, isoquinolinyl, benzofuryl, benzothiazolyl, benzotriazolyl, benzoimidazolyl, benzooxazinyl, benzothiazinyl, benzothienyl and the like. Preferred heteroaryl groups are pyridinyl and pyrazolyl.

The phrase "heteroaryl substituted by", alone or in combination with other groups, refers to a heteroaryl group that is substituted by one or multiple substituents, preferably 1-4 substituents, whereby substitution at each ring atom individually is possible, individually selected from the group consisting of amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, COO-lower alkyl, CO—N(lower alkyl,H)-lower alkyl, CO—N(lower alkyl,lower alkyl)-lower alkyl, CO—NH$_2$-lower alkyl, lower alkyl-CO— and the like. Preferred substituents are H, F and Me. Preferred "heteroaryl substituted by" are lower alkyl-heteroaryl, methyl-heteroaryl, halogen-pyridinyl, halogen-heteroaryl and fluoro-heteroaryl. Most preferred are 1-methyl-pyrazolyl and 5-fluoro-pyridin-2-yl.

The term "heterocyclyl", alone or in combination with other groups, refers to a 4 to 8 membered ring containing 1, 2 or 3 ring heteroatoms individually selected from N, O and S. 1 or 2 ring heteroatoms are preferred. The heterocyclyl can be part of a bicyclic spiro ring. Preferred are 4 to 6 membered heterocyclyl, more preferred 5 to 6 membered heterocyclyl, each containing 1 or 2 ring heteroatoms selected from N, O and S. An S heteroatom can be substituted by oxo such as SO$_2$. Examples of such heterocyclyl groups include pyrrolidinyl (pyrrolidinyl), tetrahydrofuryl, tetrahydrothienyl, tetrahydropyridyl (tetrahydropyridinyl), tetrahydropyryl, azetidyl (azetidinyl), thiazolidyl (thiazolidinyl), oxazolidyl (oxazolidinyl), piperidyl (piperidinyl), morpholinyl, thiomorpholinyl, piperazinyl, azepanyl, diazepanyl, 2-oxa-6-aza-spiro[3.3]heptyl, oxetanyl, oxazepanyl and the like. Preferred heterocyclyl groups are oxetanyl, azetidinyl, morpholinyl, 2-oxa-6-aza-spiro[3.3]heptyl, tetrahydrofuryl, tetrahydropyryl, pyrrolidinyl and piperidinyl. Most preferred heterocyclyl groups are oxetanyl, azetidinyl, morpholinyl, 2-oxa-6-aza-spiro[3.3]heptyl, 1,1-dioxo-1,6-thiomorpholin-4-yl tetrahydrofuryl, tetrahydropyryl, pyrrolidinyl and piperidinyl.

The phrase "heterocyclyl substituted by", alone or in combination with other groups, refers to a heterocyclyl group that is substituted by one or multiple substituents, preferably 1-4 substituents, whereby substitution at each ring atom individually is possible, with a substituent individually selected from the group consisting of amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, —COO-lower alkyl, CO—N(lower alkyl,H)-lower alkyl, CO—N(lower alkyl,lower alkyl)-lower alkyl, CO—NH$_2$-lower alkyl, lower alkyl-CO— and the like. Preferred substituents are hydroxy, fluoro and methyl. Preferred "heterocyclyl substituted by" are hydroxy-heterocyclyl, halogen-heterocyclyl, fluoro-heterocyclyl, lower alkyl-heterocyclyl and methyl-heterocyclyl. Most preferred are 3-hydroxy-azetidinyl, fluoro-piperidyl, 4,4-difluoro-piperidyl, methyl-tetrahydropyryl and 2,2-dimethyl-tetrahydropyryl.

The term "cycloalkyl", alone or in combination with other groups, refers to a 3 to 8 membered alicyclic carbon ring, for example cyclopropyl, cyclobutyl, cyclopentyl, cyclohexyl, cycloheptyl or cyclooctyl. Preferred cycloalkyl are cyclopropyl, cyclobutyl and cyclopentyl.

The phrase "cycloalkyl substituted by", alone or in combination with other groups, refers to a cycloalkyl group that is substituted by one or multiple substituents, preferably 1-4 substituents, whereby substitution at each ring atom individually is possible, with a substituent individually selected from the group consisting of halogen, halogen-lower alkoxy, halogen-lower alkyl, hydroxy, hydroxy-lower alkyl, lower alkoxy, lower alkoxy-lower alkyl, lower alkyl, (lower alkyl,lower alkyl)N—, (lower alkyl,H)N—, nitro, lower alkyl-S(O)$_2$— and the like. Preferred substituent is hydroxy. Preferred "cycloalkyl substituted by" is hydroxy-cycloalkyl. Most preferred is 2-hydroxy-cyclopentyl.

The term "lower alkoxy", alone or in combination with other groups, stands for a "—O-lower alkyl" radical that is be linear or branched, with single or multiple branching, whereby the alkyl group in general contains 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), iso-pentyloxy (i-pentyloxy) and the like. Preferred alkoxy groups are groups with 1 to 4 carbon atoms. Most preferred is methoxy.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salts" refers to salts that are suitable for use in contact with the tissues of humans and animals without undue toxicity, irritation, allergic response, and the like. Examples of suitable salts with inorganic and organic acids are, but are not limited to, hydrochloric acid, nitric acid, sulfuric acid, phosphoric acid, sulphuric acid, citric acid, formic acid, fumaric acid, maleic acid, lactic acid, malic acid, acetic acid, succinic acid, tartaric acid, methane-sulfonic acid, p-toluenesulphonic acid, trifluoroacetic acid and the like.

The term "pharmaceutically acceptable esters" refers to a conventionally esterified compound having a carboxyl group. Examples of ester groups which are for example cleaved in vivo to the corresponding carboxylic acids are those in which the cleaved hydrogen is replaced with-lower alkyl, which is un-substituted or substituted with heterocyclyl, cycloalkyl, etc. Examples of substituted lower alkyl esters are those in which-lower alkyl is substituted with pyrrolidine, piperidine, morpholine, N-methylpiperazine, etc. Furthermore, the term "pharmaceutically acceptable esters" refers to a conventionally esterified compound having a hydroxy group. The hydroxy compounds can be converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which acids are non-toxic to living organisms.

The terms "pharmaceutically acceptable carrier" and "pharmaceutically acceptable auxiliary substance" refer to carriers and auxiliary substances such as diluents or excipients that are compatible with the other ingredients of the formulation and not deleterious to the recipient thereof.

"Therapeutically effective amount" means an amount that is effective to prevent, alleviate or ameliorate symptoms of disease or prolong the survival of the subject being treated.

The compounds of formula I can contain one or more asymmetric centres and can therefore occur as racemates, racemic mixtures, single enantiomers, diastereomeric mixtures and individual diastereomers. Additional asymmetric centres can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to comprehend all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

Substituents at a double bond or a ring can be present in cis (=Z—) or trans (=E-) form, unless the stereochemistry is explicitly depicted in the corresponding compound formula I.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The following table lists abbreviations used within the present document.

TABLE 1

| abbreviations | |
|---|---|
| AIBN | N,N-Azobisisobutyronitril |
| AD Mix-α | 1.6 mmol hydroquinine 1,4-phthalazinediyl diether |
| | 0.4988 mol potassium carbonate, powder |
| | 0.4988 mol potassium ferricyanide |
| | 0.7 mmol potassium osmate dihydrate |

TABLE 1-continued

| abbreviations | |
|---|---|
| AcOH | acetic acid |
| brine | water saturated with sodium chloride |
| BuLi | butyl lithium |
| CDI | 1,1'-carbonyldiimidazole |
| DCM | dichloromethane |
| DIPEA | N,N-diisopropylethylamine |
| DMAP | N,N-dimethylamino-4-pyridine |
| DMF | N,N-dimethylformamide |
| DMSO | dimethylsulfoxide |
| EDAC | 1-ethyl-3-(3-dimethylaminopropyl) carbodiimide hydrochloride |
| EDCI | N-Ethyl-N,N'-(dimethylaminopropyl)-carbodiimid |
| EI | electron ionization |
| HCl | hydrochloride |
| HOBt | N-1-hydroxybenzotriazole |
| KCl, CaCl$_2$, MgCl$_2$ | potassium chloride, calcium chloride, magnesium chloride |
| LiHMDS | Lithium bis(trimethylsilyl)amide |
| LiOH, NaOH | lithium hydroxide, sodium hydroxide |
| m/e | mass-to-charge ratio of ionized atoms or molecules |
| Me$_3$Al | trimethylaluminium |
| MeOH, EtOH | methanol, ethanol |
| MS | mass spectrum |
| NaCNBH$_3$ | sodium cyanoborohydride |
| PPh$_3$ | triphenylphosphine |
| PCC | pyridinium chlorochromate |
| on | overnight |
| rt | room temperature |
| Seignette's salt | potassium sodium tartrate |
| SiO$_2$ | silicium dioxide |
| SOCl$_2$ | thionylchloride |
| TBD | 1,5,7-triazabicyclo[4.4.0]dec-5-ene |
| TBTU | O-(Benzotriazol-1-yl)-N,N,N',N'-tetramethyluronium tetrafluoroborate |
| THF | tetrahydrofuran |
| Tris | Tris(hydroxymethyl)-aminomethane |

The invention also provides pharmaceutical compositions, methods of using the compounds of the invention, and methods of preparing the aforementioned compounds.

While the present invention has been described with reference to the specific embodiments thereof, it should be understood by those skilled in the art that various changes can be made and equivalents can be substituted without departing from the true spirit and scope of the invention. In addition, many modifications can be made to adapt a particular situation, material, composition of matter, process, process step or steps, to the objective spirit and scope of the present invention. All such modifications are intended to be within the scope of the claims appended hereto. All separate embodiments can be combined.

The invention therefore also relates to pharmaceutical compositions comprising a compound as defined herewithin and a pharmaceutically acceptable carrier and/or adjuvant.

One embodiment of the invention provides compounds of formula I,

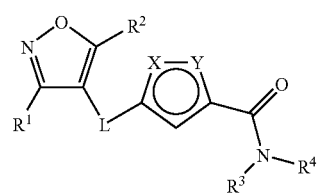

I wherein
L is —CH$_2$—O—, —CH$_2$—NH— or —CH=CH—;
X is N—R$^5$ and Y is N, or X is N and Y is N—R$^6$;

$R^1$ is selected from the group consisting of
  i) lower alkyl,
  ii) lower alkyl substituted by 1-5 halogen atoms,
  iii) aryl,
  iv) aryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl, lower alkyl)-lower alkyl, N(lower alkyl,H)-lower alkyl, nitro, lower alkyl-S(O)$_2$—, carboxy, carboxy-lower alkyl, lower alkyl-COO-lower alkyl, COO-lower alkyl, CO—N(lower alkyl,H)-lower alkyl, CO—N(lower alkyl,lower alkyl)-lower alkyl, CO—NH$_2$-lower alkyl and lower alkyl-CO—,
  v) heteroaryl,
  vi) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl,H)N—, N(lower alkyl, lower alkyl)-lower alkyl, N(lower alkyl,H)-lower alkyl, nitro, lower alkyl-S(O)$_2$—, carboxy, carboxy-lower alkyl, lower alkyl-COO-lower alkyl, lower alkyl-COO—, CO—N(lower alkyl,H)-lower alkyl, CO—N(lower alkyl,lower alkyl)-lower alkyl, CO—NH$_2$-lower alkyl and lower alkyl-CO—, and
  vii) heterocyclyl;
$R^2$ is H, lower alkyl or lower alkyl substituted by 1-5 substituents individually selected from halogen and hydroxy;
$R^3$ is selected from the group consisting of
  i) H,
  ii) lower alkyl,
  iii) lower alkyl substituted by 1-5 substituents individually selected from acetamidyl, acetyl, acetylamino, amido, amino, carboxy, cyano, cycloalkyl, halogen, halogen-lower alkoxy, heterocyclyl, hydroxy, lower alkoxy, (lower alkyl,lower alkyl)N—, (lower alkyl,H)N—, nitro and lower alkyl-S(O)$_2$—,
  iv) heteroaryl,
  v) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl,H)N—, N(lower alkyl, lower alkyl)-lower alkyl, N(lower alkyl,H)-lower alkyl, nitro, lower alkyl-S(O)$_2$—, carboxy, carboxy-lower alkyl, lower alkyl-COO-lower alkyl, lower alkyl-COO—, CO—N(lower alkyl,H)-lower alkyl, CO—N(lower alkyl,lower alkyl)-lower alkyl, CO—NH$_2$-lower alkyl, and lower alkyl-CO—,
  vi) cycloalkyl,
  vii) cycloalkyl substituted by 1-4 substituents individually selected from halogen and hydroxy,
  viii) heterocyclyl,
  ix) heterocyclyl substituted by 1-4 substituents individually selected from halogen and lower alkyl, and
  x) —NR$^7$R$^8$;
$R^4$ is H, lower alkyl or lower alkyl substituted by 1-5 halogen atoms;
or $R^3$ and $R^4$ together with the nitrogen to which they are attached form a heterocyclyl or a heterocyclyl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, lower alkyl-COO—, CO—N(lower alkyl,H)-lower alkyl, CO—N(lower alkyl,lower alkyl)-lower alkyl, CO—NH$_2$-lower alkyl and lower alkyl-CO—;
$R^5$ is H or lower alkyl;
$R^6$ is H or lower alkyl;
$R^7$ is lower alkyl; and
$R^8$ is lower alkyl,
or a pharmaceutically acceptable salt or ester thereof.

One further embodiment of the invention provides compounds of formula I, wherein
L is —CH$_2$—O— or —CH=CH—;
X is N—R$^5$ and Y is N, or X is N and Y is N—R$^6$;
$R^1$ is selected from the group consisting of
  i) lower alkyl,
  ii) lower alkyl substituted by 1-5 halogen atoms,
  iii) aryl,
  iv) aryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl,H)N—, N(lower alkyl, lower alkyl)-lower alkyl, N(lower alkyl,H)-lower alkyl, nitro lower alkyl-S(O)$_2$—, carboxy, carboxy-lower alkyl, lower alkyl-COO-lower alkyl, COO-lower alkyl, CO—N(lower alkyl,H)-lower alkyl, CO—N(lower alkyl,lower alkyl)-lower alkyl, CO—NH$_2$-lower alkyl and lower alkyl-CO—,
  v) heteroaryl,
  vi) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl,H)N—, N(lower alkyl, lower alkyl)-lower alkyl, N(lower alkyl,H)-lower alkyl, nitro, lower alkyl-S(O)$_2$—, carboxy, carboxy-lower alkyl, lower alkyl-COO-lower alkyl, —COO-lower alkyl, CO—N(lower alkyl,H)-lower alkyl, CO—N(lower alkyl,lower alkyl)-lower alkyl, CO—NH$_2$-lower alkyl and lower alkyl-CO—, and
  vii) heterocyclyl;
$R^2$ is H, lower alkyl or lower alkyl substituted by 1-5 substituents individually selected from halogen and hydroxy;
$R^3$ is selected from the group consisting of
  i) H,
  ii) lower alkyl,
  iii) lower alkyl substituted by 1-4 substituents individually selected from acetamidyl, acetyl, acetylamino, amido, amino, carboxy, cyano, cycloalkyl, halogen, halogen-lower alkoxy, heterocyclyl, hydroxy, lower alkoxy, (lower alkyl,lower alkyl)N—, (lower alkyl,H)N—, nitro and lower alkyl-S(O)$_2$—,
  iv) heteroaryl,
  v) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl,H)N—, N(lower alkyl, lower alkyl)-lower alkyl, N(lower alkyl,H)-lower alkyl, nitro, lower alkyl-S(O)$_2$—, carboxy, carboxy-lower alkyl, lower alkyl-COO-lower alkyl, lower alkyl-COO—, CO—N(lower alkyl,H)-lower alkyl, CO—N(lower alkyl,lower alkyl)-lower alkyl, CO—NH$_2$-lower alkyl and lower alkyl-CO—,
vi) cycloalkyl,
vii) cycloalkyl substituted by 1-4 substituents individually selected from halogen and hydroxy,
viii) heterocyclyl,
ix) heterocyclyl substituted by 1-4 substituents individually selected from halogen and lower alkyl, and
x) —NR$^7$R$^8$;

R$^4$ is H, lower alkyl or lower alkyl substituted by 1-5 halogen atoms;
or R$^3$ and R$^4$ together with the nitrogen to which they are attached form a heterocyclyl or a heterocyclyl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, lower alkyl-COO—, CO—N(lower alkyl,H)-lower alkyl, CO—N(lower alkyl,lower alkyl)-lower alkyl, CO—NH$_2$-lower alkyl and lower alkyl-CO—;
R$^5$ is H or lower alkyl;
R$^6$ is H or lower alkyl;
R$^7$ is lower alkyl; and
R$^8$ is lower alkyl,
or a pharmaceutically acceptable salt or ester thereof.

One certain embodiment of the invention provides compounds of formula I, wherein L is —CH$_2$—O— or CH$_2$—NH—.

One certain embodiment of the invention provides compounds of formula I, wherein L is —CH$_2$—O—.

One certain embodiment of the invention provides compounds of formula I, wherein L attached to the isoxazole moiety is "-isoxazole-CH$_2$—O—".

One certain embodiment of the invention provides compounds of formula I, wherein L is —CH═CH—.

One certain embodiment of the invention provides compounds of formula I, wherein L is —CH═CH— in cis configuration.

One certain embodiment of the invention provides compounds of formula I, wherein L is —CH═CH— in trans configuration.

One certain embodiment of the invention provides compounds of formula I, wherein L is —CH$_2$—NH—.

One certain embodiment of the invention provides compounds of formula I, wherein L attached to the isoxazole moiety is "-isoxazole-CH$_2$—NH—".

One certain embodiment of the invention provides compounds of formula I, wherein X is N—R$^5$, Y is N and R$^5$ is H or lower alkyl.

One certain embodiment of the invention provides compounds of formula I, wherein R$^5$ is H or methyl.

One certain embodiment of the invention provides compounds of formula I, wherein R$^5$ is H.

One certain embodiment of the invention provides compounds of formula I, wherein R$^5$ is methyl.

One certain embodiment of the invention provides compounds of formula I, wherein X is N, Y is N—R$^6$ and R$^6$ is H or lower alkyl.

One certain embodiment of the invention provides compounds of formula I, wherein R$^6$ is H or methyl.

One certain embodiment of the invention provides compounds of formula I, wherein R$^6$ is H.

One certain embodiment of the invention provides compounds of formula I, wherein R$^6$ is methyl.

One certain embodiment of the invention provides compounds of formula I, wherein R$^1$ is aryl, aryl substituted by 1-2 halogen atoms individually selected from fluoro and chloro, heteroaryl or heteroaryl substituted by 1-2 fluoro atoms.

One certain embodiment of the invention provides compounds of formula I, wherein R$^1$ is phenyl, chloro-phenyl, fluoro-phenyl, pyridinyl or fluoro-pyridinyl.

One certain embodiment of the invention provides compounds of formula I, wherein R$^1$ is lower alkyl, aryl, aryl substituted by 1-2 halogen atoms, heteroaryl, heteroaryl substituted by 1-2 halogen atoms, or heterocyclyl.

One certain embodiment of the invention provides compounds of formula I, wherein R$^1$ is aryl, chloro-aryl, fluoro-aryl, heteroaryl or fluoro-heteroaryl.

One certain embodiment of the invention provides compounds of formula I, wherein R$^1$ is lower alkyl, aryl, aryl substituted by one or multiple halogen, heteroaryl, heteroaryl substituted by one or multiple halogen, or heterocyclyl.

One certain embodiment of the invention provides compounds of formula I, wherein R$^1$ is n-butyl, phenyl, halogen-phenyl, pyridinyl, halogen-pyridinyl, or tetrahydropyryl.

One certain embodiment of the invention provides compounds of formula I, wherein R$^1$ is n-butyl, phenyl, chloro-phenyl, fluoro-phenyl, pyridinyl, fluoro-pyridinyl, or tetrahydropyryl.

One certain embodiment of the invention provides compounds of formula I, wherein R$^1$ is lower alkyl.

One certain embodiment of the invention provides compounds of formula I, wherein R$^1$ is n-butyl.

One certain embodiment of the invention provides compounds of formula I, wherein R$^1$ is aryl.

One certain embodiment of the invention provides compounds of formula I, wherein R$^1$ is phenyl.

One certain embodiment of the invention provides compounds of formula I, wherein R$^1$ is halogen-aryl.

One certain embodiment of the invention provides compounds of formula I, wherein R$^1$ is halogen-phenyl.

One certain embodiment of the invention provides compounds of formula I, wherein R$^1$ is 4-fluoro-phenyl.

One certain embodiment of the invention provides compounds of formula I, wherein R$^1$ is 4-chloro-phenyl.

One certain embodiment of the invention provides compounds of formula I, wherein R$^1$ is heteroaryl.

One certain embodiment of the invention provides compounds of formula I, wherein R$^1$ is pyridinyl.

One certain embodiment of the invention provides compounds of formula I, wherein R$^1$ is halogen-heteroaryl.

One certain embodiment of the invention provides compounds of formula I, wherein R$^1$ is halogen-pyridinyl.

One certain embodiment of the invention provides compounds of formula I, wherein R$^1$ is 5-fluoro-pyridin-2-yl.

One certain embodiment of the invention provides compounds of formula I, wherein R$^2$ is H, lower alkyl or hydroxy-lower alkyl.

One certain embodiment of the invention provides compounds of formula I, wherein R$^2$ is H, methyl or hydroxy-methyl.

One certain embodiment of the invention provides compounds of formula I, wherein R$^2$ is lower alkyl or hydroxy-lower alkyl.

One certain embodiment of the invention provides compounds of formula I, wherein R$^2$ is H.

One certain embodiment of the invention provides compounds of formula I, wherein $R^2$ is methyl.

One certain embodiment of the invention provides compounds of formula I, wherein $R^2$ is hydroxy-methyl.

One certain embodiment of the invention provides compounds of formula I, wherein $R^3$ and $R^4$ together with the nitrogen to which they are attached form a heterocyclyl or a heterocyclyl substituted by 1-4 substituents individually selected from halogen and hydroxy.

One certain embodiment of the invention provides compounds of formula I, wherein $R^3$ and $R^4$ together with the nitrogen to which they are attached form a heterocyclyl or a heterocyclyl substituted by one or multiple substituents individually selected from halogen and hydroxy.

One certain embodiment of the invention provides compounds of formula I, wherein $R^3$ and $R^4$ together with the nitrogen to which they are attached form a morpholino, 3-hydroxy-azetidinyl, 2-oxa-6-aza-spiro[3.3]heptyl or 4,4-difluoro-piperidyl.

One certain embodiment of the invention provides compounds of formula I, wherein $R^3$ and $R^4$ together with the nitrogen to which they are attached form a heterocyclyl.

One certain embodiment of the invention provides compounds of formula I, wherein $R^3$ and $R^4$ together with the nitrogen to which they are attached form a morpholino.

One certain embodiment of the invention provides compounds of formula I, wherein $R^3$ and $R^4$ together with the nitrogen to which they are attached form a hydroxy-heterocyclyl.

One certain embodiment of the invention provides compounds of formula I, wherein $R^3$ and $R^4$ together with the nitrogen to which they are attached form a 3-hydroxy-azetidinyl.

One certain embodiment of the invention provides compounds of formula I, wherein $R^3$ and $R^4$ together with the nitrogen to which they are attached form a 2-oxa-6-aza-spiro[3.3]heptyl.

One certain embodiment of the invention provides compounds of formula I, wherein $R^3$ and $R^4$ together with the nitrogen to which they are attached form a halogen-heterocyclyl.

One certain embodiment of the invention provides compounds of formula I, wherein $R^3$ and $R^4$ together with the nitrogen to which they are attached form a 4,4-difluoro-piperidyl.

One certain embodiment of the invention provides compounds of formula I, wherein $R^3$ is lower alkyl, heterocyclyl-lower alkyl, hydroxy-lower alkyl or heterocyclyl.

One certain embodiment of the invention provides compounds of formula I, wherein $R^3$ is lower alkyl, heterocyclyl-lower alkyl or heterocyclyl.

One certain embodiment of the invention provides compounds of formula I, wherein $R^3$ is 1-oxetanyl-ethyl, 2-hydroxy-2-methyl-propyl, isopropyl, morpholino, tetrahydrofuryl or tetrahydropyryl.

One certain embodiment of the invention provides compounds of formula I, wherein $R^3$ is isopropyl, 1-oxetanyl-ethyl, morpholino, tetrahydropyryl or tetrahydrofuryl.

One certain embodiment of the invention provides compounds of formula I, wherein $R^3$ is
  i) H,
  ii) lower alkyl,
  iii) lower alkyl substituted by 1-5 substituents individually selected from acetylamino, cycloalkyl, halogen, heterocyclyl, hydroxy and lower alkoxy,
  iv) heteroaryl substituted by 1-4 substituents individually selected from halogen and lower alkyl,
  v) cycloalkyl,
  vi) cycloalkyl substituted by 1-4 hydroxy groups,
  vii) heterocyclyl,
  viii) heterocyclyl substituted by 1-4 lower alkyl groups, or
  ix) —N(lower alkyl)$_2$.

One certain embodiment of the invention provides compounds of formula I, wherein $R^3$ is 1-hydroxy-cyclopropyl-methyl, 1-hydroxymethyl-propyl, 1-hydroxymethyl-propyl, 1-methyl-1H-pyrazolyl, 1-methyl-pyrazolyl, 1-oxetanyl-ethyl, 2,2,2-trifluoro-1-methyl-ethyl, 2,2,2-trifluoro-ethyl, 2,2,3,3,3-pentafluoro-propyl, 2,2-dimethyl-tetrahydro-pyryl, 2-acetylamino-ethyl, 2-hydroxy-1,1-dimethyl-ethyl, 2-hydroxy-1-hydroxymethyl-ethyl, 2-hydroxy-1-methyl-ethyl, 2-hydroxy-1-methyl-ethyl, 2-hydroxy-1-methyl-ethyl, 2-hydroxy-2-methyl-propyl, 2-hydroxy-cyclopentyl, 2-hydroxy-ethyl, 2-methoxy-ethyl, 3,3,3-trifluoro-2-hydroxy-propyl, 3,3,3-trifluoro-2-hydroxy-propyl, 3-hydroxy-2,2-dimethyl-propyl, cyclobutyl, cyclopropyl, H, isopropyl, morpholino, —N(CH$_3$)$_2$, piperidinyl, pyrrolidinyl, t-butyl, tetrahydrofuryl or tetrahydropyryl.

One certain embodiment of the invention provides compounds of formula I, wherein $R^3$ is lower alkyl, heterocyclyl-lower alkyl or heterocyclyl.

One certain embodiment of the invention provides compounds of formula I, wherein $R^3$ is H.

One certain embodiment of the invention provides compounds of formula I, wherein $R^3$ is lower alkyl.

One certain embodiment of the invention provides compounds of formula I, wherein $R^3$ is isopropyl.

One certain embodiment of the invention provides compounds of formula I, wherein $R^3$ is t-butyl.

One certain embodiment of the invention provides compounds of formula I, wherein $R^3$ is 2-hydroxy-ethyl.

One certain embodiment of the invention provides compounds of formula I, wherein $R^3$ is 2,2,2-trifluoro-ethyl.

One certain embodiment of the invention provides compounds of formula I, wherein $R^3$ is 2,2,2-trifluoro-1-methyl-ethyl.

One certain embodiment of the invention provides compounds of formula I, wherein $R^3$ is 2-hydroxy-1,1-dimethyl-ethyl.

One certain embodiment of the invention provides compounds of formula I, wherein $R^3$ is 1-oxetanyl-ethyl.

One certain embodiment of the invention provides compounds of formula I, wherein $R^3$ is 2-methoxy-ethyl.

One certain embodiment of the invention provides compounds of formula I, wherein $R^3$ is 2-acetylamino-ethyl.

One certain embodiment of the invention provides compounds of formula I, wherein $R^3$ is 2-hydroxy-2-cyclopropyl-ethyl.

One certain embodiment of the invention provides compounds of formula I, wherein $R^3$ is hydroxy-isopropyl.

One certain embodiment of the invention provides compounds of formula I, wherein $R^3$ is dihydroxy-isopropyl.

One certain embodiment of the invention provides compounds of formula I, wherein $R^3$ is 3,3,3-trifluoro-2-hydroxy-propyl.

One certain embodiment of the invention provides compounds of formula I, wherein $R^3$ is 2,2,3,3,3-pentafluoro-propyl.

One certain embodiment of the invention provides compounds of formula I, wherein $R^3$ is 3-hydroxy-2,2-dimethyl-propyl.

One certain embodiment of the invention provides compounds of formula I, wherein $R^3$ is 2-hydroxy-2-methyl-propyl.

One certain embodiment of the invention provides compounds of formula I, wherein $R^3$ is 1-hydroxymethyl-propyl.

One certain embodiment of the invention provides compounds of formula I, wherein $R^4$ is H.

One certain embodiment of the invention provides compounds of formula I, wherein $R^4$ is lower alkyl.

One certain embodiment of the invention provides compounds of formula I, wherein $R^7$ is H.

One certain embodiment of the invention provides compounds of formula I, wherein $R^7$ is lower alkyl.

One certain embodiment of the invention provides compounds of formula I, wherein $R^7$ is methyl.

One certain embodiment of the invention provides compounds of formula I, wherein $R^8$ is H.

One certain embodiment of the invention provides compounds of formula I, wherein $R^8$ is lower alkyl.

One certain embodiment of the invention provides compounds of formula I, wherein $R^8$ is methyl.

One certain embodiment of the invention provides compounds of formula I selected from the group consisting of
[5-(5-Methyl-3-phenyl-isoxazol-4-ylmethoxy)-2H-pyrazol-3-yl]-morpholin-4-yl-methanone,
5-(5-Methyl-3-phenyl-isoxazol-4-ylmethoxy)-2H-pyrazole-3-carboxylic acid isopropylamide,
5-(5-Methyl-3-phenyl-isoxazol-4-ylmethoxy)-2H-pyrazole-3-carboxylic acid (tetrahydro-pyran-4-yl)-amide,
5-(5-Methyl-3-phenyl-isoxazol-4-ylmethoxy)-2H-pyrazole-3-carboxylic acid (tetrahydro-furan-3-yl)-amide,
5-(5-Methyl-3-phenyl-isoxazol-4-ylmethoxy)-2H-pyrazole-3-carboxylic acid N',N'-dimethyl-hydrazide,
5-(5-Methyl-3-phenyl-isoxazol-4-ylmethoxy)-2H-pyrazole-3-carboxylic acid (2-hydroxy-ethyl)-amide,
5-(5-Methyl-3-phenyl-isoxazol-4-ylmethoxy)-2H-pyrazole-3-carboxylic acid amide,
5-[3-(4-Fluoro-phenyl)-5-methyl-isoxazol-4-ylmethoxy]-2H-pyrazole-3-carboxylic acid morpholin-4-ylamide,
5-[3-(4-Fluoro-phenyl)-5-methyl-isoxazol-4-ylmethoxy]-2H-pyrazole-3-carboxylic acid piperidin-1-ylamide,
5-[3-(4-Fluoro-phenyl)-5-methyl-isoxazol-4-ylmethoxy]-2H-pyrazole-3-carboxylic acid pyrrolidin-1-ylamide,
5-[3-(4-Fluoro-phenyl)-5-methyl-isoxazol-4-ylmethoxy]-2H-pyrazole-3-carboxylic acid N',N'-dimethyl-hydrazide,
5-[3-(4-Fluoro-phenyl)-5-methyl-isoxazol-4-ylmethoxy]-2H-pyrazole-3-carboxylic acid isopropylamide,
5-[3-(4-Fluoro-phenyl)-5-methyl-isoxazol-4-ylmethoxy]-2H-pyrazole-3-carboxylic acid (tetrahydro-pyran-4-yl)-amide,
5-(5-Methyl-3-pyridin-2-yl-isoxazol-4-ylmethoxy)-1H-pyrazole-3-carboxylic acid isopropylamide,
5-(5-Methyl-3-pyridin-2-yl-isoxazol-4-ylmethoxy)-1H-pyrazole-3-carboxylic acid (tetrahydro-pyran-4-yl)-amide,
5-(5-Methyl-3-pyridin-2-yl-isoxazol-4-ylmethoxy)-1H-pyrazole-3-carboxylic acid ((S)-2-hydroxy-1-methyl-ethyl)-amide,
5-[3-(5-Fluoro-pyridin-2-yl)-5-methyl-isoxazol-4-ylmethoxy]-2H-pyrazole-3-carboxylic acid (2,2,2-trifluoro-ethyl)-amide,
5-[3-(5-Fluoro-pyridin-2-yl)-5-methyl-isoxazol-4-ylmethoxy]-2H-pyrazole-3-carboxylic acid (tetrahydro-furan-3-yl)-amide,
5-[3-(5-Fluoro-pyridin-2-yl)-5-methyl-isoxazol-4-ylmethoxy]-2H-pyrazole-3-carboxylic acid tert-butylamide,
5-[3-(5-Fluoro-pyridin-2-yl)-5-methyl-isoxazol-4-ylmethoxy]-2H-pyrazole-3-carboxylic acid (2-hydroxy-ethyl)-amide,
5-[3-(5-Fluoro-pyridin-2-yl)-5-methyl-isoxazol-4-ylmethoxy]-2H-pyrazole-3-carboxylic acid isopropylamide,
5-[3-(5-Fluoro-pyridin-2-yl)-5-methyl-isoxazol-4-ylmethoxy]-2H-pyrazole-3-carboxylic acid N',N'-dimethyl-hydrazide,
5-[3-(5-Fluoro-pyridin-2-yl)-5-methyl-isoxazol-4-ylmethoxy]-2H-pyrazole-3-carboxylic acid morpholin-4-ylamide,
5-[3-(5-Fluoro-pyridin-2-yl)-5-methyl-isoxazol-4-ylmethoxy]-2H-pyrazole-3-carboxylic acid pyrrolidin-1-ylamide,
5-[3-(5-Fluoro-pyridin-2-yl)-isoxazol-4-ylmethoxy]-2H-pyrazole-3-carboxylic acid morpholin-4-ylamide,
5-(3-Butyl-5-methyl-isoxazol-4-ylmethoxy)-2H-pyrazole-3-carboxylic acid (tetrahydro-pyran-4-yl)-amide,
5-(3-Butyl-5-methyl-isoxazol-4-ylmethoxy)-2H-pyrazole-3-carboxylic acid ((S)-2-hydroxy-1-methyl-ethyl)-amide,
5-(3-Butyl-5-methyl-isoxazol-4-ylmethoxy)-2H-pyrazole-3-carboxylic acid (tetrahydro-furan-3-yl)-amide,
5-(3-Butyl-5-methyl-isoxazol-4-ylmethoxy)-2H-pyrazole-3-carboxylic acid (2-hydroxy-1-hydroxymethyl-ethyl)-amide,
5-(3-Butyl-5-methyl-isoxazol-4-ylmethoxy)-2H-pyrazole-3-carboxylic acid ((R)-2-hydroxy-1-methyl-ethyl)-amide,
5-(3-Butyl-5-methyl-isoxazol-4-ylmethoxy)-2H-pyrazole-3-carboxylic acid (2,2,2-trifluoro-ethyl)-amide,
5-(3-Butyl-5-methyl-isoxazol-4-ylmethoxy)-2H-pyrazole-3-carboxylic acid isopropylamide,
5-(3-Butyl-5-methyl-isoxazol-4-ylmethoxy)-2H-pyrazole-3-carboxylic acid (2-hydroxy-ethyl)-amide,
(S)-3-((3-butyl-5-methylisoxazol-4-yl)methoxy)-N-(tetrahydrofuran-3-yl)-1H-pyrazole-5-carboxamide,
(R)-3-((3-butyl-5-methylisoxazol-4-yl)methoxy)-N-(tetrahydrofuran-3-yl)-1H-pyrazole-5-carboxamide,
[5-(3-Butyl-5-methyl-isoxazol-4-ylmethoxy)-2H-pyrazol-3-yl]-morpholin-4-yl-methanone,
5-(3-Butyl-5-methyl-isoxazol-4-ylmethoxy)-2H-pyrazole-3-carboxylic acid (2,2-dimethyl-tetrahydro-pyran-4-yl)-amide,
5-(3-Butyl-5-methyl-isoxazol-4-ylmethoxy)-2H-pyrazole-3-carboxylic acid N',N'-dimethyl-hydrazide,
5-(3-Butyl-5-methyl-isoxazol-4-ylmethoxy)-2H-pyrazole-3-carboxylic acid morpholin-4-ylamide,
5-(3-Butyl-5-methyl-isoxazol-4-ylmethoxy)-2H-pyrazole-3-carboxylic acid pyrrolidin-1-ylamide,
5-(3-Butyl-5-methyl-isoxazol-4-ylmethoxy)-2H-pyrazole-3-carboxylic acid piperidin-1-ylamide,
2-Methyl-5-(5-methyl-3-phenyl-isoxazol-4-ylmethoxy)-2H-pyrazole-3-carboxylic acid (2-hydroxy-ethyl)-amide,
2-Methyl-5-(5-methyl-3-phenyl-isoxazol-4-ylmethoxy)-2H-pyrazole-3-carboxylic acid (tetrahydro-furan-3-yl)-amide,
2-Methyl-5-(5-methyl-3-phenyl-isoxazol-4-ylmethoxy)-2H-pyrazole-3-carboxylic acid (tetrahydro-pyran-4-yl)-amide,
2-Methyl-5-(5-methyl-3-phenyl-isoxazol-4-ylmethoxy)-2H-pyrazole-3-carboxylic acid amide,
2-Methyl-5-(5-methyl-3-phenyl-isoxazol-4-ylmethoxy)-2H-pyrazole-3-carboxylic acid isopropylamide,
2-Methyl-5-(5-methyl-3-phenyl-isoxazol-4-ylmethoxy)-2H-pyrazole-3-carboxylic acid N',N'-dimethyl-hydrazide,
5-[3-(4-Fluoro-phenyl)-5-methyl-isoxazol-4-ylmethoxy]-2-methyl-2H-pyrazole-3-carboxylic acid N',N'-dimethyl-hydrazide,
5-[3-(4-Fluoro-phenyl)-5-methyl-isoxazol-4-ylmethoxy]-2-methyl-2H-pyrazole-3-carboxylic acid piperidin-1-ylamide, 5-[3-(4-Fluoro-phenyl)-5-methyl-isoxazol-4-ylmethoxy]-2-methyl-2H-pyrazole-3-carboxylic acid morpholin-4-ylamide,
5-[3-(4-Fluoro-phenyl)-5-methyl-isoxazol-4-ylmethoxy]-2-methyl-2H-pyrazole-3-carboxylic acid pyrrolidin-1-ylamide,
5-[3-(4-Fluoro-phenyl)-5-methyl-isoxazol-4-ylmethoxy]-2-methyl-2H-pyrazole-3-carboxylic acid isopropylamide,
5-[3-(4-Fluoro-phenyl)-5-methyl-isoxazol-4-ylmethoxy]-2-methyl-2H-pyrazole-3-carboxylic acid (tetrahydro-pyran-4-yl)-amide,
5-[3-(4-Fluoro-phenyl)-5-methyl-isoxazol-4-ylmethoxy]-2-methyl-2H-pyrazole-3-carboxylic acid amide,
5-[3-(4-Fluoro-phenyl)-5-methyl-isoxazol-4-ylmethoxy]-2-methyl-2H-pyrazole-3-carboxylic acid (2-hydroxy-1,1-dimethyl-ethyl)-amide,
5-[3-(4-Fluoro-phenyl)-5-methyl-isoxazol-4-ylmethoxy]-2-methyl-2H-pyrazole-3-carboxylic acid ((S)-2,2,2-trifluoro-1-methyl-ethyl)-amide,
5-[3-(4-Fluoro-phenyl)-5-methyl-isoxazol-4-ylmethoxy]-2-methyl-2H-pyrazole-3-carboxylic acid (2,2,2-trifluoro-ethyl)-amide,
5-[3-(4-Fluoro-phenyl)-5-methyl-isoxazol-4-ylmethoxy]-2-methyl-2H-pyrazole-3-carboxylic acid (3-methyl-oxetan-3-yl)-amide,
5-[3-(4-Fluoro-phenyl)-5-methyl-isoxazol-4-ylmethoxy]-2-methyl-2H-pyrazole-3-carboxylic acid (3,3,3-trifluoro-2-hydroxy-propyl)-amide,
5-[3-(4-Fluoro-phenyl)-5-methyl-isoxazol-4-ylmethoxy]-2-methyl-2H-pyrazole-3-carboxylic acid (2-methoxy-ethyl)-amide,
5-[3-(4-Fluoro-phenyl)-5-methyl-isoxazol-4-ylmethoxy]-2-methyl-2H-pyrazole-3-carboxylic acid (1-hydroxy-cyclopropylmethyl)-amide,
5-[3-(4-Fluoro-phenyl)-5-methyl-isoxazol-4-ylmethoxy]-2-methyl-2H-pyrazole-3-carboxylic acid (2-hydroxy-ethyl)-amide,
5-[3-(4-Fluoro-phenyl)-5-methyl-isoxazol-4-ylmethoxy]-2-methyl-2H-pyrazole-3-carboxylic acid (1-methyl-1H-pyrazol-3-yl)-amide,
5-[3-(4-Fluoro-phenyl)-5-methyl-isoxazol-4-ylmethoxy]-2-methyl-2H-pyrazole-3-carboxylic acid (2-acetylamino-ethyl)-amide,
5-[3-(4-Fluoro-phenyl)-5-methyl-isoxazol-4-ylmethoxy]-2-methyl-2H-pyrazole-3-carboxylic acid (3-hydroxy-2,2-dimethyl-propyl)-amide,
5-[3-(4-Fluoro-phenyl)-5-methyl-isoxazol-4-ylmethoxy]-2-methyl-2H-pyrazole-3-carboxylic acid (2-hydroxy-2-methyl-propyl)-amide,
5-[3-(4-Fluoro-phenyl)-5-methyl-isoxazol-4-ylmethoxy]-2-methyl-2H-pyrazole-3-carboxylic acid ((S or R)-3,3,3-trifluoro-2-hydroxy-propyl)-amide,
5-[3-(4-Fluoro-phenyl)-5-methyl-isoxazol-4-ylmethoxy]-2-methyl-2H-pyrazole-3-carboxylic acid ((R or S)-3,3,3-trifluoro-2-hydroxy-propyl)-amide,
5-[3-(4-Fluoro-phenyl)-5-methyl-isoxazol-4-ylmethoxy]-2-methyl-2H-pyrazole-3-carboxylic acid ((R or S)-1-hydroxymethyl-propyl)-amide,
5-[3-(4-Fluoro-phenyl)-5-methyl-isoxazol-4-ylmethoxy]-2-methyl-2H-pyrazole-3-carboxylic acid ((S or R)-1-hydroxymethyl-propyl)-amide,
{5-[3-(4-Fluoro-phenyl)-5-methyl-isoxazol-4-ylmethoxy]-2-methyl-2H-pyrazol-3-yl}-(3-hydroxy-azetidin-1-yl)-methanone,
5-[3-(4-Fluoro-phenyl)-5-methyl-isoxazol-4-ylmethoxy]-2-methyl-2H-pyrazole-3-carboxylic acid (tetrahydro-furan-3-yl)-amide,
5-[3-(4-Fluoro-phenyl)-5-methyl-isoxazol-4-ylmethoxy]-2-methyl-2H-pyrazole-3-carboxylic acid ((1R,2R)-2-hydroxy-cyclopentyl)-amide and/or
5-[3-(4-Fluoro-phenyl)-5-methyl-isoxazol-4-ylmethoxy]-2-methyl-2H-pyrazole-3-carboxylic acid ((1S,2S)-2-hydroxy-cyclopentyl)-amide,
5-[3-(4-Fluoro-phenyl)-5-methyl-isoxazol-4-ylmethoxy]-2-methyl-2H-pyrazole-3-carboxylic acid ((1S,2S)-2-hydroxy-cyclopentyl)-amide and/or
5-[3-(4-Fluoro-phenyl)-5-methyl-isoxazol-4-ylmethoxy]-2-methyl-2H-pyrazole-3-carboxylic acid ((1R,2R)-2-hydroxy-cyclopentyl)-,
5-[3-(4-Fluoro-phenyl)-5-methyl-isoxazol-4-ylmethoxy]-2-methyl-2H-pyrazole-3-carboxylic acid ((R)-2-hydroxy-1-methyl-ethyl)-amide or
5-[3-(4-Fluoro-phenyl)-5-methyl-isoxazol-4-ylmethoxy]-2-methyl-2H-pyrazole-3-carboxylic acid ((S)-2-hydroxy-1-methyl-ethyl)-amide,
5-[3-(4-Fluoro-phenyl)-5-methyl-isoxazol-4-ylmethoxy]-2-methyl-2H-pyrazole-3-carboxylic acid ((S)-2-hydroxy-1-methyl-ethyl)-amide or
5-[3-(4-Fluoro-phenyl)-5-methyl-isoxazol-4-ylmethoxy]-2-methyl-2H-pyrazole-3-carboxylic acid ((R)-2-hydroxy-1-methyl-ethyl)-amide,
{5-[3-(4-Fluoro-phenyl)-5-methyl-isoxazol-4-ylmethoxy]-2-methyl-2H-pyrazol-3-yl}-(2-oxa-6-aza-spiro[3.3]hept-6-yl)-methanone,
2-Methyl-5-(5-methyl-3-pyridin-2-yl-isoxazol-4-ylmethoxy)-2H-pyrazole-3-carboxylic acid isopropylamide,
2-Methyl-5-(5-methyl-3-pyridin-2-yl-isoxazol-4-ylmethoxy)-2H-pyrazole-3-carboxylic acid (tetrahydro-pyran-4-yl)-amide,
2-Methyl-5-(5-methyl-3-pyridin-2-yl-isoxazol-4-ylmethoxy)-2H-pyrazole-3-carboxylic acid ((S)-2-hydroxy-1-methyl-ethyl)-amide,
5-[3-(5-Fluoro-pyridin-2-yl)-5-methyl-isoxazol-4-ylmethoxy]-2-methyl-2H-pyrazole-3-carboxylic acid (tetrahydro-furan-3-yl)-amide,
5-[3-(5-Fluoro-pyridin-2-yl)-5-methyl-isoxazol-4-ylmethoxy]-2-methyl-2H-pyrazole-3-carboxylic acid #N!',#N!'-dimethyl-hydrazide,
5-[3-(5-Fluoro-pyridin-2-yl)-5-methyl-isoxazol-4-ylmethoxy]-2-methyl-2H-pyrazole-3-carboxylic acid (2-hydroxy-ethyl)-amide,
5-[3-(5-Fluoro-pyridin-2-yl)-5-methyl-isoxazol-4-ylmethoxy]-2-methyl-2H-pyrazole-3-carboxylic acid (tetrahydro-pyran-4-yl)-amide,
5-(3-Butyl-5-methyl-isoxazol-4-ylmethoxy)-2-methyl-2H-pyrazole-3-carboxylic acid (2-hydroxy-ethyl)-amide,
5-(3-Butyl-5-methyl-isoxazol-4-ylmethoxy)-2-methyl-2H-pyrazole-3-carboxylic acid isopropylamide,
5-(3-Butyl-5-methyl-isoxazol-4-ylmethoxy)-2-methyl-2H-pyrazole-3-carboxylic acid (2-hydroxy-1-methyl-ethyl)-amide,
5-(3-Butyl-5-methyl-isoxazol-4-ylmethoxy)-2-methyl-2H-pyrazole-3-carboxylic acid (tetrahydro-pyran-4-yl)-amide,
5-(3-Butyl-5-methyl-isoxazol-4-ylmethoxy)-2-methyl-2H-pyrazole-3-carboxylic acid (tetrahydro-furan-3-yl)-amide,
2-Methyl-5-[5-methyl-3-(tetrahydro-pyran-4-yl)-isoxazol-4-ylmethoxy]-2H-pyrazole-3-carboxylic acid (tetrahydro-pyran-4-yl)-amide,
5-[3-(4-Fluoro-phenyl)-5-hydroxymethyl-isoxazol-4-ylmethoxy]-2-methyl-2H-pyrazole-3-carboxylic acid (tetrahydro-pyran-4-yl)-amide, 5-[3-(4-Fluoro-phenyl)-5-hydroxymethyl-isoxazol-4-yl-methoxy]-2-methyl-2H-pyrazole-3-carboxylic acid isopropylamide,
5-[3-(4-Fluoro-phenyl)-5-hydroxymethyl-isoxazol-4-yl-methoxy]-2-methyl-2H-pyrazole-3-carboxylic acid amide,
5-[3-(4-Fluoro-phenyl)-5-hydroxymethyl-isoxazol-4-yl-methoxy]-2-methyl-2H-pyrazole-3-carboxylic acid (2,2,2-trifluoro-ethyl)-amide,
5-[3-(4-Fluoro-phenyl)-5-hydroxymethyl-isoxazol-4-yl-methoxy]-2-methyl-2H-pyrazole-3-carboxylic acid (2,2,3,3,3-pentafluoro-propyl)-amide,
5-[3-(4-Fluoro-phenyl)-5-hydroxymethyl-isoxazol-4-yl-methoxy]-2-methyl-2H-pyrazole-3-carboxylic acid (1-methyl-1H-pyrazol-3-yl)-amide,
5-[3-(4-Fluoro-phenyl)-5-hydroxymethyl-isoxazol-4-yl-methoxy]-2-methyl-2H-pyrazole-3-carboxylic acid (tetrahydro-furan-3-yl)-amide,
5-[3-(4-Fluoro-phenyl)-5-hydroxymethyl-isoxazol-4-yl-methoxy]-2-methyl-2H-pyrazole-3-carboxylic acid (3-methyl-oxetan-3-yl)-amide,
{5-[3-(4-Fluoro-phenyl)-5-hydroxymethyl-isoxazol-4-yl-methoxy]-2-methyl-2H-pyrazol-3-yl}-(2-oxa-6-aza-spiro[3.3]hept-6-yl)-methanone,
5-[3-(4-Chloro-phenyl)-5-hydroxymethyl-isoxazol-4-yl-methoxy]-2-methyl-2H-pyrazole-3-carboxylic acid isopropylamide,
5-[3-(4-Chloro-phenyl)-5-hydroxymethyl-isoxazol-4-yl-methoxy]-2-methyl-2H-pyrazole-3-carboxylic acid (tetrahydro-pyran-4-yl)-amide,
5-[3-(4-Chloro-phenyl)-5-hydroxymethyl-isoxazol-4-yl-methoxy]-2-methyl-2H-pyrazole-3-carboxylic acid amide,
5-[3-(4-Chloro-phenyl)-5-hydroxymethyl-isoxazol-4-yl-methoxy]-2-methyl-2H-pyrazole-3-carboxylic acid (2,2,2-trifluoro-ethyl)-amide,
5-[3-(4-Chloro-phenyl)-5-hydroxymethyl-isoxazol-4-yl-methoxy]-2-methyl-2H-pyrazole-3-carboxylic acid (2,2,3,3,3-pentafluoro-propyl)-amide,
5-[3-(4-Chloro-phenyl)-5-hydroxymethyl-isoxazol-4-yl-methoxy]-2-methyl-2H-pyrazole-3-carboxylic acid cyclopropylamide,
5-[3-(4-Chloro-phenyl)-5-hydroxymethyl-isoxazol-4-yl-methoxy]-2-methyl-2H-pyrazole-3-carboxylic acid ((S)-2,2,2-trifluoro-1-methyl-ethyl)-amide,
5-[3-(4-Chloro-phenyl)-5-hydroxymethyl-isoxazol-4-yl-methoxy]-2-methyl-2H-pyrazole-3-carboxylic acid (2-hydroxy-1,1-dimethyl-ethyl)-amide,
5-[3-(4-Chloro-phenyl)-5-hydroxymethyl-isoxazol-4-yl-methoxy]-2-methyl-2H-pyrazole-3-carboxylic acid (3-methyl-oxetan-3-yl)-amide,
{5-[3-(4-Chloro-phenyl)-5-hydroxymethyl-isoxazol-4-yl-methoxy]-2-methyl-2H-pyrazol-3-yl}-(2-oxa-6-aza-spiro[3.3]hept-6-yl)-methanone,
5-[3-(4-Chloro-phenyl)-5-hydroxymethyl-isoxazol-4-yl-methoxy]-2-methyl-2H-pyrazole-3-carboxylic acid (tetrahydro-furan-3-yl)-amide,
{5-[3-(4-Chloro-phenyl)-5-hydroxymethyl-isoxazol-4-yl-methoxy]-2-methyl-2H-pyrazol-3-yl}-(4,4-difluoro-piperidin-1-yl)-methanone,
5-(3-Butyl-5-hydroxymethyl-isoxazol-4-ylmethoxy)-2-methyl-2H-pyrazole-3-carboxylic acid (2,2,2-trifluoro-ethyl)-amide,
5-(3-Butyl-5-hydroxymethyl-isoxazol-4-ylmethoxy)-2-methyl-2H-pyrazole-3-carboxylic acid cyclobutylamide,
1-Methyl-5-(5-methyl-3-pyridin-2-yl-isoxazol-4-yl-methoxy)-1H-pyrazole-3-carboxylic acid ((S)-2-hydroxy-1-methyl-ethyl)-amide,
1-Methyl-5-(5-methyl-3-pyridin-2-yl-isoxazol-4-yl-methoxy)-1H-pyrazole-3-carboxylic acid isopropylamide,
1-Methyl-5-(5-methyl-3-pyridin-2-yl-isoxazol-4-yl-methoxy)-1H-pyrazole-3-carboxylic acid (tetrahydro-pyran-4-yl)-amide,
5-[3-(5-Fluoro-pyridin-2-yl)-5-methyl-isoxazol-4-yl-methoxy]-1-methyl-1H-pyrazole-3-carboxylic acid ((S)-2-hydroxy-1-methyl-ethyl)-amide,
5-[(E)-2-(5-Methyl-3-phenyl-isoxazol-4-yl)-vinyl]-2H-pyrazole-3-carboxylic acid isopropylamide,
5-[(Z)-2-(5-Methyl-3-phenyl-isoxazol-4-yl)-vinyl]-2H-pyrazole-3-carboxylic acid isopropylamide,
5-{(Z)-2-[3-(4-Fluoro-phenyl)-5-methyl-isoxazol-4-yl]-vinyl}-2-methyl-2H-pyrazole-3-carboxylic acid isopropylamide,
5-{(Z)-2-[3-(4-Fluoro-phenyl)-5-methyl-isoxazol-4-yl]-vinyl}-2-methyl-2H-pyrazole-3-carboxylic acid (2-hydroxy-1-methyl-ethyl)-amide,
5-{(E)-2-[3-(4-Fluoro-phenyl)-5-methyl-isoxazol-4-yl]-vinyl}-2-methyl-2H-pyrazole-3-carboxylic acid isopropylamide,
5-{(E)-2-[3-(4-Fluoro-phenyl)-5-methyl-isoxazol-4-yl]-vinyl}-2-methyl-2H-pyrazole-3-carboxylic acid ethylamide,
5-{(E)-2-[3-(4-Fluoro-phenyl)-5-methyl-isoxazol-4-yl]-vinyl}-2-methyl-2H-pyrazole-3-carboxylic acid (2-hydroxy-2-methyl-propyl)-amide,
5-{(E)-2-[3-(4-Fluoro-phenyl)-5-methyl-isoxazol-4-yl]-vinyl}-2-methyl-2H-pyrazole-3-carboxylic acid (tetrahydro-pyran-4-yl)-amide,
5-{(E)-2-[3-(4-Fluoro-phenyl)-5-methyl-isoxazol-4-yl]-vinyl}-2-methyl-2H-pyrazole-3-carboxylic acid amide,
(1,1-Dioxo-1,6-thiomorpholin-4-yl)-(5-{(E)-2-[3-(4-fluoro-phenyl)-5-methyl-isoxazol-4-yl]-vinyl}-2-methyl-2H-pyrazol-3-yl)-methanone,
5-{(E)-2-[3-(4-Fluoro-phenyl)-5-methyl-isoxazol-4-yl]-vinyl}-2-methyl-2H-pyrazole-3-carboxylic acid (2,2,2-trifluoro-ethyl)-amide,
(5-{(E)-2-[3-(4-Fluoro-phenyl)-5-methyl-isoxazol-4-yl]-vinyl}-2-methyl-2H-pyrazol-3-yl)-morpholin-4-yl-methanone,
5-{(E)-2-[3-(4-Fluoro-phenyl)-5-methyl-isoxazol-4-yl]-vinyl}-2-methyl-2H-pyrazole-3-carboxylic acid (2-hydroxy-1-methyl-ethyl)-amide,
(1,1-Dioxo-1,6-thiomorpholin-4-yl)-(5-{(E)-2-[3-(4-fluoro-phenyl)-5-methyl-isoxazol-4-yl]-vinyl}-2H-pyrazol-3-yl)-methanone,
(5-{(E)-2-[3-(4-Fluoro-phenyl)-5-methyl-isoxazol-4-yl]-vinyl}-2H-pyrazol-3-yl)-morpholin-4-yl-methanone,
5-{(E)-2-[3-(4-Fluoro-phenyl)-5-methyl-isoxazol-4-yl]-vinyl}-2H-pyrazole-3-carboxylic acid (2,2,2-trifluoro-ethyl)-amide,
5-{(E)-2-[3-(4-Fluoro-phenyl)-5-methyl-isoxazol-4-yl]-vinyl}-2H-pyrazole-3-carboxylic acid isopropylamide,
(5-{(E)-2-[3-(4-Fluoro-phenyl)-5-methyl-isoxazol-4-yl]-vinyl}-2-methyl-2H-pyrazol-3-yl)-(2-oxa-6-aza-spiro[3.3]hept-6-yl)-methanone,
5-{(E)-2-[3-(4-Fluoro-phenyl)-5-methyl-isoxazol-4-yl]-vinyl}-2H-pyrazole-3-carboxylic acid (tetrahydro-pyran-4-yl)-amide,
(5-{(E)-2-[3-(4-Fluoro-phenyl)-5-methyl-isoxazol-4-yl]-vinyl}-2H-pyrazol-3-yl)-(2-oxa-6-aza-spiro[3.3]hept-6-yl)-methanone, 5-{(E)-2-[3-(4-Fluoro-phenyl)-5-methyl-isoxazol-4-yl]-vinyl}-2H-pyrazole-3-carboxylic acid (2-hydroxy-1,1-dimethyl-ethyl)-amide,
5-{(E)-2-[3-(4-Fluoro-phenyl)-5-methyl-isoxazol-4-yl]-vinyl}-2H-pyrazole-3-carboxylic acid (2-hydroxy-1-methyl-ethyl)-amide,
5-{(E)-2-[3-(4-Fluoro-phenyl)-5-methyl-isoxazol-4-yl]-vinyl}-2H-pyrazole-3-carboxylic acid (2-hydroxy-2-methyl-propyl)-amide,
5-{(E)-2-[3-(4-Fluoro-phenyl)-5-methyl-isoxazol-4-yl]-vinyl}-2H-pyrazole-3-carboxylic acid ethylamide,
5-{(E)-2-[3-(4-Fluoro-phenyl)-5-methyl-isoxazol-4-yl]-vinyl}-2H-pyrazole-3-carboxylic acid amide,
5-{(E)-2-[3-(4-Fluoro-phenyl)-5-methyl-isoxazol-4-yl]-vinyl}-2-methyl-2H-pyrazole-3-carboxylic acid (2-hydroxy-1,1-dimethyl-ethyl)-amide,
5-{[3-(4-Fluoro-phenyl)-5-methyl-isoxazol-4-ylmethyl]-amino}-2-methyl-2H-pyrazole-3-carboxylic acid (2-hydroxy-2-methyl-propyl)-amide,
5-{[3-(4-Fluoro-phenyl)-5-methyl-isoxazol-4-ylmethyl]-amino}-2-methyl-2H-pyrazole-3-carboxylic acid amide,
5-{[3-(4-Fluoro-phenyl)-5-methyl-isoxazol-4-ylmethyl]-amino}-2-methyl-2H-pyrazole-3-carboxylic acid (2,2,2-trifluoro-ethyl)-amide,
5-{[3-(4-Fluoro-phenyl)-5-methyl-isoxazol-4-ylmethyl]-amino}-2-methyl-2H-pyrazole-3-carboxylic acid (tetrahydro-pyran-4-yl)-amide,
5-{[3-(4-Fluoro-phenyl)-5-methyl-isoxazol-4-ylmethyl]-amino}-2-methyl-2H-pyrazole-3-carboxylic acid (3-methyl-oxetan-3-yl)-amide,
(5-{[3-(4-Fluoro-phenyl)-5-methyl-isoxazol-4-ylmethyl]-amino}-2-methyl-2H-pyrazol-3-yl)-(2-oxa-6-aza-spiro[3.3]hept-6-yl)-methanone,
5-{[3-(4-Fluoro-phenyl)-5-methyl-isoxazol-4-ylmethyl]-amino}-2-methyl-2H-pyrazole-3-carboxylic acid (2-hydroxy-1-methyl-ethyl)-amide,
5-{[3-(4-Fluoro-phenyl)-5-methyl-isoxazol-4-ylmethyl]-amino}-2-methyl-2H-pyrazole-3-carboxylic acid isopropylamide,
5-{[3-(4-Fluoro-phenyl)-5-methyl-isoxazol-4-ylmethyl]-amino}-2H-pyrazole-3-carboxylic acid (2-hydroxy-2-methyl-propyl)-amide,
5-{[3-(4-Fluoro-phenyl)-5-methyl-isoxazol-4-ylmethyl]-amino}-2H-pyrazole-3-carboxylic acid amide,
5-{[3-(4-Fluoro-phenyl)-5-methyl-isoxazol-4-ylmethyl]-amino}-2H-pyrazole-3-carboxylic acid isopropylamide,
5-{[3-(4-Fluoro-phenyl)-5-methyl-isoxazol-4-ylmethyl]-amino}-2H-pyrazole-3-carboxylic acid ethylamide,
5-{[3-(4-Fluoro-phenyl)-5-methyl-isoxazol-4-ylmethyl]-amino}-2H-pyrazole-3-carboxylic acid (tetrahydro-pyran-4-yl)-amide,
5-{[3-(4-Fluoro-phenyl)-5-methyl-isoxazol-4-ylmethyl]-amino}-2H-pyrazole-3-carboxylic acid (2-hydroxy-1-methyl-ethyl)-amide,
(5-{[3-(4-Fluoro-phenyl)-5-methyl-isoxazol-4-ylmethyl]-amino}-2H-pyrazol-3-yl)-(2-oxa-6-aza-spiro[3.3]hept-6-yl)-methanone,
N-isopropyl-1-methyl-3-((5-methyl-3-(pyridin-2-yl)isoxazol-4-yl)methylamino)-1H-pyrazole-5-carboxamide,
2-Methyl-5-[(5-methyl-3-pyridin-2-yl-isoxazol-4-ylmethyl)-amino]-2H-pyrazole-3-carboxylic acid (tetrahydro-pyran-4-yl)-amide,
1-methyl-3-((5-methyl-3-(pyridin-2-yl)isoxazol-4-yl)methylamino)-N-morpholino-1H-pyrazole-5-carboxamide,
1-methyl-3-((5-methyl-3-(pyridin-2-yl)isoxazol-4-yl)methylamino)-N-(3-methyloxetan-3-yl)-1H-pyrazole-5-carboxamide,
3-((3-(5-fluoropyridin-2-yl)-5-methylisoxazol-4-yl)methylamino)-N-isopropyl-1-methyl-1H-pyrazole-5-carboxamide,
3-((3-(5-fluoropyridin-2-yl)-5-methylisoxazol-4-yl)methylamino)-1-methyl-N-(tetrahydro-2H-pyran-4-yl)-1H-pyrazole-5-carboxamide,
N-cyclopropyl-3-((3-(5-fluoropyridin-2-yl)-5-methylisoxazol-4-yl)methylamino)-1-methyl-1H-pyrazole-5-carboxamide,
N-(cyclopropylmethyl)-3-((3-(5-fluoropyridin-2-yl)-5-methylisoxazol-4-yl)methylamino)-1-methyl-1H-pyrazole-5-carboxamide,
3-((3-(5-fluoropyridin-2-yl)-5-methylisoxazol-4-yl)methylamino)-1-methyl-N-(3-methyloxetan-3-yl)-1H-pyrazole-5-carboxamide and
(3-((3-(5-fluoropyridin-2-yl)-5-methylisoxazol-4-yl)methylamino)-1-methyl-1H-pyrazol-5-yl)(2-oxa-6-azaspiro[3.3]heptan-6-yl)methanone,
or a pharmaceutically acceptable salt or ester thereof.

One certain embodiment of the invention provides compounds of formula I selected from the group consisting of
[5-(5-Methyl-3-phenyl-isoxazol-4-ylmethoxy)-2H-pyrazol-3-yl]-morpholin-4-yl-methanone,
5-(5-Methyl-3-phenyl-isoxazol-4-ylmethoxy)-2H-pyrazole-3-carboxylic acid isopropylamide,
5-(5-Methyl-3-phenyl-isoxazol-4-ylmethoxy)-2H-pyrazole-3-carboxylic acid (tetrahydro-pyran-4-yl)-amide,
5-(5-Methyl-3-phenyl-isoxazol-4-ylmethoxy)-2H-pyrazole-3-carboxylic acid (tetrahydro-furan-3-yl)-amide,
5-(5-Methyl-3-phenyl-isoxazol-4-ylmethoxy)-2H-pyrazole-3-carboxylic acid N',N'-dimethyl-hydrazide,
5-(5-Methyl-3-phenyl-isoxazol-4-ylmethoxy)-2H-pyrazole-3-carboxylic acid (2-hydroxy-ethyl)-amide,
5-(5-Methyl-3-phenyl-isoxazol-4-ylmethoxy)-2H-pyrazole-3-carboxylic acid amide,
5-[3-(4-Fluoro-phenyl)-5-methyl-isoxazol-4-ylmethoxy]-2H-pyrazole-3-carboxylic acid morpholin-4-ylamide,
5-[3-(4-Fluoro-phenyl)-5-methyl-isoxazol-4-ylmethoxy]-2H-pyrazole-3-carboxylic acid piperidin-1-ylamide,
5-[3-(4-Fluoro-phenyl)-5-methyl-isoxazol-4-ylmethoxy]-2H-pyrazole-3-carboxylic acid pyrrolidin-1-ylamide,
5-[3-(4-Fluoro-phenyl)-5-methyl-isoxazol-4-ylmethoxy]-2H-pyrazole-3-car-boxylic acid N',N'-dimethyl-hydrazide,
5-[3-(4-Fluoro-phenyl)-5-methyl-isoxazol-4-ylmethoxy]-2H-pyrazole-3-carboxylic acid isopropylamide,
5-[3-(4-Fluoro-phenyl)-5-methyl-isoxazol-4-ylmethoxy]-2H-pyrazole-3-carboxylic acid (tetra-hydro-pyran-4-yl)-amide,
5-(5-Methyl-3-pyridin-2-yl-isoxazol-4-ylmethoxy)-1H-pyrazole-3-carboxylic acid iso-propylamide,
5-(5-Methyl-3-pyridin-2-yl-isoxazol-4-ylmethoxy)-1H-pyrazole-3-carboxylic acid (tetrahydro-pyran-4-yl)-amide,
5-(5-Methyl-3-pyridin-2-yl-isoxazol-4-ylmethoxy)-1H-pyrazole-3-carboxylic acid ((S)-2-hydroxy-1-methyl-ethyl)-amide,
5-[3-(5-Fluoro-pyridin-2-yl)-5-methyl-isoxazol-4-yl-methoxy]-2H-pyrazole-3-carboxylic acid (2,2,2-trifluoro-ethyl)-amide,
5-[3-(5-Fluoro-pyridin-2-yl)-5-methyl-isoxazol-4-ylmethoxy]-2H-pyrazole-3-carboxylic acid (tetrahydro-furan-3-yl)-amide,
5-[3-(5-Fluoro-pyridin-2-yl)-5-methyl-isoxazol-4-ylmethoxy]-2H-pyrazole-3-carboxylic acid tert-butylamide, 5-[3-(5-Fluoro-pyridin-2-yl)-5-methyl-isoxazol-4-yl-methoxy]-2H-pyrazole-3-carboxylic acid (2-hydroxy-ethyl)-amide,
5-[3-(5-Fluoro-pyridin-2-yl)-5-methyl-isoxazol-4-yl-methoxy]-2H-pyrazole-3-carboxylic acid isopropylamide,
5-[3-(5-Fluoro-pyridin-2-yl)-5-methyl-isoxazol-4-yl-methoxy]-2H-pyrazole-3-carboxylic acid N',N'-dimethyl-hydrazide,
5-[3-(5-Fluoro-pyridin-2-yl)-5-methyl-isoxazol-4-yl-methoxy]-2H-pyrazole-3-carboxylic acid morpholin-4-ylamide,
5-[3-(5-Fluoro-pyridin-2-yl)-5-methyl-isoxazol-4-yl-methoxy]-2H-pyrazole-3-carboxylic acid pyrrolidin-1-ylamide,
5-[3-(5-Fluoro-pyridin-2-yl)-isoxazol-4-ylmethoxy]-2H-pyrazole-3-carboxylic acid morpholin-4-ylamide,
5-(3-Butyl-5-methyl-isoxazol-4-ylmethoxy)-2H-pyrazole-3-carboxylic acid (tetrahydro-pyran-4-yl)-amide,
5-(3-Butyl-5-methyl-isoxazol-4-ylmethoxy)-2H-pyrazole-3-carboxylic acid ((S)-2-hydroxy-1-methyl-ethyl)-amide,
5-(3-Butyl-5-methyl-isoxazol-4-ylmethoxy)-2H-pyrazole-3-carboxylic acid (tetrahydro-furan-3-yl)-amide,
5-(3-Butyl-5-methyl-isoxazol-4-ylmethoxy)-2H-pyrazole-3-carboxylic acid (2-hydroxy-1-hydroxy-methyl-ethyl)-amide,
5-(3-Butyl-5-methyl-isoxazol-4-ylmethoxy)-2H-pyrazole-3-carboxylic acid ((R)-2-hydroxy-1-methyl-ethyl)-amide,
5-(3-Butyl-5-methyl-isoxazol-4-ylmethoxy)-2H-pyrazole-3-carboxylic acid (2,2,2-trifluoro-ethyl)-amide,
5-(3-Butyl-5-methyl-isoxazol-4-ylmethoxy)-2H-pyrazole-3-carboxylic acid isopropylamide,
5-(3-Butyl-5-methyl-isoxazol-4-ylmethoxy)-2H-pyrazole-3-carboxylic acid (2-hydroxy-ethyl)-amide,
(S)-3-((3-butyl-5-methylisoxazol-4-yl)methoxy)-N-(tetrahydrofuran-3-yl)-1H-pyrazole-5-carboxamide,
(R)-3-((3-butyl-5-methyl-isoxazol-4-yl)methoxy)-N-(tetrahydrofuran-3-yl)-1H-pyrazole-5-carboxamide,
[5-(3-Butyl-5-methyl-isoxazol-4-ylmethoxy)-2H-pyrazol-3-yl]-morpholin-4-yl-methanone,
5-(3-Butyl-5-methyl-isoxazol-4-ylmethoxy)-2H-pyrazole-3-carboxylic acid (2,2-dimethyl-tetrahydro-pyran-4-yl)-amide,
5-(3-Butyl-5-methyl-isoxazol-4-ylmethoxy)-2H-pyrazole-3-carboxylic acid N',N'-dimethyl-hydrazide,
5-(3-Butyl-5-methyl-isoxazol-4-ylmethoxy)-2H-pyrazole-3-carboxylic acid morpholin-4-ylamide,
5-(3-Butyl-5-methyl-isoxazol-4-ylmethoxy)-2H-pyrazole-3-carboxylic acid pyrrolidin-1-ylamide,
5-(3-Butyl-5-methyl-isoxazol-4-ylmethoxy)-2H-pyrazole-3-carboxylic acid piperidin-1-ylamide,
2-Methyl-5-(5-methyl-3-phenyl-isoxazol-4-ylmethoxy)-2H-pyrazole-3-carboxylic acid (2-hydroxy-ethyl)-amide,
2-Methyl-5-(5-methyl-3-phenyl-isoxazol-4-ylmethoxy)-2H-pyrazole-3-carboxylic acid (tetra-hydro-furan-3-yl)-amide,
2-Methyl-5-(5-methyl-3-phenyl-isoxazol-4-ylmethoxy)-2H-pyrazole-3-carboxylic acid (tetra-hydro-pyran-4-yl)-amide,
2-Methyl-5-(5-methyl-3-phenyl-isoxazol-4-ylmethoxy)-2H-pyrazole-3-carboxylic acid amide,
2-Methyl-5-(5-methyl-3-phenyl-isoxazol-4-ylmethoxy)-2H-pyrazole-3-carboxylic acid isopropylamide,
2-Methyl-5-(5-methyl-3-phenyl-isoxazol-4-ylmethoxy)-2H-pyrazole-3-carboxylic acid N',N'-dimethyl-hydrazide,
5-[3-(4-Fluoro-phenyl)-5-methyl-isoxazol-4-ylmethoxy]-2-methyl-2H-pyrazole-3-carboxylic acid N',N'-dimethyl-hydrazide,
5-[3-(4-Fluoro-phenyl)-5-methyl-isoxazol-4-ylmethoxy]-2-methyl-2H-pyrazole-3-carboxylic acid piperidin-1-ylamide,
5-[3-(4-Fluoro-phenyl)-5-methyl-isoxazol-4-ylmethoxy]-2-methyl-2H-pyrazole-3-carboxylic acid morpholin-4-ylamide,
5-[3-(4-Fluoro-phenyl)-5-methyl-isoxazol-4-ylmethoxy]-2-methyl-2H-pyrazole-3-carboxylic acid pyrrolidin-1-ylamide,
5-[3-(4-Fluoro-phenyl)-5-methyl-isoxazol-4-ylmethoxy]-2-methyl-2H-pyrazole-3-carboxylic acid isopropylamide,
5-[3-(4-Fluoro-phenyl)-5-methyl-isoxazol-4-ylmethoxy]-2-methyl-2H-pyrazole-3-carboxylic acid (tetrahydro-pyran-4-yl)-amide,
5-[3-(4-Fluoro-phenyl)-5-methyl-isoxazol-4-ylmethoxy]-2-methyl-2H-pyrazole-3-carboxylic acid amide,
5-[3-(4-Fluoro-phenyl)-5-methyl-isoxazol-4-ylmethoxy]-2-methyl-2H-pyrazole-3-carboxylic acid (2-hydroxy-1,1-dimethyl-ethyl)-amide,
5-[3-(4-Fluoro-phenyl)-5-methyl-isoxazol-4-ylmethoxy]-2-methyl-2H-pyrazole-3-carboxylic acid ((S)-2,2,2-trifluoro-1-methyl-ethyl)-amide,
5-[3-(4-Fluoro-phenyl)-5-methyl-isoxazol-4-ylmethoxy]-2-methyl-2H-pyrazole-3-carboxylic acid (2,2,2-trifluoro-ethyl)-amide,
5-[3-(4-Fluoro-phenyl)-5-methyl-isoxazol-4-ylmethoxy]-2-methyl-2H-pyrazole-3-carboxylic acid (3-methyl-oxetan-3-yl)-amide,
5-[3-(4-Fluoro-phenyl)-5-methyl-isoxazol-4-ylmethoxy]-2-methyl-2H-pyrazole-3-carboxylic acid (3,3,3-trifluoro-2-hydroxy-propyl)-amide,
5-[3-(4-Fluoro-phenyl)-5-methyl-isoxazol-4-ylmethoxy]-2-methyl-2H-pyrazole-3-carboxylic acid (2-methoxy-ethyl)-amide,
5-[3-(4-Fluoro-phenyl)-5-methyl-isoxazol-4-ylmethoxy]-2-methyl-2H-pyrazole-3-carboxylic acid (1-hydroxy-cyclopropylmethyl)-amide,
5-[3-(4-Fluoro-phenyl)-5-methyl-isoxazol-4-ylmethoxy]-2-methyl-2H-pyrazole-3-carboxylic acid (2-hydroxy-ethyl)-amide,
5-[3-(4-Fluoro-phenyl)-5-methyl-isoxazol-4-ylmethoxy]-2-methyl-2H-pyrazole-3-carboxylic acid (1-methyl-1H-pyrazol-3-yl)-amide,
5-[3-(4-Fluoro-phenyl)-5-methyl-isoxazol-4-ylmethoxy]-2-methyl-2H-pyrazole-3-carboxylic acid (2-acetylamino-ethyl)-amide,
5-[3-(4-Fluoro-phenyl)-5-methyl-isoxazol-4-ylmethoxy]-2-methyl-2H-pyrazole-3-carboxylic acid (3-hydroxy-2,2-dimethyl-propyl)-amide,
5-[3-(4-Fluoro-phenyl)-5-methyl-isoxazol-4-ylmethoxy]-2-methyl-2H-pyrazole-3-carboxylic acid (2-hydroxy-2-methyl-propyl)-amide,
5-[3-(4-Fluoro-phenyl)-5-methyl-isoxazol-4-ylmethoxy]-2-methyl-2H-pyrazole-3-carboxylic acid ((S)-3,3,3-trifluoro-2-hydroxy-propyl)-amide,
5-[3-(4-Fluoro-phenyl)-5-methyl-isoxazol-4-ylmethoxy]-2-methyl-2H-pyrazole-3-carboxylic acid ((R)-3,3,3-trifluoro-2-hydroxy-propyl)-amide,
5-[3-(4-Fluoro-phenyl)-5-methyl-isoxazol-4-yl-methoxy]-2-methyl-2H-pyrazole-3-carboxylic acid ((R)-1-hydroxymethyl-propyl)-amide,
5-[3-(4-Fluoro-phenyl)-5-methyl-isoxazol-4-ylmethoxy]-2-methyl-2H-pyrazole-3-carboxylic acid ((S)-1-hydroxymethyl-propyl)-amide,
{5-[3-(4-Fluoro-phenyl)-5-methyl-isoxazol-4-ylmethoxy]-2-methyl-2H-pyrazol-3-yl}-(3-hydroxy-azetidin-1-yl)-methanone, 5-[3-(4-Fluoro-phenyl)-5-methyl-isoxazol-4-ylmethoxy]-2-methyl-2H-pyrazole-3-carboxylic acid (tetrahydro-furan-3-yl)-amide,
5-[3-(4-Fluoro-phenyl)-5-methyl-isoxazol-4-ylmethoxy]-2-methyl-2H-pyrazole-3-car-boxylic acid ((1R,2R)-2-hydroxy-cyclopentyl)-amide,
5-[3-(4-Fluoro-phenyl)-5-methyl-isoxazol-4-ylmethoxy]-2-methyl-2H-pyrazole-3-carboxylic acid ((1S,2S)-2-hydroxy-cyclopentyl)-amide,
5-[3-(4-Fluoro-phenyl)-5-methyl-isoxazol-4-ylmethoxy]-2-methyl-2H-pyrazole-3-carboxylic acid ((R)-2-hydroxy-1-methyl-ethyl)-amide,
5-[3-(4-Fluoro-phenyl)-5-methyl-isoxazol-4-ylmethoxy]-2-methyl-2H-pyrazole-3-carboxylic acid ((S)-2-hydroxy-1-methyl-ethyl)-amide,
{5-[3-(4-Fluoro-phenyl)-5-methyl-isoxazol-4-ylmethoxy]-2-methyl-2H-pyrazol-3-yl}-(2-oxa-6-aza-spiro[3.3]-hept-6-yl)-methanone,
2-Methyl-5-(5-methyl-3-pyridin-2-yl-isoxazol-4-ylmethoxy)-2H-pyrazole-3-carboxylic acid isopropylamide,
2-Methyl-5-(5-methyl-3-pyridin-2-yl-isoxazol-4-ylmethoxy)-2H-pyrazole-3-carboxylic acid (tetrahydro-pyran-4-yl)-amide,
2-Methyl-5-(5-methyl-3-pyridin-2-yl-isoxazol-4-ylmethoxy)-2H-pyrazole-3-carboxylic acid ((5)-2-hydroxy-1-methyl-ethyl)-amide,
5-[3-(5-Fluoro-pyridin-2-yl)-5-methyl-isoxazol-4-ylmethoxy]-2-methyl-2H-pyrazole-3-carboxylic acid (tetrahydro-furan-3-yl)-amide,
5-[3-(5-Fluoro-pyridin-2-yl)-5-methyl-isoxazol-4-ylmethoxy]-2-methyl-2H-pyrazole-3-carboxylic acid N',N-dimethyl-hydrazide,
5-[3-(5-Fluoro-pyridin-2-yl)-5-methyl-isoxazol-4-ylmethoxy]-2-methyl-2H-pyrazole-3-carboxylic acid (2-hydroxy-ethyl)-amide,
5-[3-(5-Fluoro-pyridin-2-yl)-5-methyl-isoxazol-4-ylmethoxy]-2-methyl-2H-pyrazole-3-carboxylic acid (tetrahydro-pyran-4-yl)-amide,
5-(3-Butyl-5-methyl-isoxazol-4-ylmethoxy)-2-methyl-2H-pyrazole-3-carboxylic acid (2-hydroxy-ethyl)-amide,
5-(3-Butyl-5-methyl-isoxazol-4-ylmethoxy)-2-methyl-2H-pyrazole-3-carboxylic acid iso-propylamide,
5-(3-Butyl-5-methyl-isoxazol-4-ylmethoxy)-2-methyl-2H-pyrazole-3-carboxylic acid (2-hydroxy-1-methyl-ethyl)-amide,
5-(3-Butyl-5-methyl-isoxazol-4-ylmethoxy)-2-methyl-2H-pyrazole-3-carboxylic acid (tetra-hydro-pyran-4-yl)-amide,
5-(3-Butyl-5-methyl-isoxazol-4-ylmethoxy)-2-methyl-2H-pyrazole-3-carboxylic acid (tetra-hydro-furan-3-yl)-amide,
2-Methyl-5-[5-methyl-3-(tetrahydro-pyran-4-yl)-isoxazol-4-ylmethoxy]-2H-pyrazole-3-carboxylic acid (tetrahydro-pyran-4-yl)-amide,
5-[3-(4-Fluoro-phenyl)-5-hydroxymethyl-isoxazol-4-yl-methoxy]-2-methyl-2H-pyrazole-3-carboxylic acid (tetrahydro-pyran-4-yl)-amide,
5-[3-(4-Fluoro-phenyl)-5-hydroxymethyl-isoxazol-4-yl-methoxy]-2-methyl-2H-pyrazole-3-carboxylic acid iso-propylamide,
5-[3-(4-Fluoro-phenyl)-5-hydroxymethyl-isoxazol-4-yl-methoxy]-2-methyl-2H-pyrazole-3-carboxylic acid amide,
5-[3-(4-Fluoro-phenyl)-5-hydroxymethyl-isoxazol-4-yl-methoxy]-2-methyl-2H-pyrazole-3-carboxylic acid (2,2,2-trifluoro-ethyl)-amide,
5-[3-(4-Fluoro-phenyl)-5-hydroxymethyl-isoxazol-4-yl-methoxy]-2-methyl-2H-pyrazole-3-carboxylic acid (2,2,3,3,3-pentafluoro-propyl)-amide,
5-[3-(4-Fluoro-phenyl)-5-hydroxymethyl-isoxazol-4-yl-methoxy]-2-methyl-2H-pyrazole-3-carboxylic acid (1-methyl-1H-pyrazol-3-yl)-amide,
5-[3-(4-Fluoro-phenyl)-5-hydroxymethyl-isoxazol-4-yl-methoxy]-2-methyl-2H-pyrazole-3-carboxylic acid (tetrahydro-furan-3-yl)-amide,
5-[3-(4-Fluoro-phenyl)-5-hydroxymethyl-isoxazol-4-yl-methoxy]-2-methyl-2H-pyrazole-3-carboxylic acid (3-methyl-oxetan-3-yl)-amide,
{5-[3-(4-Fluoro-phenyl)-5-hydroxymethyl-isoxazol-4-yl-methoxy]-2-methyl-2H-pyrazol-3-yl}-(2-oxa-6-aza-spiro[3.3]hept-6-yl)-methanone,
5-[3-(4-Chloro-phenyl)-5-hydroxymethyl-isoxazol-4-yl-methoxy]-2-methyl-2H-pyrazole-3-carboxylic acid iso-propylamide,
5-[3-(4-Chloro-phenyl)-5-hydroxymethyl-isoxazol-4-yl-methoxy]-2-methyl-2H-pyrazole-3-carboxylic acid (tetrahydro-pyran-4-yl)-amide,
5-[3-(4-Chloro-phenyl)-5-hydroxymethyl-isoxazol-4-yl-methoxy]-2-methyl-2H-pyrazole-3-carboxylic acid amide,
5-[3-(4-Chloro-phenyl)-5-hydroxymethyl-isoxazol-4-yl-methoxy]-2-methyl-2H-pyrazole-3-carboxylic acid (2,2,2-trifluoro-ethyl)-amide,
5-[3-(4-Chloro-phenyl)-5-hydroxymethyl-isoxazol-4-yl-methoxy]-2-methyl-2H-pyrazole-3-carboxylic acid (2,2,3,3,3-pentafluoro-propyl)-amide,
5-[3-(4-Chloro-phenyl)-5-hydroxymethyl-isoxazol-4-yl-methoxy]-2-methyl-2H-pyrazole-3-carboxylic acid cyclopropylamide,
5-[3-(4-Chloro-phenyl)-5-hydroxymethyl-isoxazol-4-yl-methoxy]-2-methyl-2H-pyrazole-3-carboxylic acid ((S)-2,2,2-trifluoro-1-methyl-ethyl)-amide,
5-[3-(4-Chloro-phenyl)-5-hydroxymethyl-isoxazol-4-yl-methoxy]-2-methyl-2H-pyrazole-3-carboxylic acid (2-hydroxy-1,1-dimethyl-ethyl)-amide,
5-[3-(4-Chloro-phenyl)-5-hydroxymethyl-isoxazol-4-yl-methoxy]-2-methyl-2H-pyrazole-3-carboxylic acid (3-methyl-oxetan-3-yl)-amide,
{5-[3-(4-Chloro-phenyl)-5-hydroxymethyl-isoxazol-4-yl-methoxy]-2-methyl-2H-pyrazol-3-yl}-(2-oxa-6-aza-spiro[3.3]hept-6-yl)-methanone,
5-[3-(4-Chloro-phenyl)-5-hydroxymethyl-isoxazol-4-yl-methoxy]-2-methyl-2H-pyrazole-3-carboxylic acid (tetrahydro-furan-3-yl)-amide,
{5-[3-(4-Chloro-phenyl)-5-hydroxymethyl-isoxazol-4-yl-methoxy]-2-methyl-2H-pyrazol-3-yl}-(4,4-difluoro-piperidin-1-yl)-methanone,
5-(3-Butyl-5-hydroxymethyl-isoxazol-4-ylmethoxy)-2-methyl-2H-pyrazole-3-carboxylic acid (2,2,2-trifluoro-ethyl)-amide,
5-(3-Butyl-5-hydroxymethyl-isoxazol-4-ylmethoxy)-2-methyl-2H-pyrazole-3-carboxylic acid cyclobutylamide,
1-Methyl-5-(5-methyl-3-pyridin-2-yl-isoxazol-4-yl-methoxy)-1H-pyrazole-3-carboxylic acid ((5)-2-hydroxy-1-methyl-ethyl)-amide,
1-Methyl-5-(5-methyl-3-pyridin-2-yl-isoxazol-4-yl-methoxy)-1H-pyrazole-3-carboxylic acid isopropylamide,
1-Methyl-5-(5-methyl-3-pyridin-2-yl-isoxazol-4-yl-methoxy)-1H-pyrazole-3-carboxylic acid (tetrahydro-pyran-4-yl)-amide,
5-[3-(5-Fluoro-pyridin-2-yl)-5-methyl-isoxazol-4-yl-methoxy]-1-methyl-1H-pyrazole-3-carboxylic acid ((S)-2-hydroxy-1-methyl-ethyl)-amide, 5-[(E)-2-(5-Methyl-3-phenyl-isoxazol-4-yl)-vinyl]-2H-pyrazole-3-carboxylic acid iso-propylamide and
5-[(Z)-2-(5-Methyl-3-phenyl-isoxazol-4-yl)-vinyl]-2H-pyrazole-3-carboxylic acid iso-propylamide,
or a pharmaceutically acceptable salt or ester thereof.

One certain embodiment of the invention provides compounds of formula I selected from the group consisting of
5-(5-Methyl-3-pyridin-2-yl-isoxazol-4-ylmethoxy)-1H-pyrazole-3-carboxylic acid isopropylamide,
5-(5-Methyl-3-pyridin-2-yl-isoxazol-4-ylmethoxy)-1H-pyrazole-3-carboxylic acid (tetrahydro-pyran-4-yl)-amide and
5-(5-Methyl-3-pyridin-2-yl-isoxazol-4-ylmethoxy)-1H-pyrazole-3-carboxylic acid ((S)-2-hydroxy-1-methyl-ethyl)-amide,
or a pharmaceutically acceptable salt or ester thereof.

One certain embodiment of the invention provides compounds of formula I selected from the group consisting of
1-Methyl-5-(5-methyl-3-pyridin-2-yl-isoxazol-4-yl-methoxy)-1H-pyrazole-3-carboxylic acid ((S)-2-hydroxy-1-methyl-ethyl)-amide,
1-Methyl-5-(5-methyl-3-pyridin-2-yl-isoxazol-4-yl-methoxy)-1H-pyrazole-3-carboxylic acid isopropylamide,
1-Methyl-5-(5-methyl-3-pyridin-2-yl-isoxazol-4-yl-methoxy)-1H-pyrazole-3-carboxylic acid (tetrahydro-pyran-4-yl)-amide and
5-[3-(5-Fluoro-pyridin-2-yl)-5-methyl-isoxazol-4-yl-methoxy]-1-methyl-1H-pyrazole-3-carboxylic acid ((S)-2-hydroxy-1-methyl-ethyl)-amide,
or a pharmaceutically acceptable salt or ester thereof.

One certain embodiment of the invention provides compounds of formula I selected from the group consisting of
(R)-3-((3-Butyl-5-methylisoxazol-4-yl)methoxy)-N-(tetrahydrofuran-3-yl)-1H-pyrazole-5-carboxamide,
(S)-3-((3-Butyl-5-methylisoxazol-4-yl)methoxy)-N-(tetrahydrofuran-3-yl)-1H-pyrazole-5-carboxamide,
[5-(3-Butyl-5-methyl-isoxazol-4-ylmethoxy)-2H-pyrazol-3-yl]-morpholin-4-yl-methanone,
[5-(5-Methyl-3-phenyl-isoxazol-4-ylmethoxy)-2H-pyrazol-3-yl]-morpholin-4-yl-methanone,
5-(3-Butyl-5-methyl-isoxazol-4-ylmethoxy)-2H-pyrazole-3-carboxylic acid (tetrahydro-pyran-4-yl)-amide,
5-(3-Butyl-5-methyl-isoxazol-4-ylmethoxy)-2H-pyrazole-3-carboxylic acid ((S)-2-hydroxy-1-methyl-ethyl)-amide,
5-(3-Butyl-5-methyl-isoxazol-4-ylmethoxy)-2H-pyrazole-3-carboxylic acid (tetrahydro-furan-3-yl)-amide,
5-(3-Butyl-5-methyl-isoxazol-4-ylmethoxy)-2H-pyrazole-3-carboxylic acid (2-hydroxy-1-hydroxymethyl-ethyl)-amide,
5-(3-Butyl-5-methyl-isoxazol-4-ylmethoxy)-2H-pyrazole-3-carboxylic acid ((R)-2-hydroxy-1-methyl-ethyl)-amide,
5-(3-Butyl-5-methyl-isoxazol-4-ylmethoxy)-2H-pyrazole-3-carboxylic acid (2,2,2-trifluoro-ethyl)-amide,
5-(3-Butyl-5-methyl-isoxazol-4-ylmethoxy)-2H-pyrazole-3-carboxylic acid isopropylamide,
5-(3-Butyl-5-methyl-isoxazol-4-ylmethoxy)-2H-pyrazole-3-carboxylic acid (2-hydroxy-ethyl)-amide,
5-(3-Butyl-5-methyl-isoxazol-4-ylmethoxy)-2H-pyrazole-3-carboxylic acid (2,2-dimethyl-tetrahydro-pyran-4-yl)-amide,
5-(3-Butyl-5-methyl-isoxazol-4-ylmethoxy)-2H-pyrazole-3-carboxylic acid N',N'-dimethyl-hydrazide,
5-(3-Butyl-5-methyl-isoxazol-4-ylmethoxy)-2H-pyrazole-3-carboxylic acid morpholin-4-ylamide,
5-(3-Butyl-5-methyl-isoxazol-4-ylmethoxy)-2H-pyrazole-3-carboxylic acid pyrrolidin-1-ylamide,
5-(3-Butyl-5-methyl-isoxazol-4-ylmethoxy)-2H-pyrazole-3-carboxylic acid piperidin-1-ylamide,
5-(5-Methyl-3-phenyl-isoxazol-4-ylmethoxy)-2H-pyrazole-3-carboxylic acid isopropylamide,
5-(5-Methyl-3-phenyl-isoxazol-4-ylmethoxy)-2H-pyrazole-3-carboxylic acid (tetrahydro-pyran-4-yl)-amide,
5-(5-Methyl-3-phenyl-isoxazol-4-ylmethoxy)-2H-pyrazole-3-carboxylic acid (tetrahydro-furan-3-yl)-amide,
5-(5-Methyl-3-phenyl-isoxazol-4-ylmethoxy)-2H-pyrazole-3-carboxylic acid N',N'-dimethyl-hydrazide,
5-(5-Methyl-3-phenyl-isoxazol-4-ylmethoxy)-2H-pyrazole-3-carboxylic acid (2-hydroxy-ethyl)-amide,
5-(5-Methyl-3-phenyl-isoxazol-4-ylmethoxy)-2H-pyrazole-3-carboxylic acid amide,
5-[3-(4-Fluoro-phenyl)-5-methyl-isoxazol-4-ylmethoxy]-2H-pyrazole-3-carboxylic acid morpholin-4-ylamide,
5-[3-(4-Fluoro-phenyl)-5-methyl-isoxazol-4-ylmethoxy]-2H-pyrazole-3-carboxylic acid piperidin-1-ylamide,
5-[3-(4-Fluoro-phenyl)-5-methyl-isoxazol-4-ylmethoxy]-2H-pyrazole-3-carboxylic acid pyrrolidin-1-ylamide,
5-[3-(4-Fluoro-phenyl)-5-methyl-isoxazol-4-ylmethoxy]-2H-pyrazole-3-carboxylic acid N',N'-dimethyl-hydrazide,
5-[3-(4-Fluoro-phenyl)-5-methyl-isoxazol-4-ylmethoxy]-2H-pyrazole-3-carboxylic acid isopropylamide,
5-[3-(4-Fluoro-phenyl)-5-methyl-isoxazol-4-ylmethoxy]-2H-pyrazole-3-carboxylic acid (tetrahydro-pyran-4-yl)-amide,
5-[3-(5-Fluoro-pyridin-2-yl)-5-methyl-isoxazol-4-yl-methoxy]-2H-pyrazole-3-carboxylic acid (2,2,2-trifluoro-ethyl)-amide,
5-[3-(5-Fluoro-pyridin-2-yl)-5-methyl-isoxazol-4-yl-methoxy]-2H-pyrazole-3-carboxylic acid (tetrahydro-furan-3-yl)-amide,
5-[3-(5-Fluoro-pyridin-2-yl)-5-methyl-isoxazol-4-yl-methoxy]-2H-pyrazole-3-carboxylic acid tert-butylamide,
5-[3-(5-Fluoro-pyridin-2-yl)-5-methyl-isoxazol-4-yl-methoxy]-2H-pyrazole-3-carboxylic acid (2-hydroxy-ethyl)-amide,
5-[3-(5-Fluoro-pyridin-2-yl)-5-methyl-isoxazol-4-yl-methoxy]-2H-pyrazole-3-carboxylic acid isopropyl-amide,
5-[3-(5-Fluoro-pyridin-2-yl)-5-methyl-isoxazol-4-yl-methoxy]-2H-pyrazole-3-carboxylic acid N',N'-dimethyl-hydrazide,
5-[3-(5-Fluoro-pyridin-2-yl)-5-methyl-isoxazol-4-yl-methoxy]-2H-pyrazole-3-carboxylic acid morpholin-4-ylamide,
5-[3-(5-Fluoro-pyridin-2-yl)-5-methyl-isoxazol-4-yl-methoxy]-2H-pyrazole-3-carboxylic acid pyrrolidin-1-ylamide and
5-[3-(5-Fluoro-pyridin-2-yl)-isoxazol-4-ylmethoxy]-2H-pyrazole-3-carboxylic acid morpholin-4-ylamide,
or a pharmaceutically acceptable salt or ester thereof.

One certain embodiment of the invention provides compounds of formula I selected from the group consisting of
{5-[3-(4-Chloro-phenyl)-5-hydroxymethyl-isoxazol-4-yl-methoxy]-2-methyl-2H-pyrazol-3-yl}-(2-oxa-6-aza-spiro[3.3]hept-6-yl)-methanone,
{5-[3-(4-Chloro-phenyl)-5-hydroxymethyl-isoxazol-4-yl-methoxy]-2-methyl-2H-pyrazol-3-yl}-(4,4-difluoro-piperidin-1-yl)-methanone,
{5-[3-(4-Fluoro-phenyl)-5-hydroxymethyl-isoxazol-4-yl-methoxy]-2-methyl-2H-pyrazol-3-yl}-(2-oxa-6-aza-spiro[3.3]hept-6-yl)-methanone,
{5-[3-(4-Fluoro-phenyl)-5-methyl-isoxazol-4-yl-methoxy]-2-methyl-2H-pyrazol-3-yl}-(3-hydroxy-azetidin-1-yl)-methanone, {5-[3-(4-Fluoro-phenyl)-5-methyl-isoxazol-4-ylmethoxy]-2-methyl-2H-pyrazol-3-yl}-(2-oxa-6-aza-spiro[3.3]-hept-6-yl)-methanone, 2-Methyl-5-(5-methyl-3-phenyl-isoxazol-4-ylmethoxy)-2H-pyrazole-3-carboxylic acid (2-hydroxy-ethyl)-amide, 2-Methyl-5-(5-methyl-3-phenyl-isoxazol-4-ylmethoxy)-2H-pyrazole-3-carboxylic acid (tetrahydro-furan-3-yl)-amide, 2-Methyl-5-(5-methyl-3-phenyl-isoxazol-4-ylmethoxy)-2H-pyrazole-3-carboxylic acid (tetrahydro-pyran-4-yl)-amide, 2-Methyl-5-(5-methyl-3-phenyl-isoxazol-4-ylmethoxy)-2H-pyrazole-3-carboxylic acid amide, 2-Methyl-5-(5-methyl-3-phenyl-isoxazol-4-ylmethoxy)-2H-pyrazole-3-carboxylic acid isopropyl amide, 2-Methyl-5-(5-methyl-3-phenyl-isoxazol-4-ylmethoxy)-2H-pyrazole-3-carboxylic acid N',N'-dimethyl-hydrazide, 2-Methyl-5-(5-methyl-3-pyridin-2-yl-isoxazol-4-ylmethoxy)-2H-pyrazole-3-carboxylic acid isopropylamide, 2-Methyl-5-(5-methyl-3-pyridin-2-yl-isoxazol-4-ylmethoxy)-2H-pyrazole-3-carboxylic acid (tetrahydro-pyran-4-yl)-amide, 2-Methyl-5-(5-methyl-3-pyridin-2-yl-isoxazol-4-ylmethoxy)-2H-pyrazole-3-carboxylic acid ((S)-2-hydroxy-1-methyl-ethyl)-amide, 2-Methyl-5-[5-methyl-3-(tetrahydro-pyran-4-yl)-isoxazol-4-ylmethoxy]-2H-pyrazole-3-carboxylic acid (tetrahydro-pyran-4-yl)-amide, 5-(3-Butyl-5-hydroxymethyl-isoxazol-4-ylmethoxy)-2-methyl-2H-pyrazole-3-carboxylic acid (2,2,2-trifluoro-ethyl)-amide, 5-(3-Butyl-5-hydroxymethyl-isoxazol-4-ylmethoxy)-2-methyl-2H-pyrazole-3-carboxylic acid cyclobutylamide, 5-(3-Butyl-5-methyl-isoxazol-4-ylmethoxy)-2-methyl-2H-pyrazole-3-car-boxylic acid (2-hydroxy-ethyl)-amide, 5-(3-Butyl-5-methyl-isoxazol-4-ylmethoxy)-2-methyl-2H-pyrazole-3-carboxylic acid isopropylamide, 5-(3-Butyl-5-methyl-isoxazol-4-ylmethoxy)-2-methyl-2H-pyrazole-3-carboxylic acid (2-hydroxy-1-methyl-ethyl)-amide, 5-(3-Butyl-5-methyl-isoxazol-4-ylmethoxy)-2-methyl-2H-pyrazole-3-carboxylic acid (tetrahydro-pyran-4-yl)-amide, 5-(3-Butyl-5-methyl-isoxazol-4-ylmethoxy)-2-methyl-2H-pyrazole-3-carboxylic acid (tetra-hydro-furan-3-yl)-amide, 5-[3-(4-Chloro-phenyl)-5-hydroxymethyl-isoxazol-4-ylmethoxy]-2-methyl-2H-pyrazole-3-carboxylic acid isopropylamide, 5-[3-(4-Chloro-phenyl)-5-hydroxy-methyl-isoxazol-4-ylmethoxy]-2-methyl-2H-pyrazole-3-carboxylic acid (tetrahydro-pyran-4-yl)-amide, 5-[3-(4-Chloro-phenyl)-5-hydroxymethyl-isoxazol-4-ylmethoxy]-2-methyl-2H-pyrazole-3-carboxylic acid amide, 5-[3-(4-Chloro-phenyl)-5-hydroxymethyl-isoxazol-4-ylmethoxy]-2-methyl-2H-pyrazole-3-carboxylic acid (2,2,2-trifluoro-ethyl)-amide, 5-[3-(4-Chloro-phenyl)-5-hydroxymethyl-isoxazol-4-ylmethoxy]-2-methyl-2H-pyrazole-3-carboxylic acid (2,2,3,3,3-pentafluoro-propyl)-amide, 5-[3-(4-Chloro-phenyl)-5-hydroxymethyl-isoxazol-4-ylmethoxy]-2-methyl-2H-pyrazole-3-carboxylic acid cyclopropylamide, 5-[3-(4-Chloro-phenyl)-5-hydroxymethyl-isoxazol-4-ylmethoxy]-2-methyl-2H-pyrazole-3-carboxylic acid ((S)-2,2,2-trifluoro-1-methyl-ethyl)-amide, 5-[3-(4-Chloro-phenyl)-5-hydroxymethyl-isoxazol-4-ylmethoxy]-2-methyl-2H-pyrazole-3-carboxylic acid (2-hydroxy-1,1-dimethyl-ethyl)-amide, 5-[3-(4-Chloro-phenyl)-5-hydroxymethyl-isoxazol-4-yl-methoxy]-2-methyl-2H-pyrazole-3-carboxylic acid (3-methyl-oxetan-3-yl)-amide, 5-[3-(4-Chloro-phenyl)-5-hydroxymethyl-isoxazol-4-ylmethoxy]-2-methyl-2H-pyrazole-3-carboxylic acid (tetrahydro-furan-3-yl)-amide, 5-[3-(4-Fluoro-phenyl)-5-hydroxymethyl-isoxazol-4-ylmethoxy]-2-methyl-2H-pyrazole-3-carboxylic acid (tetrahydro-pyran-4-yl)-amide, 5-[3-(4-Fluoro-phenyl)-5-hydroxymethyl-isoxazol-4-ylmethoxy]-2-methyl-2H-pyrazole-3-carboxylic acid isopropylamide, 5-[3-(4-Fluoro-phenyl)-5-hydroxymethyl-isoxazol-4-ylmethoxy]-2-methyl-2H-pyrazole-3-carboxylic acid amide, 5-[3-(4-Fluoro-phenyl)-5-hydroxymethyl-isoxazol-4-ylmethoxy]-2-methyl-2H-pyrazole-3-carboxylic acid (2,2,2-trifluoro-ethyl)-amide, 5-[3-(4-Fluoro-phenyl)-5-hydroxymethyl-isoxazol-4-ylmethoxy]-2-methyl-2H-pyrazole-3-carboxylic acid (2,2,3,3,3-pentafluoro-propyl)-amide, 5-[3-(4-Fluoro-phenyl)-5-hydroxymethyl-isoxazol-4-ylmethoxy]-2-methyl-2H-pyrazole-3-carboxylic acid (1-methyl-1H-pyrazol-3-yl)-amide, 5-[3-(4-Fluoro-phenyl)-5-hydroxymethyl-isoxazol-4-ylmethoxy]-2-methyl-2H-pyrazole-3-carboxylic acid (tetrahydro-furan-3-yl)-amide, 5-[3-(4-Fluoro-phenyl)-5-hydroxymethyl-isoxazol-4-ylmethoxy]-2-methyl-2H-pyrazole-3-carboxylic acid (3-methyl-oxetan-3-yl)-amide, 5-[3-(4-Fluoro-phenyl)-5-methyl-isoxazol-4-ylmethoxy]-2-methyl-2H-pyrazole-3-carboxylic acid N',N'-dimethyl-hydrazide, 5-[3-(4-Fluoro-phenyl)-5-methyl-isoxazol-4-ylmethoxy]-2-methyl-2H-pyrazole-3-carboxylic acid piperidin-1-ylamide, 5-[3-(4-Fluoro-phenyl)-5-methyl-isoxazol-4-ylmethoxy]-2-methyl-2H-pyrazole-3-carboxylic acid morpholin-4-ylamide, 5-[3-(4-Fluoro-phenyl)-5-methyl-isoxazol-4-ylmethoxy]-2-methyl-2H-pyrazole-3-carboxylic acid pyrrolidin-1-ylamide, 5-[3-(4-Fluoro-phenyl)-5-methyl-isoxazol-4-ylmethoxy]-2-methyl-2H-pyrazole-3-carboxylic acid isopropylamide, 5-[3-(4-Fluoro-phenyl)-5-methyl-isoxazol-4-ylmethoxy]-2-methyl-2H-pyrazole-3-carboxylic acid (tetrahydro-pyran-4-yl)-amide, 5-[3-(4-Fluoro-phenyl)-5-methyl-isoxazol-4-ylmethoxy]-2-methyl-2H-pyrazole-3-car-boxylic acid amide, 5-[3-(4-Fluoro-phenyl)-5-methyl-isoxazol-4-ylmethoxy]-2-methyl-2H-pyrazole-3-carboxylic acid (2-hydroxy-1,1-dimethyl-ethyl)-amide, 5-[3-(4-Fluoro-phenyl)-5-methyl-isoxazol-4-ylmethoxy]-2-methyl-2H-pyrazole-3-carboxylic acid ((S)-2,2,2-trifluoro-1-methyl-ethyl)-amide, 5-[3-(4-Fluoro-phenyl)-5-methyl-isoxazol-4-ylmethoxy]-2-methyl-2H-pyrazole-3-carboxylic acid (2,2,2-trifluoro-ethyl)-amide, 5-[3-(4-Fluoro-phenyl)-5-methyl-isoxazol-4-ylmethoxy]-2-methyl-2H-pyrazole-3-carboxylic acid (3-methyl-oxetan-3-yl)-amide, 5-[3-(4-Fluoro-phenyl)-5-methyl-isoxazol-4-ylmethoxy]-2-methyl-2H-pyrazole-3-carboxylic acid (3,3,3-trifluoro-2-hydroxy-propyl)-amide, 5-[3-(4-Fluoro-phenyl)-5-methyl-isoxazol-4-yl-methoxy]-2-methyl-2H-pyrazole-3-carboxylic acid (2-methoxy-ethyl)-amide, 5-[3-(4-Fluoro-phenyl)-5-methyl-isoxazol-4-ylmethoxy]-2-methyl-2H-pyrazole-3-carboxylic acid (1-hydroxy-cyclopropylmethyl)-amide, 5-[3-(4-Fluoro-phenyl)-5-methyl-isoxazol-4-ylmethoxy]-2-methyl-2H-pyrazole-3-carboxylic acid (2-hydroxy-ethyl)-amide, 5-[3-(4-Fluoro-phenyl)-5-methyl-isoxazol-4-ylmethoxy]-2-methyl-2H-pyrazole-3-carboxylic acid (1-methyl-1H-pyrazol-3-yl)-amide, 5-[3-(4-Fluoro-phenyl)-5-methyl-isoxazol-4-ylmethoxy]-2-methyl-2H-pyrazole-3-carboxylic acid (2-acetylamino-ethyl)-amide, 5-[3-(4-Fluoro-phenyl)-5-methyl-isoxazol-4-ylmethoxy]-2-methyl-2H-pyrazole-3-carboxylic acid (3-hydroxy-2,2-dimethyl-propyl)-amide, 5-[3-(4-Fluoro-phenyl)-5-methyl-isoxazol-4-ylmethoxy]-2-methyl-2H-pyrazole-3-carboxylic acid (2-hydroxy-2-methyl-propyl)-amide, 5-[3-(4-Fluoro-phenyl)-5-methyl-isoxazol-4-ylmethoxy]-2-methyl-2H-pyrazole-3-carboxylic acid ((S or R)-3,3,3-trifluoro-2-hydroxy-propyl)-amide, 5-[3-(4-Fluoro-phenyl)-5-methyl-isoxazol-4-ylmethoxy]-2-methyl-2H-pyrazole-3-carboxylic acid ((R or S)-3,3,3-trifluoro-2-hydroxy-propyl)-amide, 5-[3-(4-Fluoro-phenyl)-5-methyl-isoxazol-4-ylmethoxy]-2-methyl-2H-pyrazole-3-carboxylic acid ((R or S)-1-hydroxymethyl-propyl)-amide, 5-[3-(4-Fluoro-phenyl)-5-methyl-isoxazol-4-ylmethoxy]-2-methyl-2H-pyrazole-3-carboxylic acid ((S or R)-1-hydroxymethyl-propyl)-amide, 5-[3-(4-Fluoro-phenyl)-5-methyl-isoxazol-4-ylmethoxy]-2-methyl-2H-pyrazole-3-carboxylic acid (tetrahydro-furan-3-yl)-amide, 5-[3-(4-Fluoro-phenyl)-5-methyl-isoxazol-4-ylmethoxy]-2-methyl-2H-pyrazole-3-carboxylic acid (1R,2R)-2-hydroxy-cyclopentyl)-amide, 5-[3-(4-Fluoro-phenyl)-5-methyl-isoxazol-4-yl-methoxy]-2-methyl-2H-pyrazole-3-carboxylic acid ((1S,2S)-2-hydroxy-cyclopentyl)-amide, 5-[3-(4-Fluoro-phenyl)-5-methyl-isoxazol-4-ylmethoxy]-2-methyl-2H-pyrazole-3-carboxylic acid ((1S,2S)-2-hydroxy-cyclopentyl)-amide, 5-[3-(4-Fluoro-phenyl)-5-methyl-isoxazol-4-yl-methoxy]-2-methyl-2H-pyrazole-3-carboxylic acid ((1R,2R)-2-hydroxy-cyclopentyl)-amide, 5-[3-(4-Fluoro-phenyl)-5-methyl-isoxazol-4-ylmethoxy]-2-methyl-2H-pyrazole-3-carboxylic acid ((R)-2-hydroxy-1-methyl-ethyl)-amide, 5-[3-(4-Fluoro-phenyl)-5-methyl-isoxazol-4-ylmethoxy]-2-methyl-2H-pyrazole-3-carboxylic acid ((S)-2-hydroxy-1-methyl-ethyl)-amide, 5-[3-(4-Fluoro-phenyl)-5-methyl-isoxazol-4-ylmethoxy]-2-methyl-2H-pyrazole-3-carboxylic acid ((R)-2-hydroxy-1-methyl-ethyl)-amide, 5-[3-(4-Fluoro-phenyl)-5-methyl-isoxazol-4-ylmethoxy]-2-methyl-2H-pyrazole-3-carboxylic acid ((S)-2-hydroxy-1-methyl-ethyl)-amide, 5-[3-(5-Fluoro-pyridin-2-yl)-5-methyl-isoxazol-4-yl-methoxy]-2-methyl-2H-pyrazole-3-carboxylic acid (tetrahydro-furan-3-yl)-amide, 5-[3-(5-Fluoro-pyridin-2-yl)-5-methyl-isoxazol-4-yl-methoxy]-2-methyl-2H-pyrazole-3-carboxylic acid N',N'-dimethyl-hydrazide, 5-[3-(5-Fluoro-pyridin-2-yl)-5-methyl-isoxazol-4-yl-methoxy]-2-methyl-2H-pyrazole-3-carboxylic acid (2-hydroxy-ethyl)-amide and 5-[3-(5-Fluoro-pyridin-2-yl)-5-methyl-isoxazol-4-yl-methoxy]-2-methyl-2H-pyrazole-3-carboxylic acid (tetrahydro-pyran-4-yl)-amide, or a pharmaceutically acceptable salt or ester thereof.

One certain embodiment of the invention provides compounds of formula I selected from the group consisting of
{5-[3-(4-Chloro-phenyl)-5-hydroxymethyl-isoxazol-4-yl-methoxy]-2-methyl-2H-pyrazol-3-yl}-(2-oxa-6-aza-spiro[3.3]hept-6-yl)-methanone, {5-[3-(4-Fluoro-phenyl)-5-methyl-isoxazol-4-yl-methoxy]-2-methyl-2H-pyrazol-3-yl}-(2-oxa-6-aza-spiro[3.3]hept-6-yl)-methanone, 2-Methyl-5-(5-methyl-3-phenyl-isoxazol-4-ylmethoxy)-2H-pyrazole-3-carboxylic acid (tetrahydro-pyran-4-yl)-amide, 2-Methyl-5-(5-methyl-3-pyridin-2-yl-isoxazol-4-yl-methoxy)-2H-pyrazole-3-car-boxylic acid (tetrahydro-pyran-4-yl)-amide, 5-[3-(4-Chloro-phenyl)-5-hydroxymethyl-isoxazol-4-yl-methoxy]-2-methyl-2H-pyrazole-3-carboxylic acid (tetrahydro-pyran-4-yl)-amide, 5-[3-(4-Chloro-phenyl)-5-hydroxymethyl-isoxazol-4-yl-methoxy]-2-methyl-2H-pyrazole-3-carboxylic acid (3-methyl-oxetan-3-yl)-amide, 5-[3-(4-Chloro-phenyl)-5-hydroxymethyl-isoxazol-4-yl-methoxy]-2-methyl-2H-pyrazole-3-carboxylic acid (tetrahydro-furan-3-yl)-amide, 5-[3-(4-Fluoro-phenyl)-5-hydroxymethyl-isoxazol-4-yl-methoxy]-2-methyl-2H-pyrazole-3-carboxylic acid (tetrahydro-pyran-4-yl)-amide, 5-[3-(4-Fluoro-phenyl)-5-hydroxymethyl-isoxazol-4-yl-methoxy]-2-methyl-2H-pyrazole-3-carboxylic acid iso-propylamide, 5-[3-(4-Fluoro-phenyl)-5-hydroxymethyl-isoxazol-4-yl-methoxy]-2-methyl-2H-pyrazole-3-carboxylic acid (tetrahydro-furan-3-yl)-amide, 5-[3-(4-Fluoro-phenyl)-5-methyl-isoxazol-4-ylmethoxy]-2-methyl-2H-pyrazole-3-carboxylic acid morpholin-4-ylamide, 5-[3-(4-Fluoro-phenyl)-5-methyl-isoxazol-4-ylmethoxy]-2-methyl-2H-pyrazole-3-carboxylic acid (tetrahydro-pyran-4-yl)-amide and 5-[3-(5-Fluoro-pyridin-2-yl)-5-methyl-isoxazol-4-yl-methoxy]-2-methyl-2H-pyrazole-3-carboxylic acid (tetrahydro-pyran-4-yl)-amide or a pharmaceutically acceptable salt or ester thereof.

One certain embodiment of the invention is 5-[3-(4-Chloro-phenyl)-5-hydroxymethyl-isoxazol-4-ylmethoxy]-2-methyl-2H-pyrazole-3-carboxylic acid (tetrahydro-pyran-4-yl)-amide.

One certain embodiment of the invention provides compounds of formula I selected from the group consisting of
5-[(E)-2-(5-Methyl-3-phenyl-isoxazol-4-yl)-vinyl]-2H-pyrazole-3-carboxylic acid iso-propylamide and 5-[(Z)-2-(5-Methyl-3-phenyl-isoxazol-4-yl)-vinyl]-2H-pyrazole-3-carboxylic acid iso-propylamide, or a pharmaceutically acceptable salt or ester thereof.

One certain embodiment of the invention provides compounds of formula I selected from the group consisting of
5-{[3-(4-Fluoro-phenyl)-5-methyl-isoxazol-4-ylmethyl]-amino}-2H-pyrazole-3-carboxylic acid (2-hydroxy-2-methyl-propyl)-amide, 5-{[3-(4-Fluoro-phenyl)-5-methyl-isoxazol-4-ylmethyl]-amino}-2H-pyrazole-3-carboxylic acid amide, 5-{[3-(4-Fluoro-phenyl)-5-methyl-isoxazol-4-ylmethyl]-amino}-2H-pyrazole-3-carboxylic acid isopropylamide,
5-{[3-(4-Fluoro-phenyl)-5-methyl-isoxazol-4-ylmethyl]-amino}-2H-pyrazole-3-carboxylic acid ethylamide,
5-{[3-(4-Fluoro-phenyl)-5-methyl-isoxazol-4-ylmethyl]-amino}-2H-pyrazole-3-carboxylic acid (tetrahydro-pyran-4-yl)-amide,
5-{[3-(4-Fluoro-phenyl)-5-methyl-isoxazol-4-ylmethyl]-amino}-2H-pyrazole-3-carboxylic acid (2-hydroxy-1-methyl-ethyl)-amide, and
(5-{[3-(4-Fluoro-phenyl)-5-methyl-isoxazol-4-ylmethyl]-amino}-2H-pyrazol-3-yl)-(2-oxa-6-aza-spiro[3.3]hept-6-yl)-methanone,
or a pharmaceutically acceptable salt or ester thereof.

One certain embodiment of the invention provides compounds of formula I selected from the group consisting of
5-{[3-(4-Fluoro-phenyl)-5-methyl-isoxazol-4-ylmethyl]-amino}-2-methyl-2H-pyrazole-3-carboxylic acid (2-hydroxy-2-methyl-propyl)-amide,
5-{[3-(4-Fluoro-phenyl)-5-methyl-isoxazol-4-ylmethyl]-amino}-2-methyl-2H-pyrazole-3-carboxylic acid amide,
5-{[3-(4-Fluoro-phenyl)-5-methyl-isoxazol-4-ylmethyl]-amino}-2-methyl-2H-pyrazole-3-carboxylic acid (2,2,2-trifluoro-ethyl)-amide,
5-{[3-(4-Fluoro-phenyl)-5-methyl-isoxazol-4-ylmethyl]-amino}-2-methyl-2H-pyrazole-3-carboxylic acid (tetrahydro-pyran-4-yl)-amide,
5-{[3-(4-Fluoro-phenyl)-5-methyl-isoxazol-4-ylmethyl]-amino}-2-methyl-2H-pyrazole-3-carboxylic acid (3-methyl-oxetan-3-yl)-amide,
(5-{[3-(4-Fluoro-phenyl)-5-methyl-isoxazol-4-ylmethyl]-amino}-2-methyl-2H-pyrazol-3-yl)-(2-oxa-6-aza-spiro[3.3]hept-6-yl)-methanone,
5-{[3-(4-Fluoro-phenyl)-5-methyl-isoxazol-4-ylmethyl]-amino}-2-methyl-2H-pyrazole-3-carboxylic acid (2-hydroxy-1-methyl-ethyl)-amide,
5-{[3-(4-Fluoro-phenyl)-5-methyl-isoxazol-4-ylmethyl]-amino}-2-methyl-2H-pyrazole-3-carboxylic acid isopropylamide,
N-isopropyl-1-methyl-3-((5-methyl-3-(pyridin-2-yl)isoxazol-4-yl)methylamino)-1H-pyrazole-5-carboxamide,
2-Methyl-5-[(5-methyl-3-pyridin-2-yl-isoxazol-4-ylmethyl)-amino]-2H-pyrazole-3-carboxylic acid (tetrahydro-pyran-4-yl)-amide,
1-methyl-3-((5-methyl-3-(pyridin-2-yl)isoxazol-4-yl)methylamino)-N-morpholino-1H-pyrazole-5-carboxamide,
1-methyl-3-((5-methyl-3-(pyridin-2-yl)isoxazol-4-yl)methylamino)-N-(3-methyloxetan-3-yl)-1H-pyrazole-5-carboxamide,
3-((3-(5-fluoropyridin-2-yl)-5-methylisoxazol-4-yl)methylamino)-N-isopropyl-1-methyl-1H-pyrazole-5-carboxamide,
3-((3-(5-fluoropyridin-2-yl)-5-methylisoxazol-4-yl)methylamino)-1-methyl-N-(tetrahydro-2H-pyran-4-yl)-1H-pyrazole-5-carboxamide,
N-cyclopropyl-3-((3-(5-fluoropyridin-2-yl)-5-methylisoxazol-4-yl)methylamino)-1-methyl-1H-pyrazole-5-carboxamide,
N-(cyclopropylmethyl)-3-((3-(5-fluoropyridin-2-yl)-5-methylisoxazol-4-yl)methylamino)-1-methyl-1H-pyrazole-5-carboxamide,
3-((3-(5-fluoropyridin-2-yl)-5-methylisoxazol-4-yl)methylamino)-1-methyl-N-(3-methyloxetan-3-yl)-1H-pyrazole-5-carboxamide, and
(3-((3-(5-fluoropyridin-2-yl)-5-methylisoxazol-4-yl)methylamino)-1-methyl-1H-pyrazol-5-yl)(2-oxa-6-azaspiro[3.3]heptan-6-yl)methanone,
or a pharmaceutically acceptable salt or ester thereof.

One certain embodiment of the invention provides compounds of formula I selected from the group consisting of
5-{[3-(4-Fluoro-phenyl)-5-methyl-isoxazol-4-ylmethyl]-amino}-2-methyl-2H-pyrazole-3-carboxylic acid (2-hydroxy-2-methyl-propyl)-amide,
5-{[3-(4-Fluoro-phenyl)-5-methyl-isoxazol-4-ylmethyl]-amino}-2-methyl-2H-pyrazole-3-carboxylic acid (tetrahydro-pyran-4-yl)-amide,
5-{[3-(4-Fluoro-phenyl)-5-methyl-isoxazol-4-ylmethyl]-amino}-2-methyl-2H-pyrazole-3-carboxylic acid (3-methyl-oxetan-3-yl)-amide,
2-Methyl-5-[(5-methyl-3-pyridin-2-yl-isoxazol-4-ylmethyl)-amino]-2H-pyrazole-3-carboxylic acid (tetrahydro-pyran-4-yl)-amide,
1-methyl-3-((5-methyl-3-(pyridin-2-yl)isoxazol-4-yl)methylamino)-N-morpholino-1H-pyrazole-5-carboxamide,
3-((3-(5-fluoropyridin-2-yl)-5-methylisoxazol-4-yl)methylamino)-1-methyl-N-(tetrahydro-2H-pyran-4-yl)-1H-pyrazole-5-carboxamide, and
3-((3-(5-fluoropyridin-2-yl)-5-methylisoxazol-4-yl)methylamino)-1-methyl-N-(3-methyloxetan-3-yl)-1H-pyrazole-5-carboxamide,
or a pharmaceutically acceptable salt or ester thereof.

One certain embodiment of the invention provides compounds of formula I selected from the group consisting of
5-[(E)-2-(5-Methyl-3-phenyl-isoxazol-4-yl)-vinyl]-2H-pyrazole-3-carboxylic acid isopropylamide,
5-[(Z)-2-(5-Methyl-3-phenyl-isoxazol-4-yl)-vinyl]-2H-pyrazole-3-carboxylic acid isopropylamide,
(1,1-Dioxo-1,6-thiomorpholin-4-yl)-(5-{(E)-2-[3-(4-fluoro-phenyl)-5-methyl-isoxazol-4-yl]-vinyl}-2H-pyrazol-3-yl)-methanone,
(5-{(E)-2-[3-(4-Fluoro-phenyl)-5-methyl-isoxazol-4-yl]-vinyl}-2H-pyrazol-3-yl)-morpholin-4-yl-methanone,
5-{(E)-2-[3-(4-Fluoro-phenyl)-5-methyl-isoxazol-4-yl]-vinyl}-2H-pyrazole-3-carboxylic acid (2,2,2-trifluoro-ethyl)-amide,
5-{(E)-2-[3-(4-Fluoro-phenyl)-5-methyl-isoxazol-4-yl]-vinyl}-2H-pyrazole-3-carboxylic acid isopropylamide,
5-{(E)-2-[3-(4-Fluoro-phenyl)-5-methyl-isoxazol-4-yl]-vinyl}-2H-pyrazole-3-carboxylic acid (tetrahydro-pyran-4-yl)-amide,
(5-{(E)-2-[3-(4-Fluoro-phenyl)-5-methyl-isoxazol-4-yl]-vinyl}-2H-pyrazol-3-yl)-(2-oxa-6-aza-spiro[3.3]hept-6-yl)-methanone,
5-{(E)-2-[3-(4-Fluoro-phenyl)-5-methyl-isoxazol-4-yl]-vinyl}-2H-pyrazole-3-carboxylic acid (2-hydroxy-1,1-dimethyl-ethyl)-amide,
5-{(E)-2-[3-(4-Fluoro-phenyl)-5-methyl-isoxazol-4-yl]-vinyl}-2H-pyrazole-3-carboxylic acid (2-hydroxy-1-methyl-ethyl)-amide,
5-{(E)-2-[3-(4-Fluoro-phenyl)-5-methyl-isoxazol-4-yl]-vinyl}-2H-pyrazole-3-carboxylic acid (2-hydroxy-2-methyl-propyl)-amide,
5-{(E)-2-[3-(4-Fluoro-phenyl)-5-methyl-isoxazol-4-yl]-vinyl}-2H-pyrazole-3-carboxylic acid ethylamide, and
5-{(E)-2-[3-(4-Fluoro-phenyl)-5-methyl-isoxazol-4-yl]-vinyl}-2H-pyrazole-3-carboxylic acid amide, or a pharmaceutically acceptable salt or ester thereof.

One certain embodiment of the invention provides compounds of formula I selected from the group consisting of
5-{(Z)-2-[3-(4-Fluoro-phenyl)-5-methyl-isoxazol-4-yl]-vinyl}-2-methyl-2H-pyrazole-3-carboxylic acid isopropylamide, 5-{(Z)-2-[3-(4-Fluoro-phenyl)-5-methyl-isoxazol-4-yl]-vinyl}-2-methyl-2H-pyrazole-3-carboxylic acid (2-hydroxy-1-methyl-ethyl)-amide,
5-{(E)-2-[3-(4-Fluoro-phenyl)-5-methyl-isoxazol-4-yl]-vinyl}-2-methyl-2H-pyrazole-3-carboxylic acid isopropylamide,
5-{(E)-2-[3-(4-Fluoro-phenyl)-5-methyl-isoxazol-4-yl]-vinyl}-2-methyl-2H-pyrazole-3-carboxylic acid ethylamide,
5-{(E)-2-[3-(4-Fluoro-phenyl)-5-methyl-isoxazol-4-yl]-vinyl}-2-methyl-2H-pyrazole-3-carboxylic acid (2-hydroxy-2-methyl-propyl)-amide,
5-{(E)-2-[3-(4-Fluoro-phenyl)-5-methyl-isoxazol-4-yl]-vinyl}-2-methyl-2H-pyrazole-3-carboxylic acid (tetrahydro-pyran-4-yl)-amide,
5-{(E)-2-[3-(4-Fluoro-phenyl)-5-methyl-isoxazol-4-yl]-vinyl}-2-methyl-2H-pyrazole-3-carboxylic acid amide,
(1,1-Dioxo-1,6-thiomorpholin-4-yl)-(5-{(E)-2-[3-(4-fluoro-phenyl)-5-methyl-isoxazol-4-yl]-vinyl}-2-methyl-2H-pyrazol-3-yl)-methanone,
5-{(E)-2-[3-(4-Fluoro-phenyl)-5-methyl-isoxazol-4-yl]-vinyl}-2-methyl-2H-pyrazole-3-carboxylic acid (2,2,2-trifluoro-ethyl)-amide,
(5-{(E)-2-[3-(4-Fluoro-phenyl)-5-methyl-isoxazol-4-yl]-vinyl}-2-methyl-2H-pyrazol-3-yl)-morpholin-4-yl-methanone,
5-{(E)-2-[3-(4-Fluoro-phenyl)-5-methyl-isoxazol-4-yl]-vinyl}-2-methyl-2H-pyrazole-3-carboxylic acid (2-hydroxy-1-methyl-ethyl)-amide,
(5-{(E)-2-[3-(4-Fluoro-phenyl)-5-methyl-isoxazol-4-yl]-vinyl}-2-methyl-2H-pyrazol-3-yl)-(2-oxa-6-aza-spiro[3.3]hept-6-yl)-methanone, and
5-{(E)-2-[3-(4-Fluoro-phenyl)-5-methyl-isoxazol-4-yl]-vinyl}-2-methyl-2H-pyrazole-3-carboxylic acid (2-hydroxy-1,1-dimethyl-ethyl)-amide,
or a pharmaceutically acceptable salt or ester thereof.

One certain embodiment of the invention provides compounds of formula I selected from the group consisting of
2-Methyl-5-(5-methyl-3-phenyl-isoxazol-4-ylmethoxy)-2H-pyrazole-3-carboxylic acid (tetrahydro-pyran-4-yl)-amide,
5-[3-(4-Fluoro-phenyl)-5-methyl-isoxazol-4-ylmethoxy]-2-methyl-2H-pyrazole-3-carboxylic acid morpholin-4-ylamide,
5-[3-(4-Fluoro-phenyl)-5-methyl-isoxazol-4-ylmethoxy]-2-methyl-2H-pyrazole-3-carboxylic acid (tetrahydro-pyran-4-yl)-amide,
{5-[3-(4-Fluoro-phenyl)-5-methyl-isoxazol-4-ylmethoxy]-2-methyl-2H-pyrazol-3-yl}-(2-oxa-6-aza-spiro[3.3]hept-6-yl)-methanone,
2-Methyl-5-(5-methyl-3-pyridin-2-yl-isoxazol-4-ylmethoxy)-2H-pyrazole-3-carboxylic acid (tetrahydro-pyran-4-yl)-amide,
5-[3-(5-Fluoro-pyridin-2-yl)-5-methyl-isoxazol-4-ylmethoxy]-2-methyl-2H-pyrazole-3-carboxylic acid (tetrahydro-pyran-4-yl)-amide,
5-[3-(4-Fluoro-phenyl)-5-hydroxymethyl-isoxazol-4-ylmethoxy]-2-methyl-2H-pyrazole-3-carboxylic acid (tetrahydro-pyran-4-yl)-amide,
5-[3-(4-Fluoro-phenyl)-5-hydroxymethyl-isoxazol-4-ylmethoxy]-2-methyl-2H-pyrazole-3-carboxylic acid isopropylamide,
5-[3-(4-Fluoro-phenyl)-5-hydroxymethyl-isoxazol-4-ylmethoxy]-2-methyl-2H-pyrazole-3-carboxylic acid (tetrahydro-furan-3-yl)-amide,
5-[3-(4-Chloro-phenyl)-5-hydroxymethyl-isoxazol-4-ylmethoxy]-2-methyl-2H-pyrazole-3-carboxylic acid (tetrahydro-pyran-4-yl)-amide,
5-[3-(4-Chloro-phenyl)-5-hydroxymethyl-isoxazol-4-ylmethoxy]-2-methyl-2H-pyrazole-3-carboxylic acid (3-methyl-oxetan-3-yl)-amide,
{5-[3-(4-Chloro-phenyl)-5-hydroxymethyl-isoxazol-4-ylmethoxy]-2-methyl-2H-pyrazol-3-yl}-(2-oxa-6-aza-spiro[3.3]hept-6-yl)-methanone,
5-[3-(4-Chloro-phenyl)-5-hydroxymethyl-isoxazol-4-ylmethoxy]-2-methyl-2H-pyrazole-3-carboxylic acid (tetrahydro-furan-3-yl)-amide,
5-{[3-(4-Fluoro-phenyl)-5-methyl-isoxazol-4-ylmethyl]-amino}-2-methyl-2H-pyrazole-3-carboxylic acid (2-hydroxy-2-methyl-propyl)-amide,
5-{[3-(4-Fluoro-phenyl)-5-methyl-isoxazol-4-ylmethyl]-amino}-2-methyl-2H-pyrazole-3-carboxylic acid (tetrahydro-pyran-4-yl)-amide,
5-{[3-(4-Fluoro-phenyl)-5-methyl-isoxazol-4-ylmethyl]-amino}-2-methyl-2H-pyrazole-3-carboxylic acid (3-methyl-oxetan-3-yl)-amide,
2-Methyl-5-[(5-methyl-3-pyridin-2-yl-isoxazol-4-ylmethyl)-amino]-2H-pyrazole-3-carboxylic acid (tetrahydro-pyran-4-yl)-amide,
1-methyl-3-((5-methyl-3-(pyridin-2-yl)isoxazol-4-yl)methylamino)-N-morpholino-1H-pyrazole-5-carboxamide,
3-((3-(5-fluoropyridin-2-yl)-5-methylisoxazol-4-yl)methylamino)-1-methyl-N-(tetrahydro-2H-pyran-4-yl)-1H-pyrazole-5-carboxamide,
3-((3-(5-fluoropyridin-2-yl)-5-methylisoxazol-4-yl)methylamino)-1-methyl-N-(3-methyloxetan-3-yl)-1H-pyrazole-5-carboxamide,
or a pharmaceutically acceptable salt or ester thereof.

One certain embodiment of the invention is a process for preparing a compound of formula I as defined herewithin, which process comprises reacting a compound of formula III to a compound of formula IV, which then reacts with a compound of formula II to a compound of formula I, or, alternatively, a compound of formula III reacts with a compound of formula II to a compound of formula I,

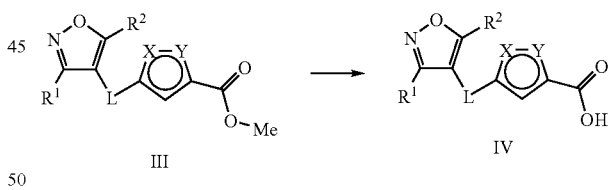

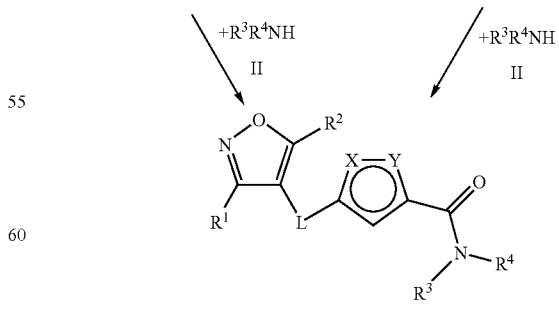

wherein any residues and variables have any of the meanings as defined herewithin.

One certain embodiment of the invention is a process for preparing a compound of formula I, which process comprises reacting a compound of formula R³R⁴NH (II) with a compound of formula III,

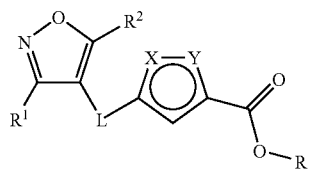

wherein any residues and variables have any of the meanings as defined herewithin and R is lower alkyl or H.

One certain embodiment of the invention is a compound as described herewithin, whenever prepared by a process as defined above.

One certain embodiment of the invention is a compound as described herewithin for the use as a medicament.

One certain embodiment of the invention is a compound as described herewithin for the use as therapeutically active substance.

One certain embodiment of the invention is a compound as described herewithin for the use for the therapeutic and/or prophylactic treatment of a disorder or condition mediated by the GABA A α5 receptor, or that can be treated via modulation of the GABA A α5 receptor.

One certain embodiment of the invention is a compound as described herewithin for the use as therapeutically active substance for the therapeutic and/or prophylactic treatment of diseases and disorders related to the GABA A α5 receptor.

One certain embodiment of the invention is a compound as described herewithin for the use for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One certain embodiment of the invention is a medicament, comprising a compound as described herewithin.

One certain embodiment of the invention is a pharmaceutical composition comprising a compound as described herewithin as an active ingredient and a pharmaceutically acceptable carrier and/or a pharmaceutically acceptable auxiliary substance.

One certain embodiment of the invention is a pharmaceutical composition, comprising a compound as described herewithin for the therapeutic and/or prophylactic treatment of a disorder or condition mediated by the GABA A α5 receptor, or that can be treated via modulation of the GABA A α5 receptor.

One certain embodiment of the invention is a pharmaceutical composition, comprising a compound as described herewithin for the manufacture of a medicament for the therapeutic and/or prophylactic treatment of diseases and disorders which are related to the GABA A α5 receptor.

One certain embodiment of the invention is a pharmaceutical composition, comprising a compound as described herewithin for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One certain embodiment of the invention is the use of a compound as described herewithin for the manufacture of a medicament for the therapeutic and/or prophylactic treatment of a disorder or condition mediated by the GABA A α5 receptor, or that can be treated via modulation of the GABA A α5 receptor.

One certain embodiment of the invention is the use of a compound as described herewithin for the therapeutic and/or prophylactic treatment of diseases and disorders which are related to the GABA A α5 receptor.

One certain embodiment of the invention is the use of a compound as described herewithin for the manufacture of a medicament for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One certain embodiment of the invention is the use of a compound as described herewithin for the therapeutic and/or prophylactic treatment of a disorder or condition mediated by the GABA A α5 receptor, or that can be treated via modulation of the GABA A α5 receptor.

One certain embodiment of the invention is the use of a compound as described herewithin for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One certain embodiment of the invention is a method for the therapeutic and/or prophylactic treatment of a disorder or condition mediated by the GABA A α5 receptor, or that can be treated via modulation of the GABA A α5 receptor, particularly for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers, which method comprises administering a compound as described herewithin to a human being or animal.

One certain embodiment of the invention is a method for the therapeutic and/or prophylactic treatment of a disorder or condition related to the GABA A α5 receptor, particularly for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers, which method comprises administering a compound as described herewithin to a human being or animal.

The preferred indications using the compounds of the present invention are cognitive disorders, schizophrenia, positive, negative and/or cognitive symptoms associated with schizophrenia and Alzheimer's disease. Most preferred indications are schizophrenia and Alzheimer's disease. Particularly preferred is the indication Alzheimer's disease.

The compounds of formula I can be prepared in accordance with the following schemes. The starting material is commercially available or can be prepared in accordance with known methods. Any previously defined residues and variables will continue to have the previously defined meaning unless otherwise indicated.

The present compounds of formula I and their pharmaceutically acceptable salts can be prepared by a process comprising the steps of:

A) Reacting a compound of formula 1 with hydroxylamine hydrochloride in a suitable solvent, such as ethanol and water in the presence of a base, such as aqueous sodium hydroxide to give a compound of formula 2, followed by reacting the compound of formula 2 with a chlorinating agent such as N-chlorosuccinimide in a suitable solvent, such as DMF to give a compound of formula 3.

Scheme 1: Synthesis of intermediates 3

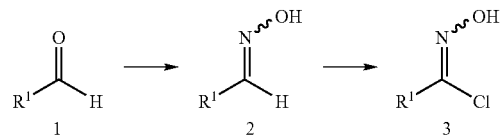

B) A compound of formula 3 is then reacted further to a compound of formula 6 by reacting i) with a compound of formula 4 in the presence of a suitable base, such as triethylamine, in a suitable solvent, such as chloroform, or ii) with a compound of formula 5 in the presence of a suitable base, such as triethylamine, in a suitable solvent, such as diethylether.

Scheme 2: Synthesis of intermediates 6

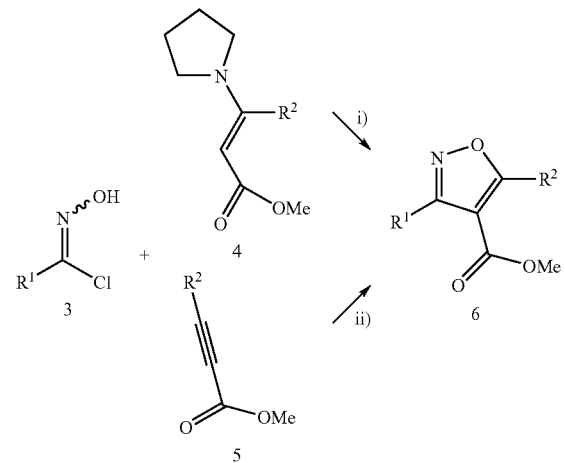

C-1) A compound of formula 6 is then reacted to a compound of formula 8 with i) a reducing agent, such as lithium aluminum hydride, in a suitable solvent, such as THF to give a compound of formula 8, or ii-1) a hydrolytic agent such as NaOH or LiOH in a suitable solvent such as THF, MeOH or EtOH, water to give a compound of formula 7, ii-2) followed by reacting a compound of formula 7 with a reducing agent, such as lithium aluminum hydride or ethylchloroformate in the presence of sodium borohydride in a suitable solvent such as THF or water.

Scheme 3: Synthesis of intermediates 8

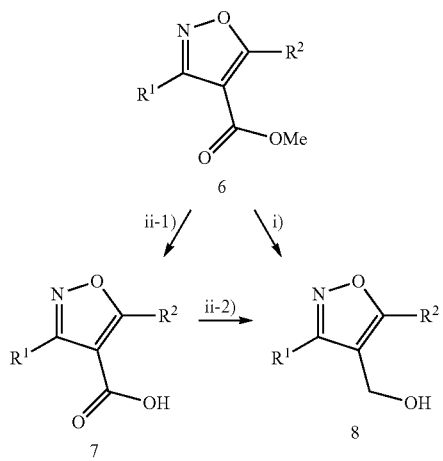

Scheme 5: Synthesis of intermediates 13

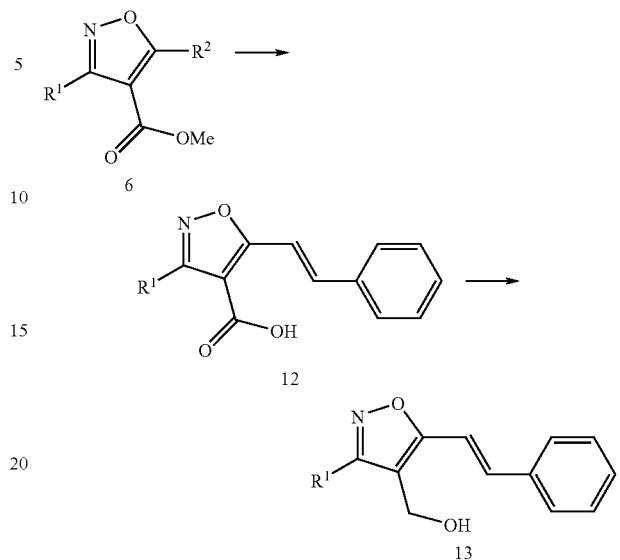

C-2) A compound of formula 8 is further reacted with a compound of formula 9 in the presence of triphenylphosphine and diethyl azodicarboxylate (or diisopropyl azodicarboxylate), in a suitable solvent, such as THF, to give a compound of formula 10. A compound of formula 10 is further reacted in the presence of a suitable base, such as cesium carbonate, in a suitable solvent, such as DMF to give a compound of formula 11.

D-2) Compounds of formula 13 can react with a compound such as 14 in the presence of triphenylphosphine and diethyl-azodicarboxylate (or diispropyl-azodicarboxylate), in a suitable solvent, such as THF to give a compound of formula 15.

Scheme 4: Synthesis of intermediates 11

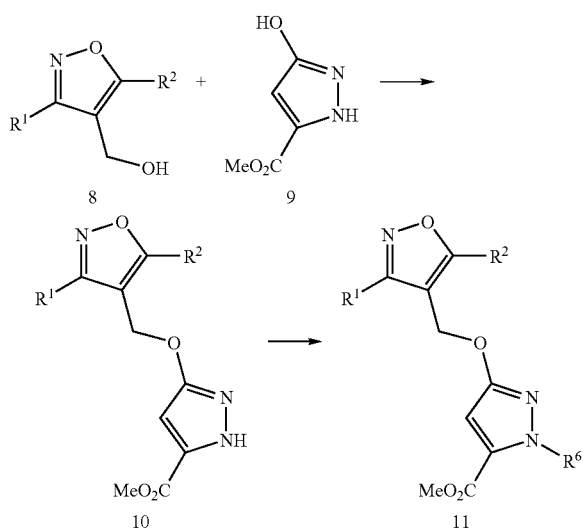

Scheme 6: Synthesis of intermediates 15

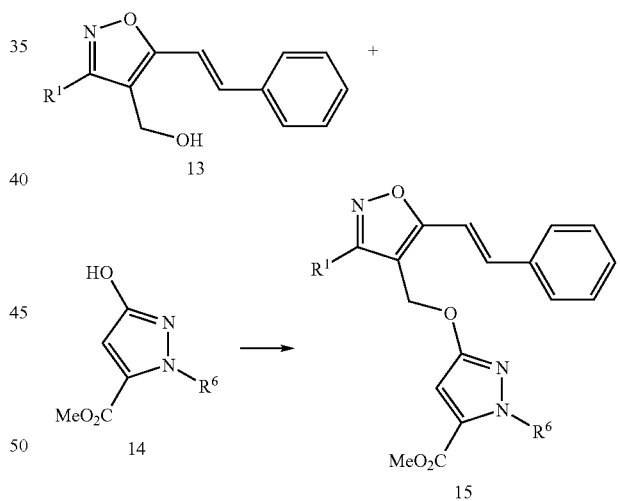

D-1) Alternatively, compounds of formula 6 can be reacted with benzaldehyde in the presence of a base such as sodium ethoxide in a suitable solvent such as ethanol under reflux to give a compound of formula 12, followed by reacting a compound of formula 12 with a reducing agent, such as lithium aluminum hydride or ethyl chloroformate in the presence of sodium borohydride and a suitable base such as triethylamine in a suitable solvent such as THF or water to give a compound of formula 13.

D-3) A compound of formula 15 can react further with
i-1) an oxidizing agent such as osmium(VIII)-oxide and sodium metaperiodate in the presence of benzyltriethylammonium chloride in the presence of a suitable solvent such as tert-butanol, dioxane and water at elevated temperatures to give a compound of formula 16,
i-2) followed by reacting a compound of formula 16 with a reducing agent, such as sodium borohydride in a suitable solvent such as methanol to give a compound of formula 17, or
ii-1) alternatively, a compound of formula 15 can be reacted with AD Mix-α with methanesulfonamide in a suitable solvent such as tert-butanol and water to give a compound of formula 18, ii-2) which can then be reacted with lead tetraacetate in a suitable solvent such as benzene and then reacted with a reducing agent such as sodium borohydride in a suitable solvent such as methanol to give a compound of formula 17.

Scheme 7: Synthesis of intermediates 17

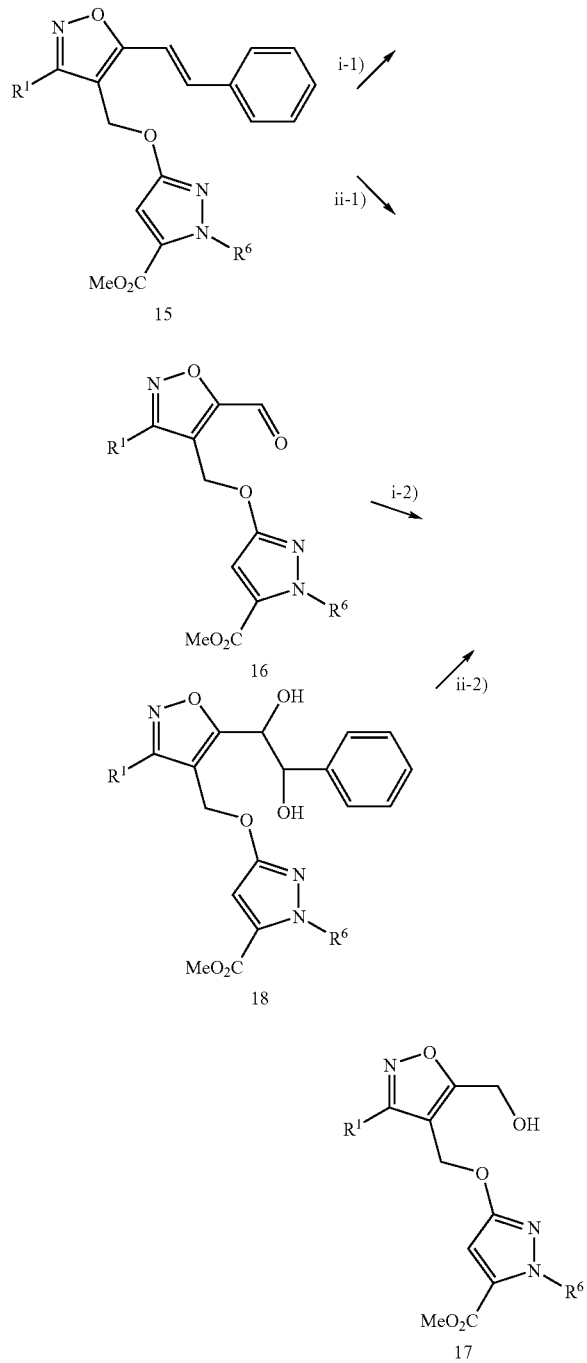

D-4) A compound of formula 17 which can be treated with a suitable base such as sodium hydroxide or lithium hydroxide in a suitable solvent, such as dioxane, water, THF or methanol to give a compound of formula 19.

Scheme 8: Synthesis of intermediates 19

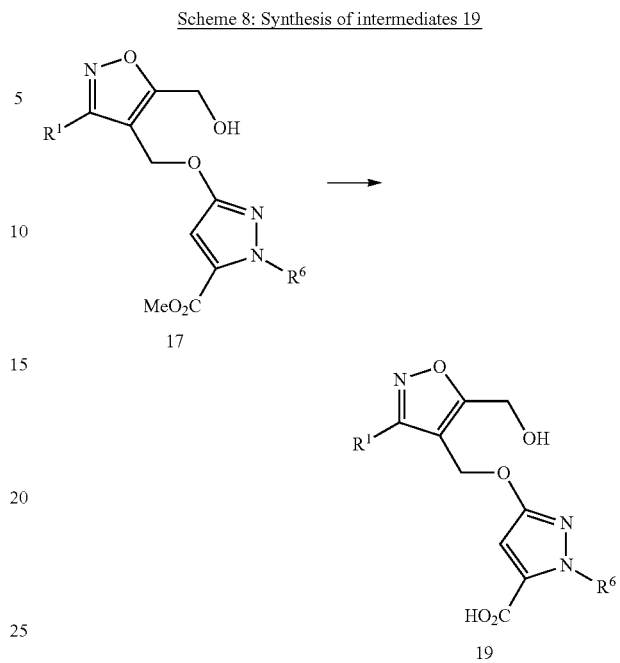

E) A compound of formula 20 can be reacted with a compound of formula 8 in the presence of triphenylphosphine and diethyl-azodicarboxylate (or diisopropyl-azodicarboxylate), in a suitable solvent, such as THF to give a compound of formula 21.

Scheme 9: Synthesis of intermediates 21

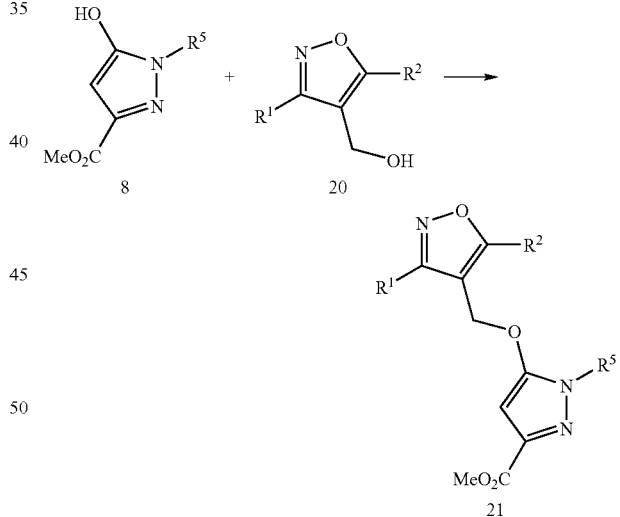

F-1) A compound of formula 8 can be converted to a compound of formula 22 by reaction with an oxidizing agent such as pyridinium chlorochromate in a suitable solvent such as DCM, which can be converted to a compound of formula 23 by reaction with tetrabromomethane in the presence of triphenylphosphine. A compound of formula 23, upon treatment with isopropylmagnesium chloride in a suitable solvent such as THF, can provide a compound of formula 24 and then reacting a compound of formula 24 with tributyltin hydride and AIBN to give a compound of formula 25, followed by reaction of compound of formula 25 with iodine in a suitable solvent such as chloroform to give a compound of formula 26.

Scheme 10: Synthesis of intermediates 26

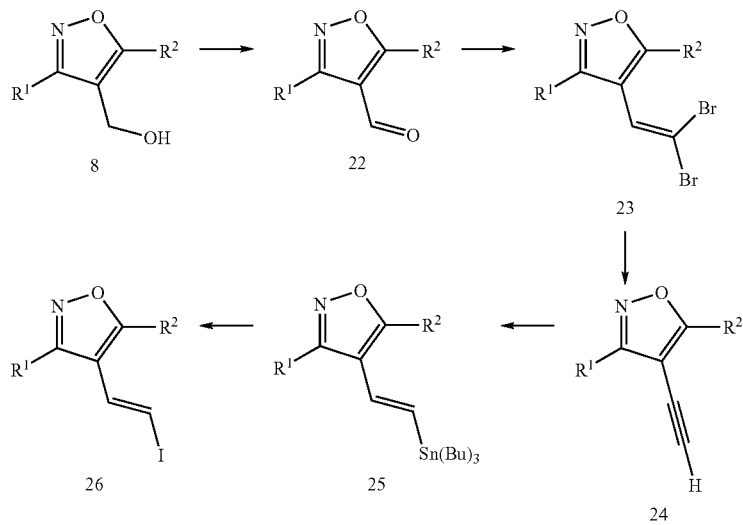

F-2) A compound of formula 26 can be reacted with a compound of formula 27 in the presence of lithium chloride, copper(I) iodide and tetrakis(triphenylphosphonium) palladium(0) in a suitable solvent such as THF to give a compound of formula 28.

Scheme 11: Synthesis of intermediates 28

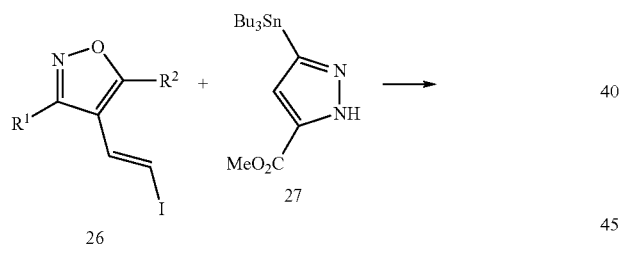

-continued

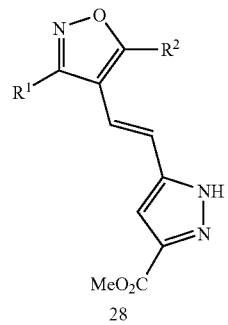

F-3) Alternatively, compounds of formula 8 can be chlorinated by e.g. thionylchloride to a compound of formula 39, which reacts further with a triphenylphosphine to the respective phosphonium salt of formula 40. A compound of formula 40 can then react with a compound of formula 41 (41-1 or 41-2), which was prepared according to scheme 12, under presence of a strong non-nucleophilic base such as LiHMDS to a compound of formula 42. Ester 42 can, after being separated into E and Z isomer, and be coupled with a suitable amine promoted by an activation agent such as EDCI to give a compound of formula 43.

Scheme 12: Synthesis of compounds 43

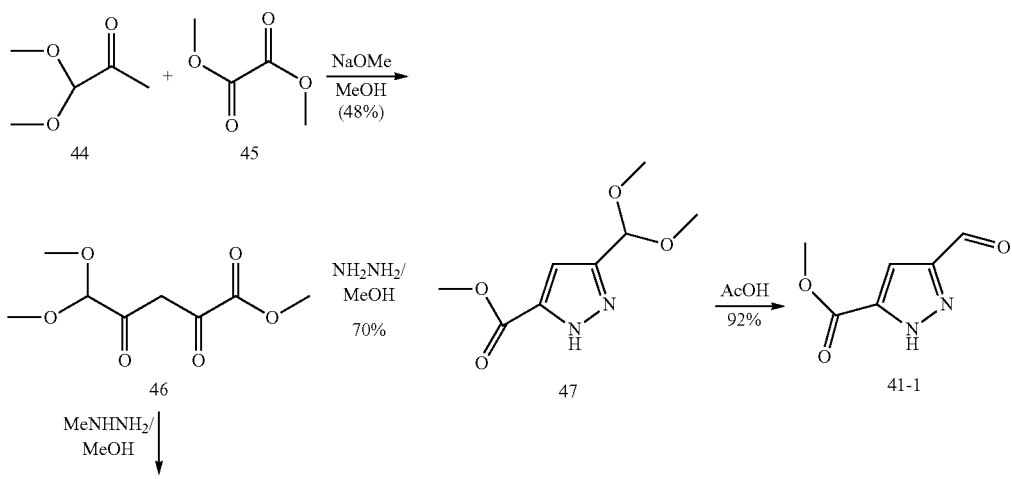

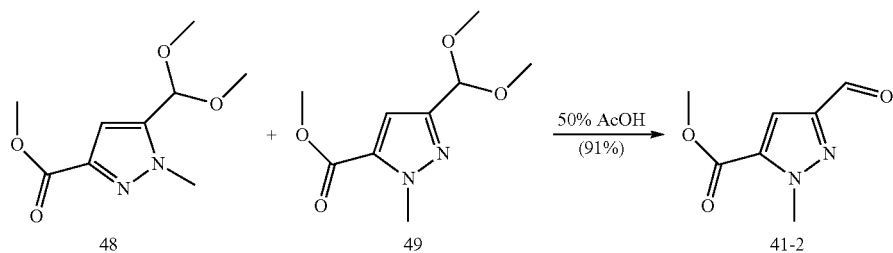
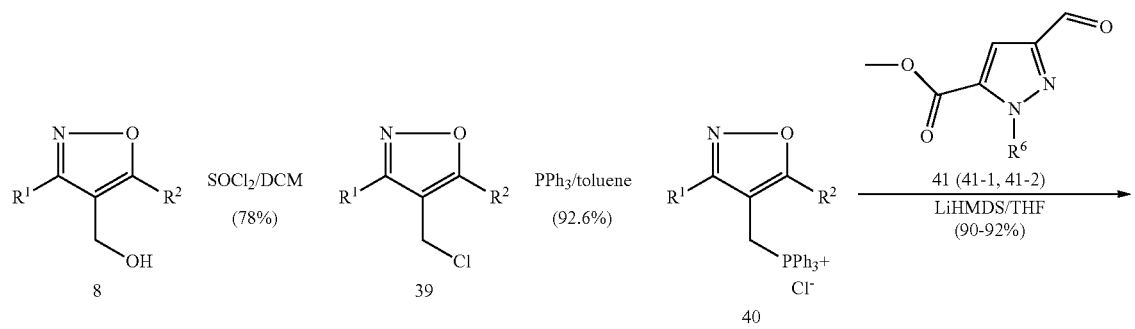
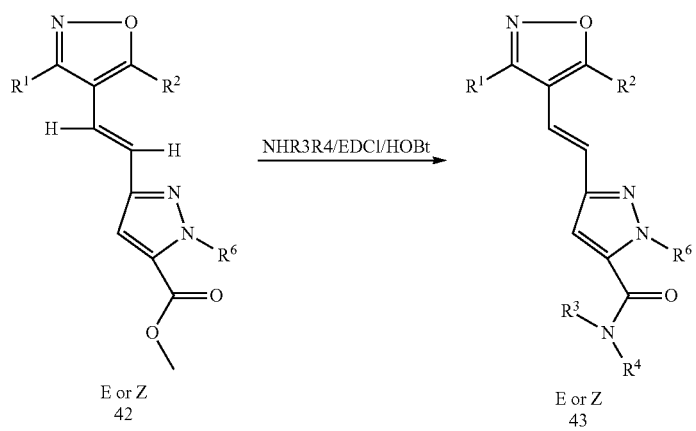
G) Compounds of formula 28 can further react with a compound of formula 29 or a compound of formula 30 to a compound of formula 50 or with a compound of formula 31 or a compound of formula 32 to a compound of formula 33,
i) under Mitsunobu inversion conditions (such as Ph$_3$P/DEAD in THF), or
ii) in a base promoted alkylation (such as Cs$_2$CO$_3$ in DMF).

Scheme 13: Synthesis of compounds 50 and 33

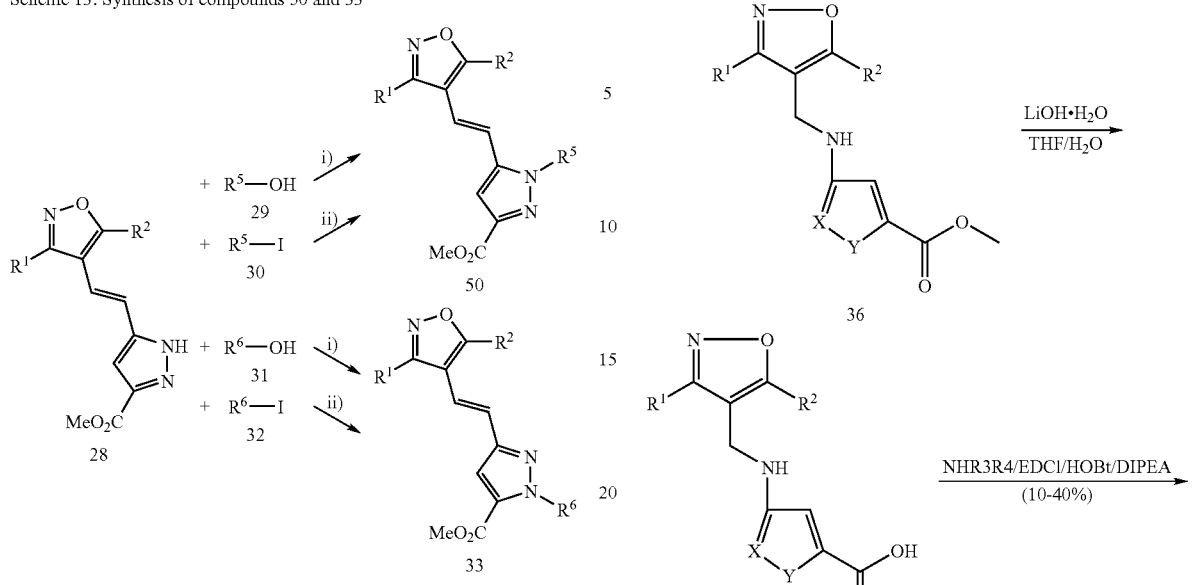

H) Compounds of formula 8 can further be oxidized by an oxidant such as PCC to a compound of formula 34, and then react with compounds of formula 35 with a suitable reducing agent such as sodium cyanoborohydride to a compound of formula 36. The ester 36 can be hydrolyzed to the acid 37 and then further coupled with a suitable amine promoted by an activation agent such as EDCI to a compound of formula 38.

Scheme 14: Synthesis of compounds 38

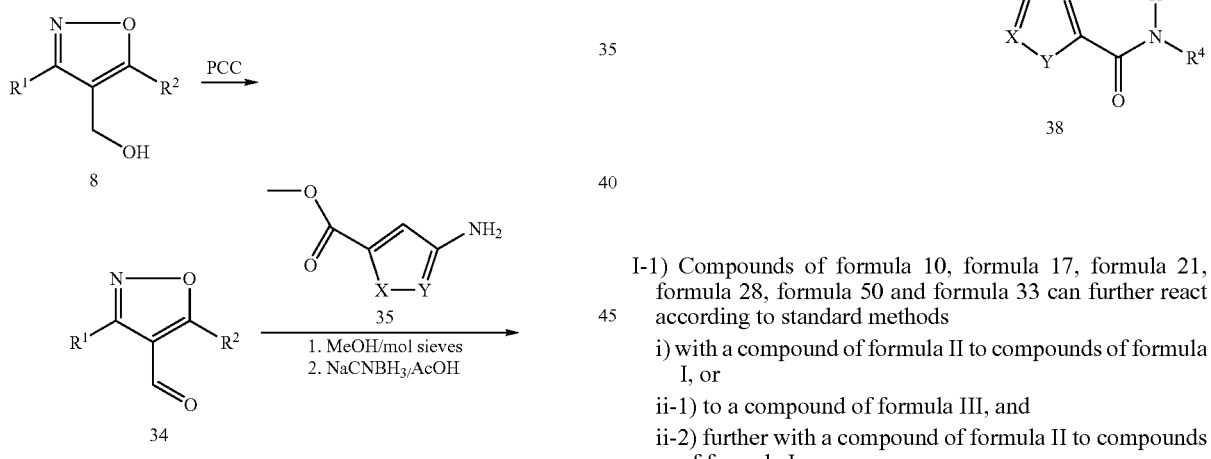

I-1) Compounds of formula 10, formula 17, formula 21, formula 28, formula 50 and formula 33 can further react according to standard methods
  i) with a compound of formula II to compounds of formula I, or
  ii-1) to a compound of formula III, and
  ii-2) further with a compound of formula II to compounds of formula I.

Scheme 15: Synthesis of compounds of formula I

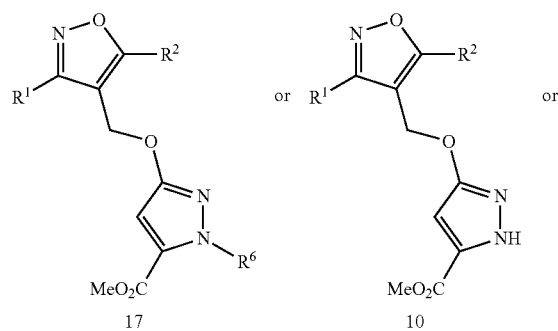

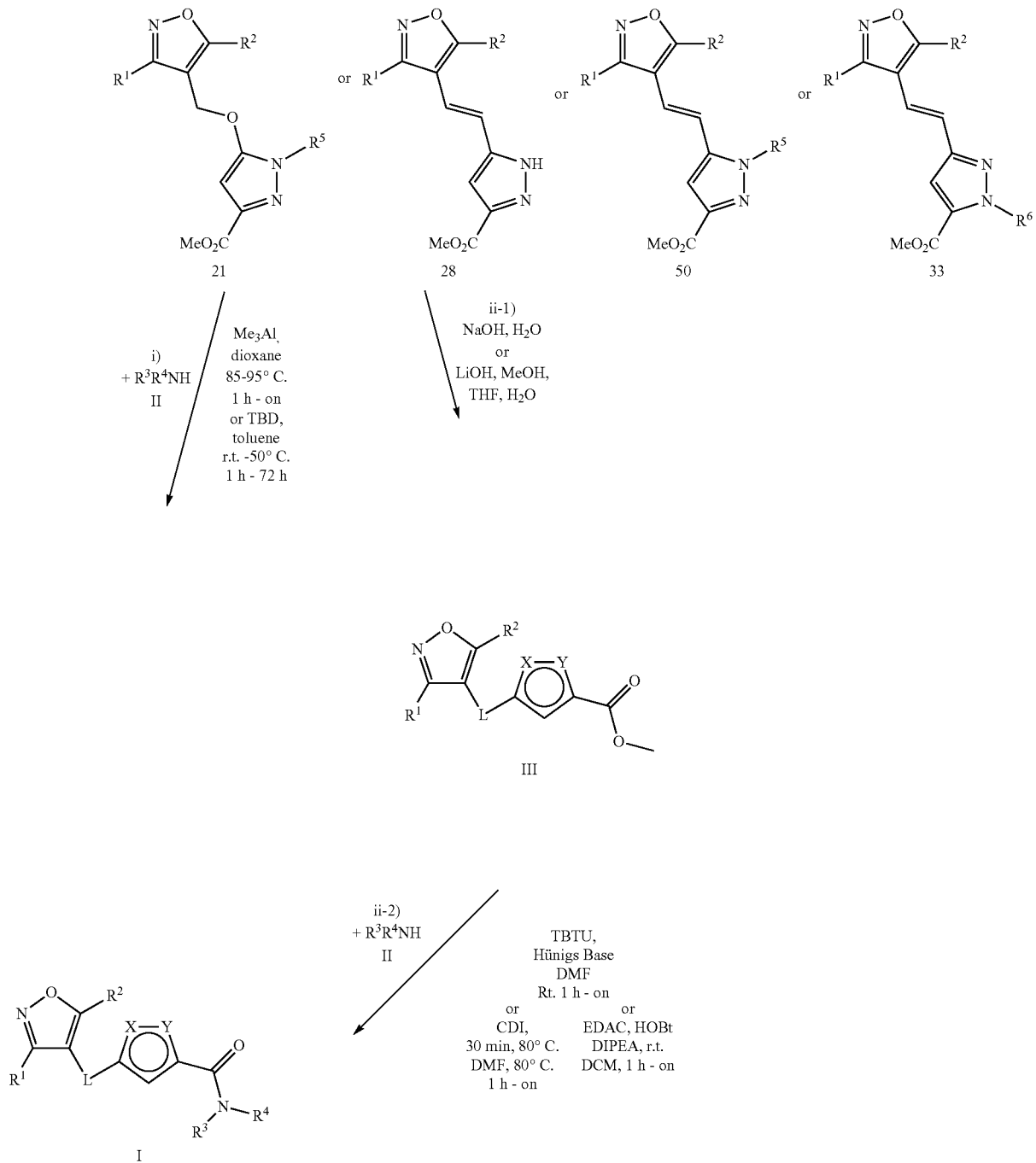
I-2) Alternatively, compounds of formula 28 can further react with a compound of formula 29 or a compound of formula 30 to a compound of formula 50 or with a compound of formula 31 or a compound of formula 32 to a compound of formula 33,
i) under Mitsunobu inversion conditions (such as Ph₃P/ DEAD in THF), or
ii) in a base promoted alkylation (such as Cs₂CO₃ in DMF).

Scheme 16: Synthesis of compounds 50 and 33

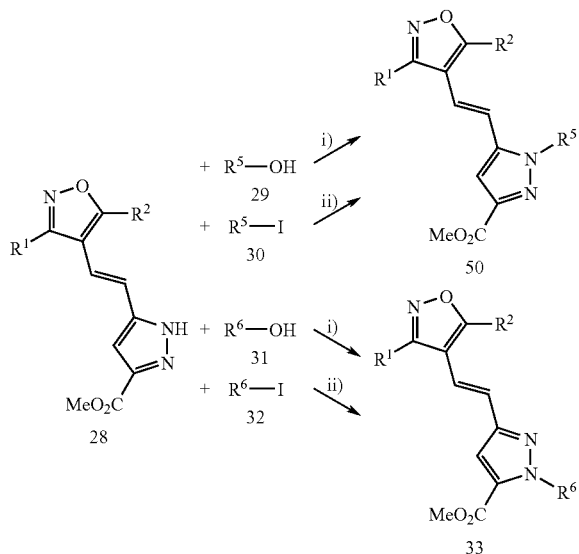

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilization.

The conversion into pharmaceutically acceptable esters of compounds of formula I bearing a carboxy group can be carried out e.g. by treatment of a suitable carboxy group with a suitable alcohol using e.g. a condensating reagent such as benzotriazol-1-yloxytris(dimethylamino)-phosphonium hexafluorophosphate (BOP), N,N-dicylohexyl-carbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoro-borate (TPTU), or by direct reaction with a suitable alcohol under acidic conditions, as for example in the presence of a strong mineral acid like hydrochloric acid, sulfuric acid and the like. The conversion into pharmaceutically acceptable esters of compounds of formula I bearing a hydroxy group can be carried out with suitable acids by analogous methods.

Insofar as their preparation is not described in the examples, the compounds of formula I as well as all intermediate products can be prepared according to analogous methods or according to the methods set forth herewithin. Starting materials are commercially available, known in the art or can be prepared by methods known in the art or in analogy thereto.

It will be appreciated that the compounds of general formula I in this invention can be derivatized at functional groups to provide derivatives which are capable of conversion back to the parent compound in vivo.

Pharmacological Tests

The compounds of formula I and their pharmaceutically acceptable salts and esters possess valuable pharmacological properties. Compounds of the present invention are ligands for GABA A receptors containing the α5 subunit and are therefore useful in the therapy where cognition enhancement is required.

The compounds were investigated in accordance with the test given hereinafter.

Membrane Preparation and Binding Assay

The affinity of compounds at GABA A receptor subtypes was measured by competition for [3H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM $CaCl_2$, 1.2 mM $MgCl_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were re-suspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, [$^3$H]flumazenil at a concentration of 1 nM for α1, α2 and α3 subunits and 0.5 nM for α5 subunits and the test compound in the range of $10-10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and the preferred compounds were found to possess a Ki value for displacement of [$^3$H]flumazenil from α5 subunits of the rat GABA A receptor of 100 nM or less. Most preferred are compounds with a Ki (nM)<35. In a preferred embodiment the compounds of the invention are binding selective for the α5 subunit relative to the α1, α2 and α3 subunit.

Representative test results are listed below.

TABLE 2 human Ki (hKi) values

| Ex. | hKi GABA A α5 (nM) |
|---|---|
| 1 | 41.3 |
| 2 | 32.4 |
| 3 | 3.1 |
| 4 | 6.6 |
| 5 | 14.6 |
| 6 | 17.5 |
| 7 | 36.3 |
| 8 | 1.8 |
| 9 | 6.2 |
| 10 | 3.8 |
| 11 | 4.9 |
| 12 | 2.3 |
| 13 | 0.5 |
| 14 | 9.3 |
| 15 | 2.5 |

TABLE 2-continued human Ki (hKi) values

| Ex. | hKi GABA A α5 (nM) |
|---|---|
| 16 | 11.1 |
| 17 | 1.2 |
| 18 | 1.2 |
| 19 | 17.8 |
| 20 | 4 |
| 21 | 2.5 |
| 22 | 6.7 |
| 23 | 1.9 |
| 24 | 3.5 |
| 25 | 13.6 |
| 26 | 2.3 |
| 27 | 7.8 |
| 28 | 5.4 |
| 29 | 10.4 |
| 30 | 25.2 |
| 31 | 6.4 |
| 32 | 15.7 |
| 33 | 20.2 |
| 34 | 5.7 |
| 35 | 6 |
| 36 | 53.5 |
| 37 | 22 |
| 38 | 38.7 |
| 39 | 5.8 |
| 40 | 21.5 |
| 41 | 27.2 |
| 42 | 15.9 |
| 43 | 9.7 |
| 44 | 3.1 |
| 45 | 47.3 |
| 46 | 40.9 |
| 47 | 50.3 |
| 48 | 23.3 |
| 49 | 19.3 |
| 50 | 3.5 |
| 51 | 11.4 |
| 52 | 7.4 |
| 53 | 1.2 |
| 54 | 12 |
| 55 | 29.6 |
| 56 | 6.1 |
| 57 | 6.1 |
| 58 | 4.3 |
| 59 | 1.8 |
| 60 | 13.2 |
| 61 | 7.4 |
| 62 | 7.1 |
| 63 | 13.1 |
| 64 | 16.1 |
| 65 | 5.8 |
| 66 | 6.5 |
| 67 | 2.4 |
| 68 | 5.3 |
| 69 | 3.5 |
| 70 | 16.7 |
| 71 | 16.5 |
| 72 | 1.5 |
| 73 | 9.4 |
| 74 | 2 |
| 75 | 5.7 |
| 76 | 10.8 |
| 77 | 45.8 |
| 78 | 30.2 |
| 79 | 6.5 |
| 80 | 23.5 |
| 81 | 5.9 |
| 82 | 29.5 |
| 83 | 11 |
| 84 | 3.5 |
| 85 | 27.6 |
| 86 | 39.2 |
| 87 | 44.7 |
| 88 | 8.7 |
| 89 | 20.3 |
| 90 | 24.4 |
| 91 | 1 |
| 92 | 9.5 |
| 93 | 14.7 |
| 94 | 6.3 |
| 95 | 8 |
| 96 | 42.7 |
| 97 | 4.5 |
| 98 | 4.9 |
| 99 | 24 |
| 100 | 5.8 |
| 101 | 0.9 |
| 102 | 12.6 |
| 103 | 5.7 |
| 104 | 6.6 |
| 105 | 5.4 |
| 106 | 8.1 |
| 107 | 17.8 |
| 108 | 3.1 |
| 109 | 9 |
| 110 | 2.7 |
| 111 | 52.5 |
| 112 | 45.1 |
| 113 | 39.6 |
| 114 | 16.2 |
| 115 | 20.5 |
| 116 | 18.2 |
| 117 | 6.8 |
| 118 | 5.1 |
| 119 | 20.2 |
| 120 | 28.0 |
| 121 | 49.6 |
| 122 | 1.6 |
| 123 | 1.3 |
| 124 | 2.0 |
| 125 | 0.4 |
| 126 | 1.5 |
| 127 | 29.3 |
| 128 | 1.2 |
| 129 | 11.8 |
| 130 | 0.9 |
| 131 | 36.5 |
| 132 | 50.6 |
| 133 | 4.1 |
| 134 | 5.2 |
| 135 | 2.4 |
| 136 | 1.0 |
| 137 | 1.4 |
| 138 | 11.0 |
| 139 | 3.0 |
| 140 | 3.8 |
| 141 | 8.1 |
| 142 | 4.8 |
| 143 | 7.4 |
| 144 | 29.3 |
| 145 | 69.6 |
| 146 | 15.2 |
| 147 | 4.7 |
| 148 | 5.4 |
| 149 | 67.5 |
| 150 | 26.2 |
| 151 | 13.6 |
| 152 | 20.9 |
| 153 | 43.4 |
| 154 | 13.0 |
| 155 | 57.1 |
| 156 | 3.9 |
| 157 | 51.0 |
| 158 | 22.0 |
| 159 | 39.9 |
| 160 | 25.4 |
| 161 | 19.4 |
| 162 | 30.3 |
| 163 | 99.5 |
| 164 | 11.9 |
| 165 | 41.1 |

TABLE 2-continued human Ki (hKi) values

| Ex. | hKi GABA A α5 (nM) |
|---|---|
| 166 | 55.6 |
| 167 | 16.2 |
| 168 | 77.7 |

Pharmaceutical Compositions

The present invention also provides pharmaceutical compositions of the invention which contain compounds of formula I as well as their pharmaceutically acceptable salts and esters. The pharmaceutical compositions of the invention can be formulated for any route of administration, such as oral, sub-lingual, buccal, parenteral (subcutaneous, intramuscular, intravenous), rectal, topical, intranasal and trough inhalation or insufflation, and comprise at least one compound of formula I or pharmaceutically acceptable salts or esters thereof, with any pharmaceutically suitable ingredient, excipient, carrier, adjuvant or vehicle. Oral pharmaceutical compositions are e.g. tablets, coated tablets, dragées, hard gelatin capsules, soft gelatin capsules, solutions, emulsions or suspensions. Rectal pharmaceutical compositions are e.g. in the form of suppositories.

The compounds of formula I and their pharmaceutically acceptable salts and esters can be processed with pharmaceutically inert, inorganic or organic excipients for the production of tablets, coated tablets, dragées and hard gelatin capsules. Examples are lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

The pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt or ester thereof. The daily dosage can be administered as single dose or in divided doses and, in addition, the upper limit can also be exceeded when necessary.

Examples of compositions according to the invention are, but are not limited to:

Example A

Tablets of the following composition are manufactured in the usual manner:

TABLE 3 possible tablet composition

| ingredient | mg/tablet |
|---|---|
| Compound of formula I | 5 |
| Lactose | 45 |
| Corn starch | 15 |
| Microcrystalline cellulose | 34 |
| Magnesium stearate | 1 |
| Tablet weight | 100 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Example B

Capsules of the following composition are manufactured:

TABLE 4 possible capsule composition

| ingredient | mg/capsule |
|---|---|
| Compound of formula I | 10 |
| Lactose | 155 |
| Corn starch | 30 |
| Talc | 5 |
| Capsule fill weight | 200 |

Manufacturing Procedure
1. Mix items 1, 2 and 3 in a suitable mixer for 30 minutes.
2. Add item 4 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into hard gelatine capsules.

Example C

Suppositories of the following composition are manufactured:

TABLE 5 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Experimental Part

The following examples 1-119 are provided for illustration of the invention. They should not be considered as limiting the scope of the invention, but merely as being representative thereof.

Example 1

[5-(5-Methyl-3-phenyl-isoxazol-4-ylmethoxy)-2H-pyrazol-3-yl]morpholin-4-yl-methanone

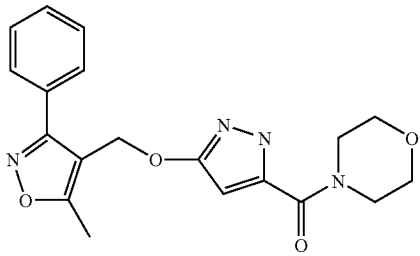

a) 5-(5-Methyl-3-phenyl-isoxazol-4-ylmethoxy)-2H-pyrazole-3-carboxylic acid methyl ester To a stirred solution of 5-hydroxy-2H-pyrazole-3-carboxylic acid methyl ester (1.30 g, 9.15 mmol) and (5-methyl-3-phenyl-isoxazol-4-yl)-methanol (1.73 g, 9.15 mmol) in THF (80 mL) at 5° C. under argon was added triphenylphosphine (3.12 g, 11.9 mmol), then diethyl azodicarboxylate (2.07 g, 11.9 mmol) was added dropwise. The reaction mixture was warmed to room temperature and stirred overnight. The reaction mixture was then evaporated. Purification by chromatography (silica, heptane:ethyl acetate=1:1 then dichloromethane:methanol=9:1) gave a colorless oil (800 mg) which was triturated with diisopropylether and further purified using a 5×50 cm Chiralpak AD column at room temperature using an isopropanol:heptane (2:8) mobile phase with UV detection at 220 nM to afford the title compound (250 mg, 9%) as a white solid. MS: m/e=328.3 [M+H]$^+$.

b) [5-(5-Methyl-3-phenyl-isoxazol-4-ylmethoxy)-2H-pyrazol-3-yl]-morpholin-4-yl-methanone A solution of trimethylaluminium (2 M in toluene, 0.92 mL, 1.3 mmol) was added dropwise (exothermic) to a solution of morpholine (111 μL, 1.3 mmol) in dioxane (3 mL) and the resulting mixture was stirred at room temperature for 1 h. Then a solution of 5-(5-methyl-3-phenyl-isoxazol-4-ylmethoxy)-2H-pyrazole-3-carboxylic acid methyl ester (100 mg, 0.32 mmol) in dioxane (2 mL) was added. The resulting mixture was heated at 90° C. overnight and then cooled to room temperature and then poured into Seignette's salt solution and extracted with ethyl acetate which was then washed with brine, dried over sodium sulfate and evaporated. Purification by chromatography (silica, dichloromethane:methanol=9:1) afforded the title compound (47 mg, 40%), which was obtained as a colorless oil. MS: m/e=369.1 [M+H]$^+$.

Example 2

5-(5-Methyl-3-phenyl-isoxazol-4-ylmethoxy)-2H-pyrazole-3-carboxylic acid isopropylamide

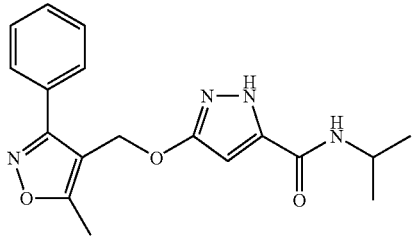

As described for example 1b, 5-(5-methyl-3-phenyl-isoxazol-4-ylmethoxy)-2H-pyrazole-3-carboxylic acid methyl ester (100 mg, 0.32 mmol) was converted, using isopropylamine instead of morpholine, to the title compound (14 mg, 13%), which was obtained as a colorless oil. MS: m/e=341.3 [M+H]$^+$.

Example 3

5-(5-Methyl-3-phenyl-isoxazol-4-ylmethoxy)-2H-pyrazole-3-carboxylic acid (tetrahydro-pyran-4-yl)-amide

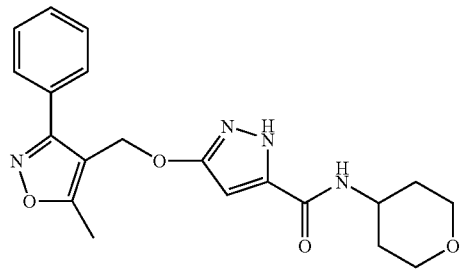

As described for example 1b, 5-(5-methyl-3-phenyl-isoxazol-4-ylmethoxy)-2H-pyrazole-3-carboxylic acid methyl ester (100 mg, 0.32 mmol) was converted, using 4-aminotetrahydropyran instead of morpholine, to the title compound (52 mg, 43%), which was obtained as a colorless oil. MS: m/e=383.2 [M+H]$^+$.

Example 4

Rac-5-(5-Methyl-3-phenyl-isoxazol-4-ylmethoxy)-2H-pyrazole-3-carboxylic acid (tetra-hydro-furan-3-yl)-amide

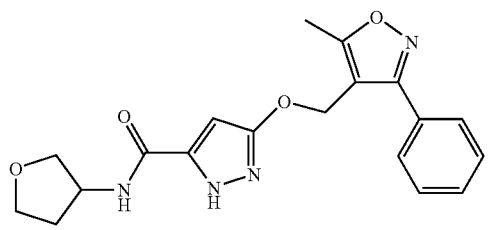

As described for example 1b, 5-(5-methyl-3-phenyl-isoxazol-4-ylmethoxy)-2H-pyrazole-3-carboxylic acid methyl ester (100 mg, 0.32 mmol) was converted, using rac-3-aminotetrahydrofuran instead of morpholine, to the title compound (39 mg, 33%), which was obtained as a white solid. MS: m/e=369.2 [M+H]+.

Example 5

5-(5-Methyl-3-phenyl-isoxazol-4-ylmethoxy)-2H-pyrazole-3-carboxylic acid N',N'-dimethyl-hydrazide

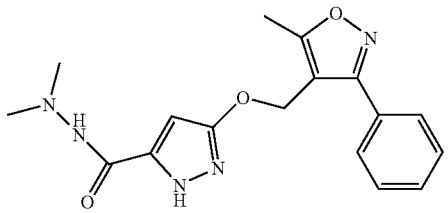

As described for example 1b, 5-(5-methyl-3-phenyl-isoxazol-4-ylmethoxy)-2H-pyrazole-3-carboxylic acid methyl ester (100 mg, 0.32 mmol) was converted, using N,N-dimethylhydrazine instead of morpholine, to the title compound (26 mg, 24%), which was obtained as a white solid. MS: m/e=342.1 [M+H]+.

Example 6

5-(5-Methyl-3-phenyl-isoxazol-4-ylmethoxy)-2H-pyrazole-3-carboxylic acid (2-hydroxy-ethyl)-amide

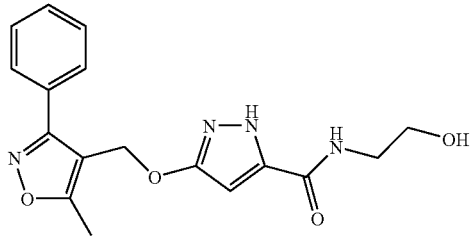

To a solution of 5-(5-methyl-3-phenyl-isoxazol-4-ylmethoxy)-2H-pyrazole-3-carboxylic acid methyl ester (100 mg, 0.32 mmol) and ethanolamine (29 mg, 0.47 mmol) in toluene (1 mL) was added 1,5,7-triazabicyclo[4.4.0]dec-5-ene (16 mg, 0.11 mmol) and the reaction was heated at 90° C. under argon overnight. After cooling to room temperature, the mixture was evaporated and purification by chromatography (silica, dichloromethane:methanol=100:0 to 9:1) afforded the title compound (30 mg, 28%), which was obtained as a white solid. MS: m/e=343.2 [M+H]+.

Example 7

5-(5-Methyl-3-phenyl-isoxazol-4-ylmethoxy)-2H-pyrazole-3-carboxylic acid amide

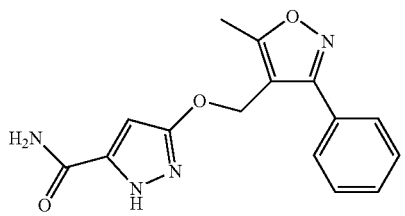

As described for example 6, 5-(5-methyl-3-phenyl-isoxazol-4-ylmethoxy)-2H-pyrazole-3-carboxylic acid methyl ester (100 mg, 0.32 mmol) was converted, using ammonia in methanol instead of ethanolamine, to the title compound (15 mg, 16%), which was obtained as a white solid. MS: m/e=299.4 [M+H]+.

Example 8

5-[3-(4-Fluoro-phenyl)-5-methyl-isoxazol-4-ylmethoxy]-2H-pyrazole-3-carboxylic acid morpholin-4-ylamide

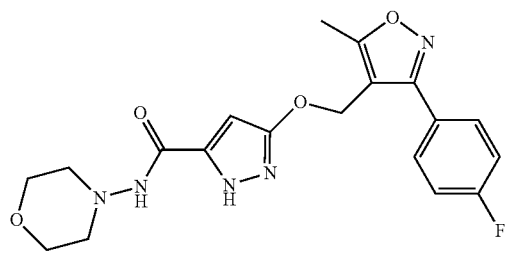

a) 5-[3-(4-Fluoro-phenyl)-5-methyl-isoxazol-4-ylmethoxy]-2H-pyrazole-3-carboxylic acid methyl ester As described for example 1a, [3-(4-fluoro-phenyl)-5-methyl-isoxazol-4-yl]-methanol (3.1 g, 15 mmol), instead of (5-methyl-3-phenyl-isoxazol-4-yl)-methanol, was converted to the title compound (420 mg, 9%), which was obtained as a white solid.
MS: m/e=332.2 [M+H]+.

b) 5-[3-(4-Fluoro-phenyl)-5-methyl-isoxazol-4-ylmethoxy]-2H-pyrazole-3-carboxylic acid morpholin-4-ylamide As described for example 1b, 5-[3-(4-fluoro-phenyl)-5-methyl-isoxazol-4-ylmethoxy]-2H-pyrazole-3-carboxylic acid methyl ester (100 mg, 0.3 mmol), instead of 5-(5-methyl-3-phenyl-isoxazol-4-ylmethoxy)-2H-pyrazole-3-carboxylic acid methyl ester, was converted, using 4-aminomorpholine instead of morpholine, to the title compound (45 mg, 37%), which was obtained as a colorless oil. MS: m/e=402.3 [M+H]+.

Example 9

5-[3-(4-Fluoro-phenyl)-5-methyl-isoxazol-4-ylmethoxy]-2H-pyrazole-3-carboxylic acid piperidin-1-ylamide

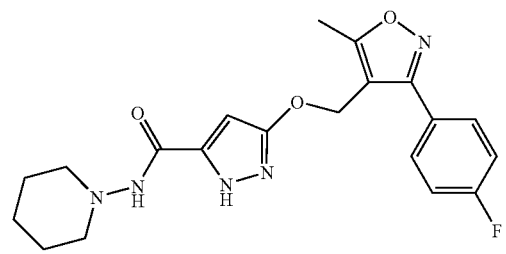

As described for example 8b, 5-[3-(4-fluoro-phenyl)-5-methyl-isoxazol-4-ylmethoxy]-2H-pyrazole-3-carboxylic acid methyl ester (100 mg, 0.3 mmol) was converted, using 1-aminopiperidine instead of 4-aminomorpholine, to the title compound (78 mg, 65%), which was obtained as a white solid. MS: m/e=400.2 [M+H]+.

Example 10

5-[3-(4-Fluoro-phenyl)-5-methyl-isoxazol-4-yl-methoxy]-2H-pyrazole-3-carboxylic acid pyrrolidin-1-ylamide

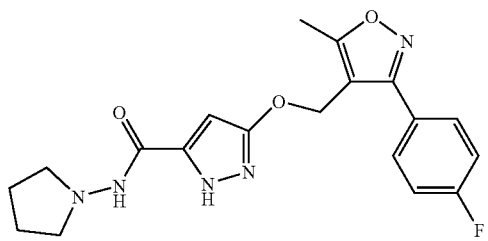

a) 5-[3-(4-Fluoro-phenyl)-5-methyl-isoxazol-4-ylmethoxy]-2H-pyrazole-3-carboxylic acid To a solution of 5-[3-(4-fluoro-phenyl)-5-methyl-isoxazol-4-ylmethoxy]-2H-pyrazole-3-carboxylic acid methyl ester (200 mg, 0.6 mmol) in dioxane (5 mL) was added aqueous sodium hydroxide (2 M, 3.0 mL, 6.0 mmol). After heating at 90° C. for 2 h the solution was cooled to room temperature and neutralized with aqueous hydrogen chloride (2 N). The precipitate was then filtered off and dried to afford the title compound (191 mg, 100%) as a white solid. MS: m/e=315.9 [M−H]⁻.

b) 5-[3-(4-Fluoro-phenyl)-5-methyl-isoxazol-4-ylmethoxy]-2H-pyrazole-3-carboxylic acid pyrrolidin-1-ylamide To a solution of 5-[3-(4-fluoro-phenyl)-5-methyl-isoxazol-4-ylmethoxy]-2H-pyrazole-3-carboxylic acid (100 mg, 0.32 mmol) in DMF (5 mL) were added 2-(1H-benzotriazole-1-yl)-1,1,3,3-tetramethyluronium tetrafluoroborate (152 mg, 0.47 mmol), N,N-diisopropyl ethyl amine (270 μL, 1.6 mmol) and N-aminopyrrolidine HCl (58 mg, 0.47 mmol). The resulting reaction mixture was stirred overnight at room temperature. The reaction mixture was then poured into aqueous sodium chloride (saturated) and extracted with ethyl acetate. The combined organic layers were then washed with water, citric acid solution and saturated sodium hydrogen carbonate solution and then dried over sodium sulfate, filtered and evaporated. Concentration and purification by chromatography (silica, dichloromethane:methanol=100:0 to 9:1) afforded the title compound (91 mg, 75%) as a white solid. MS: m/e=386.2 [M+H]⁺.

Example 11

5-[3-(4-Fluoro-phenyl)-5-methyl-isoxazol-4-ylmethoxy]-2H-pyrazole-3-carboxylic acid N',N'-dimethyl-hydrazide

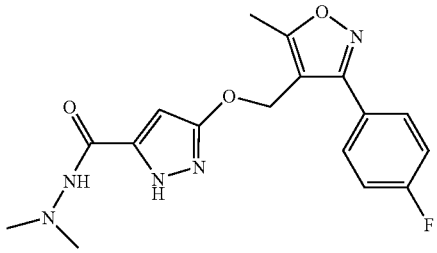

As described for example 8b, 5-[3-(4-fluoro-phenyl)-5-methyl-isoxazol-4-ylmethoxy]-2H-pyrazole-3-carboxylic acid methyl ester (100 mg, 0.3 mmol) was converted, using N,N-dimethylhydrazine instead of 4-aminomorpholine, to the title compound (25 mg, 23%), which was obtained as a white solid after recrystallization from ethyl acetate. MS: m/e=360.2 [M+H]⁺.

Example 12

5-[3-(4-Fluoro-phenyl)-5-methyl-isoxazol-4-ylmethoxy]-2H-pyrazole-3-carboxylic acid isopropylamide

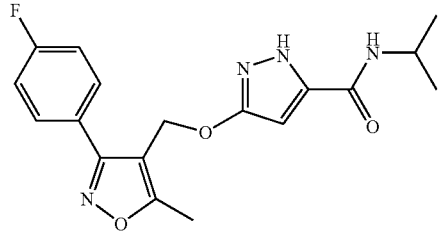

As described for example 8b, 5-[3-(4-fluoro-phenyl)-5-methyl-isoxazol-4-ylmethoxy]-2H-pyrazole-3-carboxylic acid methyl ester (100 mg, 0.3 mmol) was converted, using isopropylamine instead of 4-aminomorpholine, to the title compound (50 mg, 46%), which was obtained as a white solid. MS: m/e=359.2 [M+H]⁺.

Example 13

5-[3-(4-Fluoro-phenyl)-5-methyl-isoxazol-4-ylmethoxy]-2H-pyrazole-3-carboxylic acid (tetrahydro-pyran-4-yl)-amide

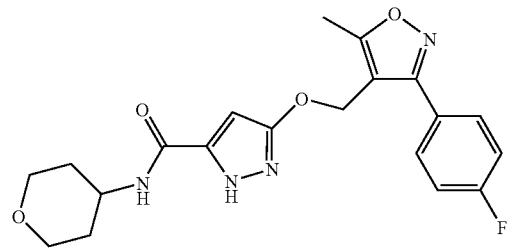

As described for example 8b, 5-[3-(4-fluoro-phenyl)-5-methyl-isoxazol-4-ylmethoxy]-2H-pyrazole-3-carboxylic acid methyl ester (100 mg, 0.3 mmol) was converted, using 4-aminotetrahydropyran instead of 4-aminomorpholine, to the title compound (100 mg, 82%), which was obtained as a white foam. MS: m/e=401.2 [M+H]⁺.

Example 14

5-(5-Methyl-3-pyridin-2-yl-isoxazol-4-ylmethoxy)-1H-pyrazole-3-carboxylic acid isopropylamide

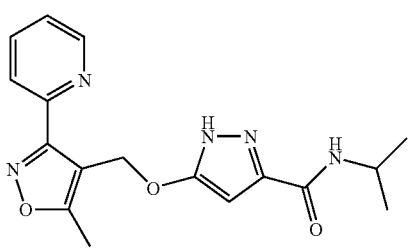

a) (E)- and/or (Z)-Pyridine-2-carbaldehyde oxime

To a suspension of 2-pyridinecarboxaldehyde (47.8 mL, 500 mmol) and hydroxylamine (38.2 g, 550 mmol) in ethanol (37 mL) and water (111 mL) was added ice (213 g). Then a solution of sodium hydroxide (50 g, 1.25 mol) in water (51 mL) was added within a 30 min period (temperature rose from −8° C. to +10° C.) whereupon most of the solid dissolves. After 1 h stirring at room temperature the resulting mixture was then acidified with HCl (5 N). The precipitate was then filtered off and dried to afford the title compound (47.7 g, 78%), which was obtained as an off white solid. MS m/e=123.3 $[M+H]^+$.

b) 5-Methyl-3-pyridin-2-yl-isoxazole-4-carboxylic acid ethyl ester

To a suspension of N-chlorosuccinimide (6.0 g, 33 mmol) in chloroform (20 mL) was added pyridine (0.26 mL, 3.3 mmol) and a solution of (E)- and/or (Z)-pyridine-2-carbaldehyde oxime (4.0 g, 33 mmol) in chloroform (103 mL) during 15 min at ambient temperature. After stirring for 30 min at this temperature a solution of ethyl (E)-3-(1-pyrrolidino)-2-butenoate (6.0 g, 33 mmol) in chloroform (4 mL) was added. The resulting suspension was warmed to 50° C. and a solution of triethylamine (12 mL, 86 mmol) in chloroform (10 mL) was added dropwise over a period of 1 h. Stirring was continued for 0.5 h at 50° C. and for 30 h at room temperature. The dark brown solution was washed with water (100 mL) and the aqueous layers were extracted with dichloromethane (50 mL) and dried over sodium sulfate and evaporated. Purification by chromatography ($SiO_2$, heptane:ethyl acetate 8:2 to 1:1) afforded the title compound (4.43 g, 58%) as a yellow oil. MS: m/e=233.3 $[M+H]^+$.

c) (5-Methyl-3-pyridin-2-yl-isoxazol-4-yl)-methanol

To a solution of 5-methyl-3-pyridin-2-yl-isoxazole-4-carboxylic acid ethyl ester (4.1 g, 18 mmol) in THF (229 mL) at 0° C. was added lithium aluminum hydride (367 mg, 10 mmol). And the resulting mixture stirred for 1 h at room temperature. Water (1.9 mL) was added carefully followed by aqueous sodium hydroxide (15%, 1.9 mL) and water (0.54 mL). The resulting suspension was stirred for 15 min at ambient temperature and filtered over Hyflo®. Concentration and trituration with heptane afforded the title compound (2.88 g, 86%) as a light yellow solid. MS: m/e=191.3 $[M+H]^+$.

d) 5-(5-Methyl-3-pyridin-2-yl-isoxazol-4-ylmethoxy)-2H-pyrazole-3-carboxylic acid methyl ester As described for example 1a, (5-methyl-3-pyridin-2-yl-isoxazol-4-yl)-methanol (500 mg, 2.6 mmol), instead of (5-methyl-3-phenyl-isoxazol-4-yl)-methanol, was converted to the title compound (281 mg, 36%), which was obtained as a white solid. MS: m/e=315.1 $[M+H]^+$.

e) 5-(5-Methyl-3-pyridin-2-yl-isoxazol-4-ylmethoxy)-1H-pyrazole-3-carboxylic acid isopropylamide As described for example 1b, 5-(5-methyl-3-pyridin-2-yl-isoxazol-4-ylmethoxy)-2H-pyrazole-3-carboxylic acid methyl ester (70 mg, 0.22 mmol), instead of 5-(5-methyl-3-phenyl-isoxazol-4-ylmethoxy)-2H-pyrazole-3-carboxylic acid methyl ester, was converted, using isopropylamine instead of morpholine, to the title compound (72 mg, 95%) which was obtained as a light yellow oil. MS: m/e=342.2 $[M+H]^+$.

Example 15

5-(5-Methyl-3-pyridin-2-yl-isoxazol-4-ylmethoxy)-1H-pyrazole-3-carboxylic acid (tetrahydropyran-4-yl)-amide

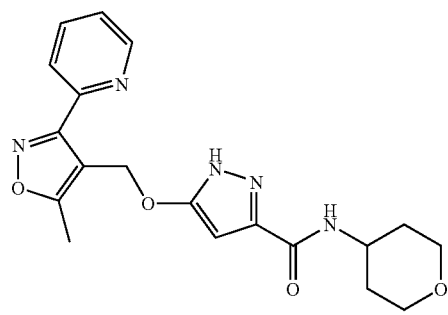

As described for example 14e, 5-(5-methyl-3-pyridin-2-yl-isoxazol-4-ylmethoxy)-2H-pyrazole-3-carboxylic acid methyl ester (70 mg, 0.22 mmol) was converted, using 4-aminotetrahydropyran instead of isopropylamine to the title compound (85 mg, 99%), which was obtained as a colorless oil. MS: m/e=384.2 $[M+H]^+$.

Example 16

5-(5-Methyl-3-pyridin-2-yl-isoxazol-4-ylmethoxy)-1H-pyrazole-3-carboxylic acid ((S)-2-hydroxy-1-methyl-ethyl)-amide

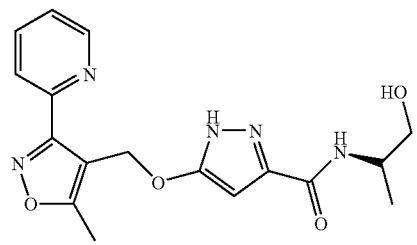

As described for example 6, 5-(5-methyl-3-pyridin-2-yl-isoxazol-4-ylmethoxy)-2H-pyrazole-3-carboxylic acid methyl ester (70 mg, 0.22 mmol), instead of 5-(5-methyl-3-phenyl-isoxazol-4-ylmethoxy)-2H-pyrazole-3-carboxylic acid methyl ester, was converted, using L-alaninol instead of ethanolamine, to the title compound (40 mg, 50%) which was obtained as a colorless oil. MS: m/e=358.2 $[M+H]^+$.

Example 17

5-[3-(5-Fluoro-pyridin-2-yl)-5-methyl-isoxazol-4-ylmethoxy]-2H-pyrazole-3-carboxylic acid (2,2,2-trifluoro-ethyl)-amide

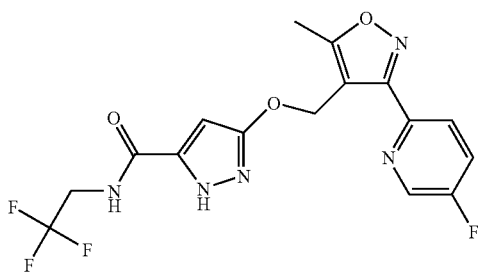

a) (E and/or Z)-5-Fluoro-pyridine-2-carbaldehyde oxime

To a solution of 5-fluoro-2-formylpyridine (5.0 g, 41 mmol) and hydroxylamine hydrochloride (3.06 g, 44 mmol) in ethanol (3.2 mL) and water (9.6 mL) was added ice (18.6 g). Then a solution of NaOH (4.0 g, 100 mmol) in water (4.6 mL) was added dropwise over 10 min keeping the temperature between −5° C. and 5° C. The reaction mixture was then stirred at room temperature for 30 min. Then HCl (4 N) was added to acidify the mixture and the resulting precipitate was filtered off and washed with water to afford the title compound (4.41 g, 79%) as a light brown solid. MS: m/e=141.0 [M+H]$^+$.

b) 3-(5-Fluoro-pyridin-2-yl)-5-methyl-isoxazole-4-carboxylic acid ethyl ester To a suspension of N-chlorosuccinimide (4.63 g, 35 mmol) in chloroform (21 mL) was added pyridine (0.28 mL, 3.5 mmol) and a solution of (E and/or Z)-5-fluoro-pyridine-2-carbaldehyde oxime (4.86 g, 35 mmol) in chloroform (110 mL) during 15 min at room temperature. After stirring for 30 min at this temperature a solution of ethyl (E)-3-(1-pyrrolidino)-2-butenoate (6.36 g, 35 mmol) in chloroform (4.4 mL) was added. The resulting suspension was warmed to 50° C. and a solution of triethylamine (4.83 mL, 35 mmol) in chloroform (4.4 mL) was added dropwise over a period of 30 min. Stirring was continued for 1.5 h at 50° C. and then cooled to ambient temperature. The solution was then diluted with ice-water (200 mL) and the aqueous layers were extracted with dichloromethane (50 mL) and dried over sodium sulfate and evaporation to give a dark brown oil. Purification by chromatography (SiO$_2$, heptane:ethyl acetate=100:0 to 20:80) afforded the title compound (5.83 g, 67%) as yellow oil. MS: m/e=251.1 [M+H]$^+$.

c) [3-(5-Fluoro-pyridin-2-yl)-5-methyl-isoxazol-4-yl]-methanol

To a solution of 3-(5-fluoro-pyridin-2-yl)-5-methyl-isoxazole-4-carboxylic acid ethyl ester (2.5 g, 10 mmol) in dry THF (34 mL), cooled to 0° C., was added lithium aluminum hydride (209 mg, 2.3 mmol) portionwise. After allowing to warm up to room temperature over 1 h, the mixture was cooled to 0° C. and water (0.2 mL) was added carefully followed by aqueous sodium hydroxide (15%, 0.2 mL) and water (0.6 mL). The resulting suspension was stirred for 4 h at ambient temperature and filtered over Hyflo®. The filtrate was then concentrated and purification by chromatography (SiO$_2$, heptane:ethyl acetate=50:50 to 0:100) afforded the title compound (1.47 g, 71%) as a light yellow solid. MS: m/e=209.1 [M+H]$^+$.

d) 5-[3-(5-Fluoro-pyridin-2-yl)-5-methyl-isoxazol-4-ylmethoxy]-2H-pyrazole-3-carboxylic acid methyl ester As described for example 1a, [3-(5-fluoro-pyridin-2-yl)-5-methyl-isoxazol-4-yl]-methanol (350 mg, 2.46 mmol), instead of (5-methyl-3-phenyl-isoxazol-4-yl)-methanol, was converted to the title compound (370 mg, 45%) which was obtained as a white solid. MS: m/e=333.0 [M+H]$^+$.

e) 5-[3-(5-Fluoro-pyridin-2-yl)-5-methyl-isoxazol-4-ylmethoxy]-2H-pyrazole-3-carboxylic acid (2,2,2-trifluoro-ethyl)-amide As described for example 1b, 5-[3-(5-fluoro-pyridin-2-yl)-5-methyl-isoxazol-4-ylmethoxy]-2H-pyrazole-3-carboxylic acid methyl ester (100 mg, 0.3 mmol), instead of 5-(5-methyl-3-phenyl-isoxazol-4-ylmethoxy)-2H-pyrazole-3-carboxylic acid methyl ester, was converted, using 2,2,2-trifluoroethylamine instead of morpholine, to the title compound (25 mg, 21%), which was obtained as a white solid. MS: m/e=400.0 [M+H]$^+$.

Example 18

Rac-5-[3-(5-Fluoro-pyridin-2-yl)-5-methyl-isoxazol-4-ylmethoxy]-2H-pyrazole-3-carboxylic acid (tetrahydro-furan-3-yl)-amide

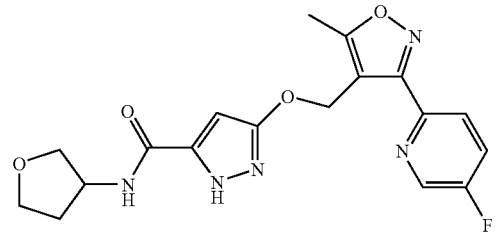

As described for example 17e, 5-[3-(5-fluoro-pyridin-2-yl)-5-methyl-isoxazol-4-ylmethoxy]-2H-pyrazole-3-carboxylic acid methyl ester (100 mg, 0.3 mmol) was converted, using rac-3-aminotetrahydrofuran instead of 2,2,2-trifluoroethylamine, to the title compound (46 mg, 40%) which was obtained as a white solid. MS: m/e=388.2 [M+H]$^+$.

Example 19

5-[3-(5-Fluoro-pyridin-2-yl)-5-methyl-isoxazol-4-ylmethoxy]-2H-pyrazole-3-carboxylic acid tert-butylamide

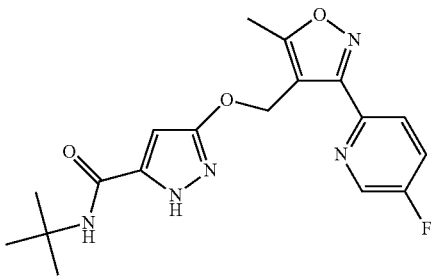

As described for example 17e, 5-[3-(5-fluoro-pyridin-2-yl)-5-methyl-isoxazol-4-ylmethoxy]-2H-pyrazole-3-carboxylic acid methyl ester (100 mg, 0.3 mmol) was converted, using tert-butylamine instead of 2,2,2-trifluoroethylamine, to the title compound (25 mg, 22%) which was obtained as a white solid. MS: m/e=374.1 [M+H]$^+$.

Example 20

5-[3-(5-Fluoro-pyridin-2-yl)-5-methyl-isoxazol-4-ylmethoxy]-2H-pyrazole-3-carboxylic acid (2-hydroxy-ethyl)-amide

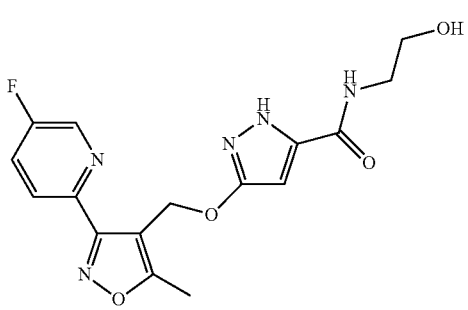

As described for example 6, 5-[3-(5-fluoro-pyridin-2-yl)-5-methyl-isoxazol-4-ylmethoxy]-2H-pyrazole-3-carboxylic acid methyl ester (70 mg, 0.21 mmol), instead of 5-(5-methyl-3-phenyl-isoxazol-4-ylmethoxy)-2H-pyrazole-3-carboxylic acid methyl ester, was converted to the title compound (37 mg, 49%) which was obtained as a white solid. MS: m/e=362.1 [M+H]$^+$.

Example 21

5-[3-(5-Fluoro-pyridin-2-yl)-5-methyl-isoxazol-4-ylmethoxy]-2H-pyrazole-3-carboxylic acid isopropylamide

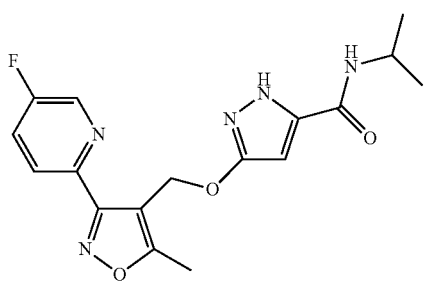

As described for example 17e, 5-[3-(5-fluoro-pyridin-2-yl)-5-methyl-isoxazol-4-ylmethoxy]-2H-pyrazole-3-carboxylic acid methyl ester (100 mg, 0.3 mmol) was converted, using isopropylamine instead of 2,2,2-trifluoroethylamine, to the title compound (31 mg, 29%) which was obtained as a white solid. MS: m/e=360.2 [M+H]$^+$.

Example 22

5-[3-(5-Fluoro-pyridin-2-yl)-5-methyl-isoxazol-4-ylmethoxy]-2H-pyrazole-3-carboxylic acid N',N'-dimethyl-hydrazide

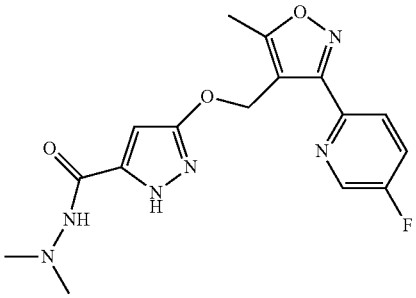

As described for example 17e, 5-[3-(5-fluoro-pyridin-2-yl)-5-methyl-isoxazol-4-ylmethoxy]-2H-pyrazole-3-carboxylic acid methyl ester (100 mg, 0.3 mmol) was converted, using N,N-dimethylhydrazine instead of 2,2,2-trifluoroethylamine, to the title compound (65 mg, 60%) which was obtained as a white solid. MS: m/e=361.2 [M+H]$^+$.

Example 23

5-[3-(5-Fluoro-pyridin-2-yl)-5-methyl-isoxazol-4-ylmethoxy]-2H-pyrazole-3-carboxylic acid morpholin-4-ylamide

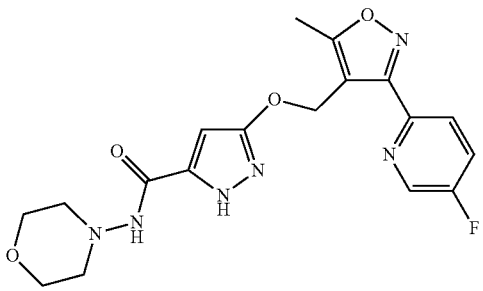

As described for example 17e, 5-[3-(5-fluoro-pyridin-2-yl)-5-methyl-isoxazol-4-ylmethoxy]-2H-pyrazole-3-carboxylic acid methyl ester (50 mg, 0.15 mmol) was converted, using 4-aminomorpholine instead of 2,2,2-trifluoroethylamine, to the title compound (57 mg, 94%) which was obtained as a colorless oil. MS: m/e=403.3 [M+H]$^+$.

Example 24

5-[3-(5-Fluoro-pyridin-2-yl)-5-methyl-isoxazol-4-ylmethoxy]-2H-pyrazole-3-carboxylic acid pyrrolidin-1-ylamide

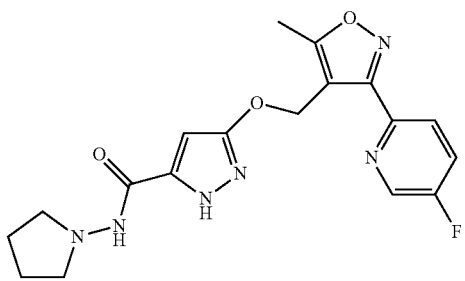

a) 5-[3-(5-Fluoro-pyridin-2-yl)-5-methyl-isoxazol-4-ylmethoxy]-2H-pyrazole-3-carboxylic acid As described for example 10a, 5-[3-(5-fluoro-pyridin-2-yl)-5-methyl-isoxazol-4-ylmethoxy]-2H-pyrazole-3-carboxylic acid methyl ester (50 mg, 0.15 mmol), instead of 5-[3-(4-fluoro-phenyl)-5-methyl-isoxazol-4-ylmethoxy]-2H-pyrazole-3-carboxylic acid methyl ester, was converted, to the title compound (38 mg, 79%) which was obtained as a white solid. MS: m/e=317.0 [M−H]⁻.

b) 5-[3-(5-Fluoro-pyridin-2-yl)-5-methyl-isoxazol-4-ylmethoxy]-2H-pyrazole-3-carboxylic acid pyrrolidin-1-ylamide As described for example 10b, 5-[3-(5-fluoro-pyridin-2-yl)-5-methyl-isoxazol-4-ylmethoxy]-2H-pyrazole-3-carboxylic acid (38 mg, 0.12 mmol), instead of 5-[3-(4-fluoro-phenyl)-5-methyl-isoxazol-4-ylmethoxy]-2H-pyrazole-3-carboxylic acid, was converted, to the title compound (18 mg, 39%) which was obtained as a white solid. MS: m/e=387.2 [M+H]⁺.

Example 25

5-[3-(5-Fluoro-pyridin-2-yl)-isoxazol-4-ylmethoxy]-2H-pyrazole-3-carboxylic acid morpholin-4-ylamide

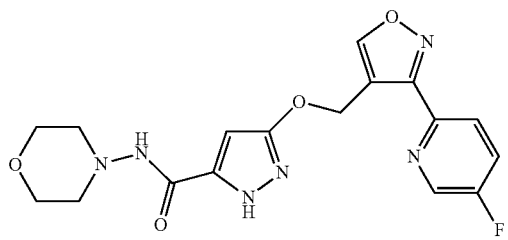

a) 5-Fluoro-pyridine-2-carbaldehyde oxime

To a solution of 5-fluoro-2-formylpyridine (5.0 g, 41 mmol) and hydroxylamine hydrochloride (3.06 g, 44 mmol) in ethanol (3.2 mL) and water (9.6 mL) was added ice (18.6 g). Then a solution of NaOH (4.0 g, 100 mmol) in water (4.6 mL) was added dropwise over 10 min keeping the temperature between −5° C. and 5° C. The reaction mixture was then stirred at room temperature for 30 min. Then HCl (4 N) was added to acidify the mixture and the resulting precipitate was filtered off and washed with water to afford the title compound (4.41 g, 79%) as a light brown solid. MS: m/e=141.0 [M+H]⁺.

b) 3-(5-Fluoro-pyridin-2-yl)-isoxazole-4-carboxylic acid ethyl ester

To a solution of N-chlorosuccinimide (17.34 g, 130 mmol) in DMF (128 mL) was added 5-fluoro-pyridine-2-carbaldehyde oxime (18.2 g, 130 mmol) portionwise over 2 h at room temperature and as the reaction warmed up to 60° C. the mixture was cooled back to room temperature with an ice-water bath and the resulting mixture was then stirred for 64 h at room temperature. To this solution was then added ethyl 3-(N,N-dimethylamino)acrylate (18.6 g, 130 mmol) and triethylamine (36.2 mL, 260 mmol) in chloroform (64 mL) and the resulting mixture was then stirred for 1 h at room temperature and poured onto a mixture of ice water and HCl (4 N, 1 L) and extracted with ethylacetate. The organic extract was then washed with water, saturated aqueous sodium hydrogen carbonate solution, brine, dried with sodium sulfate, filtered and evaporated. Purification by chromatography (silica, heptane:ethylacetate=100:0 to 1:1) afforded the title product (21.96 g, 72%), which was obtained as a yellow solid. MS: m/e=237.1 [M+H]⁺.

c) [3-(5-Fluoro-pyridin-2-yl)-isoxazol-4-yl]-methanol

To a solution of 3-(5-fluoro-pyridin-2-yl)-isoxazole-4-carboxylic acid ethyl ester (1.0 g, 4.23 mmol) in THF (52 mL) was added portionwise lithium aluminum hydride (89 mg, 2.33 mmol) at 0° C. and the reaction mixture was stirred at room temperature for 1 h. The mixture was then cooled to 0° C. and water (88 μL) added followed by sodium hydroxide (15% solution, 88 μL) and then again water (264 μL) and the mixture then stirred overnight at room temperature. The precipitate was then filtered off and washed with THF. The combined washings and filtrate were then evaporated. Purification by chromatography (silica, heptane:ethyl acetate=100:0 to 1:1) afforded the title compound (249 mg, 30%) which was obtained as a light yellow solid. MS: m/e=195.1 [M+H]⁺.

d) 5-[3-(5-Fluoro-pyridin-2-yl)-isoxazol-4-ylmethoxy]-2H-pyrazole-3-carboxylic acid methyl ester As described for example 1a, [3-(5-fluoro-pyridin-2-yl)-isoxazol-4-yl]-methanol (1.0 g, 5.2 mmol), instead of (5-methyl-3-phenyl-isoxazol-4-yl)-methanol, was converted to the title compound (444 mg, 27%) which was obtained as a white solid. MS: m/e=319.1 [M+H]⁺.

e) 5-[3-(5-Fluoro-pyridin-2-yl)-isoxazol-4-ylmethoxy]-2H-pyrazole-3-carboxylic acid morpholin-4-ylamide As described for example 1b, 5-[3-(5-fluoro-pyridin-2-yl)-isoxazol-4-ylmethoxy]-2H-pyrazole-3-carboxylic acid methyl ester (70 mg, 0.22 mmol), instead of 5-(5-methyl-3-phenyl-isoxazol-4-ylmethoxy)-2H-pyrazole-3-carboxylic acid methyl ester, was converted, using 4-aminomorpholine instead of morpholine, to the title compound (32 mg, 38%) which was obtained as a white solid. MS: m/e=389.1 [M+H]⁺.

Example 26

5-(3-Butyl-5-methyl-isoxazol-4-ylmethoxy)-2H-pyrazole-3-carboxylic acid (tetrahydropyran-4-yl)-amide

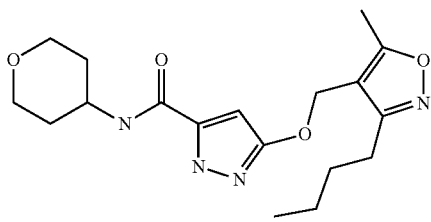

a) 3-Butyl-5-methyl-isoxazole-4-carboxylic acid ethyl ester

To a suspension of N-chlorosuccinimide (16.1 g, 121 mmol) in chloroform (250 mL) at room temperature was added pyridine (0.95 g, 12.0 mmol) then a solution of pentanal oxime (12.2 g, 121 mmol) in chloroform (250 mL) was added dropwise over 20 min. The reaction mixture was stirred at 50° C. for 2 h then cooled to room temperature and a solution of ethyl(E)-3-(1-pyrrolidino)-2-butenoate (22.1 g, 121 mmol) in chloroform (120 mL) added dropwise. The reaction mixture was warmed to 50° C. and a solution of triethylamine (12.2 g, 121 mmol) in chloroform (120 mL) added dropwise. After 15 h the reaction mixture was cooled and extracted with water then citric acid (10% w/w aqueous solution). The combined aqueous phases were extracted with dichloromethane, and then the combined organic phases were dried, filtered and concentrated. Purification by chromatography (silica, heptane:ethyl acetate=100:0 to 9:1) afforded the title compound (10.9 g, 43%) as a pale yellow liquid. MS: m/e=232.2 [M+H]⁺.

b) (3-Butyl-5-methyl-isoxazol-4-yl)-methanol

To a stirred solution of 3-butyl-5-methyl-isoxazole-4-carboxylic acid ethyl ester (9.8 g, 46.3 mmol) in THF (100 mL) under argon and at 0° C. was added lithium aluminum hydride (2.03 g, 53.4 mmol) in five portions. After 1 h the reaction mixture was quenched dropwise with Seignette's salt solution. The reaction mixture was filtered and the filtrate extracted with ethyl acetate. The combined organic extracts were washed with Seignette's salt solution then dried, filtered and concentrated. Purification by chromatography (silica, heptane:ethyl acetate=100:0 to 4:6) afforded the title compound (7.5 g, 95%) as a yellow liquid. MS: m/e=170.3 [M+H]⁺.

c) 5-(3-Butyl-5-methyl-isoxazol-4-ylmethoxy)-2H-pyrazole-3-carboxylic acid methyl ester As described for example 1a, (3-butyl-5-methyl-isoxazol-4-yl)-methanol (2.4 g, 14.2 mmol), instead of (5-methyl-3-phenyl-isoxazol-4-yl)-methanol, was converted to the title compound (1.6 g, 43%) which was obtained as a white solid. MS: m/e=294.2 [M+H]⁺.

d) 5-(3-Butyl-5-methyl-isoxazol-4-ylmethoxy)-2H-pyrazole-3-carboxylic acid (tetrahydro-pyran-4-yl)-amide As described for example 1b, 5-(3-butyl-5-methyl-isoxazol-4-ylmethoxy)-2H-pyrazole-3-carboxylic acid methyl ester (100 mg, 0.34 mmol), instead of 5-(5-methyl-3-phenyl-isoxazol-4-ylmethoxy)-2H-pyrazole-3-carboxylic acid methyl ester, was converted, using 4-aminotetrahydropyran instead of morpholine, to the title compound (23 mg, 19%) which was obtained as a white solid. MS: m/e=363.0 [M+H]⁺.

Example 27

5-(3-Butyl-5-methyl-isoxazol-4-ylmethoxy)-2H-pyrazole-3-carboxylic acid ((S)-2-hydroxy-1-methyl-ethyl)-amide

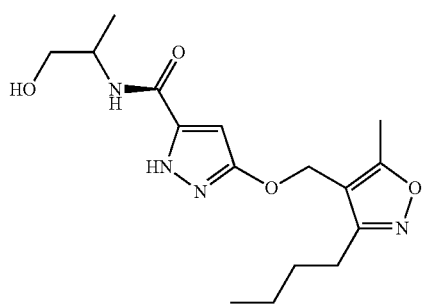

As described for example 6, 5-(3-butyl-5-methyl-isoxazol-4-ylmethoxy)-2H-pyrazole-3-carboxylic acid methyl ester (100 mg, 0.34 mmol), instead of 5-(5-methyl-3-phenyl-isoxazol-4-ylmethoxy)-2H-pyrazole-3-carboxylic acid methyl ester, was converted, using L-alaninol instead of ethanolamine, to the title compound (7 mg, 6%) which was obtained as a colorless oil. MS: m/e=337.4 [M+H]⁺.

Example 28

Rac-5-(3-Butyl-5-methyl-isoxazol-4-ylmethoxy)-2H-pyrazole-3-carboxylic acid (tetrahydrofuran-3-yl)-amide

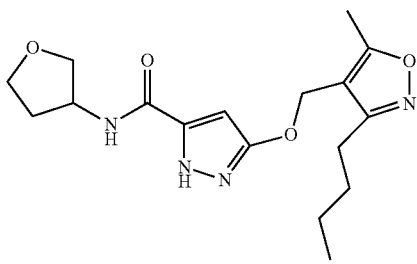

As described for example 26d, 5-(3-butyl-5-methyl-isoxazol-4-ylmethoxy)-2H-pyrazole-3-carboxylic acid methyl ester (492 mg, 1.7 mmol) was converted, using rac-3-aminotetrahydrofuran instead of 4-aminotetrahydropyran, to the title compound (280 mg, 48%) which was obtained as a colorless oil. MS: m/e=349.2 [M+H]⁺.

Example 29

5-(3-Butyl-5-methyl-isoxazol-4-ylmethoxy)-2H-pyrazole-3-carboxylic acid (2-hydroxy-1-hydroxymethyl-ethyl)-amide

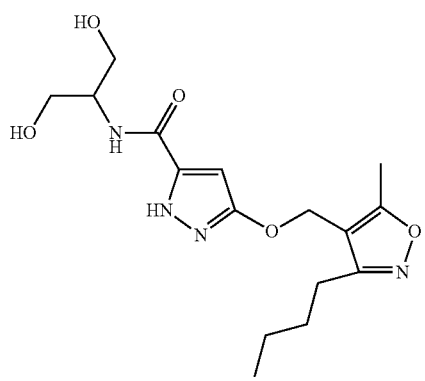

As described for example 27, 5-(3-butyl-5-methyl-isoxazol-4-ylmethoxy)-2H-pyrazole-3-carboxylic acid methyl ester (100 mg, 0.34 mmol) was converted, using 2-amino-1,3-propandiol instead of L-alaninol, to the title compound (12 mg, 10%) which was obtained as a white solid. MS: m/e=353.3 [M+H]⁺.

Example 30

5-(3-Butyl-5-methyl-isoxazol-4-ylmethoxy)-2H-pyrazole-3-carboxylic acid ((R)-2-hydroxy-1-methyl-ethyl)-amide

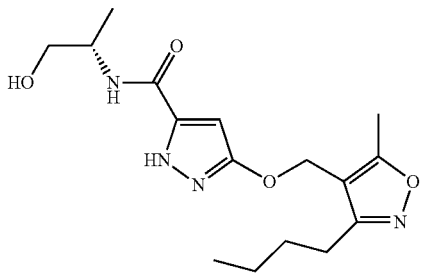

As described for example 27, 5-(3-butyl-5-methyl-isoxazol-4-ylmethoxy)-2H-pyrazole-3-carboxylic acid methyl ester (100 mg, 0.34 mmol) was converted, using D-alaninol instead of L-alaninol, to the title compound (103 mg, 90%) which was obtained as a colorless oil.
MS: m/e=337.3 [M+H]$^+$.

Example 31

5-(3-Butyl-5-methyl-isoxazol-4-ylmethoxy)-2H-pyrazole-3-carboxylic acid (2,2,2-trifluoro-ethyl)-amide

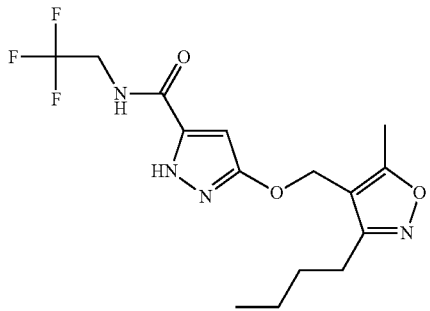

As described for example 26d, 5-(3-butyl-5-methyl-isoxazol-4-ylmethoxy)-2H-pyrazole-3-carboxylic acid methyl ester (100 mg, 0.34 mmol) was converted, using 2,2,2-trifluoroethylamine instead of 4-aminotetrahydropyran, to the title compound (120 mg, 98%) which was obtained as a colorless oil. MS: m/e=361.2 [M+H]$^+$.

Example 32

5-(3-Butyl-5-methyl-isoxazol-4-ylmethoxy)-2H-pyrazole-3-carboxylic acid isopropylamide

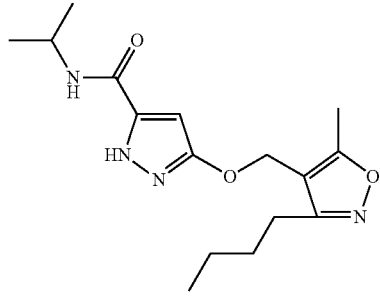

As described for example 26d, 5-(3-butyl-5-methyl-isoxazol-4-ylmethoxy)-2H-pyrazole-3-carboxylic acid methyl ester (100 mg, 0.34 mmol) was converted, using isopropylamine instead of 4-aminotetrahydropyran, to the title compound (97 mg, 89%) which was obtained as a colorless oil. MS: m/e=321.3 [M+H]$^+$.

Example 33

5-(3-Butyl-5-methyl-isoxazol-4-ylmethoxy)-2H-pyrazole-3-carboxylic acid (2-hydroxyethyl)-amide

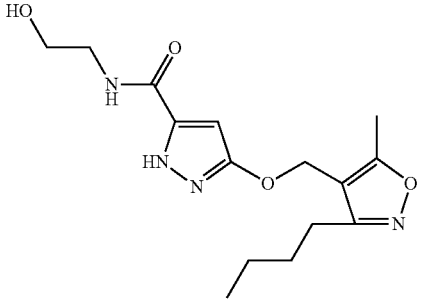

As described for example 27, 5-(3-butyl-5-methyl-isoxazol-4-ylmethoxy)-2H-pyrazole-3-carboxylic acid methyl ester (110 mg, 0.38 mmol) was converted, using ethanolamine instead of L-alaninol, to the title compound (110 mg, 91%) which was obtained as a colorless oil. MS: m/e=323.2 [M+H]$^+$.

Example 34

(−)-(S or R)-3-((3-Butyl-5-methylisoxazol-4-yl)methoxy)-N-(tetrahydrofuran-3-yl)-1H-pyrazole-5-carboxamide

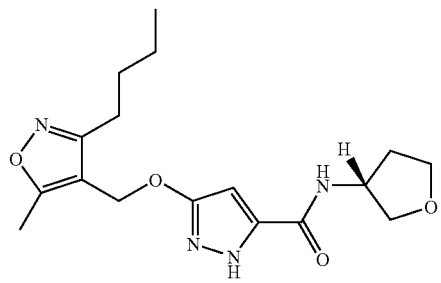

The stereoisomers of rac-5-(3-butyl-5-methyl-isoxazol-4-ylmethoxy)-2H-pyrazole-3-carboxylic acid (tetrahydro-furan-3-yl)-amide (example 28, 150 mg) in ethanol:heptane (1:1, 4 mL) were separated using a 5×50 cm Chiralpak AD column at room temperature using an isopropanol:heptane (2:8) mobile phase with UV detection at 220 nM. The least polar component (−ve sign of rotation) was obtained as a colorless oil (60 mg).

Example 35

(+)-(R or S)-3-((3-Butyl-5-methylisoxazol-4-yl)methoxy)-N-(tetrahydrofuran-3-yl)-1H-pyrazole-5-carboxamide

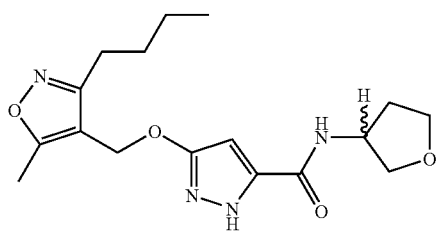

The stereoisomers of rac-5-(3-butyl-5-methyl-isoxazol-4-ylmethoxy)-2H-pyrazole-3-carboxylic acid (tetrahydro-furan-3-yl)-amide (example 28, 150 mg) in ethanol:heptane (1:1, 4 mL) were separated using a 5×50 cm Chiralpak AD column at room temperature using an isopropanol:heptane (2:8) mobile phase with UV detection at 220 nM. The least polar component (+ve sign of rotation) was obtained as a colorless oil (53 mg).

Example 36

[5-(3-Butyl-5-methyl-isoxazol-4-ylmethoxy)-2H-pyrazol-3-yl]morpholin-4-yl-methanone

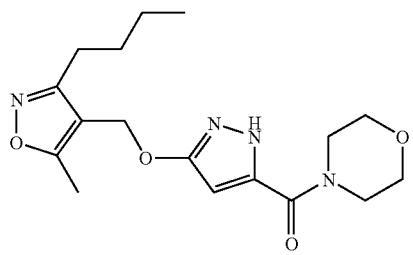

As described for example 26d, 5-(3-butyl-5-methyl-isoxazol-4-ylmethoxy)-2H-pyrazole-3-carboxylic acid methyl ester (100 mg, 0.34 mmol) was converted, using morpholine instead of 4-aminotetrahydropyran, to the title compound (61 mg, 51%) which was obtained as a colorless oil. MS: m/e=349.2 [M+H]$^+$.

Example 37

Rac-5-(3-Butyl-5-methyl-isoxazol-4-ylmethoxy)-2H-pyrazole-3-carboxylic acid (2,2-dimethyl-tetrahydro-pyran-4-yl)-amide

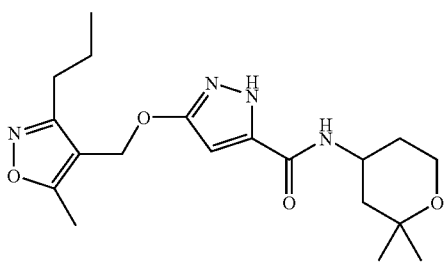

As described for example 26d, 5-(3-butyl-5-methyl-isoxazol-4-ylmethoxy)-2H-pyrazole-3-carboxylic acid methyl ester (100 mg, 0.34 mmol) was converted, using rac-2,2-dimethyltetrahydropyran instead of 4-aminotetrahydropyran, to the title compound (130 mg, 98%) which was obtained as a colorless oil. MS: m/e=391.3 [M+H]$^+$.

Example 38

5-(3-Butyl-5-methyl-isoxazol-4-ylmethoxy)-2H-pyrazole-3-carboxylic acid N',N'-dimethylhydrazide

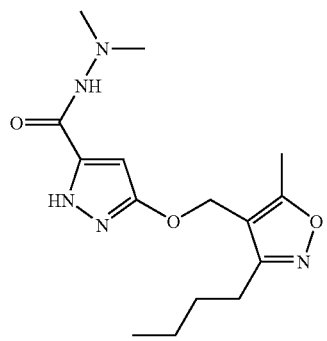

As described for example 26d, 5-(3-butyl-5-methyl-isoxazol-4-ylmethoxy)-2H-pyrazole-3-carboxylic acid methyl ester (100 mg, 0.34 mmol) was converted, using N,N-dimethylhydrazine instead of 4-aminotetrahydropyran, to the title compound (65 mg, 59%) which was obtained as a colorless oil. MS: m/e=322.3 [M+H]$^+$.

Example 39

5-(3-Butyl-5-methyl-isoxazol-4-ylmethoxy)-2H-pyrazole-3-carboxylic acid morpholin-4-ylamide

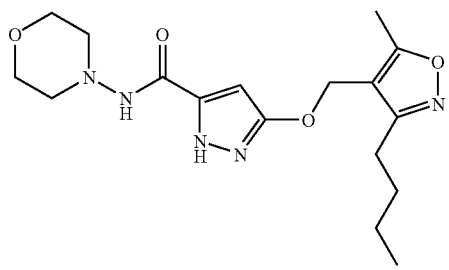

As described for example 26d, 5-(3-butyl-5-methyl-isoxazol-4-ylmethoxy)-2H-pyrazole-3-carboxylic acid methyl ester (100 mg, 0.34 mmol) was converted, using 4-aminomorpholine instead of 4-aminotetrahydropyran, to the title compound (33 mg, 27%) which was obtained as a colorless oil. MS: m/e=364.4 [M+H]$^+$.

Example 40

5-(3-Butyl-5-methyl-isoxazol-4-ylmethoxy)-2H-pyrazole-3-carboxylic acid pyrrolidin-1-ylamide

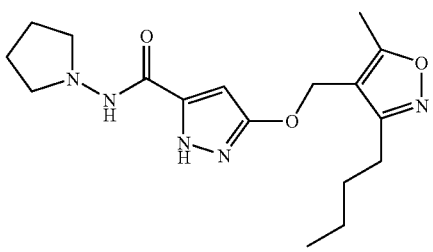

a) 5-(3-Butyl-5-methyl-isoxazol-4-ylmethoxy)-2H-pyrazole-3-carboxylic acid

As described for example 10a, 5-(3-butyl-5-methyl-isoxazol-4-ylmethoxy)-2H-pyrazole-3-carboxylic acid methyl ester (163 mg, 0.56 mmol), instead of 5-[3-(4-fluoro-phenyl)-5-methyl-isoxazol-4-ylmethoxy]-2H-pyrazole-3-carboxylic acid methyl ester, was converted, to the title compound (140 mg, 90%) which was obtained as a white solid. MS: m/e=278.0 [M−H]⁻.

b) 5-(3-Butyl-5-methyl-isoxazol-4-ylmethoxy)-2H-pyrazole-3-carboxylic acid pyrrolidin-1-ylamide As described for example 10b, 5-(3-butyl-5-methyl-isoxazol-4-ylmethoxy)-2H-pyrazole-3-carboxylic acid (140 mg, 0.5 mmol), instead of 5-[3-(4-fluoro-phenyl)-5-methyl-isoxazol-4-ylmethoxy]-2H-pyrazole-3-carboxylic acid, was converted, to the title compound (83 mg, 48%), which was obtained as a white solid. MS: m/e=348.3 [M+H]⁺.

Example 41

5-(3-Butyl-5-methyl-isoxazol-4-ylmethoxy)-2H-pyrazole-3-carboxylic acid piperidin-1-ylamide

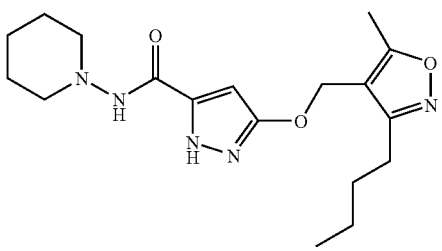

As described for example 26d, 5-(3-butyl-5-methyl-isoxazol-4-ylmethoxy)-2H-pyrazole-3-carboxylic acid methyl ester (218 mg, 0.74 mmol) was converted, using 1-aminopiperidine instead of 4-aminotetrahydropyran, to the title compound (228 mg, 85%) which was obtained as a colorless oil. MS: m/e=362.2 [M+H]⁺.

Example 42

2-Methyl-5-(5-methyl-3-phenyl-isoxazol-4-ylmethoxy)-2H-pyrazole-3-carboxylic acid (2-hydroxy-ethyl)-amide

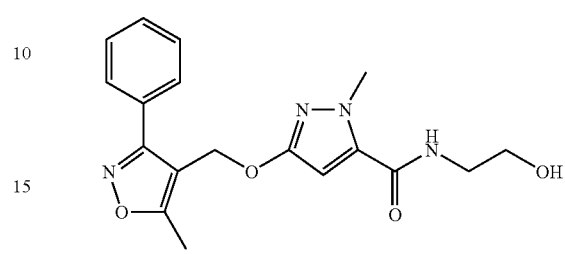

a) (E)-2-Hydrazino-but-2-enedioic acid dimethyl ester

To a solution of dimethylacetylene dicarboxylate (1.4 g, 9.9 mmol) in diethylether (40 mL) under argon was added a solution of hydrazine in THF (1 M, 10 mL) and the resulting mixture stirred at room temperature overnight. The precipitate was filtered off and dried to afford the title compound (597 mg, 35%) as a white solid. MS: m/e=175.2 [M+H]⁺.

b) 5-Hydroxy-2H-pyrazole-3-carboxylic acid methyl ester

To a solution of (E)-2-hydrazino-but-2-enedioic acid dimethyl ester (500 mg, 2.87 mmol) in xylene (10 mL) was added para-toluenesulfonic acid (45 mg, 0.24 mmol) and the resulting mixture heated at reflux for 4 h. After cooling to room temperature the mixture was stirred overnight and the resulting solid was filtered off and dried to afford the title compound (283 mg, 69%) as a white solid after trituration with dichloromethane. MS: m/e=141.1 [M+H]⁺.

c) 5-Hydroxy-2-methyl-2H-pyrazole-3-carboxylic acid methyl ester

To a solution of 5-hydroxy-2H-pyrazole-3-carboxylic acid methyl ester (2.3 g, 16 mmol) in DMF (10 mL) at room temperature was added cesium carbonate (5.27 g, 16 mmol) and methyl iodide (2.3 g, 1.0 mL, 16 mmol) and the resulting mixture stirred for 2.5 h. The mixture was then filtered off to afford the title compound (434 mg, 17%) as a white solid after trituration with ethyl acetate. MS: m/e=157.2 [M+H]⁺.

d) 2-Methyl-5-(5-methyl-3-phenyl-isoxazol-4-ylmethoxy)-2H-pyrazole-3-carboxylic acid methyl ester To a stirred solution of 5-hydroxy-2H-pyrazole-3-carboxylic acid methyl ester (200 mg, 1.28 mmol) and (5-methyl-3-phenyl-4-isoxazolyl)methanol (260 mg, 1.37 mmol) in THF (10 mL) at 5° C. under argon was added triphenylphosphine (437 mg, 1.67 mmol), then diethyl azodicarboxylate (290 mg, 1.67 mmol) was added dropwise. The reaction mixture was warmed to room temperature for 3 h. The reaction mixture was then evaporated and purification by chromatography (silica, heptane:ethyl acetate=1:1 to 6.5:3.5) afforded the title compound (128 mg, 31%) as a colorless oil. MS: m/e=328.3 [M+H]⁺.

e) 2-Methyl-5-(5-methyl-3-phenyl-isoxazol-4-yl-methoxy)-2H-pyrazole-3-carboxylic acid (2-hydroxy-ethyl)-amide As described for example 6, 2-methyl-5-(5-methyl-3-phenyl-isoxazol-4-ylmethoxy)-2H-pyrazole-3-carboxylic acid methyl ester (30 mg, 0.09 mmol), instead of 5-(5-methyl-3-phenyl-isoxazol-4-ylmethoxy)-2H-pyrazole-3-carboxylic acid methyl ester, was converted to the title compound (15 mg, 46%) which was obtained as a colorless oil. MS: m/e=357.2 [M+H]$^+$.

Example 43

Rac-2-Methyl-5-(5-methyl-3-phenyl-isoxazol-4-ylmethoxy)-2H-pyrazole-3-carboxylic acid (tetrahydro-furan-3-yl)-amide

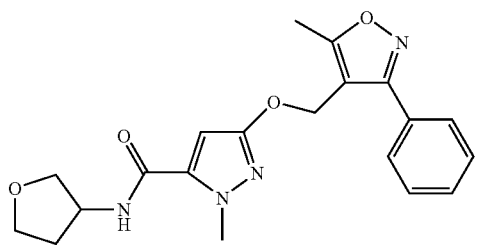

As described for example 1b, 2-methyl-5-(5-methyl-3-phenyl-isoxazol-4-ylmethoxy)-2H-pyrazole-3-carboxylic acid methyl ester (30 mg, 0.09 mmol), instead of 5-(5-methyl-3-phenyl-isoxazol-4-ylmethoxy)-2H-pyrazole-3-carboxylic acid methyl ester, was converted, using rac-3-aminotetrahydrofuran instead of morpholine, to the title compound (28 mg, 80%) which was obtained as a colorless oil. MS: m/e=383.2 [M+H]$^+$.

Example 44

2-Methyl-5-(5-methyl-3-phenyl-isoxazol-4-ylmethoxy)-2H-pyrazole-3-carboxylic acid (tetra-hydro-pyran-4-yl)-amide

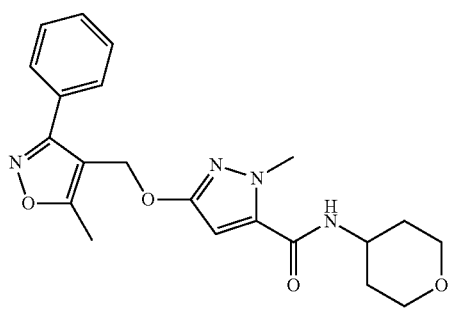

As described for example 43, 2-methyl-5-(5-methyl-3-phenyl-isoxazol-4-ylmethoxy)-2H-pyrazole-3-carboxylic acid methyl ester (30 mg, 0.09 mmol) was converted using 4-aminotetrahydropyran instead of rac-3-aminotetrahydrofuran, to the title compound (34 mg, 94%) which was obtained as a colorless oil. MS: m/e=397.1 [M+H]$^+$.

Example 45

2-Methyl-5-(5-methyl-3-phenyl-isoxazol-4-ylmethoxy)-2H-pyrazole-3-carboxylic acid amide

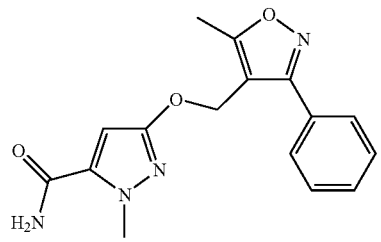

As described for example 42e, 2-methyl-5-(5-methyl-3-phenyl-isoxazol-4-ylmethoxy)-2H-pyrazole-3-carboxylic acid methyl ester (170 mg, 0.52 mmol) was converted, using ammonia in methanol instead of ethanolamine, to the title compound (32 mg, 20%) which was obtained as a white solid. MS: m/e=313.1 [M+H]$^+$.

Example 46

2-Methyl-5-(5-methyl-3-phenyl-isoxazol-4-ylmethoxy)-2H-pyrazole-3-carboxylic acid isopropylamide

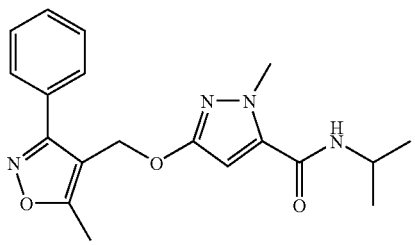

As described for example 42e, 2-methyl-5-(5-methyl-3-phenyl-isoxazol-4-ylmethoxy)-2H-pyrazole-3-carboxylic acid methyl ester (150 mg, 0.46 mmol) was converted, using isopropylamine instead of ethanolamine, to the title compound (57 mg, 35%) which was obtained as a colorless oil. MS: m/e=355.3 [M+H]$^+$.

Example 47

2-Methyl-5-(5-methyl-3-phenyl-isoxazol-4-ylmethoxy)-2H-pyrazole-3-carboxylic acid N',N'-dimethyl-hydrazide

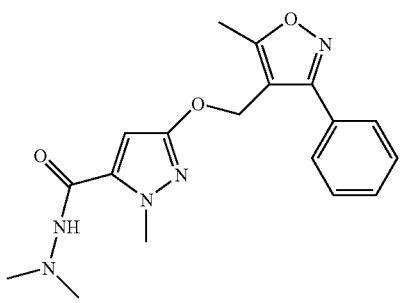

As described for example 43, 2-methyl-5-(5-methyl-3-phenyl-isoxazol-4-ylmethoxy)-2H-pyrazole-3-carboxylic acid methyl ester (120 mg, 0.37 mmol) was converted using N,N-dimethylhydrazine instead of rac-3-aminotetrahydrofuran, to the title compound (130 mg, 100%) which was obtained as a colorless oil. MS: m/e=356.2 [M+H]$^+$.

Example 48

5-[3-(4-Fluoro-phenyl)-5-methyl-isoxazol-4-yl-methoxy]-2-methyl-2H-pyrazole-3-carboxylic acid N',N'-dimethyl-hydrazide

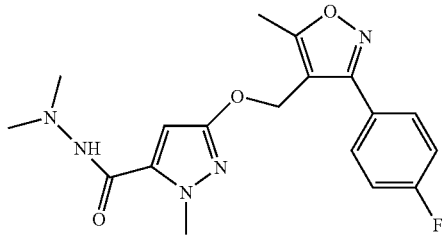

a) 5-[3-(4-Fluoro-phenyl)-5-methyl-isoxazol-4-yl-methoxy]-2H-pyrazole-3-carboxylic acid methyl ester As described for example 42d, [3-(4-fluoro-phenyl)-5-methyl-isoxazol-4-yl]-methanol (Example 8a, 3.1 g, 15 mmol), instead of (5-methyl-3-phenyl-4-isoxazolyl)methanol, was converted to the title compound (2.3 g, 53%) which was obtained as a white solid. MS: m/e=332.2 [M+H]$^+$.

b) 5-[3-(4-Fluoro-phenyl)-5-methyl-isoxazol-4-yl-methoxy]-2-methyl-2H-pyrazole-3-carboxylic acid methyl ester To a solution of 5-[3-(4-fluoro-phenyl)-5-methyl-isoxazol-4-ylmethoxy]-2H-pyrazole-3-carboxylic acid methyl ester (1.37 g, 4.1 mmol) in DMF (10 mL) at room temperature was added cesium carbonate (1.35 g, 4.1 mmol) and methyliodide (587 mg, 0.26 mL, 4.1 mmol) and the resulting mixture stirred for 30 min. The resulting mixture was then evaporated and extracted with ethyl acetate and water. The organic extract was then washed with water, brine, dried over sodium sulfate and evaporated. Purification by chromatography (silica, heptane:ethyl acetate=4:1 to 2:3) afforded the title compound (730 mg, 51%) which was obtained as a colorless oil. MS: m/e=346.1 [M+H]$^+$.

c) 5-[3-(4-Fluoro-phenyl)-5-methyl-isoxazol-4-yl-methoxy]-2-methyl-2H-pyrazole-3-carboxylic acid N',N'-dimethyl-hydrazide As described for example 1b, 5-[3-(4-fluoro-phenyl)-5-methyl-isoxazol-4-ylmethoxy]-2-methyl-2H-pyrazole-3-carboxylic acid methyl ester (110 mg, 0.32 mmol), instead of 5-(5-methyl-3-phenyl-isoxazol-4-ylmethoxy)-2H-pyrazole-3-carboxylic acid methyl ester, was converted, using N,N-dimethylhydrazine instead of morpholine, to the title compound (114 mg, 96%) which was obtained as a white foam. MS: m/e=374.2 [M+H]$^+$.

Example 49

5-[3-(4-Fluoro-phenyl)-5-methyl-isoxazol-4-yl-methoxy]-2-methyl-2H-pyrazole-3-carboxylic acid piperidin-1-ylamide

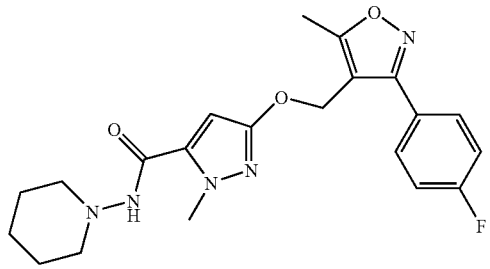

As described for example 48c, 5-[3-(4-fluoro-phenyl)-5-methyl-isoxazol-4-ylmethoxy]-2-methyl-2H-pyrazole-3-carboxylic acid methyl ester (100 mg, 0.29 mmol) was converted, using 1-aminopiperidine instead of N,N-dimethylhydrazine, to the title compound (62 mg, 52%) which was obtained as a colorless oil. MS: m/e=414.3 [M+H]$^+$.

Example 50

5-[3-(4-Fluoro-phenyl)-5-methyl-isoxazol-4-yl-methoxy]-2-methyl-2H-pyrazole-3-carboxylic acid morpholin-4-ylamide

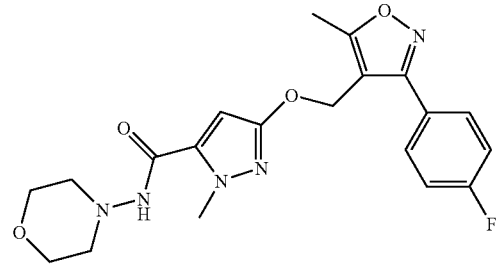

As described for example 48c, 5-[3-(4-fluoro-phenyl)-5-methyl-isoxazol-4-ylmethoxy]-2-methyl-2H-pyrazole-3-carboxylic acid methyl ester (100 mg, 0.29 mmol) was converted, using 4-aminomorpholine instead of N,N-dimethylhydrazine, to the title compound (104 mg, 87%) which was obtained as a colorless oil. MS: m/e=416.2 [M+H]$^+$.

Example 51

5-[3-(4-Fluoro-phenyl)-5-methyl-isoxazol-4-yl-methoxy]-2-methyl-2H-pyrazole-3-carboxylic acid pyrrolidin-1-ylamide

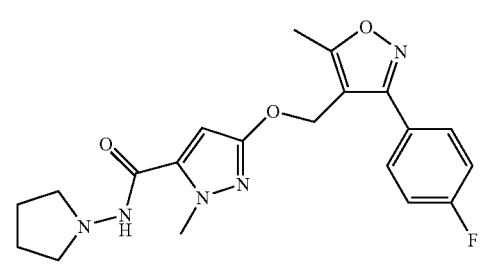

a) 5-[3-(4-Fluoro-phenyl)-5-methyl-isoxazol-4-yl-methoxy]-2-methyl-2H-pyrazole-3-carboxylic acid To a solution of 5-[3-(4-fluoro-phenyl)-5-methyl-isoxazol-4-ylmethoxy]-2-methyl-2H-pyrazole-3-carboxylic acid methyl ester (250 mg, 0.72 mmol) in dioxane (3 mL) was added aqueous sodium hydroxide (2 M, 2.0 mL, 2.0 mmol). After heating at 90° C. for 1 h the solution was cooled to room temperature and neutralized with aqueous hydrogen chloride (2 N). The resulting mixture was then extracted with ethyl acetate and water. The organic extract was then washed with water, brine, dried over sodium sulfate and evaporated to afford the title compound (222 mg, 92%) which was obtained as a white solid. MS: m/e=330.1 [M−H]$^-$.

b) 5-[3-(4-Fluoro-phenyl)-5-methyl-isoxazol-4-yl-methoxy]-2-methyl-2H-pyrazole-3-carboxylic acid pyrrolidin-1-ylamide To a solution of 5-[3-(4-fluoro-phenyl)-5-methyl-isoxazol-4-ylmethoxy]-2-methyl-2H-pyrazole-3-carboxylic acid (200 mg, 0.6 mmol) in DMF (5 mL) were added 2-(1H-benzotriazole-1-yl)-1,1,3,3-tetramethyluronium tetrafluoroborate (291 mg, 0.91 mmol), N,N-diisopropyl ethyl amine (510 µL, 3.0 mmol) and N-aminopyrrolidine HCl (111 mg, 0.91 mmol). The resulting reaction mixture was stirred overnight at room temperature. The reaction mixture was then poured into aqueous sodium chloride (saturated) and the mixture was extracted with ethyl acetate. The combined organic layers were then washed with water, citric acid solution and saturated sodium hydrogen carbonate solution and then dried over sodium sulfate, filtered and evaporated. Concentration and purification by chromatography (silica, dichloromethane) afforded the title compound (139 mg, 58%) as a colorless oil. MS: m/e=400.2 [M+H]$^+$.

Example 52

5-[3-(4-Fluoro-phenyl)-5-methyl-isoxazol-4-yl-methoxy]-2-methyl-2H-pyrazole-3-carboxylic acid isopropylamide

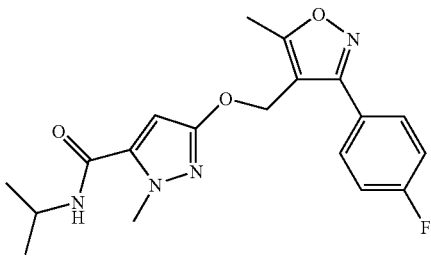

As described for example 48c, 5-[3-(4-fluoro-phenyl)-5-methyl-isoxazol-4-ylmethoxy]-2-methyl-2H-pyrazole-3-carboxylic acid methyl ester (100 mg, 0.29 mmol) was converted, using isopropylamine instead of N,N-dimethylhydrazine, to the title compound (95 mg, 88%) which was obtained as a colorless oil. MS: m/e=373.1 [M+H]$^+$.

Example 53

5-[3-(4-Fluoro-phenyl)-5-methyl-isoxazol-4-yl-methoxy]-2-methyl-2H-pyrazole-3-carboxylic acid (tetrahydro-pyran-4-yl)-amide

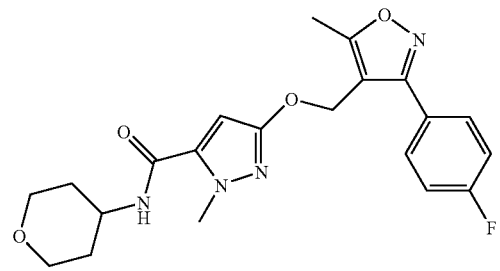

As described for example 48c, 5-[3-(4-fluoro-phenyl)-5-methyl-isoxazol-4-ylmethoxy]-2-methyl-2H-pyrazole-3-carboxylic acid methyl ester (100 mg, 0.29 mmol) was converted, using 4-aminotetrahydropyran instead of N,N-dimethylhydrazine, to the title compound (40 mg, 41%) which was obtained as a colorless oil. MS: m/e=415.3 [M+H]$^+$.

Example 54

5-[3-(4-Fluoro-phenyl)-5-methyl-isoxazol-4-yl-methoxy]-2-methyl-2H-pyrazole-3-carboxylic acid amide

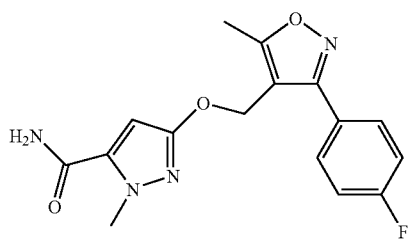

To a solution of 5-[3-(4-fluoro-phenyl)-5-methyl-isoxazol-4-ylmethoxy]-2-methyl-2H-pyrazole-3-carboxylic acid (100 mg, 0.36 mmol) in DMF (8.3 mL) was added 1,1'-carbonyldiimidazole (60.6 mg, 0.36 mmol). The resulting reaction mixture was stirred for 1 h at 60° C. and then treated with an ammonium hydroxide solution (465 µL, 3.0 mmol) and stirred overnight at room temperature. The reaction mixture was then poured into aqueous sodium chloride (saturated) and the mixture was extracted with ethyl acetate. The combined organic layers were then washed with water and saturated sodium hydrogen carbonate solution and then dried over sodium sulfate, filtered and evaporated. Concentration and purification by chromatography (silica, dichloromethane:methanol=99:1 to 95:5) afforded the title compound (79 mg, 79%) as a white solid. MS: m/e=331.2 [M+H]$^+$.

Example 55

5-[3-(4-Fluoro-phenyl)-5-methyl-isoxazol-4-yl-methoxy]-2-methyl-2H-pyrazole-3-carboxylic acid (2-hydroxy-1,1-dimethyl-ethyl)-amide

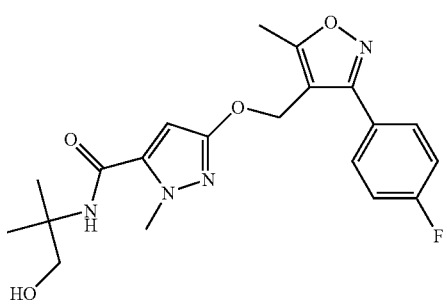

To a solution of 5-[3-(4-fluoro-phenyl)-5-methyl-isoxazol-4-ylmethoxy]-2-methyl-2H-pyrazole-3-carboxylic acid (100 mg, 0.3 mmol) in THF (2.7 mL) was added 1-hydroxybenzotriazole hydrate (47.2 mg, 0.3 mmol), N-ethyldiisopropylamine (131.9 μL, 0.76 mmol), N-(3-dimethylaminopropyl)-N'-ethylcarbodiimidazole hydrochloride (59.1 mg, 0.3 mmol) and 2-amino-2-methyl-1-propanol (27.8 mg, 0.3 mmol) and the resulting mixture stirred overnight at room temperature. The reaction mixture was then poured into aqueous sodium chloride (saturated) and the mixture was extracted with ethyl acetate. The combined organic layers were then washed with water and saturated sodium hydrogen carbonate solution and then dried over sodium sulfate, filtered and evaporated. Concentration and purification by chromatography (silica, dichloromethane:methanol=99:1 to 95:5) afforded the title compound (115 mg, 94%) as a white solid. MS: m/e=403.2 [M+H]$^+$.

Example 56

5-[3-(4-Fluoro-phenyl)-5-methyl-isoxazol-4-yl-methoxy]-2-methyl-2H-pyrazole-3-carboxylic acid ((S)-2,2,2-trifluoro-1-methyl-ethyl)-amide

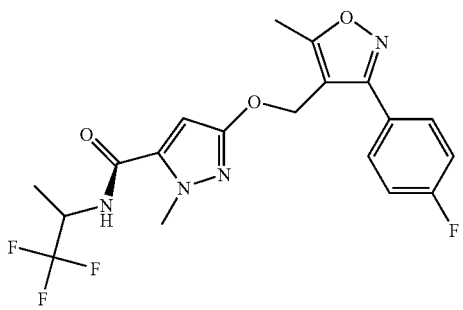

As described for example 48c, 5-[3-(4-fluoro-phenyl)-5-methyl-isoxazol-4-ylmethoxy]-2-methyl-2H-pyrazole-3-carboxylic acid methyl ester (100 mg, 0.29 mmol) was converted, using L-2,2,2-trifluoro-1-methylethylamine instead of N,N-dimethylhydrazine, to the title compound (22 mg, 18%) which was obtained as a white solid. MS: m/e=427.1 [M+H]$^+$.

Example 57

5-[3-(4-Fluoro-phenyl)-5-methyl-isoxazol-4-yl-methoxy]-2-methyl-2H-pyrazole-3-carboxylic acid (2,2,2-trifluoro-ethyl)-amide

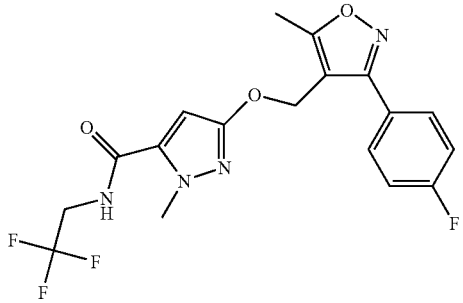

As described for example 55, 5-[3-(4-fluoro-phenyl)-5-methyl-isoxazol-4-ylmethoxy]-2-methyl-2H-pyrazole-3-carboxylic acid (100 mg, 0.3 mmol) was converted, using 2,2,2-trifluoroethylamine instead of 2-amino-2-methyl-1-propanol, to the title compound (112 mg, 90%) which was obtained as a white solid. MS: m/e=413.2 [M+H]$^+$.

Example 58

5-[3-(4-Fluoro-phenyl)-5-methyl-isoxazol-4-yl-methoxy]-2-methyl-2H-pyrazole-3-carboxylic acid (3-methyl-oxetan-3-yl)-amide

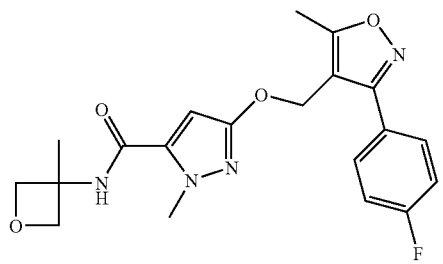

As described for example 55, 5-[3-(4-fluoro-phenyl)-5-methyl-isoxazol-4-ylmethoxy]-2-methyl-2H-pyrazole-3-carboxylic acid (100 mg, 0.3 mmol) was converted, using 3-methyl-3-oxetanamine instead of 2-amino-2-methyl-1-propanol, to the title compound (109 mg, 90%), which was obtained as a white solid. MS: m/e=401.2 [M+H]$^+$.

Example 59

Rac-5-[3-(4-Fluoro-phenyl)-5-methyl-isoxazol-4-ylmethoxy]-2-methyl-2H-pyrazole-3-carboxylic acid (3,3,3-trifluoro-2-hydroxy-propyl)-amide

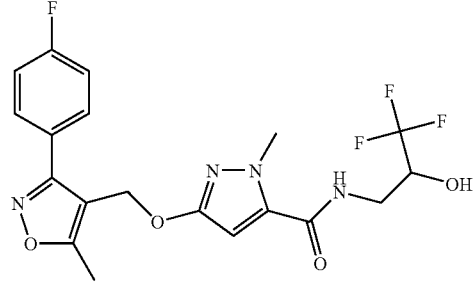

As described for example 55, 5-[3-(4-fluoro-phenyl)-5-methyl-isoxazol-4-ylmethoxy]-2-methyl-2H-pyrazole-3-carboxylic acid (100 mg, 0.3 mmol) was converted, using rac-3-amino-1,1,1-trifluoropropan-2-ol instead of 2-amino-

Example 60
5-[3-(4-Fluoro-phenyl)-5-methyl-isoxazol-4-yl-methoxy]-2-methyl-2H-pyrazole-3-carboxylic acid (2-methoxy-ethyl)-amide

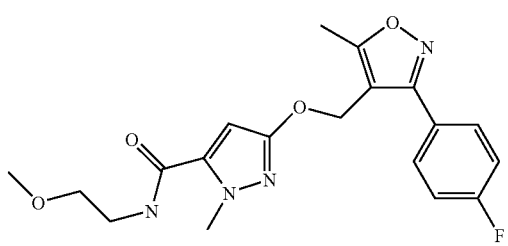

As described for example 55, 5-[3-(4-fluoro-phenyl)-5-methyl-isoxazol-4-ylmethoxy]-2-methyl-2H-pyrazole-3-carboxylic acid (100 mg, 0.3 mmol) was converted, using 2-methoxyethylamine instead of 2-amino-2-methyl-1-propanol, to the title compound (80 mg, 68%) which was obtained as a colorless gum MS: m/e=389.1 [M+H]$^+$.

Example 61
5-[3-(4-Fluoro-phenyl)-5-methyl-isoxazol-4-yl-methoxy]-2-methyl-2H-pyrazole-3-carboxylic acid (1-hydroxy-cyclopropylmethyl)-amide

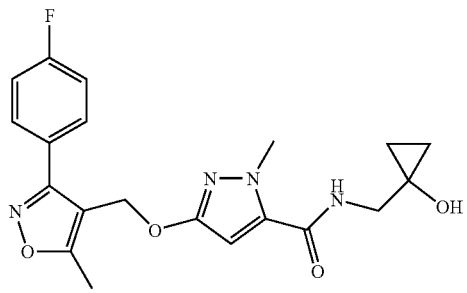

As described for example 55, 5-[3-(4-fluoro-phenyl)-5-methyl-isoxazol-4-ylmethoxy]-2-methyl-2H-pyrazole-3-carboxylic acid (100 mg, 0.3 mmol) was converted, using 1-(aminomethyl)-cyclopropan-2-ol instead of 2-amino-2-methyl-1-propanol, to the title compound (48 mg, 39%) which was obtained as a colorless gum. MS: m/e=401.2 [M+H]$^+$.

Example 62
5-[3-(4-Fluoro-phenyl)-5-methyl-isoxazol-4-yl-methoxy]-2-methyl-2H-pyrazole-3-carboxylic acid (2-hydroxy-ethyl)-amide

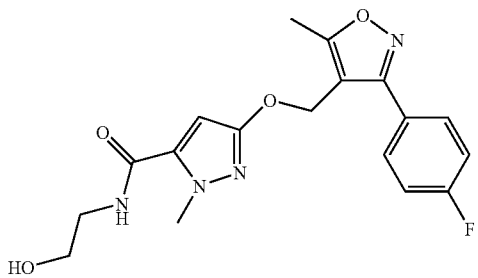

As described for example 55, 5-[3-(4-fluoro-phenyl)-5-methyl-isoxazol-4-ylmethoxy]-2-methyl-2H-pyrazole-3-carboxylic acid (100 mg, 0.3 mmol) was converted, using ethanolamine instead of 2-amino-2-methyl-1-propanol, to the title compound (70 mg, 61%) which was obtained as a white solid. MS: m/e=375.1 [M+H]$^+$.

Example 63
5-[3-(4-Fluoro-phenyl)-5-methyl-isoxazol-4-yl-methoxy]-2-methyl-2H-pyrazole-3-carboxylic acid (1-methyl-1H-pyrazol-3-yl)-amide

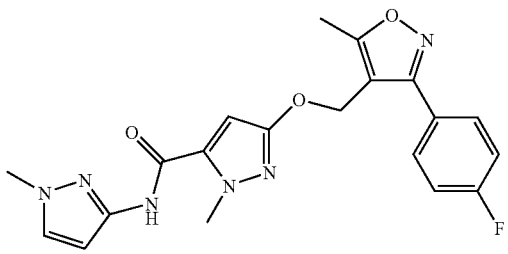

As described for example 48c, 5-[3-(4-fluoro-phenyl)-5-methyl-isoxazol-4-ylmethoxy]-2-methyl-2H-pyrazole-3-carboxylic acid methyl ester (100 mg, 0.29 mmol) was converted, using 1-methyl-1H-pyrazol-3-ylamine instead of N,N-dimethylhydrazine, to the title compound (58 mg, 48%) which was obtained as a yellow gum. MS: m/e=411.2 [M+H]$^+$.

Example 64
5-[3-(4-Fluoro-phenyl)-5-methyl-isoxazol-4-yl-methoxy]-2-methyl-2H-pyrazole-3-carboxylic acid (2-acetylamino-ethyl)-amide

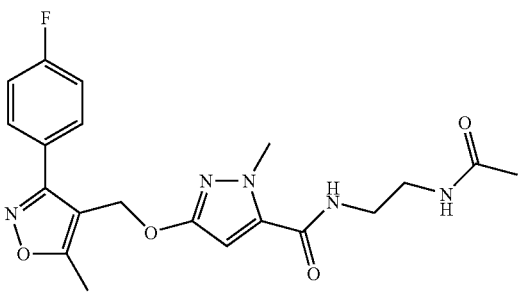

As described for example 55, 5-[3-(4-fluoro-phenyl)-5-methyl-isoxazol-4-ylmethoxy]-2-methyl-2H-pyrazole-3-carboxylic acid (100 mg, 0.3 mmol) was converted, using N-acetylethylendiamine instead of 2-amino-2-methyl-1-propanol, to the title compound (70 mg, 56%) which was obtained as a white solid. MS: m/e=414.1 [M−H]$^−$.

Example 65
5-[3-(4-Fluoro-phenyl)-5-methyl-isoxazol-4-yl-methoxy]-2-methyl-2H-pyrazole-3-carboxylic acid (3-hydroxy-2,2-dimethyl-propyl)-amide

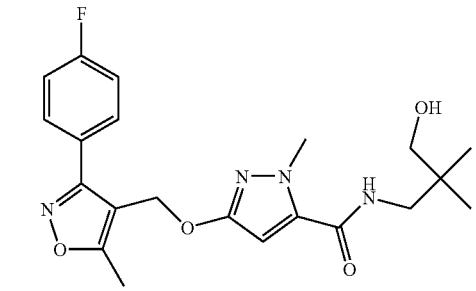

As described for example 55, 5-[3-(4-fluoro-phenyl)-5-methyl-isoxazol-4-ylmethoxy]-2-methyl-2H-pyrazole-3-carboxylic acid (100 mg, 0.3 mmol) was converted, using 3-amino-2,2-dimethyl-1-propanol instead of 2-amino-2-methyl-1-propanol, to the title compound (88 mg, 70%) which was obtained as a white solid. MS: m/e=417.2 [M+H]+.

Example 66

5-[3-(4-Fluoro-phenyl)-5-methyl-isoxazol-4-ylmethoxy]-2-methyl-2H-pyrazole-3-carboxylic acid (2-hydroxy-2-methyl-propyl)-amide

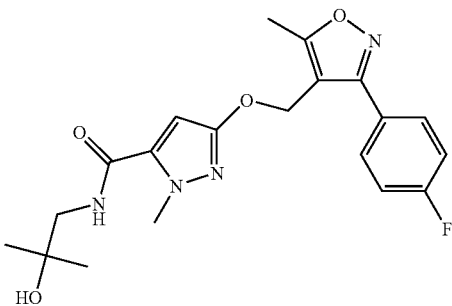

As described for example 55, 5-[3-(4-fluoro-phenyl)-5-methyl-isoxazol-4-ylmethoxy]-2-methyl-2H-pyrazole-3-carboxylic acid (100 mg, 0.3 mmol) was converted, using 1-amino-2-methyl-propan-2-ol instead of 2-amino-2-methyl-1-propanol, to the title compound (79 mg, 65%) which was obtained as a colorless gum. MS: m/e=403.2 [M+H]+.

Example 67

(+)-5-[3-(4-Fluoro-phenyl)-5-methyl-isoxazol-4-ylmethoxy]-2-methyl-2H-pyrazole-3-carboxylic acid ((S or R)-3,3,3-trifluoro-2-hydroxy-propyl)-amide or enantiomer

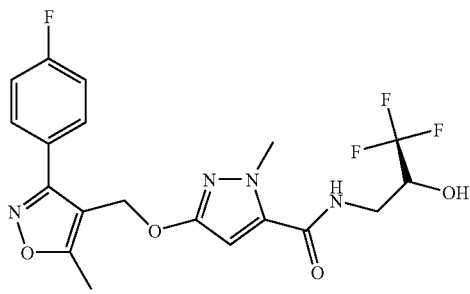

The stereoisomers of rac-5-[3-(4-fluoro-phenyl)-5-methyl-isoxazol-4-ylmethoxy]-2-methyl-2H-pyrazole-3-carboxylic acid (3,3,3-trifluoro-2-hydroxy-propyl)-amide (example 59, 70 mg) in ethanol:heptane (1:1, 2 mL) were separated using a 5×50 cm Chiralpak AD column at room temperature using an isopropanol:heptane (15:85) mobile phase with UV detection at 220 nM. The least polar component (+ve sign of rotation) was obtained as a colorless gum (18 mg). MS: m/e=441.1 [M−H]−.

Example 68

(−)-5-[3-(4-Fluoro-phenyl)-5-methyl-isoxazol-4-ylmethoxy]-2-methyl-2H-pyrazole-3-carboxylic acid ((R or S)-3,3,3-trifluoro-2-hydroxy-propyl)-amide or enantiomer

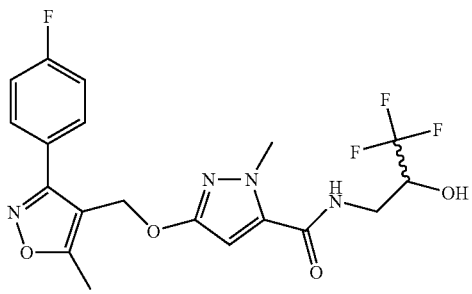

The stereoisomers of rac-5-[3-(4-fluoro-phenyl)-5-methyl-isoxazol-4-ylmethoxy]-2-methyl-2H-pyrazole-3-carboxylic acid (3,3,3-trifluoro-2-hydroxy-propyl)-amide (example 59, 70 mg) in ethanol:heptane (1:1, 2 mL) were separated using a 5×50 cm Chiralpak AD column at room temperature using an isopropanol:heptane (15:85) mobile phase with UV detection at 220 nM. The most polar component (−ve sign of rotation) was obtained as a colorless gum (13 mg). MS: m/e=441.1 [M−H]−.

Example 69

(−)-5-[3-(4-Fluoro-phenyl)-5-methyl-isoxazol-4-ylmethoxy]-2-methyl-2H-pyrazole-3-carboxylic acid ((R or S)-1-hydroxymethyl-propyl)-amide

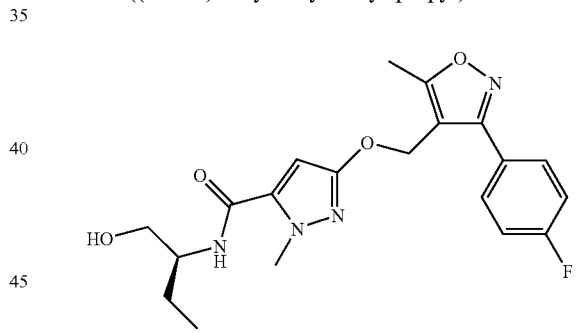

a) rac-5-[3-(4-Fluoro-phenyl)-5-methyl-isoxazol-4-ylmethoxy]-2-methyl-2H-pyrazole-3-carboxylic acid (1-hydroxymethyl-propyl)-amide As described for example 55, 5-[3-(4-fluoro-phenyl)-5-methyl-isoxazol-4-ylmethoxy]-2-methyl-2H-pyrazole-3-carboxylic acid (200 mg, 0.6 mmol) was converted, using rac-2-amino-1-butanol instead of 2-amino-2-methyl-1-propanol, to the title compound (155 mg, 63%) which was obtained as a colorless gum. MS: m/e=403.2 [M+H]+.

b) 5-[3-(4-Fluoro-phenyl)-5-methyl-isoxazol-4-ylmethoxy]-2-methyl-2H-pyrazole-3-carboxylic acid ((R or S)-1-hydroxymethyl-propyl)-amide The stereoisomers of 5-[3-(4-fluoro-phenyl)-5-methyl-isoxazol-4-ylmethoxy]-2-methyl-2H-pyrazole-3-carboxylic acid (1-hydroxymethyl-propyl)-amide (example 69a, 155 mg) in ethanol:heptane (1:1, 8 mL) were separated using a 5×50 cm Chiralpak AD column at room temperature using an isopropanol:heptane (15:85) mobile phase with UV detection at 220 nM. The least polar component (−ve sign of rotation) was obtained as a white solid (76 mg). MS: m/e=403.2 [M+H]⁺.

Example 70

(+)-5-[3-(4-Fluoro-phenyl)-5-methyl-isoxazol-4-ylmethoxy]-2-methyl-2H-pyrazole-3-carboxylic acid ((S or R)-1-hydroxymethyl-propyl)-amide

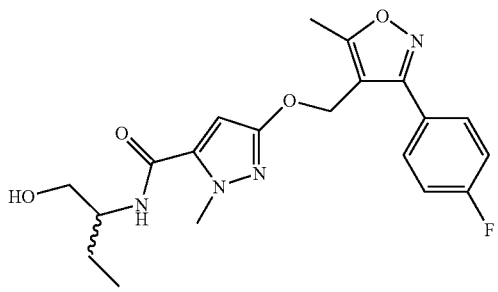

The stereoisomers of 5-[3-(4-fluoro-phenyl)-5-methyl-isoxazol-4-ylmethoxy]-2-methyl-2H-pyrazole-3-carboxylic acid (1-hydroxymethyl-propyl)-amide (example 69a, 155 mg) in ethanol:heptane (1:1, 8 mL) were separated using a 5×50 cm Chiralpak AD column at room temperature using an isopropanol:heptane (15:85) mobile phase with UV detection at 220 nM. The most polar component (+ve sign of rotation) was obtained as a white solid (43 mg). MS: m/e=403.2 [M+H]⁺.

Example 71

{5-[3-(4-Fluoro-phenyl)-5-methyl-isoxazol-4-yl-methoxy]-2-methyl-2H-pyrazol-3-yl}-(3-hydroxy-azetidin-1-yl)-methanone

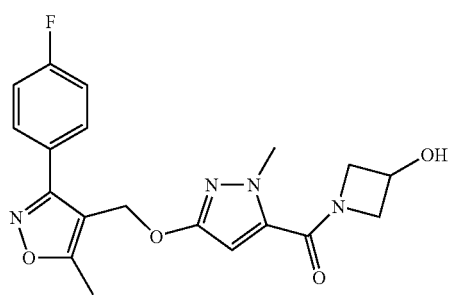

As described for example 55, 5-[3-(4-fluoro-phenyl)-5-methyl-isoxazol-4-ylmethoxy]-2-methyl-2H-pyrazole-3-carboxylic acid (100 mg, 0.3 mmol) was converted, using 3-hydroxyazetidine hydrochloride instead of 2-amino-2-methyl-1-propanol, to the title compound (20 mg, 17%) which was obtained as a colorless gum. MS: m/e=387.1 [M+H]⁺.

Example 72

Rac-5-[3-(4-Fluoro-phenyl)-5-methyl-isoxazol-4-ylmethoxy]-2-methyl-2H-pyrazole-3-carboxylic acid (tetrahydro-furan-3-yl)-amide

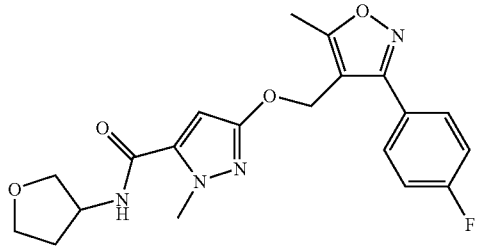

As described for example 55, 5-[3-(4-fluoro-phenyl)-5-methyl-isoxazol-4-ylmethoxy]-2-methyl-2H-pyrazole-3-carboxylic acid (100 mg, 0.3 mmol) was converted, using rac-3-aminotetrahydrofuran instead of 2-amino-2-methyl-1-propanol, to the title compound (84 mg, 69%) which was obtained as a light brown solid. MS: m/e=401.2 [M+H]⁺.

Example 73

(+5-[3-(4-Fluoro-phenyl)-5-methyl-isoxazol-4-yl-methoxy]-2-methyl-2H-pyrazole-3-carboxylic acid ((1R,2R)-2-hydroxy-cyclopentyl)-amide and/or 5-[3-(4-Fluoro-phenyl)-5-methyl-isoxazol-4-ylmethoxy]-2-methyl-2H-pyrazole-3-carboxylic acid ((1S,2S)-2-hydroxy-cyclopentyl)-amide

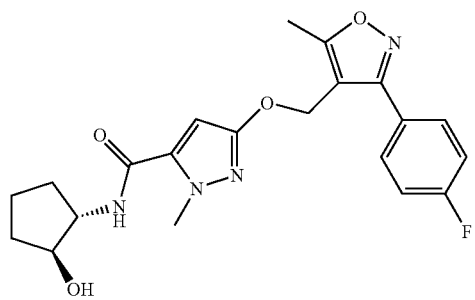

a) 5-[3-(4-Fluoro-phenyl)-5-methyl-isoxazol-4-yl-methoxy]-2-methyl-2H-pyrazole-3-carboxylic acid ((1R,2R)-2-hydroxy-cyclopentyl)-amide and/or 5-[3-(4-fluoro-phenyl)-5-methyl-isoxazol-4-ylmethoxy]-2-methyl-2H-pyrazole-3-carboxylic acid ((1S,2S)-2-hydroxy-cyclopentyl)-amide As described for example 55, 5-[3-(4-fluoro-phenyl)-5-methyl-isoxazol-4-ylmethoxy]-2-methyl-2H-pyrazole-3-carboxylic acid (80 mg, 0.24 mmol) was converted, using trans-(1R,2R)-2-aminocyclopentanol hydrochloride instead of 2-amino-2-methyl-1-propanol, to the (1R,2R) form of the title compound (93 mg, 93%) which was obtained as a white solid. MS: m/e=415.3 [M+H]⁺.

b) 5-[3-(4-Fluoro-phenyl)-5-methyl-isoxazol-4-yl-methoxy]-2-methyl-2H-pyrazole-3-carboxylic acid ((1R,2R)-2-hydroxy-cyclopentyl)-amide and/or 5-[3-(4-fluoro-phenyl)-5-methyl-isoxazol-4-ylmethoxy]-2-methyl-2H-pyrazole-3-carboxylic acid ((1S,2S)-2-hydroxy-cyclopentyl)-amide The stereoisomers of 5-[3-(4-fluoro-phenyl)-5-methyl-isoxazol-4-ylmethoxy]-2-methyl-2H-pyrazole-3-carboxylic acid ((1R,2R)-2-hydroxy-cyclopentyl)-amide and/or 5-[3-(4-fluoro-phenyl)-5-methyl-isoxazol-4-ylmethoxy]-2-methyl-2H-pyrazole-3-carboxylic acid ((1S,2S)-2-hydroxy-cyclopentyl)-amide (example 73a, 93 mg) in ethanol:heptane (1:1, 2 mL) were separated using a 5×50 cm Chiralpak AD column at room temperature using an isopropanol:heptane (1:4) mobile phase with UV detection at 220 nM. The least polar component (−ve sign of rotation) was obtained as a white solid (30 mg). MS: m/e=415.3 [M+H]⁺.

Example 74

(+)-5-[3-(4-Fluoro-phenyl)-5-methyl-isoxazol-4-ylmethoxy]-2-methyl-2H-pyrazole-3-carboxylic acid ((1S,2S)-2-hydroxy-cyclopentyl)-amide and/or 5-[3-(4-fluoro-phenyl)-5-methyl-isoxazol-4-ylmethoxy]-2-methyl-2H-pyrazole-3-carboxylic acid ((1R,2R)-2-hydroxy-cyclopentyl)-amide

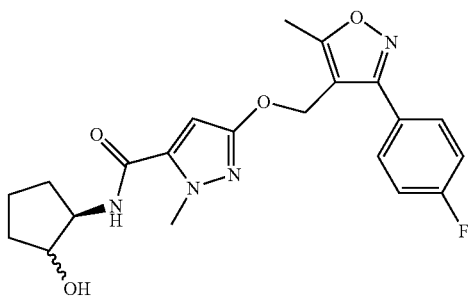

The stereoisomers of 5-[3-(4-fluoro-phenyl)-5-methyl-isoxazol-4-ylmethoxy]-2-methyl-2H-pyrazole-3-carboxylic acid ((1R,2R)-2-hydroxy-cyclopentyl)-amide and/or 5-[3-(4-fluoro-phenyl)-5-methyl-isoxazol-4-ylmethoxy]-2-methyl-2H-pyrazole-3-carboxylic acid ((1S,2S)-2-hydroxy-cyclopentyl)-amide (example 73a, 93 mg) in ethanol:heptane (1:1, 2 mL) were separated using a 5×50 cm Chiralpak AD column at room temperature using an isopropanol:heptane (1:4) mobile phase with UV detection at 220 nM. The most polar component (+ve sign of rotation) was obtained as a white solid (43 mg). MS: m/e=415.3 [M+H]⁺.

Example 75

(+)-5-[3-(4-Fluoro-phenyl)-5-methyl-isoxazol-4-ylmethoxy]-2-methyl-2H-pyrazole-3-carboxylic acid ((R)-2-hydroxy-1-methyl-ethyl)-amide or 5-[3-(4-fluoro-phenyl)-5-methyl-isoxazol-4-ylmethoxy]-2-methyl-2H-pyrazole-3-carboxylic acid ((S)-2-hydroxy-1-methyl-ethyl)-amide or enantiomer

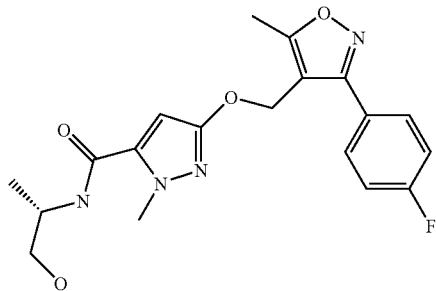

a) Rac-5-[3-(4-Fluoro-phenyl)-5-methyl-isoxazol-4-ylmethoxy]-2-methyl-2H-pyrazole-3-carboxylic acid (2-hydroxy-1-methyl-ethyl)-amide As described for example 55, 5-[3-(4-fluoro-phenyl)-5-methyl-isoxazol-4-ylmethoxy]-2-methyl-2H-pyrazole-3-carboxylic acid (200 mg, 0.6 mmol) was converted, using DL-2-amino-1-propanol instead of 2-amino-2-methyl-1-propanol, to the title compound (155 mg, 66%) which was obtained as a white solid. MS: m/e=389.1 [M+H]⁺.

b) 5-[3-(4-Fluoro-phenyl)-5-methyl-isoxazol-4-ylmethoxy]-2-methyl-2H-pyrazole-3-carboxylic acid ((R)-2-hydroxy-1-methyl-ethyl)-amide or 5-[3-(4-fluoro-phenyl)-5-methyl-isoxazol-4-ylmethoxy]-2-methyl-2H-pyrazole-3-carboxylic acid ((S)-2-hydroxy-1-methyl-ethyl)-amide The stereoisomers of 5-[3-(4-fluoro-phenyl)-5-methyl-isoxazol-4-ylmethoxy]-2-methyl-2H-pyrazole-3-carboxylic acid (2-hydroxy-1-methyl-ethyl)-amide (example 75a, 155 mg) in ethanol:heptane (1:1, 8 mL) were separated using a 5×50 cm Chiralpak AD column at room temperature using an isopropanol:heptane (12:88) mobile phase with UV detection at 220 nM. The least polar component (+ve sign of rotation) was obtained as a colorless gum (20 mg). MS: m/e=389.1 [M+H]⁺.

Example 76

(−)-5-[3-(4-Fluoro-phenyl)-5-methyl-isoxazol-4-ylmethoxy]-2-methyl-2H-pyrazole-3-carboxylic acid ((S)-2-hydroxy-1-methyl-ethyl)-amide or 5-[3-(4-fluoro-phenyl)-5-methyl-isoxazol-4-ylmethoxy]-2-methyl-2H-pyrazole-3-carboxylic acid ((R)-2-hydroxy-1-methyl-ethyl)-amide or enantiomer

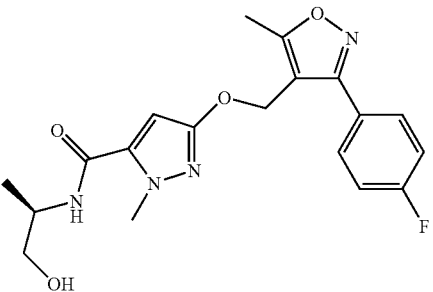

The stereoisomers of 5-[3-(4-fluoro-phenyl)-5-methyl-isoxazol-4-ylmethoxy]-2-methyl-2H-pyrazole-3-carboxylic acid (2-hydroxy-1-methyl-ethyl)-amide (example 75a, 155 mg) in ethanol:heptane (1:1, 8 mL) were separated using a 5×50 cm Chiralpak AD column at room temperature using an isopropanol:heptane (12:88) mobile phase with UV detection at 220 nM. The most polar component (−ve sign of rotation) was obtained as a colorless gum (30 mg). MS: m/e=389.1 [M+H]⁺.

Example 77

{5-[3-(4-Fluoro-phenyl)-5-methyl-isoxazol-4-yl-methoxy]-2-methyl-2H-pyrazol-3-yl}-(2-oxa-6-aza-spiro[3.3]hept-6-yl)-methanone

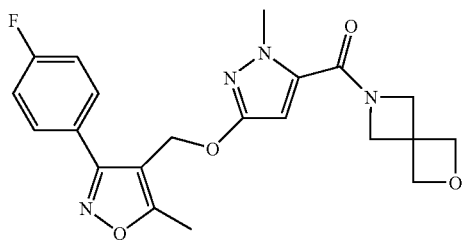

As described for example 55, 5-[3-(4-fluoro-phenyl)-5-methyl-isoxazol-4-ylmethoxy]-2-methyl-2H-pyrazole-3-carboxylic acid (100 mg, 0.3 mmol) was converted, using 2-oxa-6-azonia-spiro[3.3]heptane oxalate salt instead of 2-amino-2-methyl-1-propanol, to the title compound (61 mg, 49%) which was obtained as a white solid. MS: m/e=413.2 [M+H]$^+$.

Example 78

2-Methyl-5-(5-methyl-3-pyridin-2-yl-isoxazol-4-ylmethoxy)-2H-pyrazole-3-carboxylic acid isopropylamide

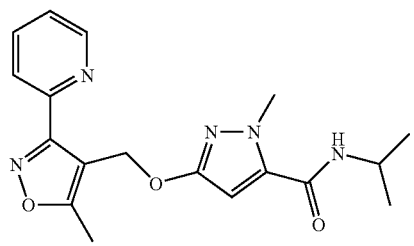

a) 2-Methyl-5-(5-methyl-3-pyridin-2-yl-isoxazol-4-ylmethoxy)-2H-pyrazole-3-carboxylic acid methyl ester To a stirred solution of 5-hydroxy-2-methyl-2H-pyrazole-3-carboxylic acid methyl ester (355 mg, 2.28 mmol) and (5-methyl-3-pyridin-2-yl-isoxazol-4-yl)-methanol (432 mg, 2.28 mmol) in THF (10 mL) at 5° C. under argon was added triphenylphosphine (775 mg, 2.95 mmol), then diethyl azodicarboxylate (515 mg, 2.95 mmol) was added dropwise. The reaction mixture was warmed to room temperature overnight. Then the reaction mixture was evaporated and purified by chromatography (silica, heptane:ethyl acetate=1:1 to 7.5:2.5) to afford the title compound (220 mg, 30%) as a white solid. MS: m/e=329.3 [M+H]$^+$.

b) 2-Methyl-5-(5-methyl-3-pyridin-2-yl-isoxazol-4-ylmethoxy)-2H-pyrazole-3-carboxylic acid isopropylamide As described for example 1b, 2-methyl-5-(5-methyl-3-pyridin-2-yl-isoxazol-4-ylmethoxy)-2H-pyrazole-3-carboxylic acid methyl ester (70 mg, 0.21 mmol), instead of 5-(5-methyl-3-phenyl-isoxazol-4-ylmethoxy)-2H-pyrazole-3-carboxylic acid methyl ester, was converted, using isopropylamine instead of morpholine, to the title compound (41 mg, 54%) which was obtained as a colorless oil. MS: m/e=356.2 [M+H]$^+$.

Example 79

2-Methyl-5-(5-methyl-3-pyridin-2-yl-isoxazol-4-ylmethoxy)-2H-pyrazole-3-carboxylic acid (tetrahydro-pyran-4-yl)-amide

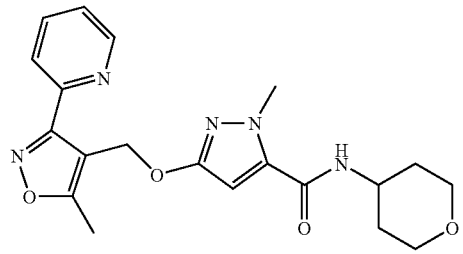

As described for example 78b, 2-methyl-5-(5-methyl-3-pyridin-2-yl-isoxazol-4-ylmethoxy)-2H-pyrazole-3-carboxylic acid methyl ester (70 mg, 0.21 mmol) was converted using 4-aminotetrahydropyran instead of isopropylamine, to the title compound (43 mg, 51%) which was obtained as a white solid. MS: m/e=398.2 [M+H]$^+$.

Example 80

2-Methyl-5-(5-methyl-3-pyridin-2-yl-isoxazol-4-ylmethoxy)-2H-pyrazole-3-carboxylic acid ((S)-2-hydroxy-1-methyl-ethyl)-amide

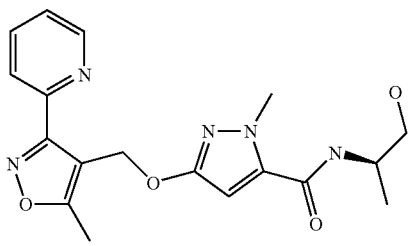

As described for example 6, 2-methyl-5-(5-methyl-3-pyridin-2-yl-isoxazol-4-ylmethoxy)-2H-pyrazole-3-carboxylic acid methyl ester (90 mg, 0.27 mmol), instead of 5-(5-methyl-3-phenyl-isoxazol-4-ylmethoxy)-2H-pyrazole-3-carboxylic acid methyl ester, was converted, using L-alaninol instead of ethanolamine, to the title compound (91 mg, 89%) which was obtained as a colorless oil. MS: m/e=372.2 [M+H]$^+$.

Example 81

Rac-5-[3-(5-fluoro-pyridin-2-yl)-5-methyl-isoxazol-4-ylmethoxy]-2-methyl-2H-pyrazole-3-carboxylic acid (tetrahydro-furan-3-yl)-amide

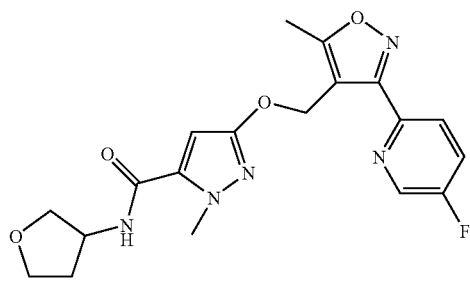

a) 5-[3-(5-Fluoro-pyridin-2-yl)-5-methyl-isoxazol-4-ylmethoxy]-2H-pyrazole-3-carboxylic acid methyl ester As described for example 17d, [3-(5-fluoro-pyridin-2-yl)-5-methyl-isoxazol-4-yl]-methanol (1.03 g, 4.95 mmol), using 5-hydroxy-2-methyl-2H-pyrazole-3-carboxylic acid methyl ester instead of 5-hydroxy-2H-pyrazole-3-carboxylic acid methyl ester, was converted to the title compound (770 mg, 47%) which was obtained as a white solid. MS: m/e=333.2 [M+H]$^+$.

b) 5-[3-(5-Fluoro-pyridin-2-yl)-5-methyl-isoxazol-4-ylmethoxy]-2-methyl-2H-pyrazole-3-carboxylic acid methyl ester To a solution of 5-[3-(5-fluoro-pyridin-2-yl)-5-methyl-isoxazol-4-ylmethoxy]-2H-pyrazole-3-carboxylic acid methyl ester (700 mg, 2.1 mmol) in DMF (10 mL) at room temperature was added cesium carbonate (686 mg, 2.1 mmol) and methyliodide (299 mg, 0.13 mL, 2.1 mmol) and the resulting mixture stirred for 30 min. The resulting mixture was then evaporated and extracted with ethyl acetate and water. The organic extract was then washed with water, brine, dried over sodium sulfate and evaporated. Purification by chromatography (silica, heptane:ethyl acetate=4:1 to 2:3) afforded the title compound (354 mg, 49%) which was obtained as a white solid.

MS: m/e=347.1 [M+H]$^+$.

c) Rac-5-[3-(5-fluoro-pyridin-2-yl)-5-methyl-isoxazol-4-ylmethoxy]-2-methyl-2H-pyrazole-3-carboxylic acid (tetrahydro-furan-3-yl)-amide As described for example 1b, 5-[3-(5-fluoro-pyridin-2-yl)-5-methyl-isoxazol-4-ylmethoxy]-2-methyl-2H-pyrazole-3-carboxylic acid methyl ester (140 mg, 0.40 mmol), instead of 5-(5-methyl-3-phenyl-isoxazol-4-ylmethoxy)-2H-pyrazole-3-carboxylic acid methyl ester, was converted, using rac-3-aminotetrahydrofuran instead of morpholine, to the title compound (96 mg, 59%) which was obtained as a white solid. MS: m/e=402.3 [M+H]$^+$.

Example 82

5-[3-(5-Fluoro-pyridin-2-yl)-5-methyl-isoxazol-4-ylmethoxy]-2-methyl-2H-pyrazole-3-carboxylic acid N',N'-dimethyl-hydrazide

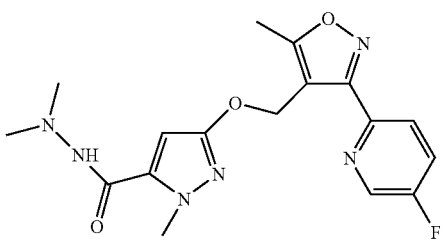

As described for example 81c, 5-[3-(5-fluoro-pyridin-2-yl)-5-methyl-isoxazol-4-ylmethoxy]-2-methyl-2H-pyrazole-3-carboxylic acid methyl ester (73 mg, 0.21 mmol) was converted, using N,N-dimethylhydrazine instead of morpholine, to the title compound (74 mg, 94%) which was obtained as a colorless oil. MS: m/e=375.2 [M+H]$^+$.

Example 83

5-[3-(5-Fluoro-pyridin-2-yl)-5-methyl-isoxazol-4-ylmethoxy]-2-methyl-2H-pyrazole-3-carboxylic acid (2-hydroxy-ethyl)-amide

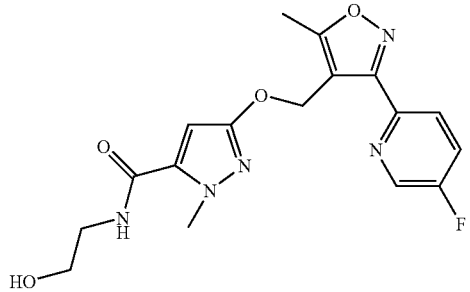

As described for example 6, 5-[3-(5-fluoro-pyridin-2-yl)-5-methyl-isoxazol-4-ylmethoxy]-2-methyl-2H-pyrazole-3-carboxylic acid methyl ester (73 mg, 0.21 mmol), instead of 5-(5-methyl-3-phenyl-isoxazol-4-ylmethoxy)-2H-pyrazole-3-carboxylic acid methyl ester, was converted to the title compound (68 mg, 86%) which was obtained as a white solid. MS: m/e=376.2 [M+H]$^+$.

Example 84

5-[3-(5-Fluoro-pyridin-2-yl)-5-methyl-isoxazol-4-ylmethoxy]-2-methyl-2H-pyrazole-3-carboxylic acid (tetrahydro-pyran-4-yl)-amide

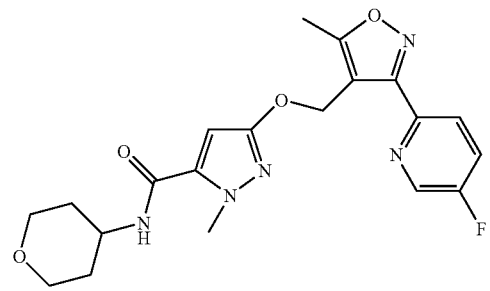

As described for example 81c, 5-[3-(5-fluoro-pyridin-2-yl)-5-methyl-isoxazol-4-ylmethoxy]-2-methyl-2H-pyrazole-3-carboxylic acid methyl ester (73 mg, 0.21 mmol) was converted, using 4-aminotetrahydropyran instead of morpholine, to the title compound (32 mg, 37%) which was obtained as a white solid. MS: m/e=416.2 [M+H]$^+$.

Example 85

5-(3-Butyl-5-methyl-isoxazol-4-ylmethoxy)-2-methyl-2H-pyrazole-3-carboxylic acid (2-hydroxy-ethyl)-amide

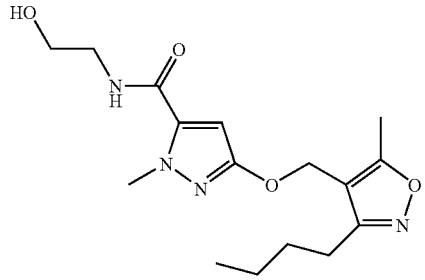

a) 5-(3-Butyl-5-methyl-isoxazol-4-ylmethoxy)-2-methyl-2H-pyrazole-3-carboxylic acid methyl ester As described for example 42d, (3-butyl-5-methyl-isoxazol-4-yl)-methanol (320 mg, 1.9 mmol), instead of (5-methyl-3-phenyl-4-isoxazolyl)methanol, was converted to the title compound (346 mg, 55%) which was obtained as a colorless oil. MS: m/e=308.2 [M+H]$^+$.

b) 5-(3-Butyl-5-methyl-isoxazol-4-ylmethoxy)-2-methyl-2H-pyrazole-3-carboxylic acid methyl ester As described for example 6, 5-(3-butyl-5-methyl-isoxazol-4-ylmethoxy)-2-methyl-2H-pyrazole-3-carboxylic acid methyl ester (60 mg, 0.2 mmol), instead of 5-(5-methyl-3-phenyl-isoxazol-4-ylmethoxy)-2H-pyrazole-3-carboxylic acid methyl ester, was converted to the title compound (50 mg, 76%) which was obtained as a colorless oil. MS: m/e=337.3 [M+H]$^+$.

Example 86

5-(3-Butyl-5-methyl-isoxazol-4-ylmethoxy)-2-methyl-2H-pyrazole-3-carboxylic acid isopropylamide

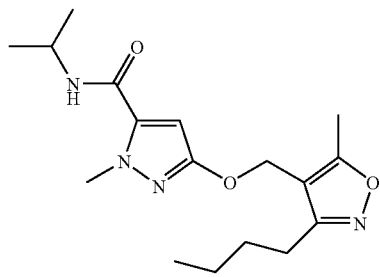

As described for example 1b, 5-(3-butyl-5-methyl-isoxazol-4-ylmethoxy)-2-methyl-2H-pyrazole-3-carboxylic acid methyl ester (60 mg, 0.2 mmol), instead of 5-(5-methyl-3-phenylisoxazol-4-ylmethoxy)-2H-pyrazole-3-carboxylic acid methyl ester, was converted, using isopropylamine instead of morpholine, to the title compound (63 mg, 97%) which was obtained as a colorless oil. MS: m/e=335.2 [M+H]$^+$.

Example 87

Rac-5-(3-Butyl-5-methyl-isoxazol-4-ylmethoxy)-2-methyl-2H-pyrazole-3-carboxylic acid (2-hydroxy-1-methyl-ethyl)-amide

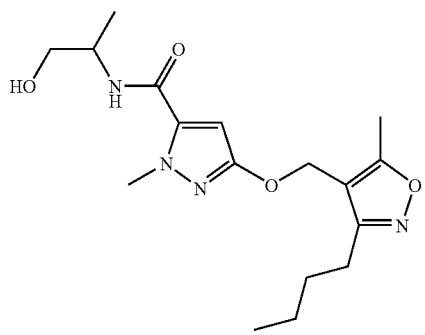

As described for example 85b, 5-(3-butyl-5-methyl-isoxazol-4-ylmethoxy)-2-methyl-2H-pyrazole-3-carboxylic acid methyl ester (60 mg, 0.2 mmol), was converted, using DL-2-amino-1-propanol instead of ethanolamine, to the title compound (48 mg, 70%) which was obtained as a colorless oil. MS: m/e=351.3 [M+H]$^+$.

Example 88

5-(3-Butyl-5-methyl-isoxazol-4-ylmethoxy)-2-methyl-2H-pyrazole-3-carboxylic acid (tetra-hydropyran-4-yl)-amide

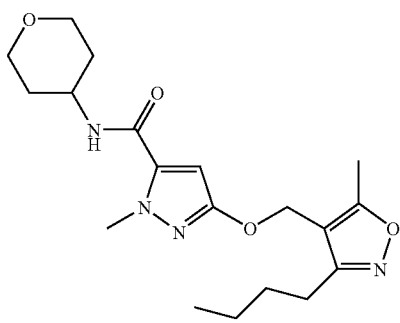

As described for example 86, 5-(3-butyl-5-methyl-isoxazol-4-ylmethoxy)-2-methyl-2H-pyrazole-3-carboxylic acid methyl ester (60 mg, 0.2 mmol) was converted, using 4-aminotetrahydropyran instead of isopropylamine, to the title compound (70 mg, 95%) which was obtained as a colorless oil. MS: m/e=377.2 [M+H]$^+$.

Example 89

Rac-5-(3-Butyl-5-methyl-isoxazol-4-ylmethoxy)-2-methyl-2H-pyrazole-3-carboxylic acid (tetrahydrofuran-3-yl)-amide

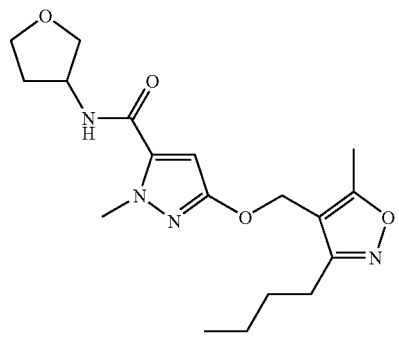

As described for example 86, 5-(3-butyl-5-methyl-isoxazol-4-ylmethoxy)-2-methyl-2H-pyrazole-3-carboxylic acid methyl ester (60 mg, 0.2 mmol) was converted, using rac-3-aminotetrahydrofuran instead of isopropylamine, to the title compound (54 mg, 76%) which was obtained as a colorless oil. MS: m/e=363.1 [M+H]$^+$.

Example 90

2-Methyl-5-[5-methyl-3-(tetrahydro-pyran-4-yl)-isoxazol-4-ylmethoxy]-2H-pyrazole-3-carboxylic acid (tetrahydro-pyran-4-yl)-amide

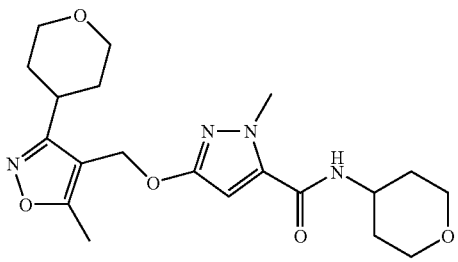

a) Tetrahydro-pyran-4-carbaldehyde oxime

To a suspension of tetrahydro-pyran-4-carbaldehyde (36.9 g, 259 mmol) and hydroxylamine (27.2 g, 388 mmol) in ethanol (246 mL) and water (246 mL) was added sodium acetate (42.9 g, 517 mmol) and the resulting mixture heated at 90° C. overnight. After cooling to room temperature the resulting mixture was then evaporated and extracted with diethylether and water. The organic extract was then washed with water, brine, dried over sodium sulfate and evaporated. Purification by chromatography (silica, heptane:ethyl acetate=1:1) afforded the title compound (16.8 g, 50%) which was obtained as a yellow liquid. MS: m/e=129.1 [M+H]$^+$.

b) 5-Methyl-3-(tetrahydro-pyran-4-yl)-isoxazole-4-carboxylic acid ethyl ester To a solution of tetrahydro-pyran-4-carbaldehyde oxime (6.5 g, 50 mmol) in DMF (47 mL) was added N-chlorosuccinimide (6.95 g, 50 mmol) at room temperature and the after 3 h the mixture was extracted with tert-butylmethylether (100 mL). The organic extract was then added dropwise over 2 h to a solution of ethyl 2-butynoate (61.2 mL, 52.5 mmol) and triethylamine (8.4 mL, 60 mmol) in tert-butylmethylether (47 mL) heated under reflux and the resulting mixture heated overnight. The reaction mixture was then cooled to room temperature and extracted with tert-butylmethylether and washed with aqueous hydrochloric acid solution (1 N). The combined organic phases were dried over sodium sulfate, filtered and concentrated. Purification by chromatography (silica, heptane:ethyl acetate=100:0 to 1:1) afforded the title compound (4.2 g, 35%) as a light yellow solid. MS: m/e=240.2 [M+H]$^+$.

c) [5-Methyl-3-(tetrahydro-pyran-4-yl)-isoxazol-4-yl]-methanol

To a solution of 5-methyl-3-(tetrahydro-pyran-4-yl)-isoxazole-4-carboxylic acid ethyl ester (4.0 g, 16.7 mmol) in THF (55 mL) at 0° C. was added lithium aluminum hydride (349 mg, 9.0 mmol). And the resulting mixture stirred for 18 h at room temperature. Water (0.5 mL) was added carefully followed by aqueous sodium hydroxide (15%, 1.0 mL) and water (2.2 mL). The resulting suspension was stirred for 15 min at ambient temperature and filtered over Hyflo®. The filtrate was then evaporated and purification by chromatography (silica, heptane:ethyl acetate=100:0 to 1:1) afforded the title compound (1.1 g, 34%) as a colorless gum.
MS: m/e=198.1 [M+H]$^+$.

d) 2-Methyl-5-[5-methyl-3-(tetrahydro-pyran-4-yl)-isoxazol-4-ylmethoxy]-2H-pyrazole-3-carboxylic acid methyl ester To a stirred solution of 5-hydroxy-2-methyl-2H-pyrazole-3-carboxylic acid methyl ester (4.68 g, 30 mmol) and [5-methyl-3-(tetrahydro-pyran-4-yl)-isoxazol-4-yl]-methanol (5.92 g, 30 mmol) in THF (400 mL) at 5° C. under argon was added triphenylphosphine (10.6 g, 39 mmol), then diisopropyl azodicarboxylate (8.23 mL, 39 mmol) was added dropwise. The reaction mixture was warmed to room temperature overnight. The reaction mixture was then extracted with ethyl acetate and the organic extract washed with water, dried over sodium sulphate, filtered and evaporated. Purification by chromatography (silica, heptane:ethyl acetate=1:1) afforded the title compound (7.26 g, 85%) as a white solid. MS: m/e=336.2 [M+H]$^+$.

e) 2-Methyl-5-[5-methyl-3-(tetrahydro-pyran-4-yl)-isoxazol-4-ylmethoxy]-2H-pyrazole-3-carboxylic acid (tetrahydro-pyran-4-yl)-amide As described for example 1b, 2-methyl-5-[5-methyl-3-(tetrahydro-pyran-4-yl)-isoxazol-4-ylmethoxy]-2H-pyrazole-3-carboxylic acid methyl ester (200 mg, 0.6 mmol), instead of 5-(5-methyl-3-phenyl-isoxazol-4-ylmethoxy)-2H-pyrazole-3-carboxylic acid methyl ester, was converted, using 4-aminotetrahydropyran instead of morpholine, to the title compound (183 mg, 76%) which was obtained as a colorless gum. MS: m/e=403.1 [M–H]$^-$.

Example 91

5-[3-(4-Fluoro-phenyl)-5-hydroxymethyl-isoxazol-4-ylmethoxy]-2-methyl-2H-pyrazole-3-carboxylic acid (tetrahydro-pyran-4-yl)-amide

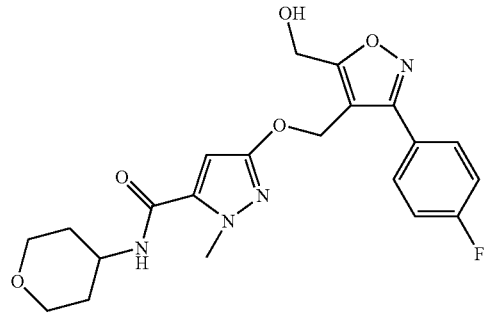

a) 3-(4-Fluoro-phenyl)-5-((E)-styryl)-isoxazole-4-carboxylic acid

To a solution of 3-(4-fluoro-phenyl)-5-methyl-isoxazole-4-carboxylic acid ethyl ester (20.0 g, 80.2 mmol) and benzaldehyde (8.19 mL, 80.2 mmol) in ethanol (113 mL) was added sodium ethoxide (2.71 M, 32.5 mL, 88.3 mmol) and the reaction mixture was heated under reflux for 1 h. Hydrochloric acid (1 N, 96.3 mL) was added and the resulting mixture was extracted with toluene. The solvent was then distilled off to afford the title compound (19.1 g, 77%) as a light yellow solid. MS: m/e=308.0 [M–H]$^-$.

b) [3-(4-Fluoro-phenyl)-5-((E)-styryl)-isoxazol-4-yl]-methanol

To a solution of 3-(4-fluoro-phenyl)-5-((E)-styryl)-isoxazole-4-carboxylic acid (19.0 g, 61.4 mmol) and triethylamine (8.6 mL, 61.4 mmol) in THF (475 mL) was added at room temperature a solution of ethyl chloroformate (5.97 mL, 61.4 mmol) in THF (55 mL). After 1 h the triethylamine hydrochloride salt was filtered off and washed with a small amount of THF. The mixture was added to a solution of sodium borohydride (6.05 g, 154 mmol) and water (55 mL).

After stirring overnight at room temperature aqueous sodium hydroxide solution (1 N, 180 mL) was added. Extraction with tert-butylmethylether, removal of the solvent by distillation and chromatography (silica, dichloromethane:methanol=1:0 to 95:5) afforded the title compound (11.4 g, 63%) as light yellow solid. MS: m/e=296.2 [M+H]⁺.

c) 5-[3-(4-Fluoro-phenyl)-5-((E and/or Z)-styryl)-isoxazol-4-ylmethoxy]-2-methyl-2H-pyrazole-3-carboxylic acid methyl ester To a stirred solution of 5-hydroxy-2-methyl-2H-pyrazole-3-carboxylic acid methyl ester (3.59 g, 23.0 mmol) and [3-(4-fluoro-phenyl)-5-((E)-styryl)-isoxazol-4-yl]-methanol (6.8 g, 23.0 mmol) in THF (279 mL) at 5° C. under argon was added triphenylphosphine (8.1 g, 29.9 mmol), then diethyl azodicarboxylate (13.7 mL, 29.9 mmol) was added dropwise. The reaction mixture was warmed to room temperature and stirred overnight. The reaction mixture was then evaporated. Purification by chromatography (silica, heptane:ethyl acetate=1:0 to 2.7:7.5) afforded the title compound (3.42 g, 34%) as a light yellow solid. MS: m/e=434.3 [M+H]⁺.

d) 5-[3-(4-Fluoro-phenyl)-5-formyl-isoxazol-4-ylmethoxy]-2-methyl-2H-pyrazole-3-carboxylic acid methyl ester A mixture of 5-[3-(4-fluoro-phenyl)-5-((E and/or Z)-styryl)-isoxazol-4-ylmethoxy]-2-methyl-2H-pyrazole-3-carboxylic acid methyl ester (200 mg, 0.46 mmol), osmium (VIII) oxide (2.93 mg, 0.012 mmol), sodium metaperiodate (394 mg, 1.84 mmol), benzyltriethylammonium chloride (42.9 mg, 0.18 mmol) in dioxane (3 mL) and water (1 mL) was heated for 25 min at 120° C. in a microwave. Water was then added to the reaction mixture and the resulting mixture extracted with ethyl acetate. The organic extract was then evaporated and the residue purified by chromatography (silica, ethyl acetate:heptane=1:4 to 9:1) to afford the title compound (120 mg, 72%) as a yellow oil. MS: m/e=418.1 [M+OAc]⁻.
Alternatively:

e) 5-[5-((1S,2R)-1,2-Dihydroxy-2-phenyl-ethyl)-3-(4-fluoro-phenyl)-isoxazol-4-ylmethoxy]-2-methyl-2H-pyrazole-3-carboxylic acid methyl ester To a solution of 5-[3-(4-fluoro-phenyl)-5-([E and/or Z]-styryl)-isoxazol-4-ylmethoxy]-2-methyl-2H-pyrazole-3-carboxylic acid methyl ester (100 mg, 0.23 mmol) in dioxane (1 mL) was added N-Methylmorpholine N-Oxide (27.9 mg, 0.23 mmol), water (250 μL) and osmium(VIII) oxide (2.5% w/v solution in t-butanol/939 μL, 0.92 mmol) at 0° C. The reaction mixture was stirred at room temperature overnight. The mixture was partitioned between ethyl acetate and saturated sodium thiosulfate. The combined organic extracts were washed with brine, dried, filtered and evaporated. The organic extract was then evaporated and the residue purified by chromatography (silica, ethyl acetate:heptane=1:4 to 9:1) afforded the title compound (40 mg, 37%) as a white solid. MS: m/e=466.1 [M+H]⁺.

f) 5-[3-(4-Fluoro-phenyl)-5-formyl-isoxazol-4-ylmethoxy]-2-methyl-2H-pyrazole-3-carboxylic acid methyl ester Sodium (meta)periodate (3.67 g, 17.2 mmol) was added at 0° C. to a mixture of 5-[5-((1S,2R)-1,2-dihydroxy-2-phenyl-ethyl)-3-(4-fluoro-phenyl)-isoxazol-4-ylmethoxy]-2-methyl-2H-pyrazole-3-carboxylic acid methyl ester (5.35 g, 11.4 mmol) in THF (29.6 ml) and water (6.1 ml) and the resulting mixture stirred at 0° C. over night. The reaction mixture was extracted with water and ethyl acetate, and the organic phases were washed with brine, dried over sodium sulfate, filtered and evaporated. Purification by chromatography (silica, heptane:ethyl acetate=1:0 to 4:1) afforded the title compound (3.63 g, 88%) as a white solid. MS: m/e=418.1 [M+OAc]⁻.

g) 5-[3-(4-Fluoro-phenyl)-5-hydroxymethyl-isoxazol-4-ylmethoxy]-2-methyl-2H-pyrazole-3-carboxylic acid methyl ester A solution of 5-[3-(4-fluoro-phenyl)-5-formyl-isoxazol-4-ylmethoxy]-2-methyl-2H-pyrazole-3-carboxylic acid methyl ester (720 mg, 2.0 mmol) and sodium borohydride (158 mg, 4.0 mmol) in methanol (36 mL) were stirred for 1 h at room temperature. Addition of 10% aqueous citric acid (100 mL) was followed by extraction with ethyl acetate. The combined organic extracts were washed with brine, dried over sodium sulfate, filtered and evaporated. Purification by chromatography (silica, heptane:ethyl acetate=4:1 to 1:1) afforded the title compound (510 mg, 70%) as a white solid. MS: m/e=420.3 [M+OAc]⁻.

h) 5-[3-(4-Fluoro-phenyl)-5-hydroxymethyl-isoxazol-4-ylmethoxy]-2-methyl-2H-pyrazole-3-carboxylic acid (tetrahydro-pyran-4-yl)-amide As described for example 1b, 5-[3-(4-fluoro-phenyl)-5-hydroxymethyl-isoxazol-4-ylmethoxy]-2-methyl-2H-pyrazole-3-carboxylic acid methyl ester (150 mg, 0.42 mmol), instead of 5-(5-methyl-3-phenyl-isoxazol-4-ylmethoxy)-2H-pyrazole-3-carboxylic acid methyl ester, was converted, using 4-aminotetrahydropyran instead of morpholine, to the title compound (120 mg, 67%) which was obtained as a white solid. MS: m/e=429.1 [M−H]⁻.

Example 92

5-[3-(4-Fluoro-phenyl)-5-hydroxymethyl-isoxazol-4-ylmethoxy]-2-methyl-2H-pyrazole-3-carboxylic acid isopropylamide

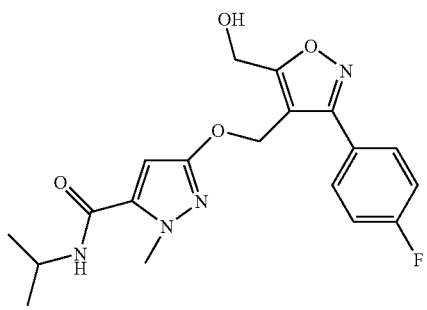

As described for example 91h, 5-[3-(4-fluoro-phenyl)-5-hydroxymethyl-isoxazol-4-ylmethoxy]-2-methyl-2H-pyrazole-3-carboxylic acid methyl ester (150 mg, 0.42 mmol) was converted, using isopropylamine instead of 4-aminotetrahydropyran, to the title compound (90 mg, 56%) which was obtained as a white solid. MS: m/e=387.0 [M−H]⁻.

Example 93

5-[3-(4-Fluoro-phenyl)-5-hydroxymethyl-isoxazol-4-ylmethoxy]-2-methyl-2H-pyrazole-3-carboxylic acid amide

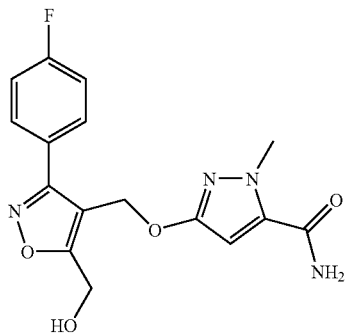

a) 5-[3-(4-Fluoro-phenyl)-5-hydroxymethyl-isoxazol-4-ylmethoxy]-2-methyl-2H-pyrazole-3-carboxylic acid To 5-[3-(4-fluoro-phenyl)-5-hydroxymethyl-isoxazol-4-ylmethoxy]-2-methyl-2H-pyrazole-3-carboxylic acid methyl ester (250 mg, 0.69 mmol) in THF (1.17 mL), methanol (391 µL) and water (1.17 mL) was added lithium hydroxide (33.8 mg, 1.4 mmol). The reaction mixture was stirred for 2 h at room temperature. Addition of aqueous hydrochloride solution (1 N, 25 mL) and extraction with ethyl acetate yielded the title compound (220 mg, 92%) as a light brown solid. MS: m/e=346.0 [M−H]⁻.

b) 5-[3-(4-Fluoro-phenyl)-5-hydroxymethyl-isoxazol-4-ylmethoxy]-2-methyl-2H-pyrazole-3-carboxylic acid amide To a solution of 5-[3-(4-fluoro-phenyl)-5-hydroxymethyl-isoxazol-4-ylmethoxy]-2-methyl-2H-pyrazole-3-carboxylic acid (200 mg, 0.58 mmol) in DMF (16.7 mL) was added 1,1'-carbonyldiimidazole (116 mg, 0.69 mmol). The resulting reaction mixture was stirred for 1 h at 60° C. and then treated with an ammonium hydroxide solution (887 µL, 5.8 mmol) and stirred overnight at room temperature. The reaction mixture was then poured into aqueous sodium chloride (saturated) and the mixture was extracted with ethyl acetate. The combined organic layers were then washed with water and saturated sodium hydrogen carbonate solution and then dried over sodium sulfate, filtered and evaporated. Concentration and purification by chromatography (silica, dichloromethane:methanol=98:2 to 9:1) afforded the title compound (170 mg, 85%) as a white solid. MS: m/e=345.0 [M−H]⁻.

Example 94

5-[3-(4-Fluoro-phenyl)-5-hydroxymethyl-isoxazol-4-ylmethoxy]-2-methyl-2H-pyrazole-3-carboxylic acid (2,2,2-trifluoro-ethyl)-amide

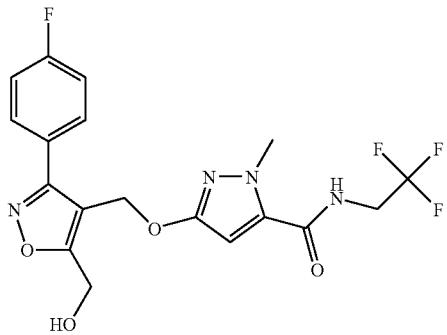

As described for example 91h, 5-[3-(4-fluoro-phenyl)-5-hydroxymethyl-isoxazol-4-ylmethoxy]-2-methyl-2H-pyrazole-3-carboxylic acid methyl ester (100 mg, 0.28 mmol) was converted, using 2,2,2-trifluoroethylamine instead of 4-aminotetrahydropyran, to the title compound (115 mg, 97%) which was obtained as a brown solid. MS: m/e=427.0 [M−]⁻.

Example 95

5-[3-(4-Fluoro-phenyl)-5-hydroxymethyl-isoxazol-4-ylmethoxy]-2-methyl-2H-pyrazole-3-carboxylic acid (2,2,3,3,3-pentafluoro-propyl)-amide

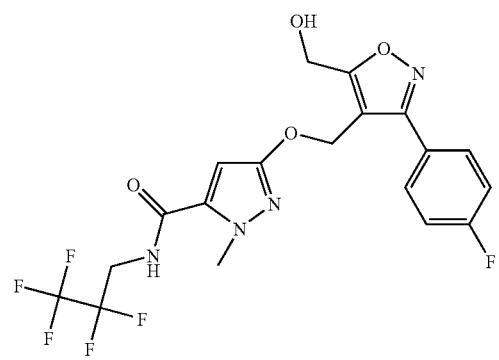

As described for example 91h, 5-[3-(4-fluoro-phenyl)-5-hydroxymethyl-isoxazol-4-ylmethoxy]-2-methyl-2H-pyrazole-3-carboxylic acid methyl ester (100 mg, 0.28 mmol) was converted, using 2,2,3,3,3-pentafluoropropylamine instead of 4-aminotetrahydropyran, to the title compound (115 mg, 87%) which was obtained as a brown oil. MS: m/e=477.0 [M−]⁻.

Example 96

5-[3-(4-Fluoro-phenyl)-5-hydroxymethyl-isoxazol-4-ylmethoxy]-2-methyl-2H-pyrazole-3-carboxylic acid (1-methyl-1H-pyrazol-3-yl)-amide

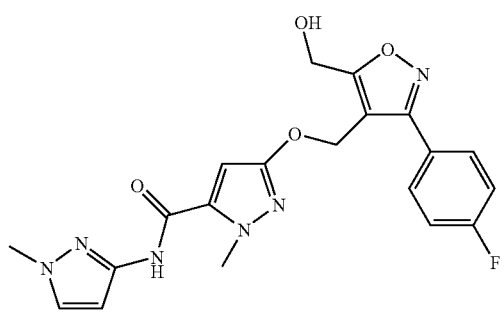

As described for example 91h, 5-[3-(4-fluoro-phenyl)-5-hydroxymethyl-isoxazol-4-ylmethoxy]-2-methyl-2H-pyrazole-3-carboxylic acid methyl ester (100 mg, 0.28 mmol) was converted, using 1-methyl-1H-pyrazol-3-ylamine instead of 4-aminotetrahydropyran, to the title compound (80 mg, 68%) which was obtained as a white solid. MS: m/e=425.1 [M−H]⁻.

Example 97

Rac-5-[3-(4-fluoro-phenyl)-5-hydroxymethyl-isoxazol-4-ylmethoxy]-2-methyl-2H-pyrazole-3-carboxylic acid (tetrahydro-furan-3-yl)-amide

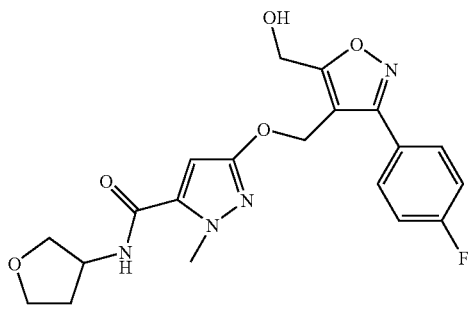

To a solution of 5-[3-(4-fluoro-phenyl)-5-hydroxymethyl-isoxazol-4-ylmethoxy]-2-methyl-2H-pyrazole-3-carboxylic acid (100 mg, 0.29 mmol) in THF (10 mL) was added 1-hydroxybenzotriazole hydrate (45.0 mg, 0.29 mmol), N-ethyldiisopropylamine (126 µL, 0.76 mmol), N-(3-dimethylaminopropyl)-N'-ethylcarbodiimidazole hydrochloride (56.3 mg, 0.29 mmol) and rac-3-aminotetrahydrofuran (25.1 mg, 0.29 mmol) and the resulting mixture stirred overnight at room temperature. The reaction mixture was then poured into aqueous sodium chloride (saturated) and the mixture was extracted with ethyl acetate. The combined organic layers were then washed with water and saturated sodium hydrogen carbonate solution and then dried over sodium sulfate, filtered and evaporated. Concentration and purification by chromatography (silica, dichloromethane:methanol=99:1 to 95:5) afforded the title compound (60 mg, 50%) as a white solid. MS: m/e=415.1 [M−H]⁻.

Example 98

Rac-5-[3-(4-fluoro-phenyl)-5-hydroxymethyl-isoxazol-4-ylmethoxy]-2-methyl-2H-pyrazole-3-carboxylic acid (3-methyl-oxetan-3-yl)-amide

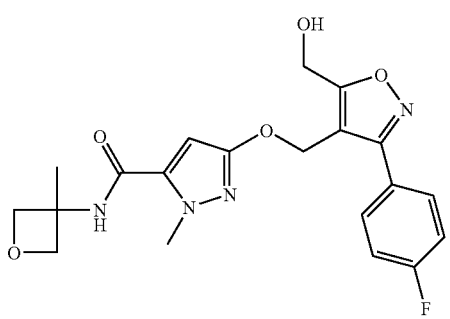

As described for example 97, 5-[3-(4-fluoro-phenyl)-5-hydroxymethyl-isoxazol-4-ylmethoxy]-2-methyl-2H-pyrazole-3-carboxylic acid (100 mg, 0.29 mmol) was converted, using 3-methyl-3-oxetanamine instead of rac-3-aminotetrahydrofuran, to the title compound (60 mg, 50%) which was obtained as a white foam. MS: m/e=415.1 [M−H]⁻.

Example 99

{5-[3-(4-Fluoro-phenyl)-5-hydroxymethyl-isoxazol-4-ylmethoxy]-2-methyl-2H-pyrazol-3-yl}-(2-oxa-6-aza-spiro[3.3]hept-6-yl)-methanone

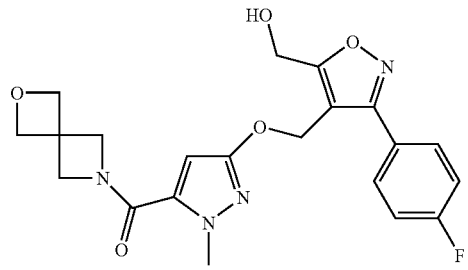

As described for example 97, 5-[3-(4-fluoro-phenyl)-5-hydroxymethyl-isoxazol-4-ylmethoxy]-2-methyl-2H-pyrazole-3-carboxylic acid (100 mg, 0.29 mmol) was converted, using 2-oxa-6-azonia-spiro[3.3]heptane oxalate salt instead of rac-3-aminotetrahydrofuran, to the title compound (35 mg, 28%) which was obtained as a white solid. MS: m/e=487.3 [M+OAc]⁻.

Example 100

5-[3-(4-Chloro-phenyl)-5-hydroxymethyl-isoxazol-4-ylmethoxy]-2-methyl-2H-pyrazole-3-carboxylic acid isopropylamide

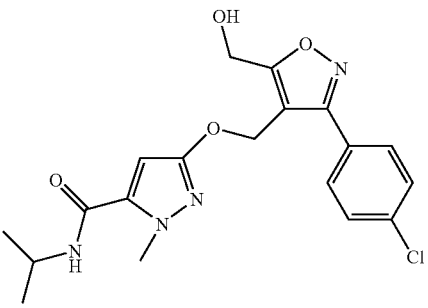

a) 3-(4-Chloro-phenyl)-5-([E]-styryl)-isoxazole-4-carboxylic acid

To a stirred solution of 3-(4-chloro-phenyl)-5-methyl-isoxazole-4-carboxylic acid ethyl ester (9.6 g, 36.1 mmol) and benzaldehyde (3.69 mL, 36.1 mmol) in ethanol (54 mL) was added sodium ethoxide (2.71 M, 14.6 mL, 39.7 mmol) and the reaction was heated under reflux for 10 min. Hydrochloric acid (1 N, 43.4 mL) was added and the resulting mixture was then triturated with dichloromethane and filtered to afford the title compound (6.21 g, 53%) as a light yellow solid. MS: m/e=324.1 [M−H]⁻.

b) [3-(4-Chloro-phenyl)-5-([E]-styryl)-isoxazol-4-yl]-methanol

To a solution of 3-(4-chloro-phenyl)-5-([E]-styryl)-isoxazole-4-carboxylic acid (6.0 g, 18.4 mmol) and triethylamine (2.58 mL, 18.4 mmol) in THF (150 mL) was added at room temperature a solution of ethyl chloroformate (1.8 mL, 18.4 mmol) in THF (17.4 mL). After 1 h triethylamine hydrochloride salt was filtered off, and washed with a small amount of THF. The solution was then added to a solution of sodium borohydride (1.82 g, 46.1 mmol) in water (18 mL). After stirring overnight at room temperature sodium hydroxide solution (1 N) was added. Extraction with tert-butylmethylether and purification by chromatography (silica, dichloromethane) afforded the title compound (4.52 g, 79%) as a white solid. MS: m/e=369.9 [M+CH₃COO]⁻.

c) 5-[3-(4-Chloro-phenyl)-5-((E and/or Z)-styryl)-isoxazol-4-ylmethoxy]-2-methyl-2H-pyrazole-3-carboxylic acid methyl ester As described for example 91c, [3-(4-chloro-phenyl)-5-((E)-styryl)-isoxazol-4-yl]-methanol (100 mg, 0.29 mmol), instead of 3-(4-fluoro-phenyl)-5-((E)-styryl)-isoxazol-4-yl]-methanol, was converted to the title compound (150 mg, 43%) which was obtained as a white solid. MS: m/e=450.2 [M+H]+.

d) 5-[3-(4-Chloro-phenyl)-5-formyl-isoxazol-4-ylmethoxy]-2-methyl-2H-pyrazole-3-carboxylic acid methyl ester As described for example 91d, 5-[3-(4-chloro-phenyl)-5-((E and/or Z)-styryl)-isoxazol-4-ylmethoxy]-2-methyl-2H-pyrazole-3-carboxylic acid methyl ester (3.0 g, 6.7 mmol), instead of 5-[3-(4-fluoro-phenyl)-5-((E and/or Z)-styryl)-isoxazol-4-ylmethoxy]-2-methyl-2H-pyrazole-3-carboxylic acid methyl ester, was converted to the title compound (2.4 g, 100%) which was obtained as a white solid. MS: m/e=376.1 [M+H]+.

e) 5-[3-(4-Chloro-phenyl)-5-hydroxymethyl-isoxazol-4-ylmethoxy]-2-methyl-2H-pyrazole-3-carboxylic acid methyl ester As described for example 91g, 5-[3-(4-chloro-phenyl)-5-formyl-isoxazol-4-ylmethoxy]-2-methyl-2H-pyrazole-3-carboxylic acid methyl ester (2.4 g, 6.6 mmol), instead of 5-[3-(4-fluoro-phenyl)-5-formyl-isoxazol-4-ylmethoxy]-2-methyl-2H-pyrazole-3-carboxylic acid methyl ester, was converted to the title compound (2.4 g, 100%) which was obtained as a white solid. MS: m/e=378.2 [M+H]+.

f) 5-[3-(4-Chloro-phenyl)-5-hydroxymethyl-isoxazol-4-ylmethoxy]-2-methyl-2H-pyrazole-3-carboxylic acid isopropylamide As described for example 91h, 5-[3-(4-chloro-phenyl)-5-hydroxymethyl-isoxazol-4-ylmethoxy]-2-methyl-2H-pyrazole-3-carboxylic acid methyl ester (100 mg, 0.27 mmol), instead of 5-[3-(4-fluoro-phenyl)-5-hydroxymethyl-isoxazol-4-ylmethoxy]-2-methyl-2H-pyrazole-3-carboxylic acid methyl ester, was converted, using isopropylamine instead of 4-aminotetrahydropyran, to the title compound (60 mg, 56%) which was obtained as a white solid. MS: m/e=405.3 [M+H]+.

Example 101

5-[3-(4-Chloro-phenyl)-5-hydroxymethyl-isoxazol-4-ylmethoxy]-2-methyl-2H-pyrazole-3-carboxylic acid (tetrahydro-pyran-4-yl)-amide

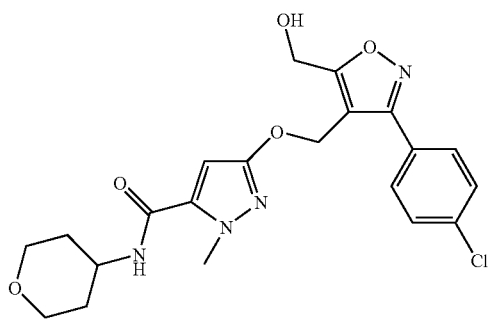

As described for example 100f, 5-[3-(4-chloro-phenyl)-5-hydroxymethyl-isoxazol-4-ylmethoxy]-2-methyl-2H-pyrazole-3-carboxylic acid methyl ester (100 mg, 0.27 mmol) was converted, using 4-aminotetrahydropyran instead of isopropylamine, to the title compound (50 mg, 42%) which was obtained as a white solid. MS: m/e=447.3 [M+H]+.

Example 102

5-[3-(4-Chloro-phenyl)-5-hydroxymethyl-isoxazol-4-ylmethoxy]-2-methyl-2H-pyrazole-3-carboxylic acid amide

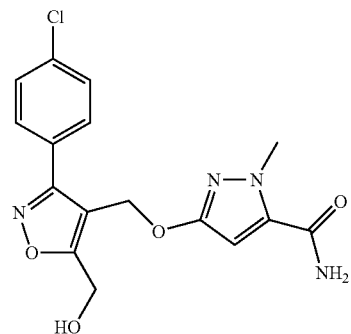

a) 5-[3-(4-Chloro-phenyl)-5-hydroxymethyl-isoxazol-4-ylmethoxy]-2-methyl-2H-pyrazole-3-carboxylic acid As described for example 93a, 5-[3-(4-chloro-phenyl)-5-hydroxymethyl-isoxazol-4-ylmethoxy]-2-methyl-2H-pyrazole-3-carboxylic acid methyl ester (500 mg, 1.32 mmol), instead of 5-[3-(4-fluoro-phenyl)-5-hydroxymethyl-isoxazol-4-ylmethoxy]-2-methyl-2H-pyrazole-3-carboxylic acid methyl ester, was converted to the title compound (440 mg, 91%) which was obtained as a white solid. MS: m/e=361.9 [M−H]−.

b) 5-[3-(4-Chloro-phenyl)-5-hydroxymethyl-isoxazol-4-ylmethoxy]-2-methyl-2H-pyrazole-3-carboxylic acid amide As described for example 93b, 5-[3-(4-chloro-phenyl)-5-hydroxymethyl-isoxazol-4-ylmethoxy]-2-methyl-2H-pyrazole-3-carboxylic acid (100 mg, 0.28 mmol), instead of 5-[3-(4-fluoro-phenyl)-5-hydroxymethyl-isoxazol-4-ylmethoxy]-2-methyl-2H-pyrazole-3-carboxylic acid, was converted to the title compound (25 mg, 25%) which was obtained as a white solid. MS: m/e=363.1 [M+H]+.

Example 103

5-[3-(4-Chloro-phenyl)-5-hydroxymethyl-isoxazol-4-ylmethoxy]-2-methyl-2H-pyrazole-3-carboxylic acid (2,2,2-trifluoro-ethyl)-amide

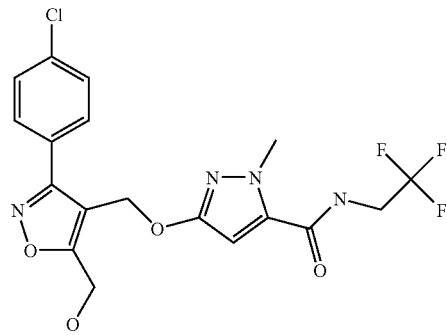

113

As described for example 100f, 5-[3-(4-chloro-phenyl)-5-hydroxymethyl-isoxazol-4-ylmethoxy]-2-methyl-2H-pyrazole-3-carboxylic acid methyl ester (100 mg, 0.27 mmol) was converted, using 2,2,2-trifluoroethylamine instead of isopropylamine, to the title compound (38 mg, 32%) which was obtained as a white solid. MS: m/e=443.0 [M−H]⁻.

Example 104

5-[3-(4-Chloro-phenyl)-5-hydroxymethyl-isoxazol-4-ylmethoxy]-2-methyl-2H-pyrazole-3-carboxylic acid (2,2,3,3,3-pentafluoro-propyl)-amide

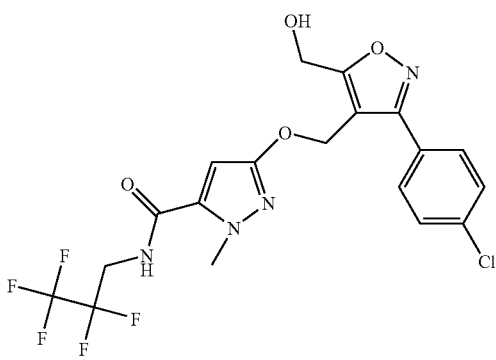

As described for example 100f, 5-[3-(4-chloro-phenyl)-5-hydroxymethyl-isoxazol-4-ylmethoxy]-2-methyl-2H-pyrazole-3-carboxylic acid methyl ester (100 mg, 0.27 mmol) was converted, using 2,2,3,3,3-pentafluoropropylamine instead of isopropylamine, to the title compound (35 mg, 26%) which was obtained as a white solid. MS: m/e=495.1 [M+H]⁺.

Example 105

5-[3-(4-Chloro-phenyl)-5-hydroxymethyl-isoxazol-4-ylmethoxy]-2-methyl-2H-pyrazole-3-carboxylic acid cyclopropylamide

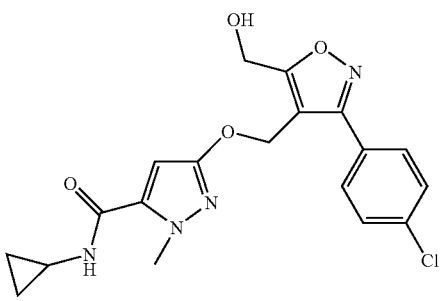

As described for example 100f, 5-[3-(4-chloro-phenyl)-5-hydroxymethyl-isoxazol-4-ylmethoxy]-2-methyl-2H-pyrazole-3-carboxylic acid methyl ester (100 mg, 0.27 mmol) was converted, using cyclopropylamine instead of isopropylamine, to the title compound (32 mg, 30%) which was obtained as a white solid. MS: m/e=403.2 [M+H]⁺.

114

Example 106

5-[3-(4-Chloro-phenyl)-5-hydroxymethyl-isoxazol-4-ylmethoxy]-2-methyl-2H-pyrazole-3-carboxylic acid ((S)-2,2,2-trifluoro-1-methyl-ethyl)-amide

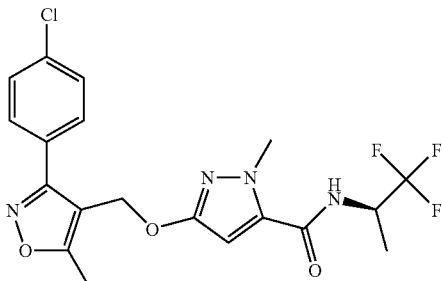

As described for example 100f, 5-[3-(4-chloro-phenyl)-5-hydroxymethyl-isoxazol-4-ylmethoxy]-2-methyl-2H-pyrazole-3-carboxylic acid methyl ester (100 mg, 0.27 mmol) was converted, using L-2,2,2-trifluoro-1-(methyl)ethylamine instead of isopropylamine, to the title compound (21 mg, 17%) which was obtained as a colorless gum. MS: m/e=459.3 [M+H]⁺.

Example 107

5-[3-(4-Chloro-phenyl)-5-hydroxymethyl-isoxazol-4-ylmethoxy]-2-methyl-2H-pyrazole-3-carboxylic acid (2-hydroxy-1,1-dimethyl-ethyl)-amide

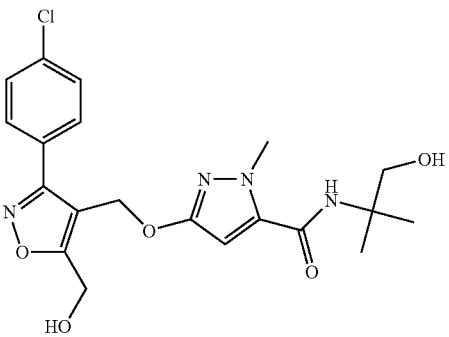

To a solution of 5-[3-(4-chloro-phenyl)-5-hydroxymethyl-isoxazol-4-ylmethoxy]-2-methyl-2H-pyrazole-3-carboxylic acid (100 mg, 0.28 mmol) in THF (2.7 mL) was added 1-hydroxybenzotriazole hydrate (43.0 mg, 0.28 mmol), N-ethyldiisopropylamine (120 µL, 0.69 mmol), N-(3-dimethylaminopropyl)-N'-ethylcarbodiimidazole hydrochloride (43.0 mg, 0.28 mmol) and 2-amino-2-methyl-1-propanol (25.3 mg, 0.28 mmol) and the resulting mixture stirred overnight at room temperature. The reaction mixture was then poured into aqueous sodium chloride (saturated) and the mixture was extracted with ethyl acetate. The combined organic layers were then washed with water and saturated sodium hydrogen carbonate solution and then dried over sodium sulfate, filtered and evaporated. Concentration and purification by chromatography (silica, dichloromethane:methanol=99:1 to 95:5) afforded the title compound (32 mg, 26%) as a white solid. MS: m/e=435.3 [M+H]⁺.

Example 108

5-[3-(4-Chloro-phenyl)-5-hydroxymethyl-isoxazol-4-ylmethoxy]-2-methyl-2H-pyrazole-3-carboxylic acid (3-methyl-oxetan-3-yl)-amide

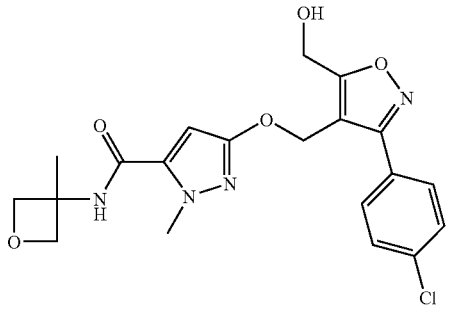

As described for example 107, 5-[3-(4-chloro-phenyl)-5-hydroxymethyl-isoxazol-4-ylmethoxy]-2-methyl-2H-pyrazole-3-carboxylic acid (100 mg, 0.28 mmol) was converted, using 3-methyl-3-oxetanamine instead of 2-amino-2-methyl-1-propanol, to the title compound (39 mg, 32%) which was obtained as a white solid. MS: m/e=433.3 [M+H]$^+$.

Example 109

{5-[3-(4-Chloro-phenyl)-5-hydroxymethyl-isoxazol-4-ylmethoxy]-2-methyl-2H-pyrazol-3-yl}-(2-oxa-6-aza-spiro[3.3]hept-6-yl)-methanone

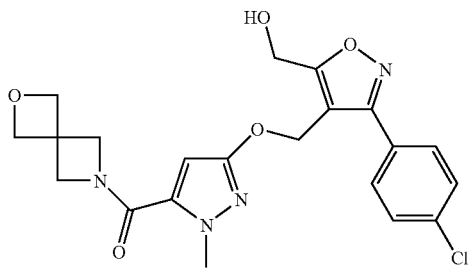

As described for example 107, 5-[3-(4-chloro-phenyl)-5-hydroxymethyl-isoxazol-4-ylmethoxy]-2-methyl-2H-pyrazole-3-carboxylic acid (65 mg, 0.18 mmol) was converted, using 2-oxa-6-azonia-spiro[3.3]heptane oxalate salt instead of 2-amino-2-methyl-1-propanol, to the title compound (38 mg, 48%) which was obtained as a colorless gum. MS: m/e=445.3 [M+H]$^+$.

Example 110

Rac-5-[3-(4-Chloro-phenyl)-5-hydroxymethyl-isoxazol-4-ylmethoxy]-2-methyl-2H-pyrazole-3-carboxylic acid (tetrahydro-furan-3-yl)-amide

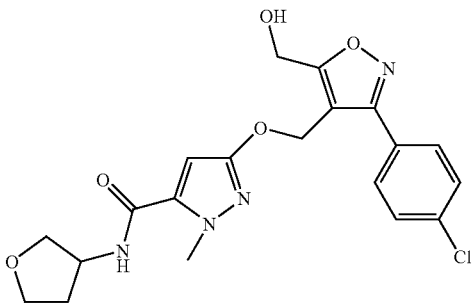

As described for example 107, 5-[3-(4-chloro-phenyl)-5-hydroxymethyl-isoxazol-4-ylmethoxy]-2-methyl-2H-pyrazole-3-carboxylic acid (100 mg, 0.28 mmol) was converted, using rac-3-aminotetrahydrofuran instead of 2-amino-2-methyl-1-propanol, to the title compound (73 mg, 61%) which was obtained as a colorless gum. MS: m/e=433.3 [M+H]$^+$.

Example 111

{5-[3-(4-Chloro-phenyl)-5-hydroxymethyl-isoxazol-4-ylmethoxy]-2-methyl-2H-pyrazol-3-yl}-(4,4-difluoro-piperidin-1-yl)-methanone

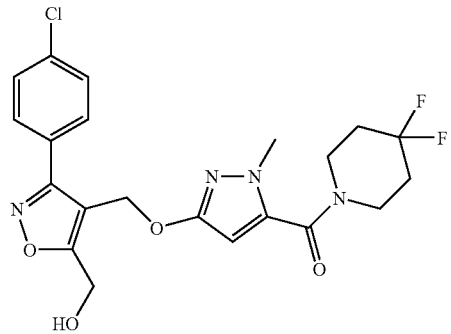

As described for example 107, 5-[3-(4-chloro-phenyl)-5-hydroxymethyl-isoxazol-4-ylmethoxy]-2-methyl-2H-pyrazole-3-carboxylic acid (100 mg, 0.28 mmol) was converted, using 4,4-difluoropiperidine hydrochloride instead of 2-amino-2-methyl-1-propanol, to the title compound (87 mg, 67%) which was obtained as a colorless gum. MS: m/e=467.2 [M+H]$^+$.

Example 112

5-(3-Butyl-5-hydroxymethyl-isoxazol-4-ylmethoxy)-2-methyl-2H-pyrazole-3-carboxylic acid (2,2,2-trifluoro-ethyl)-amide

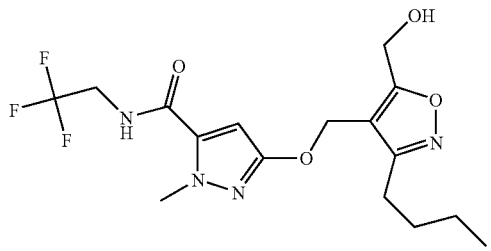

a) 3-Butyl-5-([E]-styryl)-isoxazole-4-carboxylic acid

To a solution of 3-butyl-5-methyl-isoxazole-4-carboxylic acid ethyl ester (15.0 g, 71.0 mmol) and benzaldehyde (7.2 mL, 71.0 mmol) in ethanol (100 mL) was added sodium ethoxide solution (21% in ethanol, 29.1 mL, 78.0 mmol) and the reaction mixture was stirred at reflux for 2 h, cooled to room temperature and stirred for 17 h. Hydrochloric acid (1 N, 85 mL) was added and the resulting mixture was extracted twice with dichloromethane. The combined phases were washed with brine, dried over sodium sulfate and filtered. The filtrate was concentrated to a bright yellow pasty solid and recrystallized from hot heptane/ethyl acetate to afford the title compound (8.0 g, 42%) as a yellow solid. MS: m/e=270.4 [M−H]$^-$.

b) [3-Butyl-5-([E]-styryl)-isoxazol-4-yl]-methanol

To a solution of 3-butyl-5-([E]-styryl)-isoxazole-4-carboxylic acid (7.0 g, 25.8 mmol) and triethylamine (3.8 mL, 27.0 mmol) in THF (30 mL) was added at 0° C. ethyl chloroformate (2.6 mL, 27.0 mmol). After 1 h the triethylamine hydrochloride salt was filtered off and washed with a small amount of THF. The filtrate was concentrated, the residue taken up in ethanol (70 mL) and added to a solution of sodium borohydride (2.4 g, 63.4 mmol) in water (35 mL) at 0° C. After stirring at room temperature for 2.5 days, the reaction was quenched with aqueous sodium hydroxide (1 M, 40 mL) and extracted twice with tert-butylmethylether. The combined phases were washed with brine, dried over sodium sulfate and filtered. The filtrate was concentrated to a yellow oil and purified by flash chromatography (silica, dichloromethane:methanol 100:0 to 97:3) to afford the title compound (6.9 g, 98%) as an orange oil. MS: m/e=258.1 [M+H]+.

c) 5-[3-Butyl-5-(1,2-dihydroxy-2-phenyl-ethyl)-isoxazol-4-ylmethoxy]-2-methyl-2H-pyrazole-3-carboxylic acid methyl ester To a stirred solution of 5-hydroxy-2H-pyrazole-3-carboxylic acid methyl ester (937 mg, 6.0 mmol) and [3-butyl-5-([E]-styryl)-isoxazol-4-yl]-methanol (1.54 g, 6.0 mmol) in THF (120 mL) at 5° C. under argon was added triphenylphosphine (2.1 g, 7.8 mmol), then diethyl azodicarboxylate (1.06 g, 6.0 mmol) was added dropwise. The reaction mixture was warmed to room temperature overnight. The reaction mixture was then poured into aqueous sodium chloride (saturated) and the mixture was extracted with ethyl acetate. The combined organic layers were then washed with water and saturated sodium hydrogen carbonate solution and then dried over sodium sulfate, filtered and evaporated. Concentration and purification by chromatography (silica, heptane:ethyl acetate=4:1 to 7:3) afforded the intermediate product (1.07 g, 45%) as a yellow oil. MS: m/e=396.2 [M+H]+. To a solution of the intermediate product (0.79 g, 2.0 mmol) in tert-butanol (50 mL) was added AD Mix-α (2.8 g) with water (50 mL). The reaction mixture was stirred at room temperature overnight and extracted with ethyl acetate. The combined organic phases were washed with brine, dried over sodium sulfate and concentrated to a yellow oil. The crude material was purified by flash chromatography (silica gel, heptane:ethyl acetate 7:3 to 1:1) to afford the title compound (440 mg, 51%) as a colorless oil. MS: m/e=430.2 [M+H]+.

d) 5-(3-Butyl-5-hydroxymethyl-isoxazol-4-ylmethoxy)-2-methyl-2H-pyrazole-3-carboxylic acid methyl ester To a solution of 5-[3-butyl-5-(1,2-dihydroxy-2-phenylethyl)-isoxazol-4-ylmethoxy]-2-methyl-2H-pyrazole-3-carboxylic acid methyl ester (440 mg, 1.03 mmol) in benzene (2 mL) was added lead tetraacetate (545 mg, 1.23 mmol) with benzene (2 mL) and the reaction was stirred at room temperature for 1 h and then lead tetraacetate (136 mg, 0.3 mmol) and benzene (1.5 mL) added. After 30 min, the suspension was filtered over Celite® and the filtrate was concentrated to give crude 5-(3-butyl-5-formyl-isoxazol-4-ylmethoxy)-2-methyl-2H-pyrazole-3-carboxylic acid methyl ester as a yellow oil (330 mg). The oil was taken up in methanol (12 mL) and sodium borohydride (97 mg, 2.57 mmol) was added in portions over 3 min. Upon addition, the reaction became a clear light yellow solution containing a black precipitate. After stirring at room temperature for 15 min, the mixture was filtered over Celite® and the filter cake was washed with methanol. The filtrate was concentrated and the residue was portioned between 0.5M aqueous hydrochloric acid and ethyl acetate. The aqueous phase was extracted two times with ethyl acetate and the combined organic phases were washed with brine, dried over sodium sulfate and concentrated to afford a yellow oil. The crude material was purified by chromatography (silica, heptane:ethyl acetate 1:0 to 1:1) to afford the title compound (256 mg, 77%) as a colorless oil. MS: m/e=322.2 [M+H]+.

Alternatively:

e) 5-(3-Butyl-5-formyl-isoxazol-4-ylmethoxy)-2-methyl-2H-pyrazole-3-carboxylic acid methyl ester A mixture of 5-[3-butyl-5-((E and/or Z)-styryl)-isoxazol-4-ylmethoxy]-2-methyl-2H-pyrazole-3-carboxylic acid methyl ester (1.0 g, 2.5 mmol), osmium(VIII) oxide (25 mg, 0.1 mmol), sodium metaperiodate (2.16 g, 10 mmol), benzyltriethylammonium chloride (230 mg, 0.96 mmol) in dioxane (24 mL) and water (8 mL) was heated for 5.5 h at 120° C. Water was then added to the reaction mixture and the resulting mixture extracted with ethyl acetate. The organic extract was then evaporated and the residue purified by chromatography (silica, ethyl acetate:heptane=1:4 to 9:1) to afford the title compound (80 mg, 10%) as a yellow oil. MS: m/e=322.2 [M+X]+.

f) 5-(3-Butyl-5-hydroxymethyl-isoxazol-4-ylmethoxy)-2-methyl-2H-pyrazole-3-carboxylic acid methyl ester To a solution of 5-(3-butyl-5-formyl-isoxazol-4-ylmethoxy)-2-methyl-2H-pyrazole-3-carboxylic acid methyl ester (80 mg, 0.25 mmol) in methanol (4 mL) was added sodium borohydride (18.8 mg, 0.5 mmol) in portions over 3 min. Upon addition, the reaction became a clear light yellow solution containing a black precipitate. After stirring at room temperature for 1.5 h, the mixture was filtered over Celite® and the filter cake was washed with methanol. The filtrate was concentrated and the residue was portioned between 0.5M aqueous hydrochloric acid and ethyl acetate. The aqueous phase was extracted two times with ethyl acetate and the combined organic phases were washed with brine, dried over sodium sulfate and concentrated to a yellow oil. The crude material was purified by chromatography (silica, heptane:acetone 7.5:2.5) to afford the title compound (37 mg, 46%) as a dark brown oil. MS: m/e=324.3 [M+H]+.

g) 5-(3-Butyl-5-hydroxymethyl-isoxazol-4-ylmethoxy)-2-methyl-2H-pyrazole-3-carboxylic acid To a solution of 5-(3-butyl-5-hydroxymethyl-isoxazol-4-ylmethoxy)-2-methyl-2H-pyrazole-3-carboxylic acid methyl ester (260 mg, 0.81 mmol) in dioxane (15 mL) was added aqueous sodium hydroxide (2 M, 7.0 mL, 7.0 mmol). After heating at 90° C. for 1.5 h the solution was cooled to room temperature, diluted with water, extracted with ethyl acetate and the combined organic phases were washed with brine, dried over sodium sulfate, filtered and concentrated to afford the title compound (250 mg, 100%) as a white solid. MS: m/e=308.5 [M−H]−.

h) 5-(3-Butyl-5-hydroxymethyl-isoxazol-4-ylmethoxy)-2-methyl-2H-pyrazole-3-carboxylic acid (2,2,2-trifluoro-ethyl)-amide To a solution of 5-(3-butyl-5-hydroxymethyl-isoxazol-4-ylmethoxy)-2-methyl-2H-pyrazole-3-carboxylic acid (50 mg, 0.16 mmol) in DMF (2 mL) were added 2-(1H-benzotriazole-1-yl)-1,1,3,3-tetramethyluronium tetrafluoroborate (57 mg, 0.18 mmol), N,N-diisopropyl ethyl amine (138 μL, 0.8 mmol) and 2,2,2-trifluoroethylamine HCl (24 mg, 0.18 mmol). The resulting reaction mixture was stirred overnight at room temperature. Concentration and purification by chromatography (silica, dichloromethane:methanol=100:0 to 95:5) afforded the title compound (47 mg, 75%) as a colorless oil. MS: m/e=391.2 [M+H]$^+$.\

Example 113

5-(3-Butyl-5-hydroxymethyl-isoxazol-4-ylmethoxy)-2-methyl-2H-pyrazole-3-carboxylic acid cyclobutylamide

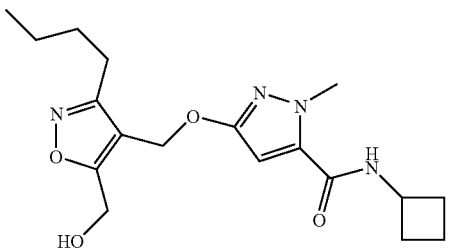

As described for example 112h, 5-(3-butyl-5-hydroxymethyl-isoxazol-4-ylmethoxy)-2-methyl-2H-pyrazole-3-carboxylic acid (50 mg, 0.16 mmol) was converted, using cyclobutylamine instead of 2,2,2-trifluoroethylamine HCl, to the title compound (45 mg, 78%) which was obtained as a colorless oil. MS: m/e=363.3 [M+H]$^+$.

Example 114

1-Methyl-5-(5-methyl-3-pyridin-2-yl-isoxazol-4-ylmethoxy)-1H-pyrazole-3-carboxylic acid ((S)-2-hydroxy-1-methyl-ethyl)-amide

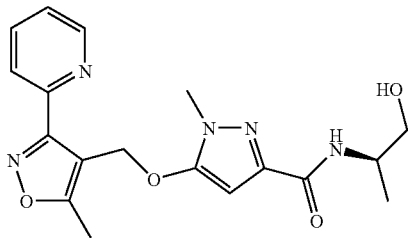

a) (E)-2-(N-Methyl-hydrazino)-but-2-enedioic acid dimethyl ester

To a solution of dimethylacetylene dicarboxylate (50.0 g, 344.8 mmol) in diethylether (1 L) under argon at 0° C. was added a solution of methylhydrazine (18.52 mL, 344.8 mL) in diethylether (100 mL) and the resulting mixture stirred for 2 h. The precipitate was filtered off, dissolved in ethanol (300 mL) at 50° C. and then the solution cooled to −20° C. whereupon the solid was filtered off and dried to afford the title compound (46.8 g, 72%) as a light yellow solid. MS: m/e=189.3 [M+H]$^+$.

b) 5-Hydroxy-1-methyl-1H-pyrazole-3-carboxylic acid methyl ester

To a solution of (E)-2-(N-methyl-hydrazino)-but-2-enedioic acid dimethyl ester (12.2 g, 65 mmol) in xylene (65 mL) was added para-toluenesulfonic acid (0.9 g, 4.7 mmol) and the resulting mixture heated at reflux for 6 h. After cooling to room temperature the mixture was stirred overnight and the resulting solid was filtered off and dissolved in ethyl acetate and the organic extract washed with sodium hydrogen carbonate, brine, dried over sodium sulfate, filtered and concentrated to afford the title compound (7.49, 74%) as a light brown solid after trituration with diisopropylether. MS: m/e=157.2 [M+H]$^+$.

c) 1-Methyl-5-(5-methyl-3-pyridin-2-yl-isoxazol-4-ylmethoxy)-1H-pyrazole-3-carboxylic acid methyl ester To a stirred solution of 5-hydroxy-1-methyl-1H-pyrazole-3-carboxylic acid methyl ester (400 mg, 2.6 mmol) and (5-methyl-3-pyridin-2-yl-isoxazol-4-yl)-methanol (500 mg, 2.6 mmol) in THF (10 mL) at 5° C. under argon was added triphenylphosphine (862 mg, 3.3 mmol), then diethyl azodicarboxylate (573 mg, 3.3 mmol) was added dropwise. The reaction mixture was warmed to room temperature and stirred overnight. The reaction mixture was then evaporated. Purification by chromatography (silica, dichloromethane:methanol=9:1) then purification using a 5×50 cm Chiralpak AD column at room temperature using an isopropanol:heptane (2:8) mobile phase with UV detection at 220 nM afforded the title compound (400 mg, 48%) as a white solid. MS: m/e=328.3 [M+H]$^+$.

d) 1-Methyl-5-(5-methyl-3-pyridin-2-yl-isoxazol-4-ylmethoxy)-1H-pyrazole-3-carboxylic acid ((S)-2-hydroxy-1-methyl-ethyl)-amide To a solution of 1-methyl-5-(5-methyl-3-pyridin-2-yl-isoxazol-4-ylmethoxy)-1H-pyrazole-3-carboxylic acid methyl ester (80 mg, 0.24 mmol) and L-alaninol (24 mg, 0.32 mmol) in toluene (1 mL) was added 1,5,7-triazabicyclo[4.4.0]dec-5-ene (14 mg, 0.1 mmol) and the reaction was stirred at room temperature under argon overnight. The mixture was evaporated and purification by chromatography (silica, dichloromethane:methanol=100:0 to 9:1) afforded the title compound (87 mg, 96%) which was obtained as a colorless oil. MS: m/e=372.2 [M+H]$^+$.

Example 115

1-Methyl-5-(5-methyl-3-pyridin-2-yl-isoxazol-4-ylmethoxy)-1H-pyrazole-3-carboxylic acid isopropylamide

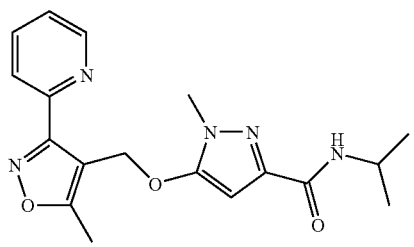

As described for example 1b, 1-methyl-5-(5-methyl-3-pyridin-2-yl-isoxazol-4-ylmethoxy)-1H-pyrazole-3-carboxylic acid methyl ester (70 mg, 0.21 mmol), instead of 5-(5-methyl-3-phenyl-isoxazol-4-ylmethoxy)-2H-pyrazole-3-carboxylic acid methyl ester, was converted, using isopropylamine instead of morpholine, to the title compound (66 mg, 87%) which was obtained as a colorless oil. MS: m/e=356.2 [M+H]$^+$.

Example 116

1-Methyl-5-(5-methyl-3-pyridin-2-yl-isoxazol-4-ylmethoxy)-1H-pyrazole-3-carboxylic acid (tetrahydro-pyran-4-yl)-amide

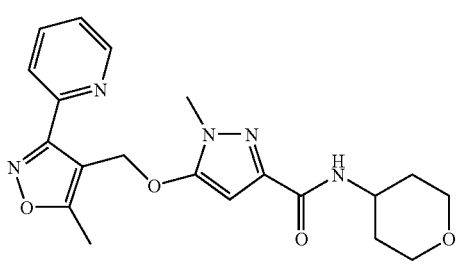

As described for example 115, 1-methyl-5-(5-methyl-3-pyridin-2-yl-isoxazol-4-ylmethoxy)-1H-pyrazole-3-carboxylic acid methyl ester (70 mg, 0.21 mmol) was converted, using 4-aminotetrahydropyran instead of isopropylamine, to the title compound (76 mg, 90%) which was obtained as a colorless oil. MS: m/e=398.2 [M+H]$^+$.

Example 117

5-[3-(5-Fluoro-pyridin-2-yl)-5-methyl-isoxazol-4-ylmethoxy]-1-methyl-1H-pyrazole-3-carboxylic acid ((S)-2-hydroxy-1-methyl-ethyl)-amide

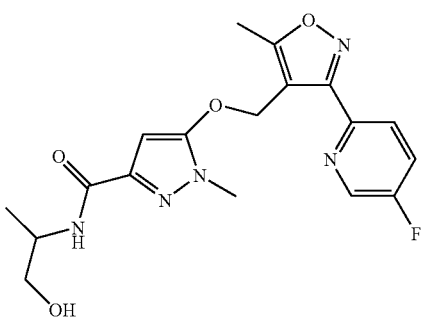

a) 5-[3-(5-Fluoro-pyridin-2-yl)-5-methyl-isoxazol-4-ylmethoxy]-1-methyl-1H-pyrazole-3-car-boxylic acid methyl ester As described for example 114c, [3-(5-fluoro-pyridin-2-yl)-5-methyl-isoxazol-4-yl]-methanol (500 mg, 2.4 mmol), instead of (5-methyl-3-pyridin-2-yl-isoxazol-4-yl)-methanol, was converted, to the title compound (410 mg, 49%) which was obtained as a white solid.
MS: m/e=347.1 [M+H]$^+$.

b) 5-[3-(5-Fluoro-pyridin-2-yl)-5-methyl-isoxazol-4-ylmethoxy]-1-methyl-1H-pyrazole-3-car-boxylic acid ((S)-2-hydroxy-1-methyl-ethyl)-amide As described for example 114d, 5-[3-(5-fluoro-pyridin-2-yl)-5-methyl-isoxazol-4-ylmethoxy]-1-methyl-1H-pyrazole-3-carboxylic acid methyl ester (100 mg, 0.29 mmol), instead of 1-methyl-5-(5-methyl-3-pyridin-2-yl-isoxazol-4-ylmethoxy)-1H-pyrazole-3-carboxylic acid methyl ester, was converted, to the title compound (66 mg, 59%) which was obtained as a colorless oil. MS: m/e=390.1 [M+H]$^+$.

Example 118

5-[(E)-2-(5-Methyl-3-phenyl-isoxazol-4-yl)-vinyl]-2H-pyrazole-3-carboxylic acid iso-propylamide

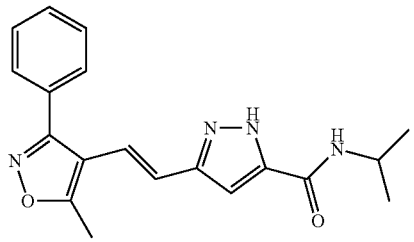

a) 5-Methyl-3-phenyl-isoxazole-4-carbaldehyde

To a stirred solution of pyridinium chlorochromate (19.4 g, 90.0 mmol) and anhydrous magnesium sulfate (36 g) in dichloromethane (100 mL) was added a solution of (5-methyl-3-phenyl-4-isoxazolyl)methanol (14.0 g, 74.0 mmol) in dichloromethane (50 mL) and the resulting solution stirred under argon for 2 h. The solution was then dissolved in diethylether (100 mL), filtered through silica and concentrated to give a viscous brown oil. Purification by chromatography (silica, heptane:ethyl acetate 9:1 to 3:2) afforded the title compound (10.5 g, 76%) which was obtained as a white solid. MS: m/e=188.2 [M+H]$^+$.

b) 4-(2,2-Dibromo-vinyl)-5-methyl-3-phenyl-isoxazole

To a stirred solution of 5-methyl-3-phenyl-isoxazole-4-carbaldehyde (5.20 g, 27.8 mmol) was added tetrabromomethane (12.9 g, 38.9 mmol) and then triphenylphosphine (14.57 g, 55.5 mmol) and the resulting mixture stirred under argon for 2 h at 0° C. The solution was concentrated to approximately 90 mL and the resulting precipitate filtered, washed with dichloromethane and discarded. This was repeated until the majority of the triphenylphospine oxide and bromide was removed. Purification by chromatography (silica, heptane:ethyl acetate 9:1 to 2:3) afforded the title compound (7.9 g, 83%) which was obtained as a colorless oil. MS: m/e=344.0 [M+H]$^+$.

c) 4-Ethynyl-5-methyl-3-phenyl-isoxazole

To a stirred solution of 4-(2,2-dibromo-vinyl)-5-methyl-3-phenyl-isoxazole (1.0 g, 2.92 mmol) in THF (6 mL) was added dropwise isopropylmagnesium chloride solution (2M in THF, 2.92 mL, 5.84 mmol) and the resulting solution stirred under argon for 1 h at 0° C. Saturated aqueous ammonium chloride (15 mL) was added and the resulting mixture extracted with ethyl acetate (3×25 mL). The combined organic layers were then dried over sodium sulfate, filtered and concentrated. Purification by chromatography (silica, heptane) afforded the title compound (486 mg, 91%) which was obtained as a yellow oil. MS: m/e=184.2 [M+H]$^+$.

d) 5-[(E)-2-(5-Methyl-3-phenyl-isoxazol-4-yl)-vinyl]-2H-pyrazole-3-carboxylic acid iso-propylamide Step A: A stirred solution of 4-ethynyl-5-methyl-3-phenyl-isoxazole (400 mg, 2.2 mmol), tributyltin hydride (1.3 g, 4.0 mmol) and AIBN (5 mg) was heated under reflux until all starting material was consumed. After cooling to room temperature, the mixture was concentrated. Purification by chromatography (silica, heptane:ethyl acetate 1:0 to 9:1) afforded the vinylstannane product (595 mg, 57%) which was obtained as a colorless oil. MS: m/e=475.3 [M+H]$^+$.

Step B: To a stirred solution of vinylstannane (300 mg, 0.63 mmol) in chloroform (60 mL) at 0° C. was added dropwise a solution of iodine (321 mg, 1.26 mmol) in chloroform (15 mL) until a pink solution resulted (approx 9 mL used). The solution was then washed with a 10% solution of sodium hydrogen sulfite (20 mL), dried over sodium sulfate, filtered and concentrated. Purification by chromatography (silica, heptane:ethyl acetate 1:0 to 9:1) afforded the vinyliodide product (210 mg, 92%) which was obtained as a colorless oil. MS: m/e=312.2 [M+H]$^+$.

Step C: To a stirred solution of the vinyliodide (200 mg, 0.64 mmol), ethyl 3(5)-tributylstannylpyrazole-5(3)-carboxylate (prepared according to Heterocycles, 1992, 33, 813) (414 mg, 0.96 mmol), lithium chloride (82 mg, 1.93 mmol) and copper(I) iodide (61 mg, 0.32 mmol) in tetrahydrofuran (20 mL) was added tetrakis(triphenylphosphonium)palladium(0) (15 mg) and the resulting solution stirred under argon for 16 h at 60° C. After cooling to room temperature, the mixture was concentrated. Purification by chromatography (silica, heptane:ethyl acetate 1:0 to 9:1) afforded the intermediate product (140 mg, 67%) which was obtained as a colorless oil. MS: m/e=324.3 [M+H]$^+$.

Step D: As described for example 1b, the intermediate ester step C (70 mg, 0.21 mmol), instead of 5-(5-methyl-3-phenyl-isoxazol-4-ylmethoxy)-2H-pyrazole-3-carboxylic acid methyl ester, was converted, using isopropylamine instead of morpholine, to the title compound (13 mg, 18%) which was obtained as a white solid. MS: m/e=337.4 [M+H]$^+$.

Example 119

5-[(Z)-2-(5-Methyl-3-phenyl-isoxazol-4-yl)-vinyl]-2H-pyrazole-3-carboxylic acid iso-propylamide

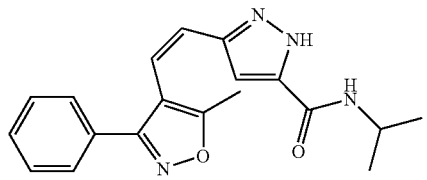

As described for example 1b, the intermediate ester (example 118d step C, 70 mg, 0.21 mmol), instead of 5-(5-methyl-3-phenyl-isoxazol-4-ylmethoxy)-2H-pyrazole-3-carboxylic acid methyl ester, was converted, using isopropylamine instead of morpholine, to the title compound (5 mg, 5.8%) which was obtained as a white solid from a small amount of the (Z-ester) present in the reaction sequence. MS: m/e=337.4 [M+H]$^+$.

Example 120

5-{(Z)-2-[3-(4-Fluoro-phenyl)-5-methyl-isoxazol-4-yl]-vinyl}-2-methyl-2H-pyrazole-3-carboxylic acid isopropylamide

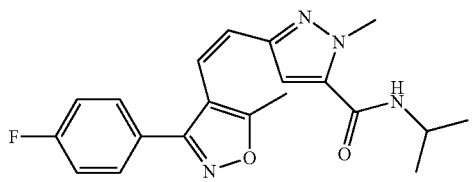

Step 1: A solution of 4-chloromethyl-3-(4-fluoro-phenyl)-5-methyl-isoxazole (5.0 g, 22.16 mmol) and triphenylphosphine (6.38 g, 24.36 mmol) in toluene (35 mL) was heated under reflux for 20 h. After cooling to room temperature the mixture was cooled and the solid was washed with diethyl-ether (150 mL) and dried to afford the chloro-phosphonium salt (10 g, 93%).

Step 2: To a solution of the chloro-phosphonium salt (2.9 g, 5.95 mmol) in dry THF (20 mL) at −78° C. was added LiHMDS (6.54 mL, 6.54 mmol) and the resulting mixture stirred at −78° C. for 1 h. The mixture was then warmed up to room temperature and a solution of 1H-pyrazole-5-carboxylic acid, 3-formyl-1-methyl-methyl ester (1.0 g, 5.95 mmol) in dry THF (15 mL) was added and the resulting mixture stirred for 2 h. Saturated aqueous ammonium chloride (15 mL) was added and the resulting mixture extracted with ethyl acetate (2×40 mL). The combined organic layers were then dried over sodium sulfate, filtered and concentrated. Purification by chromatography (silica, heptane:ethyl acetate 1:0 to 9:1) afforded, two products, 5-{(Z)-2-[3-(4-fluoro-phenyl)-5-methyl-isoxazol-4-yl]-vinyl}-2-methyl-2H-pyrazole-3-carboxylic acid methyl ester (400 mg) and ethyl 5-{(E)-2-[3-(4-fluoro-phenyl)-5-methyl-isoxazol-4-yl]-vinyl}-2-methyl-2H-pyrazole-3-carboxylic acid methyl ester (2.15 g) as off white solids.

Step 3: To a solution of 5-{(Z)-2-[3-(4-fluoro-phenyl)-5-methyl-isoxazol-4-yl]-vinyl}-2-methyl-2H-pyrazole-3-carboxylic acid methyl ester (6.29 mmol) in THF (14 mL) was added lithium hydroxide monohydrate (37.79 mmol) in water (18 mL) and the resulting mixture stirred for 12 h. After evaporation the mixture was diluted with water (10 mL) and citric acid (10%) and extracted with ethyl acetate (2×80 mL). The combined extracts were then dried with sodium sulfate, filtered and evaporated to afford 5-{(Z)-2-[3-(4-fluoro-phenyl)-5-methyl-isoxazol-4-yl]-vinyl}-2-methyl-2H-pyrazole-3-carboxylic acid (mg, 85%) as a white solid. MS: m/e=328.2 [M+H]$^+$.

Step 4: To a solution of 5-{(Z)-2-[3-(4-fluoro-phenyl)-5-methyl-isoxazol-4-yl]-vinyl}-2-methyl-2H-pyrazole-3-carboxylic acid (0.3 mmol) in DMF (7 mL) was added 1-hydroxybenzotriazole hydrate (0.45 mmol), N-ethyldiisopropylamine (1.2 mmol), N-(3-dimethylaminopropyl)-N'-ethylcarbodiimidazole hydrochloride 0.45 mmol) and isopropylamine (27.8 mg, 0.45 mmol) and the resulting mixture stirred overnight at room temperature. The reaction mixture was then poured into aqueous sodium chloride (saturated) and the mixture was extracted with ethyl acetate. The combined organic layers were then washed with water and saturated sodium hydrogen carbonate solution and then dried over sodium sulfate, filtered and evaporated. Concentration and purification by preparative HPLC afforded the title compound (35 mg, 28%) as an off white gum. MS: m/e=369.2 [M+H]$^+$.

Example 121

5-{(Z)-2-[3-(4-Fluoro-phenyl)-5-methyl-isoxazol-4-yl]vinyl}-2-methyl-2H-pyrazole-3-carboxylic acid (2-hydroxy-1-methyl-ethyl)-amide

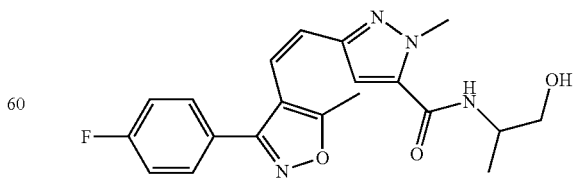

As described for example 120 (step 4), 5-{(Z)-2-[3-(4-fluoro-phenyl)-5-methyl-isoxazol-4-yl]-vinyl}-2-methyl-2H-pyrazole-3-carboxylic acid (0.3 mmol), was converted, using 2-hydroxy-1-methylethylamine instead of isopropy-

Example 122

5-{(E)-2-[3-(4-Fluoro-phenyl)-5-methyl-isoxazol-4-yl]vinyl}-2-methyl-2H-pyrazole-3-carboxylic acid isopropylamide

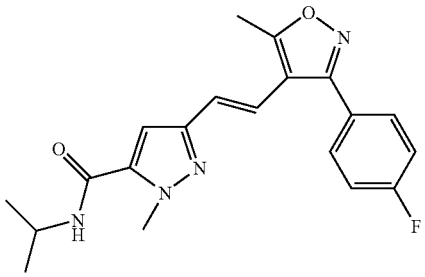

To a solution of 5-{(E)-2-[3-(4-fluoro-phenyl)-5-methyl-isoxazol-4-yl]-vinyl}-2-methyl-2H-pyrazole-3-carboxylic acid (0.3 mmol) in DMF (7 mL) was added 1-hydroxybenzotriazole hydrate (0.45 mmol), N-ethyldiisopropylamine (1.2 mmol), N-(3-dimethylaminopropyl)-N'-ethylcarbodiimidazole hydrochloride (0.45 mmol) and isopropylamine (0.45 mmol) and the resulting mixture stirred overnight at room temperature. The reaction mixture was then poured into aqueous sodium chloride (saturated) and the mixture was extracted with ethyl acetate. The combined organic layers were then washed with water and saturated sodium hydrogen carbonate solution and then dried over sodium sulfate, filtered and evaporated. Concentration and purification by preparative HPLC afforded the title compound (6.5 mg, 11%) as a white solid. MS: m/e=369.2 [M+H]$^+$.

Example 123

5-{(E)-2-[3-(4-Fluoro-phenyl)-5-methyl-isoxazol-4-yl]vinyl}-2-methyl-2H-pyrazole-3-carboxylic acid ethylamide

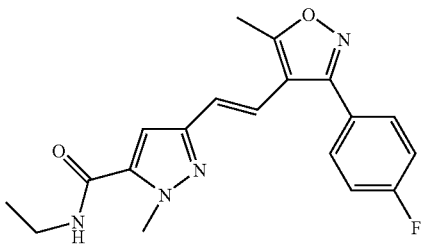

As described for example 122, 5-{(E)-2-[3-(4-fluoro-phenyl)-5-methyl-isoxazol-4-yl]-vinyl}-2-methyl-2H-pyrazole-3-carboxylic acid was converted, using ethylamine instead of isopropylamine, to the title compound (30 mg, 74%) which was obtained as a colorless gum. MS: m/e=355.0 [M+H]$^+$.

Example 124

5-{(E)-2-[3-(4-Fluoro-phenyl)-5-methyl-isoxazol-4-yl]vinyl}-2-methyl-2H-pyrazole-3-carboxylic acid (2-hydroxy-2-methyl-propyl)-amide

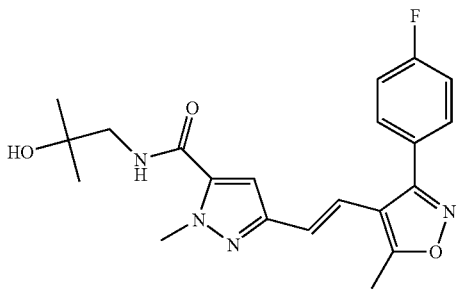

As described for example 122, 5-{(E)-2-[3-(4-fluoro-phenyl)-5-methyl-isoxazol-4-yl]-vinyl}-2-methyl-2H-pyrazole-3-carboxylic acid was converted, using 2-hydroxy-2-methyl-propylamine instead of isopropylamine, to the title compound (9.4 mg, 28%) which was obtained as a white solid. MS: m/e=399.2 [M+H]$^+$.

Example 125

5-{(E)-2-[3-(4-Fluoro-phenyl)-5-methyl-isoxazol-4-yl]vinyl}-2-methyl-2H-pyrazole-3-carboxylic acid (tetrahydro-pyran-4-yl)-amide

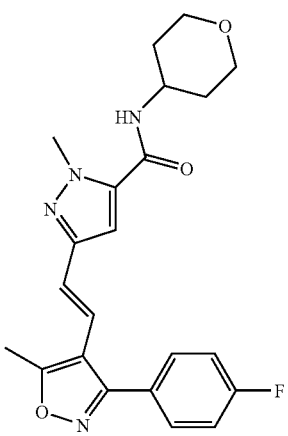

As described for example 122, 5-{(E)-2-[3-(4-fluoro-phenyl)-5-methyl-isoxazol-4-yl]-vinyl}-2-methyl-2H-pyrazole-3-carboxylic acid was converted, using 4-aminotetrahydropyran instead of isopropylamine, to the title compound (13 mg, 32%) which was obtained as a white solid. MS: m/e=411.2 [M+H]$^+$.

Example 126

5-{(E)-2-[3-(4-Fluoro-phenyl)-5-methyl-isoxazol-4-yl]vinyl}-2-methyl-2H-pyrazole-3-carboxylic acid amide

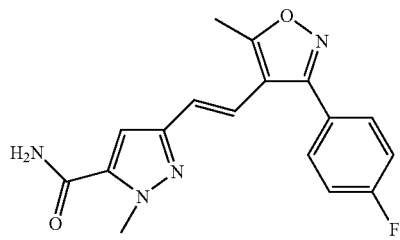

As described for example 122, 5-{(E)-2-[3-(4-fluoro-phenyl)-5-methyl-isoxazol-4-yl]-vinyl}-2-methyl-2H-pyrazole-3-carboxylic acid was converted, using ammonia instead of isopropylamine, to the title compound (19 mg, 60%) which was obtained as a white solid. MS: m/e=327.2 [M+H]$^+$.

Example 127

(1,1-Dioxo-1,6-thiomorpholin-4-yl)-(5-{(E)-2-[3-(4-fluoro-phenyl)-5-methyl-isoxazol-4-yl]-vinyl}-2-methyl-2H-pyrazol-3-yl)-methanone

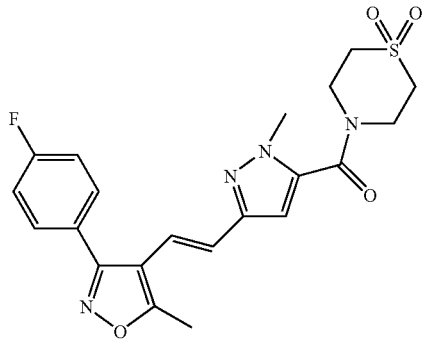

As described for example 122, 5-{(E)-2-[3-(4-fluoro-phenyl)-5-methyl-isoxazol-4-yl]-vinyl}-2-methyl-2H-pyrazole-3-carboxylic acid was converted, using thiomormorpholine S,S-dioxide instead of isopropylamine, to the title compound (37 mg, 74%) which was obtained as a white solid. MS: m/e=445.2 [M+H]$^+$.

Example 128

5-{(E)-2-[3-(4-Fluoro-phenyl)-5-methyl-isoxazol-4-yl]vinyl}-2-methyl-2H-pyrazole-3-carboxylic acid (2,2,2-trifluoro-ethyl)-amide

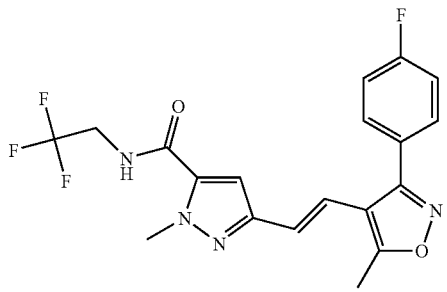

As described for example 122, 5-{(E)-2-[3-(4-fluoro-phenyl)-5-methyl-isoxazol-4-yl]-vinyl}-2-methyl-2H-pyrazole-3-carboxylic acid was converted, using 2,2,2-trifluoroethylamine instead of isopropylamine, to the title compound (30 mg, 64%) which was obtained as a white solid. MS: m/e=409.0 [M+H]$^+$.

Example 129

(5-{(E)-2-[3-(4-Fluoro-phenyl)-5-methyl-isoxazol-4-yl]vinyl}-2-methyl-2H-pyrazol-3-yl)-morpholin-4-yl-methanone

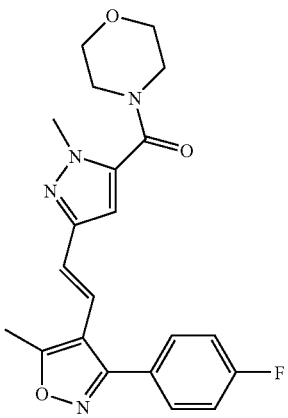

As described for example 122, 5-{(E)-2-[3-(4-fluoro-phenyl)-5-methyl-isoxazol-4-yl]-vinyl}-2-methyl-2H-pyrazole-3-carboxylic acid was converted, using morpholine instead of isopropylamine, to the title compound (8.3 mg, 25%) which was obtained as a white solid. MS: m/e=397.2 [M+H]$^+$.

Example 130

5-{(E)-2-[3-(4-Fluoro-phenyl)-5-methyl-isoxazol-4-yl]vinyl}-2-methyl-2H-pyrazole-3-carboxylic acid (2-hydroxy-1-methyl-ethyl)-amide

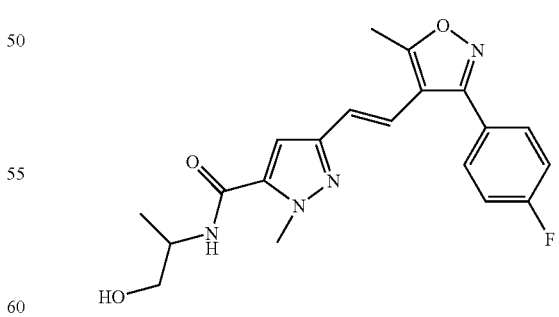

As described for example 122, 5-{(E)-2-[3-(4-fluoro-phenyl)-5-methyl-isoxazol-4-yl]-vinyl}-2-methyl-2H-pyrazole-3-carboxylic acid was converted, using 2-hydroxy-1-methyl-ethylamine instead of isopropylamine, to the title compound (6.7 mg, 17%) which was obtained as an off white solid. MS: m/e=385.2 [M+H]$^+$.

Example 131

(1,1-Dioxo-1,6-thiomorpholin-4-yl)-(5-{(E)-2-[3-(4-fluoro-phenyl)-5-methyl-isoxazol-4-yl]-vinyl}-2H-pyrazol-3-yl)-methanone

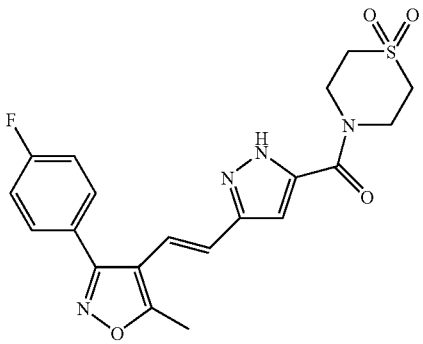

Step 1: To a solution of the chloro-phosphonium salt (2.9 g, 5.95 mmol) in dry THF (20 mL) at −78° C. was added LiHMDS (6.54 mL, 6.54 mmol) and the resulting mixture stirred at −78° C. for 1 h. The mixture was then warmed up to room temperature and a solution of 1H-pyrazole-5-carboxylic acid, 3-formyl-1-methyl-, methyl ester (5.95 mmol) in dry THF (15 mL) was added and the resulting mixture stirred for 2 h. Saturated aqueous ammonium chloride (15 mL) was added and the resulting mixture extracted with ethyl acetate (2×40 mL). The combined organic layers were then dried over sodium sulfate, filtered and concentrated. Purification by chromatography (silica, heptane:ethyl acetate 1:0 to 9:1) afforded, two products in a ~1:1 ratio, 5-{(E and Z)-2-[3-(4-fluoro-phenyl)-5-methyl-isoxazol-4-yl]-vinyl}-2H-pyrazole-3-carboxylic acid methyl ester (55%).

Step 2: As described for example 120 (step 3), 5-{(E)-2-[3-(4-fluoro-phenyl)-5-methyl-isoxazol-4-yl]-vinyl}-2H-pyrazole-3-carboxylic acid methyl ester was converted to 5-{(E)-2-[3-(4-fluoro-phenyl)-5-methyl-isoxazol-4-yl]-vinyl}-2H-pyrazole-3-carboxylic acid (165 mg, 93% which was obtained as an off white solid. MS: m/e=314.2 [M+H]$^+$.

Step 3: As described for example 122, 5-{(E)-2-[3-(4-fluoro-phenyl)-5-methyl-isoxazol-4-yl]-vinyl}-2H-pyrazole-3-carboxylic acid instead of 5-{(E)-2-[3-(4-fluoro-phenyl)-5-methyl-isoxazol-4-yl]-vinyl}-2-methyl-2H-pyrazole-3-carboxylic acid was converted, using thiomorpholine S,S-dioxide instead of isopropylamine, to the title compound (8.8 mg, 22%) which was obtained as an off white solid. MS: m/e=431.2 [M+H]$^+$.

Example 132

(5-{(E)-2-[3-(4-Fluoro-phenyl)-5-methyl-isoxazol-4-yl]vinyl}-2H-pyrazol-3-yl)-morpholin-4-yl-methanone

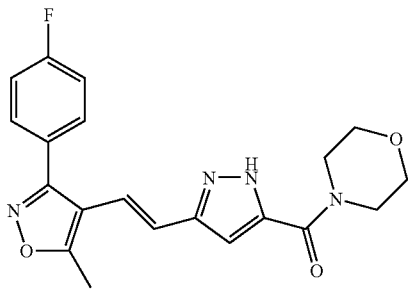

As described for example 131 (step 3), 5-{(E)-2-[3-(4-fluoro-phenyl)-5-methyl-isoxazol-4-yl]-vinyl}-2H-pyrazole-3-carboxylic acid was converted, using morpholine instead of thiomorpholine S,S-dioxide, to the title compound (18 mg, 33%) which was obtained as an off white solid. MS: m/e=383.2 [M+H]$^+$.

Example 133

5-{(E)-2-[3-(4-Fluoro-phenyl)-5-methyl-isoxazol-4-yl]vinyl}-2H-pyrazole-3-carboxylic acid (2,2,2-trifluoro-ethyl)-amide

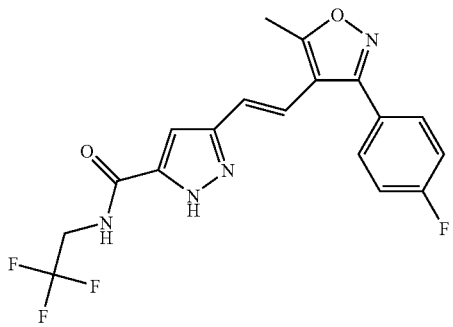

As described for example 132, 5-{(E)-2-[3-(4-fluoro-phenyl)-5-methyl-isoxazol-4-yl]-vinyl}-2H-pyrazole-3-carboxylic acid was converted, using 2,2,2-trifluoroethylamine instead of morpholine, to the title compound (18 mg, 56%) which was obtained as an off white solid. MS: m/e=395.4 [M+H]$^+$.

Example 134

5-{(E)-2-[3-(4-Fluoro-phenyl)-5-methyl-isoxazol-4-yl]-vinyl}-2H-pyrazole-3-carboxylic acid isopropylamide

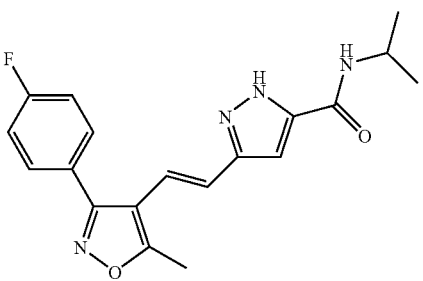

As described for example 132, 5-{(E)-2-[3-(4-fluoro-phenyl)-5-methyl-isoxazol-4-yl]-vinyl}-2H-pyrazole-3-carboxylic acid was converted, using isopropylamine instead of morpholine, to the title compound (28 mg, 53%) which was obtained as an off white solid. MS: m/e=355.2 [M+H]$^+$.

Example 135

(5-{(E)-2-[3-(4-Fluoro-phenyl)-5-methyl-isoxazol-4-yl]-vinyl}-2-methyl-2H-pyrazol-3-yl)-(2-oxa-6-aza-spiro[3.3]hept-6-yl)-methanone

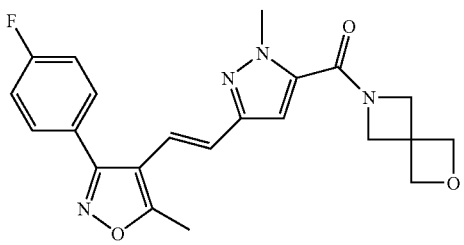

As described for example 122, 5-{(E)-2-[3-(4-fluoro-phenyl)-5-methyl-isoxazol-4-yl]-vinyl}-2-methyl-2H-pyrazole-3-carboxylic acid was converted, using 2-oxa-6-azonia-spiro[3.3]heptane oxalate salt instead of isopropylamine, to the title compound (24 mg, 70%) which was obtained as an off white solid. MS: m/e=409.0 [M+H]⁺.

Example 136

5-{(E)-2-[3-(4-Fluoro-phenyl)-5-methyl-isoxazol-4-yl]vinyl}-2H-pyrazole-3-carboxylic acid (2-hydroxy-1-methyl-ethyl)-amide

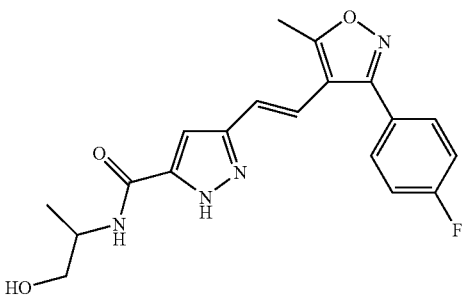

As described for example 132, 5-{(E)-2-[3-(4-fluoro-phenyl)-5-methyl-isoxazol-4-yl]-vinyl}-2H-pyrazole-3-carboxylic acid was converted, using 4-aminotetrahydropyran instead of morpholine, to the title compound (20 mg, 47%) which was obtained as a light brown solid. MS: m/e=397.2 [M+H]⁺.

Example 137

(5-{(E)-2-[3-(4-Fluoro-phenyl)-5-methyl-isoxazol-4-yl]vinyl}-2H-pyrazol-3-yl)-(2-oxa-6-aza-spiro[3.3]hept-6-yl)-methanone

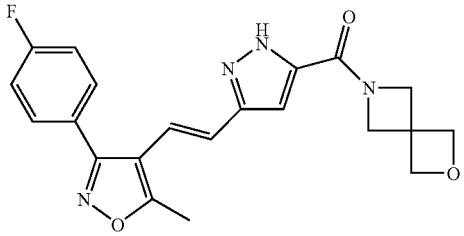

As described for example 132, 5-{(E)-2-[3-(4-fluoro-phenyl)-5-methyl-isoxazol-4-yl]-vinyl}-2H-pyrazole-3-carboxylic acid was converted, using 2-oxa-6-azonia-spiro[3.3]heptane oxalate salt instead of morpholine, to the title compound (11 mg, 37%) which was obtained as an off white solid. MS: m/e=395.4 [M+H]⁺.

Example 138

5-{(E)-2-[3-(4-Fluoro-phenyl)-5-methyl-isoxazol-4-yl]vinyl}-2H-pyrazole-3-carboxylic acid (2-hydroxy-1,1-dimethyl-ethyl)-amide

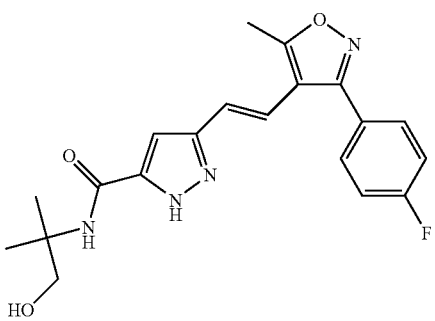

As described for example 132, 5-{(E)-2-[3-(4-fluoro-phenyl)-5-methyl-isoxazol-4-yl]-vinyl}-2H-pyrazole-3-carboxylic acid was converted, using 2-hydroxy-1,1-dimethyl-ethylamine instead of morpholine, to the title compound (11 mg, 36%) which was obtained as an off white solid. MS: m/e=385.2 [M+H]⁺.

Example 139

5-{(E)-2-[3-(4-Fluoro-phenyl)-5-methyl-isoxazol-4-yl]-vinyl}-2H-pyrazole-3-carboxylic acid (2-hydroxy-1-methyl-ethyl)-amide

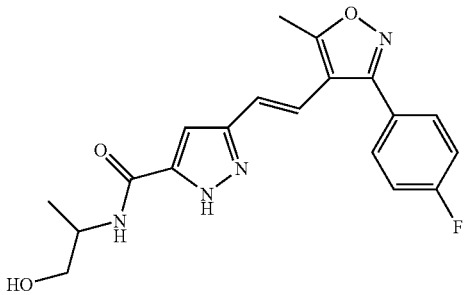

As described for example 132, 5-{(E)-2-[3-(4-fluoro-phenyl)-5-methyl-isoxazol-4-yl]-vinyl}-2H-pyrazole-3-carboxylic acid was converted, using 2-hydroxy-1-methylethylamine instead of morpholine, to the title compound (14 mg, 41%) which was obtained as an off white solid. MS: m/e=371.2 [M+H]⁺.

Example 140

5-{(E)-2-[3-(4-Fluoro-phenyl)-5-methyl-isoxazol-4-yl]vinyl}-2H-pyrazole-3-carboxylic acid (2-hydroxy-2-methyl-propyl)-amide

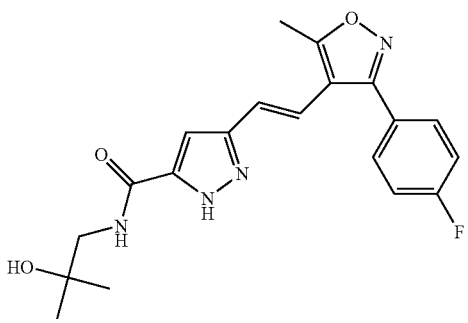

As described for example 132, 5-{(E)-2-[3-(4-fluoro-phenyl)-5-methyl-isoxazol-4-yl]-vinyl}-2H-pyrazole-3-carboxylic acid was converted, using 2-hydroxy-2-methyl-propylamine instead of morpholine, to the title compound (9.1 mg, 26%) which was obtained as a brown solid. MS: m/e=385.2 [M+H]$^+$.

Example 141

5-{(E)-2-[3-(4-Fluoro-phenyl)-5-methyl-isoxazol-4-yl]vinyl}-2H-pyrazole-3-carboxylic acid ethylamide

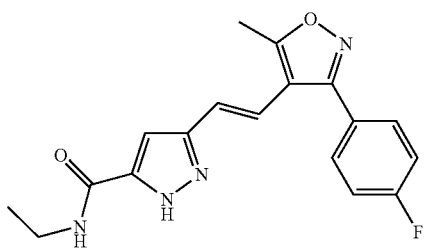

As described for example 132, 5-{(E)-2-[3-(4-fluoro-phenyl)-5-methyl-isoxazol-4-yl]-vinyl}-2H-pyrazole-3-carboxylic acid was converted, using ethylamine instead of morpholine, to the title compound (8.9 mg, 33%) which was obtained as an off white solid. MS: m/e=341.0 [M+H]$^+$.

Example 142

5-{(E)-2-[3-(4-Fluoro-phenyl)-5-methyl-isoxazol-4-yl]vinyl}-2H-pyrazole-3-carboxylic acid amide

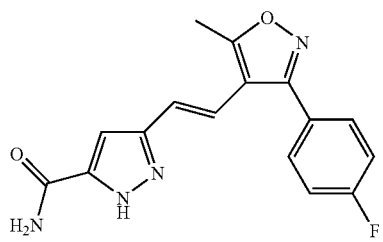

As described for example 132, 5-{(E)-2-[3-(4-fluoro-phenyl)-5-methyl-isoxazol-4-yl]-vinyl}-2H-pyrazole-3-carboxylic acid was converted, using ammonia instead of morpholine, to the title compound (12 mg, 32%) which was obtained as an off white solid. MS: m/e=313.2 [M+H]$^+$.

Example 143

5-{(E)-2-[3-(4-Fluoro-phenyl)-5-methyl-isoxazol-4-yl]vinyl}-2-methyl-2H-pyrazole-3-carboxylic acid (2-hydroxy-1,1-dimethyl-ethyl)-amide

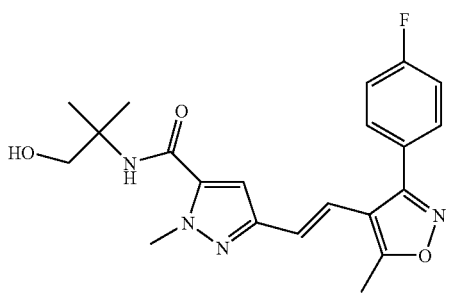

As described for example 132, 5-{(E)-2-[3-(4-fluoro-phenyl)-5-methyl-isoxazol-4-yl]-vinyl}-2H-pyrazole-3-carboxylic acid was converted, using 2-hydroxy-1,1-dimethyl-ethylamine instead of morpholine, to the title compound (5.7 mg, 70%) which was obtained as an off white solid. MS: m/e=399.2 [M+H]$^+$.

Example 144

5-{[3-(4-Fluoro-phenyl)-5-methyl-isoxazol-4-ylmethyl]-amino}-2-methyl-2H-pyrazole-3-carboxylic acid (2-hydroxy-2-methyl-propyl)-amide

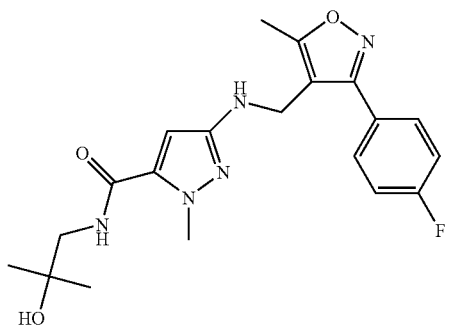

Step 1: To a solution of 3-(4-fluoro-phenyl)-5-methyl-isoxazole-4-carbaldehyde (1.32 g, 6.44 mmol) and the 5-amino-2-methyl-2H-pyrazole-3-carboxylic acid methyl ester hydrochloride (1.0 g, 6.44 mmol) in methanol (30 mL) at room temperature was added potassium carbonate (890 mg, 6.44 mmol) and then the reaction mixture was heated under reflux for 2 h. After cooling to room temperature sodium borohydride (487 mg, 12.9 mmol) was added and then the mixture heated under reflux for 12 h. The mixture was then cooled and treated with hydrochloric acid (1 N, 10 drops) and evaporated. Water was then added and the mixture extracted with ethyl acetate. The aqueous layer was acidified with hydrochloric acid (2 N) and then extracted with ethyl acetate. The combined organic extracts were then dried over sodium sulfate, filtered and evaporated to afford 5-{[3-(4-fluoro-phenyl)-5-methyl-isoxazol-4-ylmethyl]-amino}-2-methyl-2H-pyrazole-3-carboxylic acid methyl ester (27%) which was obtained as a white solid.

Step 2: As described for example 152, 5-{[3-(4-fluoro-phenyl)-5-methyl-isoxazol-4-ylmethyl]-amino}-2-methyl-2H-pyrazole-3-carboxylic acid methyl ester was converted, to 5-{[3-(4-fluoro-phenyl)-5-methyl-isoxazol-4-ylmethyl]-amino}-2-methyl-2H-pyrazole-3-carboxylic acid which was obtained as an off white solid.

Step 3: To a solution of 5-{[3-(4-fluoro-phenyl)-5-methyl-isoxazol-4-ylmethyl]-amino}-2-methyl-2H-pyrazole-3-carboxylic acid (0.212 mmol) in DMF (5 mL) was added 1-hydroxybenzotriazole hydrate (0.318 mmol), N-ethyldiisopropylamine (0.848 mmol), N-(3-dimethylaminopropyl)-N'-ethylcarbodiimidazole hydrochloride (0.318 mmol) and 2-hydroxy-2-methylpropylamine (0.318 mmol) and the resulting mixture stirred overnight at room temperature. The reaction mixture was then poured into aqueous sodium chloride (saturated) and the mixture was extracted with ethyl acetate. The combined organic layers were then washed with water and saturated sodium hydrogen carbonate solution and then dried over sodium sulfate, filtered and evaporated. Concentration and purification by preparative HPLC afforded the title compound (13 mg, 14%) as an off white solid. MS: m/e=402.2 [M+H]$^+$.

Example 145

5-{[3-(4-Fluoro-phenyl)-5-methyl-isoxazol-4-ylmethyl]-amino}-2-methyl-2H-pyrazole-3-carboxylic acid amide

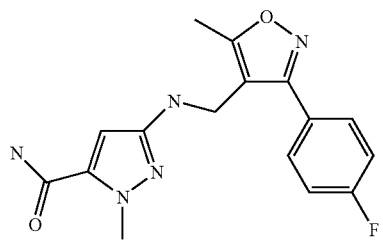

As described for example 144, 5-{[3-(4-fluoro-phenyl)-5-methyl-isoxazol-4-ylmethyl]-amino}-2-methyl-2H-pyrazole-3-carboxylic acid was converted, using ammonia instead of 2-hydroxy-2-methylpropylamine, to the title compound (12 mg, 20%) which was obtained as an off white solid. MS: m/e=330.4 [M+H]$^+$.

Example 146

5-{[3-(4-Fluoro-phenyl)-5-methyl-isoxazol-4-ylmethyl]-amino}-2-methyl-2H-pyrazole-3-carboxylic acid (2,2,2-trifluoro-ethyl)-amide

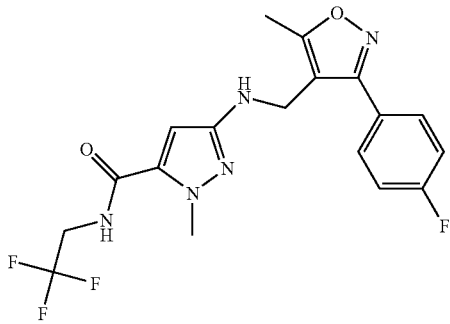

As described for example 144, 5-{[3-(4-fluoro-phenyl)-5-methyl-isoxazol-4-ylmethyl]-amino}-2-methyl-2H-pyrazole-3-carboxylic acid was converted, using 2,2,2-trifluoro-ethylamine instead of 2-hydroxy-2-methylpropylamine, to the title compound (22 mg, 20%) which was obtained as an off white solid. MS: m/e=412.4 [M+H]$^+$.

Example 147

5-{[3-(4-Fluoro-phenyl)-5-methyl-isoxazol-4-ylmethyl]-amino}-2-methyl-2H-pyrazole-3-carboxylic acid (tetrahydro-pyran-4-yl)-amide

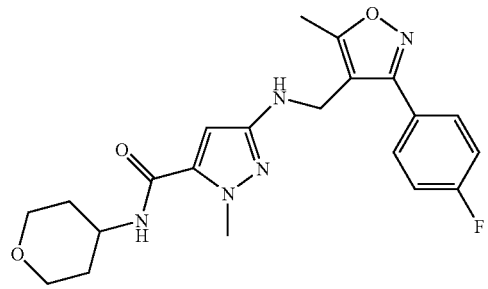

As described for example 144, 5-{[3-(4-fluoro-phenyl)-5-methyl-isoxazol-4-ylmethyl]-amino}-2-methyl-2H-pyrazole-3-carboxylic acid was converted, using 4-amiontetrahydropyran instead of 2-hydroxy-2-methylpropylamine, to the title compound (7.7 mg, 27%) which was obtained as a light yellow solid. MS: m/e=414.2 [M+H]$^+$.

Example 148

5-{[3-(4-Fluoro-phenyl)-5-methyl-isoxazol-4-ylmethyl]-amino}-2-methyl-2H-pyrazole-3-carboxylic acid (3-methyl-oxetan-3-yl)-amide

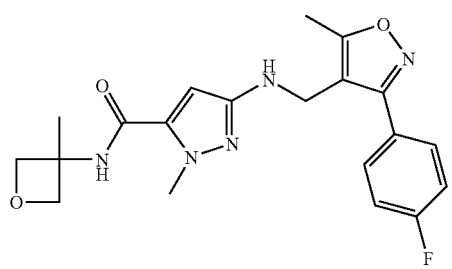

As described for example 144, 5-{[3-(4-fluoro-phenyl)-5-methyl-isoxazol-4-ylmethyl]-amino}-2-methyl-2H-pyrazole-3-carboxylic acid was converted, using 3-methyl-oxetan-3-yl-amine instead of 2-hydroxy-2-methylpropylamine, to the title compound (17 mg, 28%) which was obtained as a white solid. MS: m/e=400.3 [M+H]$^+$.

Example 149

(5-{[3-(4-Fluoro-phenyl)-5-methyl-isoxazol-4-ylmethyl]-amino}-2-methyl-2H-pyrazol-3-yl)-(2-oxa-6-aza-spiro[3.3]hept-6-yl)-methanone

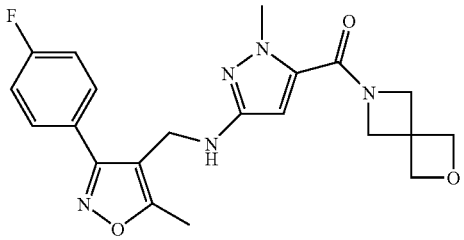

As described for example 144, 5-{[3-(4-fluoro-phenyl)-5-methyl-isoxazol-4-ylmethyl]-amino}-2-methyl-2H-pyrazole-3-carboxylic acid was converted, using 2-oxa-6-azoniaspiro[3.3]heptane oxalate salt instead of 2-hydroxy-2-methylpropylamine, to the title compound (14 mg, 22%) which was obtained as a white solid. MS: m/e=412.4 [M+H]⁺.

Example 150

5-{[3-(4-Fluoro-phenyl)-5-methyl-isoxazol-4-ylmethyl]-amino}-2-methyl-2H-pyrazole-3-carboxylic acid (2-hydroxy-1-methyl-ethyl)-amide

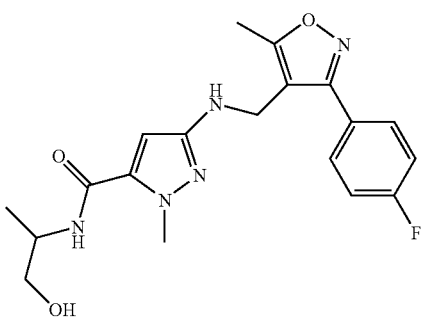

As described for example 144, 5-{[3-(4-fluoro-phenyl)-5-methyl-isoxazol-4-ylmethyl]-amino}-2-methyl-2H-pyrazole-3-carboxylic acid was converted, using 2-hydroxy-1-methylethylamine instead of 2-hydroxy-2-methylpropylamine, to the title compound (22 mg, 42%) which was obtained as a light yellow solid. MS: m/e=388.4 [M+H]⁺.

Example 151

5-{[3-(4-Fluoro-phenyl)-5-methyl-isoxazol-4-ylmethyl]-amino}-2-methyl-2H-pyrazole-3-carboxylic acid isopropylamide

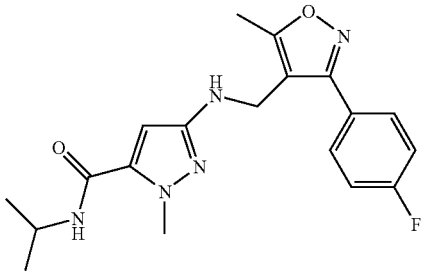

As described for example 144, 5-{[3-(4-fluoro-phenyl)-5-methyl-isoxazol-4-ylmethyl]-amino}-2-methyl-2H-pyrazole-3-carboxylic acid was converted, using isopropylamine instead of 2-hydroxy-2-methylpropylamine, to the title compound (15 mg, 21%) which was obtained as a white solid. MS: m/e=372.2 [M+H]⁺.

Example 152

5-{[3-(4-Fluoro-phenyl)-5-methyl-isoxazol-4-ylmethyl]-amino}-2H-pyrazole-3-carboxylic acid (2-hydroxy-2-methyl-propyl)-amide

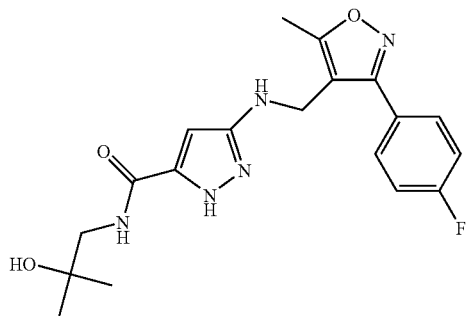

Step 1: To a solution of 3-(4-fluoro-phenyl)-5-methyl-isoxazole-4-carbaldehyde (1.75 g, 8.53 mmol) and the 5-amino-2H-pyrazole-3-carboxylic acid methyl ester hydrochloride (1.2 g, 8.53 mmol) in methanol (70 mL) at room temperature was added molecular sieves (2.5 g) and then after 1 h, acetic acid (6.8 mL, 119.4 mmol) was added. Then sodium cyanoborohydride (1.07 g, 17.1 mmol) was added portionwise and the mixture stirred at room temperature overnight. After evaporation, dichloromethane was added and the mixture washed with sodium hydrogen carbonate (saturated solution). The organic layer was then dried over sodium sulfate, filtered and evaporated. Purification by chromatography (silica, heptane:ethyl acetate 7:3 to 6:4) afforded 5-{[3-(4-fluoro-phenyl)-5-methyl-isoxazol-4-ylmethyl]-amino}-2H-pyrazole-3-carboxylic acid methyl ester (1.2 g, 44%).

Step 2: 5-{[3-(4-Fluoro-phenyl)-5-methyl-isoxazol-4-ylmethyl]-amino}-2H-pyrazole-3-carboxylic acid methyl ester (900 mg, 2.72 mmol) was then dissolved in THF (20 mL) and lithium hydroxide monohydrate (686 mg, 16.34 mmol) in water (15 mL) added and the resulting mixture stirred for 12 h. After evaporation the mixture was diluted with water (10 mL) and citric acid (10%) and extracted with ethyl acetate (2×80 mL). The combined extracts were then dried with sodium sulfate, filtered and evaporated to afford 5-{[3-(4-fluoro-phenyl)-5-methyl-isoxazol-4-ylmethyl]-amino}-2H-pyrazole-3-carboxylic acid (703 mg, 91%) as an off white solid. MS: m/e=317.4 [M+H]+.

Step 3: To a solution of 5-{[3-(4-fluoro-phenyl)-5-methyl-isoxazol-4-ylmethyl]-amino}-2H-pyrazole-3-carboxylic acid (0.212 mmol) in DMF (5 mL) was added 1-hydroxybenzotriazole hydrate (0.318 mmol), N-ethyldiisopropylamine (0.848 mmol), N-(3-dimethylaminopropyl)-N'-ethylcarbodiimidazole hydrochloride (0.318 mmol) and 2-hydroxy-2-methylpropylamine (0.318 mmol) and the resulting mixture stirred overnight at room temperature. The reaction mixture was then poured into aqueous sodium chloride (saturated) and the mixture was extracted with ethyl acetate. The combined organic layers were then washed with water and saturated sodium hydrogen carbonate solution and then dried over sodium sulfate, filtered and evaporated. Concentration and purification by preparative HPLC afforded the title compound (15 mg, 29%) as an off white solid. MS: m/e=388.4 [M+H]⁺.

Example 153

5-{[3-(4-Fluoro-phenyl)-5-methyl-isoxazol-4-ylmethyl]-amino}-2H-pyrazole-3-carboxylic acid amide

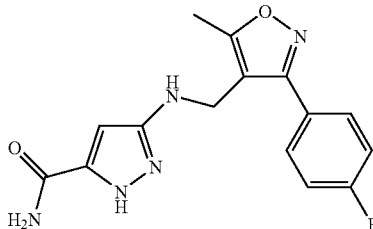

As described for example 152, 5-{[3-(4-fluoro-phenyl)-5-methyl-isoxazol-4-ylmethyl]-amino}-2H-pyrazole-3-carboxylic acid was converted, using ammonia instead of 2-hydroxy-2-methylpropylamine, to the title compound (17 mg, 29%) which was obtained as an off white solid. MS: m/e=316.4 [M+H]$^+$.

Example 154

5-{[3-(4-Fluoro-phenyl)-5-methyl-isoxazol-4-ylmethyl]-amino}-2H-pyrazole-3-carboxylic acid isopropylamide

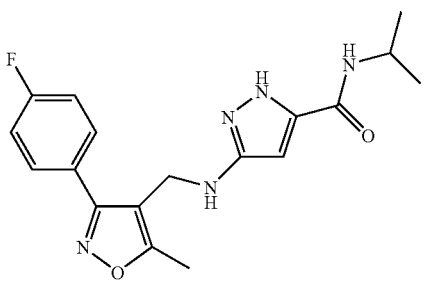

As described for example 152, 5-{[3-(4-fluoro-phenyl)-5-methyl-isoxazol-4-ylmethyl]-amino}-2H-pyrazole-3-carboxylic acid was converted, using ammonia instead of isopropylamine, to the title compound (6.4 mg, 32%) which was obtained as a white solid. MS: m/e=358.2 [M+H]$^+$.

Example 155

5-{[3-(4-Fluoro-phenyl)-5-methyl-isoxazol-4-ylmethyl]-amino}-2H-pyrazole-3-carboxylic acid ethylamide

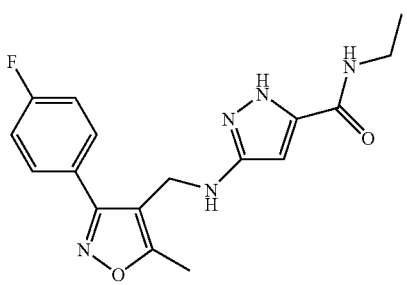

As described for example 152, 5-{[3-(4-fluoro-phenyl)-5-methyl-isoxazol-4-ylmethyl]-amino}-2H-pyrazole-3-carboxylic acid was converted, using ethylamine instead of 2-hydroxy-2-methypropylamine, to the title compound (14 mg, 41%) which was obtained as an off white solid. MS: m/e=344.2 [M+H]$^+$.

Example 156

5-{[3-(4-Fluoro-phenyl)-5-methyl-isoxazol-4-ylmethyl]-amino}-2H-pyrazole-3-carboxylic acid (tetrahydro-pyran-4-yl)-amide

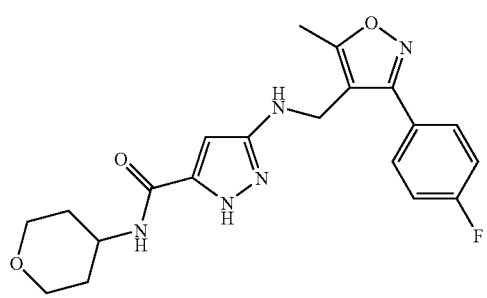

As described for example 152, 5-{[3-(4-fluoro-phenyl)-5-methyl-isoxazol-4-ylmethyl]-amino}-2H-pyrazole-3-carboxylic acid was converted, using 4-aminotetrahydropyran instead of 2-hydroxy-2-methylpropylamine, to the title compound (9.1 mg, 28%) which was obtained as an off white solid. MS: m/e=400.2 [M+H]$^+$.

Example 157

5-{[3-(4-Fluoro-phenyl)-5-methyl-isoxazol-4-ylmethyl]-amino}-2H-pyrazole-3-carboxylic acid (2-hydroxy-1-methyl-ethyl)-amide

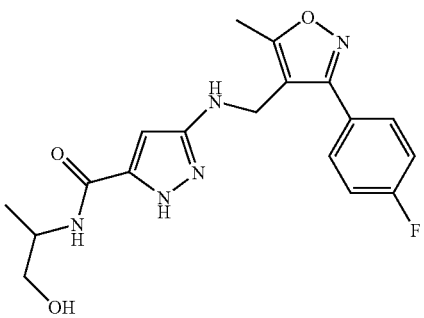

As described for example 152, 5-{[3-(4-fluoro-phenyl)-5-methyl-isoxazol-4-ylmethyl]-amino}-2H-pyrazole-3-carboxylic acid was converted, using 2-hydroxy-1-methylethylamine instead of 2-hydroxy-2-methylpropylamine, to the title compound (13 mg, 32%) which was obtained as an off white solid. MS: m/e=374.4 [M+H]$^+$.

Example 158

(5-{[3-(4-Fluoro-phenyl)-5-methyl-isoxazol-4-ylmethyl]-amino}-2H-pyrazol-3-yl)-(2-oxa-6-aza-spiro[3.3]hept-6-yl)-methanone

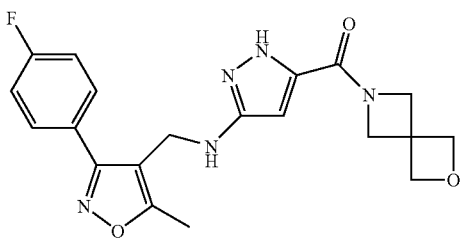

As described for example 152, 5-{[3-(4-fluoro-phenyl)-5-methyl-isoxazol-4-ylmethyl]-amino}-2H-pyrazole-3-carboxylic acid was converted, using 2-oxa-6-azonia-spiro[3.3]heptane oxalate salt instead of 2-hydroxy-2-methylpropylamine, to the title compound (11 mg, 15%) which was obtained as a white solid. MS: m/e=398.2 [M+H]⁺.

Example 159

N-isopropyl-1-methyl-3-((5-methyl-3-(pyridin-2-yl)isoxazol-4-yl)methylamino)-1H-pyrazole-5-carboxamide

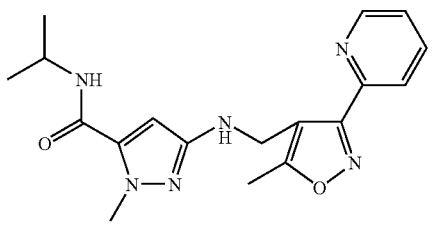

a) Ethyl 1-methyl-3-((5-methyl-3-(pyridin-2-yl)isoxazol-4-yl)methylamino)-1H-pyrazole-5-carboxylate To a mixture of 5-methyl-3-(pyridin-2-yl)isoxazole-4-carbaldehyde (811 mg, 4.31 mmol) and 5-amino-2-methyl-2H-pyrazole-3-carboxylic acid ethyl ester hydrochloride (886 mg, 4.31 mmol) in MeOH (36 mL) was added molecular sieves (1.3 g). The reaction mixture was stirred at RT for 1 h. Then acetic acid (3.45 mL, 60.3 mmol) was added. After stirring for additional 5 min, sodium cyanoborohydride (542 mg, 8.62 mmol) was added in portions over 2 min and the reaction mixture was stirred at RT for 30 min, then evaporated. The residue was extracted with dichloromethane and then washed with a saturated solution of sodium hydrogen carbonate. The organic layers were washed with water and brine, dried over sodium sulfate and evaporated. Purification by chromatography (silica, dichloromethane) afforded the title compound as a white solid (814 mg, 55%). MS: m/e=342.1 [M+H]⁺.

b) 1-Methyl-3-((5-methyl-3-(pyridin-2-yl)isoxazol-4-yl)methylamino)-1H-pyrazole-5-carboxylic acid To a solution of ethyl 1-methyl-3-((5-methyl-3-(pyridin-2-yl)isoxazol-4-yl)methylamino)-1H-pyrazole-5-carboxylate (776 mg, 2.27 mmol) in THF (8 mL) was added a solution of lithium hydroxide monohydrate (191 mg, 4.55 mmol) in water (8 mL). To get a homogeneous solution MeOH (2 mL) was added and the mixture was stirred at RT for 30 min. The organic solvents were evaporated and the residue was neutralized with 1 M HCl to get pH~5. A solid was forming. The mixture was stirred at 0° C. for 30 min, then filtered and washed with ice water. The solid was dried to give product as white solid (500 mg, 70%). The mother liquor was acidified with 1 M HCl to get pH~4. A solid was forming. Mixture was stirred at 0° C. for 30 min, then filtered and washed with water. The solid was dried to give product as white solid (189 mg, 27%). The combined solids were the title compound (689 mg, 97%) which was obtained as a white solid. MS: m/e=312.2 [M–H]⁻.

c) N-isopropyl-1-methyl-3-((5-methyl-3-(pyridin-2-yl)isoxazol-4-yl)methylamino)-1H-pyrazole-5-carboxamide To a solution of 1-methyl-3-((5-methyl-3-(pyridin-2-yl)isoxazol-4-yl)methylamino)-1H-pyrazole-5-carboxylic acid (80 mg, 255 µmol) in DMF (3 mL) were added TBTU (91 mg, 281 µmol) and N,N-diisopropyl ethyl amine (217 µL, 1.28 mmol) followed by isopropylamine (24 µL, 281 µmol). The mixture was stirred at RT for 1 h, then evaporated. The residue was purified by flash-chromatography over NH2 silica gel using gradient EtOAc/heptane 10-70% to afford the title compound (75 mg, 83%) as a white solid. MS: m/e=355.2 [M+H]⁺.

Example 160

2-Methyl-5-[(5-methyl-3-pyridin-2-yl-isoxazol-4-ylmethyl)-amino]-2H-pyrazole-3-carboxylic acid (tetrahydro-pyran-4-yl)-amide

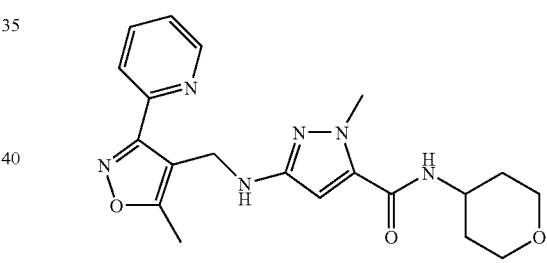

As described for example 160c, 1-methyl-3-((5-methyl-3-(pyridin-2-yl)isoxazol-4-yl)methylamino)-1H-pyrazole-5-carboxylic acid (14 mg; 44.7 µmol) was converted, using 4-aminotetrahydropyran instead of isopropylamine, to the title compound (17 mg, 96%) which was obtained as a white solid. MS: m/e=397.2 [M+H]⁺.

Example 161

1-Methyl-3-((5-methyl-3-(pyridin-2-yl)isoxazol-4-yl)methylamino)-N-morpholino-1H-pyrazole-5-carboxamide

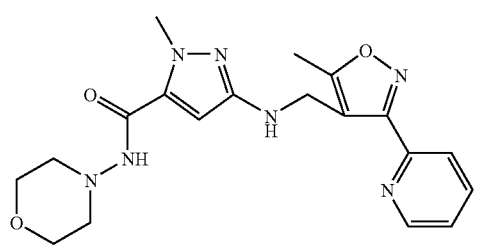

143

As described for example 160c, 1-methyl-3-((5-methyl-3-(pyridin-2-yl)isoxazol-4-yl)methylamino)-1H-pyrazole-5-carboxylic acid (80 mg; 255 μmol) was converted, using 4-aminomorpholine instead of isopropylamine, to the title compound (101 mg, 71%) which was obtained as a white solid. MS: m/e=398.2 [M+H]+.

Example 162

1-Methyl-3-((5-methyl-3-(pyridin-2-yl)isoxazol-4-yl)methylamino)-N-(3-methyloxetan-3-yl)-1H-pyrazole-5-carboxamide

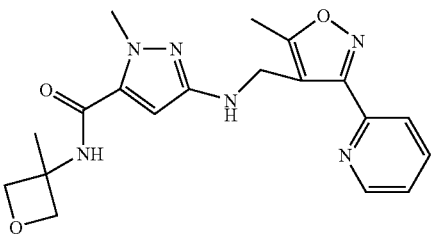

As described for example 160c, 1-methyl-3-((5-methyl-3-(pyridin-2-yl)isoxazol-4-yl)methylamino)-1H-pyrazole-5-carboxylic acid (80 mg, 255 μmol) was converted, using 3-methyl-3-oxetanamine instead of isopropylamine, to the title compound (68 mg, 70%) which was obtained as a white solid. MS: m/e=383.3 [M+H]+.

Example 163

3-((3-(5-Fluoropyridin-2-yl)-5-methylisoxazol-4-yl)methylamino)-N-isopropyl-1-methyl-1H-pyrazole-5-carboxamide

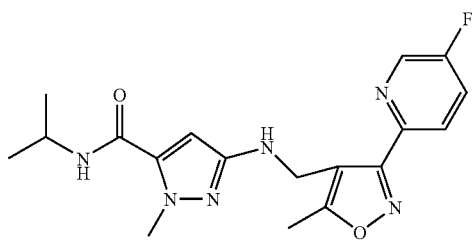

a) Ethyl 3-((3-(5-fluoropyridin-2-yl)-5-methylisoxazol-4-yl)methylamino)-1-methyl-1H-pyrazole-5-carboxylate As described for example 159a, 3-(5-fluoropyridin-2-yl)-5-methylisoxazole-4-carbaldehyde (206 mg, 1.0 mmol) was converted to the title compound (92 mg, 26%) which was obtained as a white solid. MS: m/e=360.1 [M+H]+.

b) 3-((3-(5-Fluoropyridin-2-yl)-5-methylisoxazol-4-yl)methylamino)-1-methyl-1H-pyrazole-5-carboxylic acid As described for example 159b, ethyl 3-((3-(5-fluoropyridin-2-yl)-5-methylisoxazol-4-yl)methylamino)-1-methyl-1H-pyrazole-5-carboxylate (158 mg, 0.44 mmol) was converted to the title compound (132 mg, 91%) which was obtained as a white solid. MS: m/e=330.2 [M−H]+.

144 c) 3-((3-(5-Fluoropyridin-2-yl)-5-methylisoxazol-4-yl)methylamino)-N-isopropyl-1-methyl-1H-pyrazole-5-carboxamide As described for example 160c, 3-((3-(5-fluoropyridin-2-yl)-5-methylisoxazol-4-yl)methylamino)-1-methyl-1H-pyrazole-5-carboxylic acid (38 mg, 0.12 mol) instead of 1-methyl-3-((5-methyl-3-(pyridin-2-yl)isoxazol-4-yl)methylamino)-1H-pyrazole-5-carboxylic acid was converted to the title compound (26 mg, 61%) which was obtained as a white solid. MS: m/e=373.2 [M+H]+.

Example 164

3-((3-(5-Fluoropyridin-2-yl)-5-methylisoxazol-4-yl)methylamino)-1-methyl-N-(tetrahydro-2H-pyran-4-yl)-1H-pyrazole-5-carboxamide

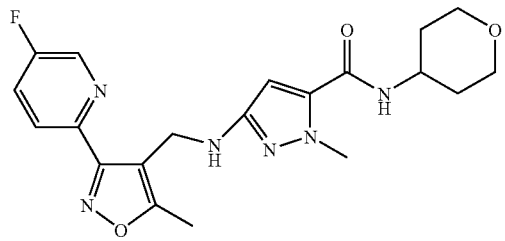

As described for example 163c, 3-((3-(5-fluoropyridin-2-yl)-5-methylisoxazol-4-yl)methylamino)-1-methyl-1H-pyrazole-5-carboxylic acid (76 mg, 0.23 mol) was converted, using 4-aminotetrahydropyran instead of isopropylamine, to the title compound (95 mg, 80%) which was obtained as a white solid. MS: m/e=415.2 [M+H]+.

Example 165

N-Cyclopropyl-3-((3-(5-fluoropyridin-2-yl)-5-methylisoxazol-4-yl)methylamino)-1-methyl-1H-pyrazole-5-carboxamide

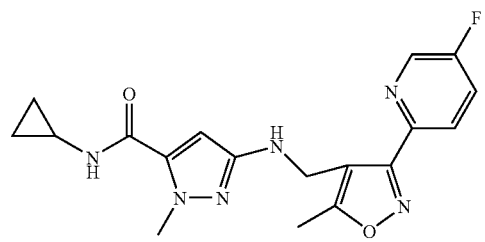

As described for example 163c, 3-((3-(5-fluoropyridin-2-yl)-5-methylisoxazol-4-yl)methylamino)-1-methyl-1H-pyrazole-5-carboxylic acid (92 mg, 0.28 mol) was converted, using cyclopropylamine instead of isopropylamine, to the title compound (78 mg, 76%) which was obtained as a white solid. MS: m/e=371.3 [M+H]+.

Example 166

N-(Cyclopropylmethyl)-3-((3-(5-fluoropyridin-2-yl)-5-methylisoxazol-4-yl)methylamino)-1-methyl-1H-pyrazole-5-carboxamide

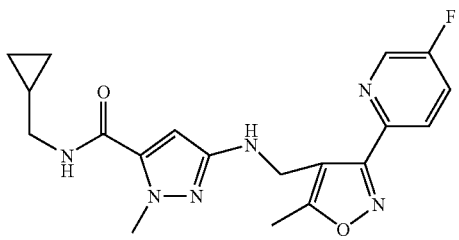

As described for example 163c, 3-((3-(5-fluoropyridin-2-yl)-5-methylisoxazol-4-yl)methylamino)-1-methyl-1H-pyrazole-5-carboxylic acid (92 mg, 0.28 mol) was converted, using aminomethylcyclopropane instead of isopropylamine, to the title compound (85 mg, 80%) which was obtained as a white solid. MS: m/e=385.2 [M+H]$^+$.

Example 167

3-((3-(5-Fluoropyridin-2-yl)-5-methylisoxazol-4-yl)methylamino)-1-methyl-N-(3-methyloxetan-3-yl)-1H-pyrazole-5-carboxamide

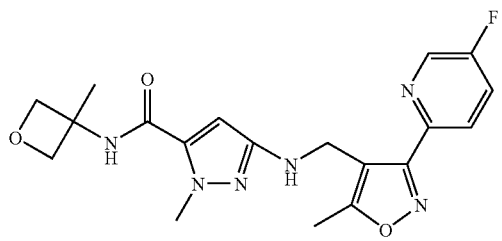

As described for example 163c, 3-((3-(5-fluoropyridin-2-yl)-5-methylisoxazol-4-yl)methylamino)-1-methyl-1H-pyrazole-5-carboxylic acid (92 mg, 0.28 mol) was converted, using 3-methyl-3-oxetanamine instead of isopropylamine, to the title compound (90 mg, 81%) which was obtained as a white solid. MS: m/e=401.3 [M+H]$^+$.

Example 168

(3-((3-(5-Fluoropyridin-2-yl)-5-methylisoxazol-4-yl)methylamino)-1-methyl-1H-pyrazol-5-yl)(2-oxa-6-azaspiro[3.3]heptan-6-yl)methanone

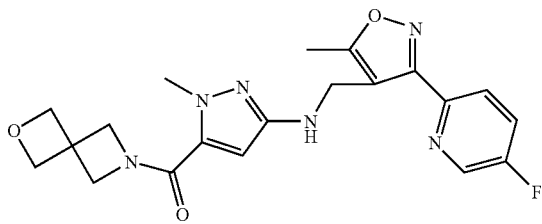

As described for example 163c, 3-((3-(5-fluoropyridin-2-yl)-5-methylisoxazol-4-yl)methylamino)-1-methyl-1H-pyrazole-5-carboxylic acid (92 mg, 0.28 mol) was converted, using 2-oxa-6-azonia-spiro[3.3]heptane oxalate salt instead of isopropylamine, to the title compound (35 mg, 31%) which was obtained as a white foam. MS: m/e=413.4 [M+H]$^+$.

The invention claimed is:
1. A compound of formula I,

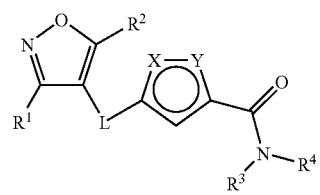

wherein
L is —CH$_2$—O—, —CH$_2$—NH— or —CH=CH—;
X is N—R$^5$ and Y is N, or X is N and Y is N—R$^6$;
R$^1$ is selected from the group consisting of
  i) lower alkyl,
  ii) lower alkyl substituted by 1-5 halogen atoms,
  iii) aryl,
  iv) aryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, COO-lower alkyl, CO—N(lower alkyl,H)-lower alkyl, CO—N(lower alkyl,lower alkyl)-lower alkyl, CO—NH$_2$-lower alkyl and lower alkyl-CO—,
  v) heteroaryl,
  vi) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, lower alkyl-COO—, CO—N(lower alkyl,H)-lower alkyl, CO—N(lower alkyl,lower alkyl)-lower alkyl, CO—NH$_2$-lower alkyl and lower alkyl-CO—, and
  vii) heterocyclyl;
R$^2$ is H, lower alkyl or lower alkyl substituted by 1-5 substituents individually selected from halogen and hydroxy;
R$^3$ is selected from the group consisting of
  i) H,
  ii) lower alkyl,
  iii) lower alkyl substituted by 1-5 substituents individually selected from acetamidyl, acetyl, acetylamino, amido, amino, carboxy, cyano, cycloalkyl, halogen, halogen-lower alkoxy, heterocyclyl, hydroxy, lower alkoxy, (lower alkyl,lower alkyl)N—, (lower alkyl,H)N—, nitro and lower alkyl-S(O)$_2$—,
  iv) heteroaryl,
  v) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, lower alkyl-COO—, CO—N(lower alkyl,H)-lower alkyl, CO—N(lower alkyl,lower alkyl)-lower alkyl, CO—NH$_2$-lower alkyl, and lower alkyl-CO—, xi) cycloalkyl, xii) cycloalkyl substituted by 1-4 substituents individually selected from halogen and hydroxy, xiii) heterocyclyl, xiv) heterocyclyl substituted by 1-4 substituents individually selected from halogen and lower alkyl, and xv) —NR$^7$R$^8$;

R$^4$ is H, lower alkyl or lower alkyl substituted by 1-5 halogen atoms;

or R$^3$ and R$^4$ together with the nitrogen to which they are attached form a heterocyclyl or a heterocyclyl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, lower alkyl-COO—, CO—N(lower alkyl,H)-lower alkyl, CO—N(lower alkyl,lower alkyl)-lower alkyl, CO—NH$_2$-lower alkyl and lower alkyl-CO—;

R$^5$ is H or lower alkyl;

R$^6$ is H or lower alkyl;

R$^7$ is lower alkyl; and

R$^8$ is lower alkyl, or a pharmaceutically acceptable salt or ester thereof.

2. The compound of claim 1 wherein

L is —CH$_2$—O— or —CH═CH—;

X is N—R$^5$ and Y is N, or X is N and Y is N—R$^6$;

R$^1$ is selected from the group consisting of i) lower alkyl, ii) lower alkyl substituted by 1-5 halogen atoms, iii) aryl, iv) aryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, COO-lower alkyl, CO—N(lower alkyl,H)-lower alkyl, CO—N(lower alkyl,lower alkyl)-lower alkyl, CO—NH$_2$-lower alkyl and lower alkyl-CO—, v) heteroaryl, vi) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, lower alkyl-COO—, CO—N(lower alkyl,H)-lower alkyl, CO—N(lower alkyl,lower alkyl)-lower alkyl, CO—NH$_2$-lower alkyl and lower alkyl-CO—, and vii) heterocyclyl;

R$^2$ is H, lower alkyl or lower alkyl substituted by 1-5 substituents individually selected from halogen and hydroxy;

R$^3$ is selected from the group consisting of i) H, ii) lower alkyl, iii) lower alkyl substituted by 1-5 substituents individually selected from acetamidyl, acetyl, acetylamino, amido, amino, carboxy, cyano, cycloalkyl, halogen, halogen-lower alkoxy, heterocyclyl, hydroxy, lower alkoxy, (lower alkyl,lower alkyl)N—, (lower alkyl,H)N—, nitro and lower alkyl-S(O)$_2$—, iv) heteroaryl, v) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, lower alkyl-COO—, CO—N(lower alkyl,H)-lower alkyl, CO—N(lower alkyl,lower alkyl)-lower alkyl, CO—NH$_2$-lower alkyl, and lower alkyl-CO—, vi) cycloalkyl, vii) cycloalkyl substituted by 1-4 substituents individually selected from halogen and hydroxy, viii) heterocyclyl, ix) heterocyclyl substituted by 1-4 substituents individually selected from halogen and lower alkyl, and x) —NR$^7$R$^8$;

R$^4$ is H, lower alkyl or lower alkyl substituted by 1-5 halogen atoms;

or R$^3$ and R$^4$ together with the nitrogen to which they are attached form a heterocyclyl or a heterocyclyl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, lower alkyl-COO—, CO—N(lower alkyl,H)-lower alkyl, CO—N(lower alkyl,lower alkyl)-lower alkyl, CO—NH$_2$-lower alkyl and lower alkyl-CO—;

R$^5$ is H or lower alkyl;

R$^6$ is H or lower alkyl;

R$^7$ is lower alkyl; and

R$^8$ is lower alkyl, or a pharmaceutically acceptable salt or ester thereof.

3. The compound of claim 1, wherein R$^1$ is lower alkyl, aryl, aryl substituted by 1-2 halogen atoms, heteroaryl, heteroaryl substituted by 1-2 halogen atoms, or heterocyclyl.

4. The compound of claim 3, wherein R$^1$ is aryl, aryl substituted by 1-2 halogen atoms individually selected from fluoro and chloro, heteroaryl or heteroaryl substituted by 1-2 fluoro atoms.

5. The compound of claim 4, wherein R$^1$ is phenyl, chlorophenyl, fluoro-phenyl, pyridinyl or fluoro-pyridinyl.

6. The compound of claim 1, wherein R$^2$ is H, lower alkyl or hydroxy-lower alkyl.

7. The compound of claim 6, wherein R$^2$ is lower alkyl or hydroxy-lower alkyl.

8. The compound of claim 6, wherein R$^2$ is H, methyl or hydroxy-methyl.

9. The compound of claim 8, wherein R$^2$ is methyl or hydroxy-methyl.

10. The compound of claim 1, wherein R$^3$ and R$^4$ together with the nitrogen atom to which they are attached form a heterocyclyl or a heterocyclyl substituted by 1-4 substituents individually selected from halogen and hydroxy.

11. The compound of claim 10, wherein $R^3$ and $R^4$ together with the nitrogen to which they are attached form a heterocyclyl.

12. The compound of claim 11, wherein $R^3$ and $R^4$ together with the nitrogen to which they are attached form a 2-oxa-6-aza-spiro[3.3]heptyl.

13. The compound of claim 1, wherein $R^4$ is H.

14. The compound of claim 1, wherein $R^3$ is
   i) H,
   ii) lower alkyl,
   iii) lower alkyl substituted by 1-5 substituents individually selected from acetylamino, cycloalkyl, halogen, heterocyclyl, hydroxy and lower alkoxy,
   iv) heteroaryl substituted by 1-4 substituents individually selected from halogen and lower alkyl,
   v) cycloalkyl,
   vi) cycloalkyl substituted by 1-4 hydroxy groups,
   vii) heterocyclyl,
   viii) heterocyclyl substituted by 1-4 lower alkyl groups, or
   ix) —N(lower alkyl)$_2$.

15. The compound of claim 1, wherein $R^3$ is lower alkyl, heterocyclyl-lower alkyl, hydroxy-lower alkyl or heterocyclyl.

16. The compound of claim 15, wherein $R^3$ is lower alkyl, heterocyclyl-lower alkyl or heterocyclyl.

17. The compound of claim 15, wherein $R^3$ is 1-oxetanyl-ethyl, 2-hydroxy-2-methyl-propyl, isopropyl, morpholino, tetrahydrofuryl or tetrahydropyryl.

18. The compound of claim 17, wherein $R^3$ is isopropyl, 1-oxetanyl-ethyl, morpholino, tetrahydropyryl or tetrahydrofuryl.

19. The compound of claim 1, wherein L is —CH$_2$—O— or —CH$_2$—NH—.

20. The compound of claim 19, wherein L is —CH$_2$—O—.

21. The compound of claim 1, wherein X is N—R$^5$, Y is N.

22. The compound of claim 21, wherein $R^5$ is H.

23. The compound of claim 22, selected from the group consisting of
   5-(5-Methyl-3-pyridin-2-yl-isoxazol-4-ylmethoxy)-1H-pyrazole-3-carboxylic acid isopropylamide,
   5-(5-Methyl-3-pyridin-2-yl-isoxazol-4-ylmethoxy)-1H-pyrazole-3-carboxylic acid (tetrahydro-pyran-4-yl)-amide, and
   5-(5-Methyl-3-pyridin-2-yl-isoxazol-4-ylmethoxy)-1H-pyrazole-3-carboxylic acid ((S)-2-hydroxy-1-methyl-ethyl)-amide,
   or a pharmaceutically acceptable salt or ester thereof.

24. The compound of claim 21, wherein $R^5$ is methyl.

25. The compound of claim 24, selected from the group consisting of
   1-Methyl-5-(5-methyl-3-pyridin-2-yl-isoxazol-4-yl-methoxy)-1H-pyrazole-3-carboxylic acid ((S)-2-hydroxy-1-methyl-ethyl)-amide,
   1-Methyl-5-(5-methyl-3-pyridin-2-yl-isoxazol-4-yl-methoxy)-1H-pyrazole-3-carboxylic acid isopropylamide,
   1-Methyl-5-(5-methyl-3-pyridin-2-yl-isoxazol-4-yl-methoxy)-1H-pyrazole-3-carboxylic acid (tetrahydro-pyran-4-yl)-amide, and
   5-[3-(5-Fluoro-pyridin-2-yl)-5-methyl-isoxazol-4-yl-methoxy]-1-methyl-1H-pyrazole-3-carboxylic acid ((S)-2-hydroxy-1-methyl-ethyl)-amide,
   or a pharmaceutically acceptable salt or ester thereof.

26. The compound of claim 20, wherein X is N, Y is N—R$^6$.

27. The compound of claim 26, wherein $R^6$ is H.

28. The compound of claim 27, selected from the group consisting of
   (R)-3-((3-Butyl-5-methylisoxazol-4-yl)methoxy)-N-(tetrahydrofuran-3-yl)-1H-pyrazole-5-carboxamide,
   (S)-3-((3-Butyl-5-methylisoxazol-4-yl)methoxy)-N-(tetrahydrofuran-3-yl)-1H-pyrazole-5-carboxamide,
   [5-(3-Butyl-5-methyl-isoxazol-4-ylmethoxy)-2H-pyrazol-3-yl]-morpholin-4-yl-methanone,
   [5-(5-Methyl-3-phenyl-isoxazol-4-ylmethoxy)-2H-pyrazol-3-yl]-morpholin-4-yl-methanone,
   5-(3-Butyl-5-methyl-isoxazol-4-ylmethoxy)-2H-pyrazole-3-carboxylic acid (tetrahydro-pyran-4-yl)-amide,
   5-(3-Butyl-5-methyl-isoxazol-4-ylmethoxy)-2H-pyrazole-3-carboxylic acid ((S)-2-hydroxy-1-methyl-ethyl)-amide,
   5-(3-Butyl-5-methyl-isoxazol-4-ylmethoxy)-2H-pyrazole-3-carboxylic acid (tetrahydro-furan-3-yl)-amide,
   5-(3-Butyl-5-methyl-isoxazol-4-ylmethoxy)-2H-pyrazole-3-carboxylic acid (2-hydroxy-1-hydroxymethyl-ethyl)-amide,
   5-(3-Butyl-5-methyl-isoxazol-4-ylmethoxy)-2H-pyrazole-3-carboxylic acid ((R)-2-hydroxy-1-methyl-ethyl)-amide, and
   5-(3-Butyl-5-methyl-isoxazol-4-ylmethoxy)-2H-pyrazole-3-carboxylic acid (2,2,2-trifluoro-ethyl)-amide
   or a pharmaceutically acceptable salt or ester thereof.

29. The compound of claim 27, selected from the group consisting of
   5-(3-Butyl-5-methyl-isoxazol-4-ylmethoxy)-2H-pyrazole-3-carboxylic acid isopropylamide,
   5-(3-Butyl-5-methyl-isoxazol-4-ylmethoxy)-2H-pyrazole-3-carboxylic acid (2-hydroxy-ethyl)-amide,
   5-(3-Butyl-5-methyl-isoxazol-4-ylmethoxy)-2H-pyrazole-3-carboxylic acid (2,2-dimethyl-tetrahydro-pyran-4-yl)-amide,
   5-(3-Butyl-5-methyl-isoxazol-4-ylmethoxy)-2H-pyrazole-3-carboxylic acid N',N'-dimethyl-hydrazide,
   5-(3-Butyl-5-methyl-isoxazol-4-ylmethoxy)-2H-pyrazole-3-carboxylic acid morpholin-4-ylamide,
   5-(3-Butyl-5-methyl-isoxazol-4-ylmethoxy)-2H-pyrazole-3-carboxylic acid pyrrolidin-1-ylamide,
   5-(3-Butyl-5-methyl-isoxazol-4-ylmethoxy)-2H-pyrazole-3-carboxylic acid piperidin-1-ylamide,
   5-(5-Methyl-3-phenyl-isoxazol-4-ylmethoxy)-2H-pyrazole-3-carboxylic acid isopropylamide,
   5-(5-Methyl-3-phenyl-isoxazol-4-ylmethoxy)-2H-pyrazole-3-carboxylic acid (tetrahydro-pyran-4-yl)-amide, and
   5-(5-Methyl-3-phenyl-isoxazol-4-ylmethoxy)-2H-pyrazole-3-carboxylic acid (tetrahydro-furan-3-yl)-amide
   or a pharmaceutically acceptable salt or ester thereof.

30. The compound of claim 27, selected from the group consisting of
   5-(5-Methyl-3-phenyl-isoxazol-4-ylmethoxy)-2H-pyrazole-3-carboxylic acid N',N'-dimethyl-hydrazide,
   5-(5-Methyl-3-phenyl-isoxazol-4-ylmethoxy)-2H-pyrazole-3-carboxylic acid (2-hydroxy-ethyl)-amide,
   5-(5-Methyl-3-phenyl-isoxazol-4-ylmethoxy)-2H-pyrazole-3-carboxylic acid amide,
   5-[3-(4-Fluoro-phenyl)-5-methyl-isoxazol-4-ylmethoxy]-2H-pyrazole-3-carboxylic acid morpholin-4-ylamide,
   5-[3-(4-Fluoro-phenyl)-5-methyl-isoxazol-4-ylmethoxy]-2H-pyrazole-3-carboxylic acid piperidin-1-ylamide,
   5-[3-(4-Fluoro-phenyl)-5-methyl-isoxazol-4-ylmethoxy]-2H-pyrazole-3-carboxylic acid pyrrolidin-1-ylamide,
   5-[3-(4-Fluoro-phenyl)-5-methyl-isoxazol-4-ylmethoxy]-2H-pyrazole-3-carboxylic acid N',N'-dimethyl-hydrazide,
   5-[3-(4-Fluoro-phenyl)-5-methyl-isoxazol-4-ylmethoxy]-2H-pyrazole-3-carboxylic acid isopropylamide, 5-[3-(4-Fluoro-phenyl)-5-methyl-isoxazol-4-ylmethoxy]-2H-pyrazole-3-carboxylic acid (tetrahydro-pyran-4-yl)-amide, and 5-[3-(5-Fluoro-pyridin-2-yl)-5-methyl-isoxazol-4-ylmethoxy]-2H-pyrazole-3-carboxylic acid (2,2,2-trifluoro-ethyl)-amide or a pharmaceutically acceptable salt or ester thereof.

31. The compound of claim 27, selected from the group consisting of

5-[3-(5-Fluoro-pyridin-2-yl)-5-methyl-isoxazol-4-ylmethoxy]-2H-pyrazole-3-carboxylic acid (tetrahydro-furan-3-yl)-amide, 5-[3-(5-Fluoro-pyridin-2-yl)-5-methyl-isoxazol-4-ylmethoxy]-2H-pyrazole-3-carboxylic acid tert-butylamide, 5-[3-(5-Fluoro-pyridin-2-yl)-5-methyl-isoxazol-4-ylmethoxy]-2H-pyrazole-3-carboxylic acid hydroxyethyl)-amide, 5-[3-(5-Fluoro-pyridin-2-yl)-5-methyl-isoxazol-4-ylmethoxy]-2H-pyrazole-3-carboxylic acid isopropylamide, 5-[3-(5-Fluoro-pyridin-2-yl)-5-methyl-isoxazol-4-ylmethoxy]-2H-pyrazole-3-carboxylic acid N',N'-dimethyl-hydrazide, 5-[3-(5-Fluoro-pyridin-2-yl)-5-methyl-isoxazol-4-ylmethoxy]-2H-pyrazole-3-carboxylic acid morpholin-4-ylamide, 5-[3-(5-Fluoro-pyridin-2-yl)-5-methyl-isoxazol-4-ylmethoxy]-2H-pyrazole-3-carboxylic acid pyrrolidin-1-ylamide, and 5-[3-(5-Fluoro-pyridin-2-yl)-isoxazol-4-ylmethoxy]-2H-pyrazole-3-carboxylic acid morpholin-4-ylamide, or a pharmaceutically acceptable salt or ester thereof.

32. The compound of claim 26, wherein $R^6$ is methyl.

33. The compound of claim 32, selected from the group consisting of

{5-[3-(4-Chloro-phenyl)-5-hydroxymethyl-isoxazol-4-ylmethoxy]-2-methyl-2H-pyrazol-3-yl}-(2-oxa-6-aza-spiro[3.3]hept-6-yl)-methanone, {5-[3-(4-Chloro-phenyl)-5-hydroxymethyl-isoxazol-4-ylmethoxy]-2-methyl-2H-pyrazol-3-yl}-(4,4-difluoro-piperidin-1-yl)-methanone, {5-[3-(4-Fluoro-phenyl)-5-hydroxymethyl-isoxazol-4-ylmethoxy]-2-methyl-2H-pyrazol-3-yl}-(2-oxa-6-aza-spiro[3.3]hept-6-yl)-methanone, {5-[3-(4-Fluoro-phenyl)-5-methyl-isoxazol-4-ylmethoxy]-2-methyl-2H-pyrazol-3-yl}-(3-hydroxy-azetidin-1-yl)-methanone, {5-[3-(4-Fluoro-phenyl)-5-methyl-isoxazol-4-ylmethoxy]-2-methyl-2H-pyrazol-3-yl}-(2-oxa-6-aza-spiro[3.3]hept-6-yl)-methanone, 2-Methyl-5-(5-methyl-3-phenyl-isoxazol-4-ylmethoxy)-2H-pyrazole-3-carboxylic acid (2-hydroxy-ethyl)-amide, 2-Methyl-5-(5-methyl-3-phenyl-isoxazol-4-ylmethoxy)-2H-pyrazole-3-carboxylic acid (tetrahydro-furan-3-yl)-amide, 2-Methyl-5-(5-methyl-3-phenyl-isoxazol-4-ylmethoxy)-2H-pyrazole-3-carboxylic acid (tetrahydro-pyran-4-yl)-amide, 2-Methyl-5-(5-methyl-3-phenyl-isoxazol-4-ylmethoxy)-2H-pyrazole-3-carboxylic acid amide, and 2-Methyl-5-(5-methyl-3-phenyl-isoxazol-4-ylmethoxy)-2H-pyrazole-3-carboxylic acid isopropylamide or a pharmaceutically acceptable salt or ester thereof.

34. The compound of claim 32, selected from the group consisting of

2-Methyl-5-(5-methyl-3-phenyl-isoxazol-4-ylmethoxy)-2H-pyrazole-3-carboxylic acid N',N'-dimethyl-hydrazide, 2-Methyl-5-(5-methyl-3-pyridin-2-yl-isoxazol-4-ylmethoxy)-2H-pyrazole-3-carboxylic acid isopropylamide, 2-Methyl-5-(5-methyl-3-pyridin-2-yl-isoxazol-4-ylmethoxy)-2H-pyrazole-3-carboxylic acid (tetrahydro-pyran-4-yl)-amide, 2-Methyl-5-(5-methyl-3-pyridin-2-yl-isoxazol-4-ylmethoxy)-2H-pyrazole-3-carboxylic acid ((S)-2-hydroxy-1-methyl-ethyl)-amide, 2-Methyl-5-[5-methyl-3-(tetrahydro-pyran-4-yl)-isoxazol-4-ylmethoxy]-2H-pyrazole-3-carboxylic acid (tetrahydro-pyran-4-yl)-amide, 5-(3-Butyl-5-hydroxymethyl-isoxazol-4-ylmethoxy)-2-methyl-2H-pyrazole-3-carboxylic acid (2,2,2-trifluoro-ethyl)-amide, 5-(3-Butyl-5-hydroxymethyl-isoxazol-4-ylmethoxy)-2-methyl-2H-pyrazole-3-carboxylic acid cyclobutylamide, 5-(3-Butyl-5-methyl-isoxazol-4-ylmethoxy)-2-methyl-2H-pyrazole-3-carboxylic acid (2-hydroxy-ethyl)-amide, 5-(3-Butyl-5-methyl-isoxazol-4-ylmethoxy)-2-methyl-2H-pyrazole-3-carboxylic acid isopropylamide, and 5-(3-Butyl-5-methyl-isoxazol-4-ylmethoxy)-2-methyl-2H-pyrazole-3-carboxylic acid (2-hydroxy-1-methyl-ethyl)-amide or a pharmaceutically acceptable salt or ester thereof.

35. The compound of claim 32, selected from the group consisting of 5-(3-Butyl-5-methyl-isoxazol-4-ylmethoxy)-2-methyl-2H-pyrazole-3-carboxylic acid (tetrahydro-pyran-4-yl)-amide, 5-(3-Butyl-5-methyl-isoxazol-4-ylmethoxy)-2-methyl-2H-pyrazole-3-carboxylic acid (tetrahydro-furan-3-yl)-amide, 5-[3-(4-Chloro-phenyl)-5-hydroxymethyl-isoxazol-4-ylmethoxy]-2-methyl-2H-pyrazole-3-carboxylic acid isopropylamide, 5-[3-(4-Chloro-phenyl)-5-hydroxymethyl-isoxazol-4-ylmethoxy]-2-methyl-2H-pyrazole-3-carboxylic acid (tetrahydro-pyran-4-yl)-amide, 5-[3-(4-Chloro-phenyl)-5-hydroxymethyl-isoxazol-4-ylmethoxy]-2-methyl-2H-pyrazole-3-carboxylic acid amide, 5-[3-(4-Chloro-phenyl)-5-hydroxymethyl-isoxazol-4-ylmethoxy]-2-methyl-2H-pyrazole-3-carboxylic acid (2,2,2-trifluoro-ethyl)-amide, 5-[3-(4-Chloro-phenyl)-5-hydroxymethyl-isoxazol-4-ylmethoxy]-2-methyl-2H-pyrazole-3-carboxylic acid (2,2,3,3,3-pentafluoro-propyl)-amide, 5-[3-(4-Chloro-phenyl)-5-hydroxymethyl-isoxazol-4-ylmethoxy]-2-methyl-2H-pyrazole-3-carboxylic acid cyclopropylamide, 5-[3-(4-Chloro-phenyl)-5-hydroxymethyl-isoxazol-4-ylmethoxy]-2-methyl-2H-pyrazole-3-carboxylic acid ((S)-2,2,2-trifluoro-1-methyl-ethyl)-amide, and 5-[3-(4-Chloro-phenyl)-5-hydroxymethyl-isoxazol-4-ylmethoxy]-2-methyl-2H-pyrazole-3-carboxylic acid (2-hydroxy-1,1-dimethyl-ethyl)-amide or a pharmaceutically acceptable salt or ester thereof.

36. The compound of claim 32, selected from the group consisting of

5-[3-(4-Chloro-phenyl)-5-hydroxymethyl-isoxazol-4-ylmethoxy]-2-methyl-2H-pyrazole-3-carboxylic acid (3-methyl-oxetan-3-yl)-amide, 5-[3-(4-Chloro-phenyl)-5-hydroxymethyl-isoxazol-4-ylmethoxy]-2-methyl-2H-pyrazole-3-carboxylic acid (tetrahydro-furan-3-yl)-amide, 5-[3-(4-Fluoro-phenyl)-5-hydroxymethyl-isoxazol-4-ylmethoxy]-2-methyl-2H-pyrazole-3-carboxylic acid (tetrahydro-pyran-4-yl)-amide, 5-[3-(4-Fluoro-phenyl)-5-hydroxymethyl-isoxazol-4-ylmethoxy]-2-methyl-2H-pyrazole-3-carboxylic acid isopropylamide, 5-[3-(4-Fluoro-phenyl)-5-hydroxymethyl-isoxazol-4-ylmethoxy]-2-methyl-2H-pyrazole-3-carboxylic acid amide, 5-[3-(4-Fluoro-phenyl)-5-hydroxymethyl-isoxazol-4-ylmethoxy]-2-methyl-2H-pyrazole-3-carboxylic acid (2,2,2-trifluoro-ethyl)-amide, 5-[3-(4-Fluoro-phenyl)-5-hydroxymethyl-isoxazol-4-ylmethoxy]-2-methyl-2H-pyrazole-3-carboxylic acid (2,2,3,3,3-pentafluoro-propyl)-amide, 5-[3-(4-Fluoro-phenyl)-5-hydroxymethyl-isoxazol-4-ylmethoxy]-2-methyl-2H-pyrazole-3-carboxylic acid (1-methyl-1H-pyrazol-3-yl)-amide, 5-[3-(4-Fluoro-phenyl)-5-hydroxymethyl-isoxazol-4-ylmethoxy]-2-methyl-2H-pyrazole-3-carboxylic acid (tetrahydro-furan-3-yl)-amide, and 5-[3-(4-Fluoro-phenyl)-5-hydroxymethyl-isoxazol-4-ylmethoxy]-2-methyl-2H-pyrazole-3-carboxylic acid (3-methyl-oxetan-3-yl)-amide or a pharmaceutically acceptable salt or ester thereof.

37. The compound of claim 32, selected from the group consisting of

5-[3-(4-Fluoro-phenyl)-5-methyl-isoxazol-4-ylmethoxy]-2-methyl-2H-pyrazole-3-carboxylic acid N',N'-dimethyl-hydrazide, 5-[3-(4-Fluoro-phenyl)-5-methyl-isoxazol-4-ylmethoxy]-2-methyl-2H-pyrazole-3-carboxylic acid piperidin-1-ylamide, 5-[3-(4-Fluoro-phenyl)-5-methyl-isoxazol-4-ylmethoxy]-2-methyl-2H-pyrazole-3-carboxylic acid morpholin-4-ylamide, 5-[3-(4-Fluoro-phenyl)-5-methyl-isoxazol-4-ylmethoxy]-2-methyl-2H-pyrazole-3-carboxylic acid pyrrolidin-1-ylamide, 5-[3-(4-Fluoro-phenyl)-5-methyl-isoxazol-4-ylmethoxy]-2-methyl-2H-pyrazole-3-carboxylic acid isopropylamide, 5-[3-(4-Fluoro-phenyl)-5-methyl-isoxazol-4-ylmethoxy]-2-methyl-2H-pyrazole-3-carboxylic acid (tetrahydro-pyran-4-yl)-amide, 5-[3-(4-Fluoro-phenyl)-5-methyl-isoxazol-4-ylmethoxy]-2-methyl-2H-pyrazole-3-carboxylic acid amide, 5-[3-(4-Fluoro-phenyl)-5-methyl-isoxazol-4-ylmethoxy]-2-methyl-2H-pyrazole-3-carboxylic acid (2-hydroxy-1,1-dimethyl-ethyl)-amide, 5-[3-(4-Fluoro-phenyl)-5-methyl-isoxazol-4-ylmethoxy]-2-methyl-2H-pyrazole-3-carboxylic acid ((S)-2,2,2-trifluoro-1-methyl-ethyl)-amide, and 5-[3-(4-Fluoro-phenyl)-5-methyl-isoxazol-4-ylmethoxy]-2-methyl-2H-pyrazole-3-carboxylic acid (2,2,2-trifluoro-ethyl)-amide or a pharmaceutically acceptable salt or ester thereof.

38. The compound of claim 32, selected from the group consisting of

5-[3-(4-Fluoro-phenyl)-5-methyl-isoxazol-4-ylmethoxy]-2-methyl-2H-pyrazole-3-carboxylic acid (3-methyl-oxetan-3-yl)-amide, 5-[3-(4-Fluoro-phenyl)-5-methyl-isoxazol-4-ylmethoxy]-2-methyl-2H-pyrazole-3-carboxylic acid (3,3,3-trifluoro-2-hydroxy-propyl)-amide, 5-[3-(4-Fluoro-phenyl)-5-methyl-isoxazol-4-ylmethoxy]-2-methyl-2H-pyrazole-3-carboxylic acid (2-methoxy-ethyl)-amide, 5-[3-(4-Fluoro-phenyl)-5-methyl-isoxazol-4-ylmethoxy]-2-methyl-2H-pyrazole-3-carboxylic acid (1-hydroxy-cyclopropylmethyl)-amide, 5-[3-(4-Fluoro-phenyl)-5-methyl-isoxazol-4-ylmethoxy]-2-methyl-2H-pyrazole-3-carboxylic acid (2-hydroxy-ethyl)-amide, 5-[3-(4-Fluoro-phenyl)-5-methyl-isoxazol-4-ylmethoxy]-2-methyl-2H-pyrazole-3-carboxylic acid (1-methyl-1H-pyrazol-3-yl)-amide, 5-[3-(4-Fluoro-phenyl)-5-methyl-isoxazol-4-ylmethoxy]-2-methyl-2H-pyrazole-3-carboxylic acid (2-acetylamino-ethyl)-amide, 5-[3-(4-Fluoro-phenyl)-5-methyl-isoxazol-4-ylmethoxy]-2-methyl-2H-pyrazole-3-carboxylic acid (3-hydroxy-2,2-dimethyl-propyl)-amide, 5-[3-(4-Fluoro-phenyl)-5-methyl-isoxazol-4-ylmethoxy]-2-methyl-2H-pyrazole-3-carboxylic acid (2-hydroxy-2-methyl-propyl)-amide, and 5-[3-(4-Fluoro-phenyl)-5-methyl-isoxazol-4-ylmethoxy]-2-methyl-2H-pyrazole-3-carboxylic acid ((S or R)-3,3,3-trifluoro-2-hydroxy-propyl)-amide or a pharmaceutically acceptable salt or ester thereof.

39. The compound of claim 32, selected from the group consisting of

5-[3-(4-Fluoro-phenyl)-5-methyl-isoxazol-4-ylmethoxy]-2-methyl-2H-pyrazole-3-carboxylic acid ((R or S)-3,3,3-trifluoro-2-hydroxy-propyl)-amide, 5-[3-(4-Fluoro-phenyl)-5-methyl-isoxazol-4-ylmethoxy]-2-methyl-2H-pyrazole-3-carboxylic acid ((R or S)-1-hydroxymethyl-propyl)-amide, 5-[3-(4-Fluoro-phenyl)-5-methyl-isoxazol-4-ylmethoxy]-2-methyl-2H-pyrazole-3-carboxylic acid ((S or R)-1-hydroxymethyl-propyl)-amide, 5-[3-(4-Fluoro-phenyl)-5-methyl-isoxazol-4-ylmethoxy]-2-methyl-2H-pyrazole-3-carboxylic acid (tetrahydro-furan-3-yl)-amide, 5-[3-(4-Fluoro-phenyl)-5-methyl-isoxazol-4-ylmethoxy]-2-methyl-2H-pyrazole-3-carboxylic acid ((1R,2R)-2-hydroxy-cyclopentyl)-amide, 5-[3-(4-Fluoro-phenyl)-5-methyl-isoxazol-4-ylmethoxy]-2-methyl-2H-pyrazole-3-carboxylic acid ((1S,2S)-2-hydroxy-cyclopentyl)-amide, 5-[3-(4-Fluoro-phenyl)-5-methyl-isoxazol-4-ylmethoxy]-2-methyl-2H-pyrazole-3-carboxylic acid ((1S,2S)-2-hydroxy-cyclopentyl)-amide, 5-[3-(4-Fluoro-phenyl)-5-methyl-isoxazol-4-ylmethoxy]-2-methyl-2H-pyrazole-3-carboxylic acid ((1R,2R)-2-hydroxy-cyclopentyl)-amide, 5-[3-(4-Fluoro-phenyl)-5-methyl-isoxazol-4-ylmethoxy]-2-methyl-2H-pyrazole-3-carboxylic acid ((R)-2-hydroxy-1-methyl-ethyl)-amide, and 5-[3-(4-Fluoro-phenyl)-5-methyl-isoxazol-4-ylmethoxy]-2-methyl-2H-pyrazole-3-carboxylic acid ((S)-2-hydroxy-1-methyl-ethyl)-amide or a pharmaceutically acceptable salt or ester thereof.

40. The compound of claim 32, selected from the group consisting of

5-[3-(4-Fluoro-phenyl)-5-methyl-isoxazol-4-ylmethoxy]-2-methyl-2H-pyrazole-3-carboxylic acid (®-2-hydroxy-1-methyl-ethyl)-amide, 5-[3-(4-Fluoro-phenyl)-5-methyl-isoxazol-4-ylmethoxy]-2-methyl-2H-pyrazole-3-carboxylic acid ((S)-2-hydroxy-1-methyl-ethyl)-amide, 5-[3-(5-Fluoro-pyridin-2-yl)-5-methyl-isoxazol-4-ylmethoxy]-2-methyl-2H-pyrazole-3-carboxylic acid (tetrahydro-furan-3-yl)-amide, 5-[3-(5-Fluoro-pyridin-2-yl)-5-methyl-isoxazol-4-ylmethoxy]-2-methyl-2H-pyrazole-3-carboxylic aci' N',N'-dimethyl-hydrazide, 5-[3-(5-Fluoro-pyridin-2-yl)-5-methyl-isoxazol-4-yl-methoxy]-2-methyl-2H-pyrazole-3-carboxylic acid (2-hydroxy-ethyl)-amide, and 5-[3-(5-Fluoro-pyridin-2-yl)-5-methyl-isoxazol-4-yl-methoxy]-2-methyl-2H-pyrazole-3-carboxylic acid (tetrahydro-pyran-4-yl)-amide, or a pharmaceutically acceptable salt or ester thereof.

41. The compound of claim 1, selected from the group consisting of

{5-[3-(4-Chloro-phenyl)-5-hydroxymethyl-isoxazol-4-yl-methoxy]-2-methyl-2H-pyrazol-3-yl}-(2-oxa-6-aza-spiro[3.3]hept-6-yl)-methanone, {5-[3-(4-Fluoro-phenyl)-5-methyl-isoxazol-4-yl-methoxy]-2-methyl-2H-pyrazol-3-yl}-(2-oxa-6-aza-spiro[3.3]hept-6-yl)-methanone, 2-Methyl-5-(5-methyl-3-phenyl-isoxazol-4-ylmethoxy)-2H-pyrazole-3-carboxylic acid (tetrahydro-pyran-4-yl)-amide, 2-Methyl-5-(5-methyl-3-pyridin-2-yl-isoxazol-4-yl-methoxy)-2H-pyrazole-3-carboxylic acid (tetrahydro-pyran-4-yl)-amide, 5-[3-(4-Chloro-phenyl)-5-hydroxymethyl-isoxazol-4-yl-methoxy]-2-methyl-2H-pyrazole-3-carboxylic acid (tetrahydro-pyran-4-yl)-amide, 5-[3-(4-Chloro-phenyl)-5-hydroxymethyl-isoxazol-4-yl-methoxy]-2-methyl-2H-pyrazole-3-carboxylic acid (3-methyl-oxetan-3-yl)-amide, 5-[3-(4-Chloro-phenyl)-5-hydroxymethyl-isoxazol-4-yl-methoxy]-2-methyl-2H-pyrazole-3-carboxylic acid (tetrahydro-furan-3-yl)-amide, 5-[3-(4-Fluoro-phenyl)-5-hydroxymethyl-isoxazol-4-yl-methoxy]-2-methyl-2H-pyrazole-3-carboxylic acid (tetrahydro-pyran-4-yl)-amide, 5-[3-(4-Fluoro-phenyl)-5-hydroxymethyl-isoxazol-4-yl-methoxy]-2-methyl-2H-pyrazole-3-carboxylic acid isopropylamide, 5-[3-(4-Fluoro-phenyl)-5-hydroxymethyl-isoxazol-4-yl-methoxy]-2-methyl-2H-pyrazole-3-carboxylic acid (tetrahydro-furan-3-yl)-amide, 5-[3-(4-Fluoro-phenyl)-5-methyl-isoxazol-4-ylmethoxy]-2-methyl-2H-pyrazole-3-carboxylic acid morpholin-4-ylamide, 5-[3-(4-Fluoro-phenyl)-5-methyl-isoxazol-4-ylmethoxy]-2-methyl-2H-pyrazole-3-carboxylic acid (tetrahydro-pyran-4-yl)-amide, and 5-[3-(5-Fluoro-pyridin-2-yl)-5-methyl-isoxazol-4-yl-methoxy]-2-methyl-2H-pyrazole-3-carboxylic acid (tetrahydro-pyran-4-yl)-amide, or a pharmaceutically acceptable salt or ester thereof.

42. The compound of claim 19, wherein L is —CH$_2$—NH—.

43. The compound of claim 42, wherein X is N, Y is N—R$^6$.

44. The compound of claim 43, wherein R$^6$ is H.

45. The compound of claim 44, selected from the group consisting of

5-{[3-(4-Fluoro-phenyl)-5-methyl-isoxazol-4-ylmethyl]-amino}-2H-pyrazole-3-carboxylic acid (2-hydroxy-2-methyl-propyl)-amide, 5-{[3-(4-Fluoro-phenyl)-5-methyl-isoxazol-4-ylmethyl]-amino}-2H-pyrazole-3-carboxylic acid amide, 5-{[3-(4-Fluoro-phenyl)-5-methyl-isoxazol-4-ylmethyl]-amino}-2H-pyrazole-3-carboxylic acid isopropylamide, 5-{[3-(4-Fluoro-phenyl)-5-methyl-isoxazol-4-ylmethyl]-amino}-2H-pyrazole-3-carboxylic acid ethylamide, 5-{[3-(4-Fluoro-phenyl)-5-methyl-isoxazol-4-ylmethyl]-amino}-2H-pyrazole-3-carboxylic acid (tetrahydro-pyran-4-yl)-amide, 5-{[3-(4-Fluoro-phenyl)-5-methyl-isoxazol-4-ylmethyl]-amino}-2H-pyrazole-3-carboxylic acid (2-hydroxy-1-methyl-ethyl)-amide, and (5-{[3-(4-Fluoro-phenyl)-5-methyl-isoxazol-4-ylmethyl]-amino}-2H-pyrazol-3-yl)-(2-oxa-6-aza-spiro[3.3]hept-6-yl)-methanone, or a pharmaceutically acceptable salt or ester thereof.

46. The compound of claim 43, wherein R$^6$ is methyl.

47. The compound of claim 46, selected from the group consisting of

5-{[3-(4-Fluoro-phenyl)-5-methyl-isoxazol-4-ylmethyl]-amino}-2-methyl-2H-pyrazole-3-carboxylic acid (2-hydroxy-2-methyl-propyl)-amide, 5-{[3-(4-Fluoro-phenyl)-5-methyl-isoxazol-4-ylmethyl]-amino}-2-methyl-2H-pyrazole-3-carboxylic acid amide, 5-{[3-(4-Fluoro-phenyl)-5-methyl-isoxazol-4-ylmethyl]-amino}-2-methyl-2H-pyrazole-3-carboxylic acid (2,2,2-trifluoro-ethyl)-amide, 5-{[3-(4-Fluoro-phenyl)-5-methyl-isoxazol-4-ylmethyl]-amino}-2-methyl-2H-pyrazole-3-carboxylic acid (tetrahydro-pyran-4-yl)-amide, 5-{[3-(4-Fluoro-phenyl)-5-methyl-isoxazol-4-ylmethyl]-amino}-2-methyl-2H-pyrazole-3-carboxylic acid (3-methyl-oxetan-3-yl)-amide, (5-{[3-(4-Fluoro-phenyl)-5-methyl-isoxazol-4-ylmethyl]-amino}-2-methyl-2H-pyrazole-3-yl)-(2-oxa-6-aza-spiro[3.3]hept-6-yl)-methanone, 5-{[3-(4-Fluoro-phenyl)-5-methyl-isoxazol-4-ylmethyl]-amino}-2-methyl-2H-pyrazole-3-carboxylic acid (2-hydroxy-1-methyl-ethyl)-amide, 5-{[3-(4-Fluoro-phenyl)-5-methyl-isoxazol-4-ylmethyl]-amino}-2-methyl-2H-pyrazole-3-carboxylic acid isopropylamide, and N-isopropyl-1-methyl-3-methyl-3-(pyridin-2-yl)isoxazol-4-yl)methylamino)-1H-pyrazole-5-carboxamide or a pharmaceutically acceptable salt or ester thereof.

48. The compound of claim 46, selected from the group consisting of

2-Methyl-5-[(5-methyl-3-pyridin-2-yl-isoxazol-4-ylmethyl)-amino]-2H-pyrazole-3-carboxylic acid (tetrahydro-pyran-4-yl)-amide, 1-Methyl-3-((5-methyl-3-(pyridin-2-yl)isoxazol-4-yl)methylamino)-N-morpholino-1H-pyrazole-5-carboxamide, 1-Methyl-3-((5-methyl-3-(pyridin-2-yl)isoxazol-4-yl)methylamino)-N-(3-methyloxetan-3-yl)-1H-pyrazole-5-carboxamide, 3-((3-(5-Fluoropyridin-2-yl)-5-methylisoxazol-4-yl)methylamino)-N-isopropyl-1-methyl-1H-pyrazole-5-carboxamide, 3-((3-(5-fluoropyridin-2-yl)-5-methylisoxazol-4-yl)methylamino)-1-methyl-N-(tetrahydro-2H-pyran-4-yl)-1H-pyrazole-5-carboxamide, N-Cyclopropyl-3-((3-(5-fluoropyridin-2-yl)-5-methyl-isoxazol-4-yl)methylamino)-1-methyl-1H-pyrazole-5-carboxamide, N-(Cyclopropylmethyl)-3-((3-(5-fluoropyridin-2-yl)-5-methylisoxazol-4-yl)methylamino)-1-methyl-1H-pyrazole-5-carboxamide, 3-((3-(5-Fluoropyridin-2-yl)-5-methylisoxazol-4-yl)methylamino)-1-methyl-N-(3-methyloxetan-3-yl)-1H-pyrazole-5-carboxamide, and (3-((3-(5-Fluoropyridin-2-yl)-5-methylisoxazol-4-yl)methylamino)-1-methyl-1H-pyrazol-5-yl)(2-oxa-6-aza-spiro[3.3]heptan-6-yl)methanone, or a pharmaceutically acceptable salt or ester thereof.

49. The compound of claim 46, selected from the group consisting of
- 5-{[3-(4-Fluoro-phenyl)-5-methyl-isoxazol-4-ylmethyl]-amino}-2-methyl-2H-pyrazole-3-carboxylic acid (2-hydroxy-2-methyl-propyl)-amide,
- 5-{[3-(4-Fluoro-phenyl)-5-methyl-isoxazol-4-ylmethyl]-amino}-2-methyl-2H-pyrazole-3-carboxylic acid (tetrahydro-pyran-4-yl)-amide,
- 5-{[3-(4-Fluoro-phenyl)-5-methyl-isoxazol-4-ylmethyl]-amino}-2-methyl-2H-pyrazole-3-carboxylic acid (3-methyl-oxetan-3-yl)-amide,
- 2-Methyl-5-[(5-methyl-3-pyridin-2-yl-isoxazol-4-ylmethyl)-amino]-2H-pyrazole-3-carboxylic acid (tetrahydro-pyran-4-yl)-amide,
- 1-Methyl-3-((5-methyl-3-(pyridin-2-yl)isoxazol-4-yl)methylamino)-N-morpholino-1H-pyrazole-5-carboxamide,
- 3-((3-(5-Fluoropyridin-2-yl)-5-methylisoxazol-4-yl)methylamino)-1-methyl-N-(tetrahydro-2H-pyran-4-yl)-1H-pyrazole-5-carboxamide, and
- 3-((3-(5-Fluoropyridin-2-yl)-5-methylisoxazol-4-yl)methylamino)-1-methyl-N-(3-methyloxetan-3-yl)-1H-pyrazole-5-carboxamide, or a pharmaceutically acceptable salt or ester thereof.

50. The compound of claim 1, wherein L is —CH═CH—.
51. The compound of claim 50, wherein X is N, Y is N—R$^6$.
52. The compound of claim 51, wherein R$^6$ is H.
53. The compound of claim 52, selected from the group consisting of
- 5-[(E)-2-(5-Methyl-3-phenyl-isoxazol-4-yl)-vinyl]-2H-pyrazole-3-carboxylic acid isopropylamide,
- 5-[(Z)-2-(5-Methyl-3-phenyl-isoxazol-4-yl)-vinyl]-2H-pyrazole-3-carboxylic acid isopropylamide,
- (1,1-Dioxo-1,6-thiomorpholin-4-yl)-(5-{(E)-2-[3-(4-fluoro-phenyl)-5-methyl-isoxazol-4-yl]-vinyl}-2H-pyrazol-3-yl)-methanone,
- (5-{(E)-2-[3-(4-Fluoro-phenyl)-5-methyl-isoxazol-4-yl]-vinyl}-2H-pyrazol-3-yl)-morpholin-4-yl-methanone,
- 5-{(E)-2-[3-(4-Fluoro-phenyl)-5-methyl-isoxazol-4-yl]-vinyl}-2H-pyrazole-3-carboxylic acid (2,2,2-trifluoro-ethyl)-amide,
- 5-{(E)-2-[3-(4-Fluoro-phenyl)-5-methyl-isoxazol-4-yl]-vinyl}-2H-pyrazole-3-carboxylic acid isopropylamide,
- 5-{(E)-2-[3-(4-Fluoro-phenyl)-5-methyl-isoxazol-4-yl]-vinyl}-2H-pyrazole-3-carboxylic acid (tetrahydro-pyran-4-yl)-amide,
- (5-{(E)-2-[3-(4-Fluoro-phenyl)-5-methyl-isoxazol-4-yl]-vinyl}-2H-pyrazol-3-yl)-(2-oxa-6-aza-spiro[3.3]hept-6-yl)-methanone,
- 5-{(E)-2-[3-(4-Fluoro-phenyl)-5-methyl-isoxazol-4-yl]-vinyl}-2H-pyrazole-3-carboxylic acid (2-hydroxy-1,1-dimethyl-ethyl)-amide,
- 5-{(E)-2-[3-(4-Fluoro-phenyl)-5-methyl-isoxazol-4-yl]-vinyl}-2H-pyrazole-3-carboxylic acid (2-hydroxy-1-methyl-ethyl)-amide,
- 5-{(E)-2-[3-(4-Fluoro-phenyl)-5-methyl-isoxazol-4-yl]-vinyl}-2H-pyrazole-3-carboxylic acid (2-hydroxy-2-methyl-propyl)-amide,
- 5-{(E)-2-[3-(4-Fluoro-phenyl)-5-methyl-isoxazol-4-yl]-vinyl}-2H-pyrazole-3-carboxylic acid ethylamide, and
- 5-{(E)-2-[3-(4-Fluoro-phenyl)-5-methyl-isoxazol-4-yl]-vinyl}-2H-pyrazole-3-carboxylic acid amide, or a pharmaceutically acceptable salt or ester thereof.

54. The compound of claim 53, selected from the group consisting of
- 5-[(E)-2-(5-Methyl-3-phenyl-isoxazol-4-yl)-vinyl]-2H-pyrazole-3-carboxylic acid isopro-pylamide, and
- 5-[(Z)-2-(5-Methyl-3-phenyl-isoxazol-4-yl)-vinyl]-2H-pyrazole-3-carboxylic acid isopro-pylamide, or a pharmaceutically acceptable salt or ester thereof.

55. The compound of claim 51, wherein R$^6$ is methyl.
56. The compound of claim 55, selected from the group consisting of
- 5-{(Z)-2-[3-(4-Fluoro-phenyl)-5-methyl-isoxazol-4-yl]-vinyl}-2-methyl-2H-pyrazole-3-carboxylic acid isopropylamide,
- 5-{(Z)-2-[3-(4-Fluoro-phenyl)-5-methyl-isoxazol-4-yl]-vinyl}-2-methyl-2H-pyrazole-3-carboxylic acid (2-hydroxy-1-methyl-ethyl)-amide,
- 5-{(E)-2-[3-(4-Fluoro-phenyl)-5-methyl-isoxazol-4-yl]-vinyl}-2-methyl-2H-pyrazole-3-carboxylic acid isopropylamide,
- 5-{(E)-2-[3-(4-Fluoro-phenyl)-5-methyl-isoxazol-4-yl]-vinyl}-2-methyl-2H-pyrazole-3-carboxylic acid ethylamide,
- 5-{(E)-2-[3-(4-Fluoro-phenyl)-5-methyl-isoxazol-4-yl]-vinyl}-2-methyl-2H-pyrazole-3-carboxylic acid (2-hydroxy-2-methyl-propyl)-amide,
- 5-{(E)-2-[3-(4-Fluoro-phenyl)-5-methyl-isoxazol-4-yl]-vinyl}-2-methyl-2H-pyrazole-3-carboxylic acid (tetrahydro-pyran-4-yl)-amide,
- 5-{(E)-2-[3-(4-Fluoro-phenyl)-5-methyl-isoxazol-4-yl]-vinyl}-2-methyl-2H-pyrazole-3-carboxylic acid amide,
- (1,1-Dioxo-1,6-thiomorpholin-4-yl)-(5-{(E)-2-[3-(4-fluoro-phenyl)-5-methyl-isoxazol-4-yl]-vinyl}-2-methyl-2H-pyrazol-3-yl)-methanone,
- 5-{(E)-2-[3-(4-Fluoro-phenyl)-5-methyl-isoxazol-4-yl]-vinyl}-2-methyl-2H-pyrazole-3-carboxylic acid (2,2,2-trifluoro-ethyl)-amide,
- (5-{(E)-2-[3-(4-Fluoro-phenyl)-5-methyl-isoxazol-4-yl]-vinyl}-2-methyl-2H-pyrazol-3-yl)-morpholin-4-yl-methanone,
- 5-{(E)-2-[3-(4-Fluoro-phenyl)-5-methyl-isoxazol-4-yl]-vinyl}-2-methyl-2H-pyrazole-3-carboxylic acid (2-hydroxy-1-methyl-ethyl)-amide,
- (5-{(E)-2-[3-(4-Fluoro-phenyl)-5-methyl-isoxazol-4-yl]-vinyl}-2-methyl-2H-pyrazol-3-yl)-(2-oxa-6-aza-spiro[3.3]hept-6-yl)-methanone, and
- 5-{(E)-2-[3-(4-Fluoro-phenyl)-5-methyl-isoxazol-4-yl]-vinyl}-2-methyl-2H-pyrazole-3-carboxylic acid (2-hydroxy-1,1-dimethyl-ethyl)-amide, or a pharmaceutically acceptable salt or ester thereof.

57. A pharmaceutical composition comprising a therapeutically effective amount of a compound of formula I

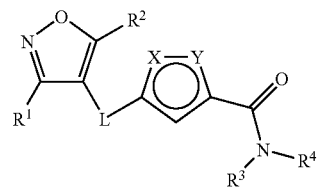

wherein
L is —CH$_2$—O—, —CH$_2$—NH— or —CH═CH—;
X is N—R$^5$ and Y is N, or X is N and Y is N—R$^6$;
R$^1$ is selected from the group consisting of
 i) lower alkyl,
 ii) lower alkyl substituted by 1-5 halogen atoms,
 iii) aryl,
 iv) aryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)
N—, N(lower alkyl,lower alkyl)-lower alkyl, N(lower
alkyl,H)-lower alkyl, nitro, lower alkyl-S(O)$_2$—, carboxy, carboxy-lower alkyl, lower alkyl-COO-lower
alkyl, COO-lower alkyl, CO—N(lower alkyl,H)-lower alkyl, CO—N(lower alkyl,lower alkyl)-lower
alkyl, CO—NH$_2$-lower alkyl and lower alkyl-CO—, v) heteroaryl, vi) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, lower alkyl-COO—, CO—N(lower alkyl,H)-lower alkyl, CO—N(lower alkyl,lower alkyl)-lower alkyl, CO—NH$_2$-lower alkyl and lower alkyl-CO—, and vii) heterocyclyl;

$R^2$ is H, lower alkyl or lower alkyl substituted by 1-5 substituents individually selected from halogen and hydroxy;

$R^3$ is selected from the group consisting of i) H, ii) lower alkyl, iii) lower alkyl substituted by 1-5 substituents individually selected from acetamidyl, acetyl, acetylamino, amido, amino, carboxy, cyano, cycloalkyl, halogen, halogen-lower alkoxy, heterocyclyl, hydroxy, lower alkoxy, (lower alkyl,lower alkyl)N—, (lower alkyl,H)N—, nitro and lower alkyl-S(O)$_2$—, iv) heteroaryl, v) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, lower alkyl-COO—, CO—N(lower alkyl,H)-lower alkyl, CO—N(lower alkyl,lower alkyl)-lower alkyl, CO—NH$_2$-lower alkyl, and lower alkyl-CO—, xvi) cycloalkyl, xvii) cycloalkyl substituted by 1-4 substituents individually selected from halogen and hydroxy, xviii) heterocyclyl, xix) heterocyclyl substituted by 1-4 substituents individually selected from halogen and lower alkyl, and xx) —NR$^7$R$^8$;

$R^4$ is H, lower alkyl or lower alkyl substituted by 1-5 halogen atoms;

or $R^3$ and $R^4$ together with the nitrogen to which they are attached form a heterocyclyl or a heterocyclyl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, lower alkyl-COO—, CO—N(lower alkyl,H)-lower alkyl, CO—N(lower alkyl,lower alkyl)-lower alkyl, CO—NH$_2$-lower alkyl and lower alkyl-CO—;

$R^5$ is H or lower alkyl;

$R^6$ is H or lower alkyl;

$R^7$ is lower alkyl; and $R^8$ is lower alkyl, or a pharmaceutically acceptable salt or ester thereof and a pharmaceutically acceptable carrier.

* * * * *